(12) United States Patent
Lockman et al.

(10) Patent No.: US 10,550,088 B2
(45) Date of Patent: Feb. 4, 2020

(54) 6-SUBSTITUTED AND 7-SUBSTITUTED MORPHINAN ANALOGS AND THE USE THEREOF

(71) Applicant: Purdue Pharma L.P., Stamford, CT (US)

(72) Inventors: Jeffrey Lockman, Princeton Junction, NJ (US); Laykea Tafesse, Robbinsville, NJ (US); Jae Hyun Park, Chandler, AZ (US); Mark A. Youngman, North Wales, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 15/108,391

(22) PCT Filed: Oct. 10, 2014

(86) PCT No.: PCT/US2014/060113
§ 371 (c)(1),
(2) Date: Jun. 27, 2016

(87) PCT Pub. No.: WO2015/099863
PCT Pub. Date: Jul. 2, 2015

(65) Prior Publication Data
US 2016/0318872 A1 Nov. 3, 2016

Related U.S. Application Data

(60) Provisional application No. 61/921,354, filed on Dec. 27, 2013.

(51) Int. Cl.
*C07D 221/28* (2006.01)
*C07D 491/18* (2006.01)
*C07C 53/18* (2006.01)

(52) U.S. Cl.
CPC ............ *C07D 221/28* (2013.01); *C07C 53/18* (2013.01); *C07D 491/18* (2013.01)

(58) Field of Classification Search
None
See application file for complete search history.

(56) References Cited

U.S. PATENT DOCUMENTS

| | | | | |
|---|---|---|---|---|
| 2,723,268 A | * | 11/1955 | Heneka et al. | C07D 221/28 546/22 |
| 4,089,855 A | * | 5/1978 | Chatterjie | C07D 221/28 514/823 |
| 6,740,641 B2 | | 5/2004 | Gao et al. | |
| 6,825,205 B2 | | 11/2004 | Kyle | |
| 6,958,398 B1 | | 10/2005 | Kupper et al. | |
| 7,084,150 B2 | | 8/2006 | Boer et al. | |
| 7,125,884 B2 | | 10/2006 | Reidenberg et al. | |
| 7,202,259 B2 | | 4/2007 | Chen | |
| 7,687,518 B2 | | 3/2010 | Chen | |
| 8,026,254 B2 | | 9/2011 | Chen | |
| 8,426,594 B2 | | 4/2013 | Kyle | |
| 8,481,743 B2 | | 7/2013 | Zhou | |
| 8,530,494 B2 | | 9/2013 | Kyle et al. | |
| 8,937,084 B2 | | 1/2015 | Park et al. | |
| 8,946,255 B2 | | 2/2015 | Kassick et al. | |
| 8,957,084 B2 | | 2/2015 | Kyle et al. | |
| 8,969,358 B2 | | 3/2015 | Goehring et al. | |

(Continued)

FOREIGN PATENT DOCUMENTS

| | | | |
|---|---|---|---|
| GB | 1006337 | * | 9/1965 |
| WO | WO-2013/093931 | | 6/2013 |

(Continued)

OTHER PUBLICATIONS

Database Caplus Chemical Abstracts Service, Columbus, Ohio, US; Database Accession No. 1956:44966, Abstract of U.S. Pat. No. 2,723,268, Farbenfabriken Bayer Akt.-Ges., Heneka et al., Nov. 8, 1955.*
Gates et al., Journal of the American Chemical Society (1956), 78, 1380-93.*
Database Caplus Chemical Abstracts Service, Columbus, Ohio, US; Database Accession No. 1963:435773, Abstract of Seki et al., Yakugaku (Year: 1963).*
Database Caplus Chemical Abstracts Service, Columbus, Ohio, US; Database Accession No. 2005:470410, Abstract of Schuetz et al., et al., Journal of Organic Chemistry (2005), 70(13), (Year: 2005).*
Database Caplus Chemical Abstracts Service, Columbus, Ohio, US; Database Accession No. 1965:431613, Abstract of JP 40010154, Sawa et al., Sawa, Yoshiro; Maeda, Shin; Tada, Harunhiko, May 24 (Year: 1965).*
Database Caplus Chemical Abstracts Service, Columbus, Ohio, US; Database Accession No. 1976:433236, Abstract of Menard et al., Canadian (Year: 1976).*

(Continued)

*Primary Examiner* — Karl J Puttlitz
(74) *Attorney, Agent, or Firm* — Purdue Pharma L.P.; Weiying Yang

(57) ABSTRACT

The application is directed to compounds of Formula I or II: and pharmaceutically acceptable salts and solvates thereof, wherein R', R", R''' $R^1$, $R^2$, $R^3$, $R^4$, $R^{4a}$, and $R^{20}$ are defined as set forth in the specification. The invention is also directed to use of compounds of Formula I or II and the pharmaceutically acceptable salts and solvates thereof to treat disorders responsive to the modulation of one or more opioid receptors. Certain compounds of the invention are especially useful for treating pain.

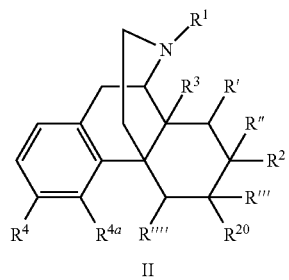

10 Claims, No Drawings

(56) References Cited

U.S. PATENT DOCUMENTS

| | | |
|---|---|---|
| 8,980,906 B2 | 3/2015 | Tafesse |
| 8,987,287 B2 | 3/2015 | Goehring et al. |
| 9,056,836 B2 | 6/2015 | Lockman et al. |
| 9,096,606 B2 | 8/2015 | Kyle |
| 9,175,000 B2 | 11/2015 | Youngman |
| 9,221,831 B2 | 12/2015 | Kyle |
| 9,273,048 B2 | 2/2016 | Goehring et al. |
| 9,315,514 B2 | 4/2016 | Reisch |
| 2005/0192308 A1 | 9/2005 | Reidenberg et al. |
| 2011/0136848 A1 | 6/2011 | Silverman |
| 2012/0010412 A1 | 1/2012 | Duncan |
| 2014/0135351 A1 | 5/2014 | Lockman et al. |
| 2015/0175571 A1 | 6/2015 | Kassick et al. |
| 2015/0183787 A1 | 7/2015 | Lockman |
| 2015/0203504 A1 | 7/2015 | Goehring et al. |
| 2015/0210646 A1 | 7/2015 | Park et al. |
| 2016/0244459 A1 | 8/2016 | Kupper |
| 2016/0318932 A1 | 11/2016 | Youngman |
| 2016/0333020 A1 | 11/2016 | Kyle |
| 2016/0340316 A1 | 11/2016 | Lockman |
| 2017/0037046 A1 | 2/2017 | Tafesse |
| 2017/0073313 A1 | 3/2017 | Tafesse |
| 2017/0107220 A1 | 4/2017 | Park |
| 2017/0190702 A1 | 7/2017 | Youngman |
| 2017/0204113 A1 | 7/2017 | Tafesse |

FOREIGN PATENT DOCUMENTS

| | | |
|---|---|---|
| WO | WO-2015/097545 | 7/2015 |
| WO | WO-2015/097547 | 7/2015 |
| WO | WO-2015/097548 | 7/2015 |
| WO | WO-2015/100092 | 7/2015 |
| WO | WO-2015/100174 | 7/2015 |
| WO | WO-2015/102682 | 7/2015 |
| WO | WO-2015/123398 | 8/2015 |
| WO | WO-2015/171553 | 11/2015 |
| WO | WO-2015/183780 | 12/2015 |
| WO | WO-2015/192039 | 12/2015 |
| WO | WO-2015/192053 | 12/2015 |
| WO | WO-2016/044546 | 3/2016 |

OTHER PUBLICATIONS

Database Caplus Chemical Abstracts Service, Columbus, Ohio, US; Database Accession No. 1963:437013, Abstract of Ikekawa et al., Scientific Papers of the Institute of Physical and Chemical (Year: 1963).*
Database Caplus Chemical Abstracts Service, Columbus, Ohio, US; Database Accession No. 1978:547121, Abstract of Chatterjie et al., U.S. Pat. No. 4,089,855, May 16, 1978 (Year: 1978).*
Foley, K.M. Pain. in: J.C. Bennett, F. Plum (Eds.) Cecil textbook of medicine. 20th ed. WB Saunders, Philadelphia; 1996:100-107.
International Search Report from corresponding PCT Application No. PCT/US14/60113 dated Feb. 3, 2015 with Written Opinion.
Negus et al., Psychopharmacology (Berl) 210:149-159 (2010).
Pande et al., Clin. Neuropharmacol. 19:451-456 (1996).
Pande et al., Clin. Neuropharmacol. 19:92-97 (1996).
Stork et al., "Regiospecific and Stereoselective Syntheses of (?) Morphine, Codeine, and Thebaine Via a Highly Stereocontrolled Intramolecular 4 + 2 Cycloaddition Leading to a Phenanthrofuran System" Journal of the American Chemical Society, 2009, vol. 131, No. 32, pp. 11402-11406.
Vanderah et al., J. Pharmacol. Exp Ther. 310:326-333 (2004).
Wadenberg, CNS Drug Rev. 9:187-198 (2003).

* cited by examiner

6-SUBSTITUTED AND 7-SUBSTITUTED MORPHINAN ANALOGS AND THE USE THEREOF

CROSS-REFERENCE TO RELATED APPLICATIONS

This application is the U.S. national phase, pursuant to 35 U.S.C. § 371, of PCT International Application Ser. No. PCT/US2014/060113, filed on Oct. 10, 2014, designating the United States and published in English on Jul. 2, 2015 as publication WO 2015/099863 A1, which claims priority to U.S. Provisional Application Ser. No. 61/921,354, filed on Dec. 27, 2013. The contents of the afore-mentioned patent applications are incorporated herein by their entirety.

BACKGROUND OF THE INVENTION

Field of the Invention

This application is in the field of medicinal chemistry. The application relates to novel 6-substituted and 7-substituted morphinan analogs, and pharmaceutical compositions comprising one or more of these compounds. The application also relates to the methods of making 6-substituted and 7-substituted morphinan analogs, and their use.

Description of the Related Art

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in *Cecil Textbook of Medicine* 100-107, J. C. Bennett and F. Plum eds., 20th ed. 1996).

Pain has traditionally been managed by administering either a non-opioid analgesic (such as acetylsalicylic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone, oxymorphone, or buprenorphine).

Until recently, there was evidence of three major classes of opioid receptors in the central nervous system (CNS), with each class having subtype receptors. These receptor classes are known as μ, δ and κ. As opiates have a high affinity to these receptors while not being endogenous to the body, research followed in order to identify and isolate the endogenous ligands to these receptors. These ligands were identified as endorphins, enkephalins, and dynorphins, respectively. Additional experimentation has led to the identification of the opioid receptor-like (ORL-1) receptor, which has a high degree of homology to the known opioid receptor classes. This more recently discovered receptor was classified as an opioid receptor based only on structural grounds, as the receptor did not exhibit pharmacological homology. It was initially demonstrated that non-selective ligands having a high affinity for μ, δ and κ receptors had low affinity for the ORL-1 receptor. This characteristic, along with the fact that an endogenous ligand had not yet been discovered, led to the ORL-1 receptor being designated as an "orphan receptor".

Kappa (κ) opioid receptor agonists have been evaluated as alternatives to existing analgesics for the treatment of pain. Centrally penetrating κ agonists produce antinociceptive effects in conventional preclinical assays of basal, inflammatory and neuropathic pain (Vanderah et al., *J. Pharmacol. Exp. Ther.* 310:326-333 (2004); Negus et al., *Psychopharmacology (Berl)* 210:149-159 (2010)). However, centrally penetrating κ agonists can also produce undesirable side-effects, such as sedative and psychotomimetic effects (Pande et al., *Clin. Neuropharmacol.* 19:92-97 (1996); Pande et al., *Clin. Neuropharmacol.* 19:451-456 (1996); and Wadenberg, *CNS Drug Rev.* 9:187-198 (2003)).

Opioid receptor agonists that do not readily cross the blood-brain barrier are peripherically restricted and distribute poorly to the central nervous system after systemic administration. Such compounds would retain an ability to produce analgesia by acting on peripheral opioid receptors, such as peripheral κ-opioid receptors, but their potency to produce centrally mediated side-effects would be reduced.

There is a need for effective analgesics that work by acting on opioid receptors. There is also a need for analgesics that work by acting on peripheral opioid receptors. There is also a need for analgesics that work by acting on central opioid receptors. There is also a need for analgesics that work by acting on κ-opioid receptors. There is also a need for analgesics that work by acting on peripheral κ-opioid receptors.

BRIEF SUMMARY OF THE INVENTION

The present invention provides novel 6-substituted and 7-substituted morphinan analog compounds represented by Formulae I, II, and I-A to I-AE below, and the pharmaceutically acceptable salts and solvates thereof, collectively referred to herein as "Compounds of the Invention" (each is individually referred to hereinafter as a "Compound of the Invention").

In another aspect, the present disclosure provides the use of Compounds of the Invention as synthesis intermediates.

In another aspect, the present disclosure provides the use of Compounds of the Invention as modulators of one or more opioid receptors. Specifically, the present disclosure provides the use of Compounds of the Invention as modulators of μ, δ, κ, and/or ORL-1 opioid receptors, and especially modulators of μ and/or κ opioid receptors.

In another aspect, the present disclosure provides a method of treating or preventing a disorder responsive to the modulation of one or more opioid receptors in a patient, comprising administering to the patient an effective amount of a Compound of the Invention.

In another aspect, the present disclosure provides a use of a Compound of the Invention as an analgesic to treat or prevent pain; or as an agent to treat or prevent withdrawal from alcohol or drug addiction; or as an agent to treat of prevent addictive disorders; or as an agent to treat a pruritic condition; or as an agent to treat or prevent constipation; or as an agent to treat or prevent diarrhea (each of pain, alcohol withdrawal, drug withdrawal, addictive disorders, pruritis, constipation, and diarrhea being a "Condition").

The present invention further provides methods of treating or preventing a Condition, comprising administering to a patient in need thereof a therapeutically effective amount of a Compound of the Invention. In certain embodiments, the Condition is pain (including acute pain, chronic pain (which includes but is not limited to, neuropathic pain, postoperative pain, and inflammatory pain), and surgical pain). The Compounds of the Invention are particularly useful for treating or preventing chronic pain.

In another aspect, the present disclosure provides a pharmaceutical composition comprising a therapeutically effective amount of a Compound of the Invention and one or more pharmaceutically acceptable carriers. Such compositions are useful for treating or preventing a Condition in a patient.

In another aspect, the present disclosure provides Compounds of the Invention for use in treatment or prevention of a disorder responsive to the modulation of one or more opioid receptors. Preferably, the disorder is responsive to modulation of the μ-opioid receptor or the κ-opioid receptor, or to modulation of a combination thereof.

In another aspect, the present disclosure provides a method of modulating one or more opioid receptors in a patient in need of said modulation, comprising administering to the patient an opioid receptor modulating amount of a Compound of the Invention.

In another aspect, the present disclosure provides Compounds of the Invention for use in treatment or prevention of one or more Conditions in a patient in need of said treatment or prevention.

In another aspect, the present disclosure provides Compounds of the Invention for use in treatment or prevention of pain in a patient, such as acute pain, chronic pain (which includes but is not limited to, neuropathic pain, postoperative pain, and inflammatory pain), or surgical pain.

In another aspect, the present disclosure provides Compounds of the Invention for use in modulation of one or more opioid receptors in a patient.

In another aspect, the present disclosure provides use of Compounds of the Invention in the manufacture of a medicament for treating or preventing a disorder responsive to the modulation of one or more opioid receptors.

In another aspect, the present disclosure provides use of Compounds of the Invention in the manufacture of a medicament for modulating of one or more opioid receptors in a patient. Preferably, the μ- or κ-opioid receptor is modulated, or both the μ- and κ-opioid receptors are modulated.

In another aspect, the present disclosure provides Compounds of the Invention for use as a medicament.

In another aspect, the present disclosure provides use of a Compound of the Invention in the manufacture of a medicament for treating or preventing a Condition in a patient.

In another aspect, the present disclosure provides use of a Compound of the Invention in the manufacture of a medicament for treating or preventing pain in a patient, such as acute pain, chronic pain, or surgical pain.

In another aspect, the present disclosure provides a pharmaceutical composition, comprising a Compound of the Invention for treating or preventing a disorder responsive to the modulation of one or more opioid receptors.

The present invention further provides methods for preparing a pharmaceutical composition, comprising admixing a Compound of the Invention and a pharmaceutically acceptable carrier to form the pharmaceutical composition.

In another aspect, the present invention provides radiolabeled Compounds of the Invention, especially $^1H$, $^{11}C$ and $^{14}C$ radiolabeled Compounds of the Invention, and the use of such compounds as radioligands to detect binding to an opioid receptor in screening assays.

In another aspect, the present invention provides a method for screening a candidate compound for the ability to bind to an opioid receptor, comprising a) introducing a fixed concentration of a radiolabeled Compound of the Invention to the receptor under conditions that permit binding of the radiolabeled compound to the receptor to form a complex; b) titrating the complex with a candidate compound; and c) determining the binding of the candidate compound to said receptor.

In a further aspect, the invention relates to a kit, comprising a sterile container containing an effective amount of a Compound of the Invention and instructions for therapeutic use.

In a further aspect, the present invention provides a method of making Compounds of the Invention.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

In one aspect, the invention provides compounds of Formula I as herein disclosed:

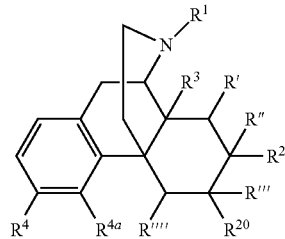

I wherein:
R', R'', R''', and R'''' are each hydrogen, or
$R^3$ and R' taken together form a double bond; or
R' and R'' taken together form a double bond; or
R'' and R''' taken together form a double bond; or
R''' and R'''' taken together form a double bond; or
$R^3$ and R' taken together form a double bond and R'' and R''' taken together form a double bond; or
$R^3$ and R' taken together form a double bond and R''' and R'''' taken together form a double bond; or
R' and R'' taken together form a double bond and R''' and R'''' taken together form a double bond;
with the proviso that when R'' and R''' taken together form a double bond or R''' and R'''' taken together form a double bond, then $R^{20}$ is not —OH;
$R^1$ is selected from the group consisting of —$(C_1-C_{10})$alkyl, —$(C_2-C_{10})$alkenyl, —$(C_2-C_{10})$alkynyl, —$(C_3-C_{12})$cycloalkyl, $(C_3-C_{12})$cycloalkyl-$(C_1-C_6)$alkyl-, —$(C_3-C_{12})$cycloalkenyl, $(C_3-C_{12})$cycloalkenyl-$(C_1-C_6)$alkyl-, -(6- to 14-membered)aryl, ((6- to 14-membered)aryl)-$(C_1-C_6)$alkyl-, diphenyl$(C_1-C_6)$alkyl-, -(3- to 12-membered)heterocycle, ((3- to 12 membered)heterocycle)-$(C_1-C_6)$alkyl-, —$(OCH_2CH_2)_s$—O—$(C_1-C_6)$alkyl, —$(CH_2CH_2O)_s$—$(C_1-C_6)$alkyl, $(C_1-C_{10})$alkoxy, C(halo)$_3$, CH(halo)$_2$, CH$_2$(halo), C(O)$R^5$, —C(O)O—$(C_1-C_{10})$alkyl, and —$(CH_2)_n$—$NR^5R^6$; each of which is optionally substituted by 1, 2 or 3 independently selected $R^9$ groups;
$R^3$ is selected from the group consisting of hydrogen, OH, halo, —$(C_1-C_{10})$alkoxy, and $NR^{17}R^{18}$; any of which is optionally substituted with 1, 2, or 3 substituents, each independently selected from OH, halo, —C(halo)$_3$, —CH(halo)$_2$, CH$_2$(halo), —$(C_1-C_{10})$alkyl-(halo)$_w$, —$NR^{17}R^{18}$, —COOH, —$(C_1-C_{10})$alkoxy, —C(═O)—$(C_1-C_{10})$alkoxy, -(5- to 12-membered)aryl, -(5- to 12-membered)heteroaryl, -(3- to 12-membered)heterocycle, —$(C_3-C_{12})$cycloalkyl, and —$(C_4-C_{12})$cycloalkenyl; wherein the -(5- to 12-membered)aryl, -(5- to 12-membered)heteroaryl, -(3- to 12-membered)heterocycle, —$(C_3-C_{12})$cycloalkyl, and —$(C_4-C_{12})$ cycloalkenyl are optionally substituted with 1, 2, or 3 independently selected $R^{40}$ groups;

$R^4$ and $R^{4a}$ are each independently selected from:
a) hydrogen, OH, halo, —C(halo)$_3$, —CH(halo)$_2$, —CH$_2$(halo), —CN, —COOH, —C(=O)NH$_2$;
b) —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_2$-C$_{10}$)alkenyloxy, —(C$_2$-C$_{10}$)alkynyloxy, any of which is optionally substituted with 1, 2, or 3 $R^{32}$ groups; or
c) —O-PG, wherein PG is a hydroxyl protecting group;

each $R^{32}$ is selected from:
a) OH, halo, haloalkyl, NR$^{17}$R$^{18}$, COOH, —(C$_1$-C$_{10}$)alkoxy, alkoxycarbonyl; or
b) -(6- to 14-membered)aryl, -(5- to 12-membered)heteroaryl, -(3- to 12-membered)heterocycle, —(C$_3$-C$_{12}$)cycloalkyl, and —(C$_3$-C$_{12}$)cycloalkenyl, any of which is optionally substituted with 1, 2, or 3 $R^{40}$ groups;

each $R^{40}$ is independently selected from the group consisting of —OH, halo, —(C$_1$-C$_{10}$)alkyl, haloalkyl, —NO$_2$, NR$^{17}$R$^{18}$, —COOH, —(C$_1$-C$_{10}$)alkoxy, and alkoxycarbonyl;

$R^5$ and $R^6$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-COOR$^7$, —CONH$_2$, and (C$_1$-C$_6$)alkyl-CONH—; and
d) -(6- to 14-membered)aryl optionally substituted with 1, 2, or 3 independently selected $R^{30}$ groups;

or $R^5$ and $R^6$ together with the nitrogen atom to which they are attached form a (3- to 12-membered)heterocycle optionally substituted with 1, 2, or 3 independently selected $R^{30}$ groups;

$R^{5a}$ and $R^{6a}$ are each independently selected from the group consisting of:
a) hydrogen, —OH, halo, —C(halo)$_3$, —CH(halo)$_2$, and —CH$_2$(halo);
b) —(C$_1$-C$_6$)alkyl, —(C$_2$-C$_6$)alkenyl, —(C$_2$-C$_6$)alkynyl, —(CH$_2$)$_n$—O—(CH$_2$)$_n$—CH$_3$, and —(C$_1$-C$_6$)alkoxy, each of which is optionally substituted with 1, 2, or 3 substituents independently selected from —OH, halo, —(C$_1$-C$_{10}$)alkyl, —(C$_2$-C$_{12}$)alkenyl, —(C$_2$-C$_{12}$)alkynyl, —(C$_1$-C$_{10}$)alkoxy, —(C$_3$-C$_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;
c) —(C$_3$-C$_8$)cycloalkyl, ((C$_3$-C$_8$)cycloalkyl)-(C$_1$-C$_6$)alkyl-, —COOR$^7$, —(C$_1$-C$_6$)alkyl-COOR$^7$, —CONH$_2$, and (C$_1$-C$_6$)alkyl-CONH—; and
d) -(6- to 14-membered)aryl optionally substituted with 1, 2, or 3 independently selected $R^{30}$ groups;

or $R^{5a}$ and $R^{6a}$ together with the nitrogen atom to which they are attached form a (3- to 12-membered)heterocycle optionally substituted with 1, 2, or 3 independently selected $R^{30}$ groups;

each $R^7$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each $R^8$ is independently selected from the group consisting of hydrogen, —(C$_1$-C$_6$)alkyl, —(C$_2$-C$_6$)alkenyl, —(C$_2$-C$_6$)alkynyl, —(C$_1$-C$_{10}$)alkoxy, —(C$_3$-C$_{12}$)cycloalkyl, —(C$_3$-C$_{12}$)cycloalkenyl, ((C$_3$-C$_{12}$)cycloalkyl)-(C$_1$-C$_6$)alkyl-, ((C$_3$-C$_{12}$)cycloalkenyl)-(C$_1$-C$_6$)alkyl-, —C(=O)(C$_1$-C$_6$)alkyl, —(C$_1$-C$_6$)alkyl-SO$_2$—(C$_1$-C$_6$)alkyl, —SO$_2$(C$_1$-C$_6$)alkyl, —SO$_2$-(6- to 14-membered)aryl, —NH$_2$, and —(C$_1$-C$_6$)alkyl-NH$_2$;

each $R^9$ is independently selected from the group consisting of —OH, halo, —(C$_1$-C$_{10}$)alkyl, —(C$_2$-C$_{10}$)alkenyl, —(C$_2$-C$_{10}$)alkynyl, —(C$_1$-C$_{10}$)alkoxy, —(C$_3$-C$_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, and CONR$^{5a}$R$^{6a}$;

each $R^7$ is independently selected from the group consisting of hydrogen, —(C$_1$-C$_6$)alkyl, —(C$_2$-C$_6$)alkenyl, —(C$_2$-C$_6$)alkynyl, —(C$_3$-C$_{12}$)cycloalkyl, —(C$_4$-C$_{12}$)cycloalkenyl, ((C$_3$-C$_{12}$)cycloalkyl)-(C$_1$-C$_6$)alkyl-, and ((C$_4$-C$_{12}$)cycloalkenyl)-(C$_1$-C$_6$)alkyl-;

each $R^{11}$ is independently selected from the group consisting of —C(halo)$_3$, —CH(halo)$_2$, —CH$_2$(halo), —(C$_2$-C$_5$)alkenyl, —(C$_2$-C$_5$)alkynyl, —(CH$_2$)$_n$—O—(CH$_2$)$_n$—CH$_3$, (6- to 14-membered)aryl, ((6- to 14-membered)aryl)-(C$_1$-C$_6$)alkyl-, and (5- to 12-membered)heteroaryl, and ((5- to 12-membered)heteroaryl)-(C$_1$-C$_6$)alkyl-; each of which is optionally substituted with 1, 2, or 3 independently selected $R^9$ groups;

each $R^{14}$ is independently selected from —COOR$^7$, —(C$_1$-C$_6$)alkyl-COOR$^7$, —C(=O)—(C$_1$-C$_6$)alkyl-COOR$^7$, —(C$_1$-C$_6$)alkyl-C(=O)—(C$_1$-C$_6$)alkyl-COOR$^7$, CONH$_2$, or —(C$_1$-C$_6$)alkyl-CONH$_2$;

each $R^{17}$ and $R^{18}$ are independently selected from the group consisting of hydrogen and —(C$_1$-C$_{10}$)alkyl;

$R^2$ is hydrogen, OH, or $Z^1$-$G^1$-$R^{10a}$;

or $R^2$ and R" taken together with the carbon atom to which they are attached form:

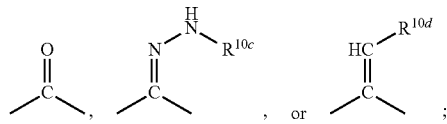

$Z^1$ is (CH$_2$)$_m$, which is optionally substituted with 1 or 2 —(C$_1$-C$_6$)alkyl;

$G^1$ is selected from:
a) a bond, —(C$_1$-C$_6$)alkylene, —(C$_2$-C$_6$)alkenylene;
b) —O—, —O—C(=O), —C(=O), =CH; or
c) NR$^8$, —NH—C(=O), —NH—C(=NH), or =N—NH;

$R^{10a}$ is selected from the group consisting of hydrogen, —(C$_1$-C$_{10}$)alkyl, —(C$_2$-C$_{12}$)alkenyl, —CH(=O), —C(=O)—(C$_1$-C$_6$)alkyl, —C(=O)—(C$_2$-C$_6$)alkenyl, —C(=O)-(6- to 14-membered)aryl, —C(=O)—(C$_1$-C$_6$)alkyl-(6- to 14-membered)aryl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, —NH(C$_1$-C$_6$)alkyl, CN, NR$^5$R$^6$, —(C$_1$-C$_6$)alkyl-NR$^5$R$^6$, —CONR$^5$R$^6$, —(C$_1$-C$_6$)alkyl-CO—NR$^5$R$^6$, —NH—C(=NH), —(C$_1$-C$_6$)alkyl-NH—C(=NH), —(C$_1$-C$_6$)alkyl-NH—C(=NH)—NR$^5$R$^6$, —COOR$^7$, —(C$_1$-C$_6$)alkyl-COOR$^7$, —(C$_1$-C$_6$)alkoxy-COOR$^7$, —CO—(CH$_2$)$_n$—COOR$^7$, —CO—(CH$_2$)$_n$—CO—NR$^5$R$^6$, —(C$_3$-C$_{12}$)cycloalkyl, ((C$_3$-C$_{12}$)cycloalkyl)-

(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(6- to 14-membered)aryl, ((6- to 14-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, and ((7- to 12-membered)bicycloheterocycle)-(C₁-C₆)alkyl-; each of which is optionally substituted with one, two, or three substituents independently selected from the group consisting of —OH, (═O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, —(C₁-C₆)alkoxy, ((C₁-C₆)alkoxy)-CO—(C₁-C₆)alkoxy-, phenyl, benzyl, —NH₂, —NH(C₁-C₆)alkyl, —(C₁-C₆)alkyl-NH(C₁-C₆)alkyl-R¹⁴, —NH—C(═NH)—NR⁵R⁶, —(C₁-C₆)alkyl-NH—C(═NH)—NR⁵R⁶, —CN, —SH, —OR¹¹, —CONR⁵R⁶, —(C₁-C₆alkyl)-C(═O)—NR⁵R⁶, —COOR⁷, —(C₁-C₆)alkyl-CO—OR⁷, —(C₁-C₆)alkoxy-CO—OR⁷, —(OCH₂CH₂)ₛ—O(C₁-C₆)alkyl, —(CH₂CH₂O)ₛ—(C₁-C₆)alkyl, (C₁-C₆)alkyl)sulfonyl, ((C₁-C₆)alkyl)sulfonyl(C₁-C₆)alkyl-, —NH—SO₂(C₁-C₆)alkyl, NH₂—SO₂(C₁-C₆)alkyl-, —N(SO₂(C₁-C₆)alkyl)₂, —C(═NH)NH₂, —NH—C(═O)—(C₁-C₆)alkyl, —NH—CO—NH₂, —NH—C(═O)—NH—(C₁-C₆)alkyl, —NH—C(═O)-(6- to 14-membered)aryl, —NH—C(═O)—(C₁-C₆)alkyl-(6- to 14-membered)aryl, —NH—(C₁-C₆)alkyl-CO—OR⁷, —NH—C(═O)—(C₁-C₆)alkyl-COOR⁷, —NH—C(═O)—CH(NH₂)—(C₁-C₆)alkyl-CO—OR⁷, —(C₃-C₁₂)cycloalkyl, ((C₃-C₁₂)cycloalkyl)-(C₁-C₆)alkyl-, -(6- to 14-membered)aryl, -(6- to 14-membered)aryloxy, —(C₁-C₆)alkoxy-C(═O)NR⁵R⁶, —NH—(C₁-C₆)alkyl-C(═O)—NR⁵R⁶, —C(═O)NH—(C₁-C₆)alkyl-COOR⁷, ((6- to 14-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

R²⁰ is hydrogen, OH, or Z²-G²-R¹⁰ᵇ;

or R²⁰ and R''' taken together with the carbon atom to which they are attached form:

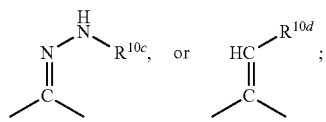

provided that:
R² and R²⁰ are not both H;
Z² is (CH₂)ₘ, which is optionally substituted with 1 or 2 —(C₁-C₆)alkyl;
G² is selected from:
 a) a bond, —(C₁-C₆)alkylene, —(C₂-C₆)alkenylene;
 b) —O—, —O—C(═O), —C(═O), ═CH; or
 c) NR⁸, —NH—C(═O), —NH—C(═NH), or ═N—NH;

R¹⁰ᵇ is selected from the group consisting of hydrogen, —(C₁-C₁₀)alkyl, —(C₂-C₁₂)alkenyl, —CH(═O), —C(═O)—(C₁-C₆)alkyl, —C(═O)—(C₂-C₆)alkenyl, —C(═O)-(6- to 14-membered)aryl, —C(═O)—(C₁-C₆)alkyl-(6- to 14-membered)aryl, —(C₂-C₁₂)alkynyl, —(C₁-C₁₀)alkoxy, —(OCH₂CH₂)ₛ—O(C₁-C₆)alkyl, —(CH₂CH₂O)ₛ—(C₁-C₆)alkyl, —NH(C₁-C₆)alkyl, CN, NR⁵R⁶, —(C₁-C₆)alkyl-NR⁵R⁶, —CONR⁵R⁶, —(C₁-C₆)alkyl-CO—NR⁵R⁶, —NH—C(═NH), —(C₁-C₆)alkyl-NH—C(═NH), —(C₁-C₆)alkyl-NH—C(═NH)—NR⁵R⁶, —COOR⁷, —(C₁-C₆)alkyl-COOR⁷, —(C₁-C₆)alkoxy-COOR⁷, —CO—(CH₂)ₙ—COOR⁷, —CO—(CH₂)ₙ—CO—NR⁵R⁶, —(C₃-C₁₂)cycloalkyl, ((C₃-C₁₂)cycloalkyl)-(C₁-C₆)alkyl-, —(C₄-C₁₂)cycloalkenyl, ((C₄-C₁₂)cycloalkenyl)-(C₁-C₆)alkyl-, —(C₆-C₁₄)bicycloalkyl, ((C₆-C₁₄)bicycloalkyl)-(C₁-C₆)alkyl-, —(C₈-C₂₀)tricycloalkyl, ((C₈-C₂₀)tricycloalkyl)-(C₁-C₆)alkyl-, —(C₇-C₁₄)bicycloalkenyl, ((C₇-C₁₄)bicycloalkenyl)-(C₁-C₆)alkyl-, —(C₈-C₂₀)tricycloalkenyl, ((C₈-C₂₀)tricycloalkenyl)-(C₁-C₆)alkyl-, -(6- to 14-membered)aryl, ((6- to 14-membered)aryl)-(C₁-C₆)alkyl-, -(7- to 12-membered)bicyclic ring system, ((7- to 12-membered)bicyclic ring system)-(C₁-C₆)alkyl-, -(7- to 12-membered)bicyclic aryl, ((7- to 12-membered)bicyclic aryl)-(C₁-C₆)alkyl-, -(5- to 12-membered)hetero aryl, ((5- to 12-membered)heteroaryl)-(C₁-C₆)alkyl-, -(3- to 12-membered)heterocycle, ((3- to 12 membered)heterocycle)-(C₁-C₆)alkyl-, -(7- to 12-membered)bicycloheterocycle, and ((7- to 12-membered)bicycloheterocycle)-(C₁-C₆)alkyl-; each of which is optionally substituted with one, two, or three substituents independently selected from the group consisting of —OH, (═O), halo, —C(halo)₃, —CH(halo)₂, —CH₂(halo), —(C₁-C₆)alkyl, halo(C₁-C₆)alkyl-, —(C₂-C₆)alkenyl, —(C₂-C₆)alkynyl, hydroxy(C₁-C₆)alkyl-, dihydroxy(C₁-C₆)alkyl-, —(C₁-C₆)alkoxy, ((C₁-C₆)alkoxy)-CO—(C₁-C₆)alkoxy-, phenyl, benzyl, —NH₂, —NH(C₁-C₆)alkyl, —(C₁-C₆)alkyl-NH(C₁-C₆)alkyl-R¹⁴, —NH—C(═NH)—NR⁵R⁶, —(C₁-C₆)alkyl-NH—C(═NH)—NR⁵R⁶, —CN, —SH, —OR¹¹, —CONR⁵R⁶, —(C₁-C₆alkyl)-C(═O)—NR⁵R⁶, —COOR⁷, —(C₁-C₆)alkyl-CO—OR⁷, —(C₁-C₆)alkoxy-CO—OR⁷, —(OCH₂CH₂)ₛ—O(C₁-C₆)alkyl, —(CH₂CH₂O)ₛ—(C₁-C₆)alkyl, (C₁-C₆)alkyl)sulfonyl, ((C₁-C₆)alkyl)sulfonyl(C₁-C₆)alkyl-, —NH—SO₂(C₁-C₆)alkyl, NH₂—SO₂(C₁-C₆)alkyl-, —N(SO₂(C₁-C₆)alkyl)₂, —C(═NH)NH₂, —NH—C(═O)—(C₁-C₆)alkyl, —NH—CO—NH₂, —NH—C(═O)—NH—(C₁-C₆)alkyl, —NH—C(═O)-(6- to 14-membered)aryl, —NH—C(═O)—(C₁-C₆)alkyl-(6- to 14-membered)aryl, —NH—(C₁-C₆)alkyl-CO—OR⁷, —NH—C(═O)—(C₁-C₆)alkyl-COOR⁷, —NH—C(═O)—CH(NH₂)—(C₁-C₆)alkyl-CO—OR⁷, —(C₃-C₁₂)cycloalkyl, ((C₃-C₁₂)cycloalkyl)-(C₁-C₆)alkyl-, -(6- to 14-membered)aryl, -(6- to 14-membered)aryloxy, —(C₁-C₆)alkoxy-C(═O)NR⁵R⁶, —NH—(C₁-C₆)alkyl-C(═O)—NR⁵R⁶, —C(═O)NH—(C₁-C₆)alkyl-COOR⁷, ((6- to 14-membered)aryl)-(C₁-C₆)alkyl-, -(5- to 12-membered)heteroaryl, ((5- to 12-membered)heteroaryl)-(C₁-C₆)alkyl-, -(3- to 12-membered)heterocycle, ((3- to 12-membered)heterocycle)-(C₁-C₆)alkyl-, -(7- to 12-membered)bicycloheterocycle, and ((7- to 12-membered)bicycloheterocycle)-(C₁-C₆)alkyl-;

or R³ and R²⁰ can be taken together to form a —(C₁-C₆)alkylene bridge or —(CH₂)w—O—(CH₂)w;

R¹⁰ᶜ is selected from the group consisting of hydrogen, —(C₁-C₁₀)alkyl, —(C₂-C₁₂)alkenyl, —CH(═O), —C(═O)—(C₁-C₆)alkyl, —C(═O)—(C₂-C₆)alkenyl, —C(═O)-(6- to 14-membered)aryl, —C(═O)—(C₁-C₆)alkyl-(6- to 14-membered)aryl, —(C₂-C₁₂)alkynyl, —(C₁-

$C_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, —NH(C$_1$-C$_6$)alkyl, CN, NR$^5$R$^6$, —(C$_1$-C$_6$)alkyl-NR$^5$R$^6$, —CONR$^5$R$^6$, —(C$_1$-C$_6$)alkyl-CO—NR$^5$R$^6$, —NH—C(=NH), —(C$_1$-C$_6$)alkyl-NH—C(=NH), —(C$_1$-C$_6$)alkyl-NH—C(=NH)—NR$^5$R$^6$, —COOR$^7$, —(C$_1$-C$_6$)alkyl-COOR$^7$, —(C$_1$-C$_6$)alkoxy-COOR$^7$, —CO—(CH$_2$)$_n$—COOR$^7$, —CO—(CH$_2$)$_n$—CO—NR$^5$R$^6$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(6- to 14-membered)aryl, ((6- to 14-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)hetero aryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; each of which is optionally substituted with one, two, or three substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)-CO—(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —NH—C(=NH)—NR$^5$R$^6$, —(C$_1$-C$_6$)alkyl-NH—C(=NH)—NR$^5$R$^6$, —CN, —SH, —OR$^{11}$, —CONR$^5$R$^6$, —(C$_1$-C$_6$alkyl)-C(=O)—NR$^5$R$^6$, —COOR$^7$, —(C$_1$-C$_6$)alkyl-CO—OR$^7$, —(C$_1$-C$_6$)alkoxy-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—C(=O)—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^7$, —NH—C(=O)—(C$_1$-C$_6$)alkyl-COOR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, —(C$_1$-C$_6$)alkoxy-C(=O)NR$^5$R$^6$, —NH—(C$_1$-C$_6$)alkyl-C(=O)—NR$^5$R$^6$, —C(=O)NH—(C$_1$-C$_6$)alkyl-COOR$^7$, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

R$^{10d}$ is selected from the group consisting of hydrogen, —(C$_1$-C$_{10}$)alkyl, —(C$_2$-C$_{12}$)alkenyl, —CH(=O), —C(=O)—(C$_1$-C$_6$)alkyl, —C(=O)—(C$_2$-C$_6$)alkenyl, —C(=O)-(6- to 14-membered)aryl, —C(=O)—(C$_1$-C$_6$)alkyl-(6- to 14-membered)aryl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$(C$_1$-C$_6$)alkyl, —NH(C$_1$-C$_6$)alkyl, CN, NR$^5$R$^6$, —(C$_1$-C$_6$)alkyl-NR$^5$R$^6$, —CONR$^5$R$^6$, —(C$_1$-C$_6$)alkyl-CO—NR$^5$R$^6$, —NH—C(=NH), —(C$_1$-C$_6$)alkyl-NH—C(=NH), —(C$_1$-C$_6$)alkyl-NH—C(=NH)—NR$^5$R$^6$, —COOR$^7$, —(C$_1$-C$_6$)alkyl-COOR$^7$, —(C$_1$-C$_6$)alkoxy-COOR$^7$, —CO—(CH$_2$)$_n$—COOR$^7$, —CO—(CH$_2$)$_n$—CO—NR$^5$R$^6$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(6- to 14-membered)aryl, ((6- to 14-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; each of which is optionally substituted with one, two, or three substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)-CO—(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —NH—C(=NH)—NR$^5$R$^6$, —(C$_1$-C$_6$)alkyl-NH—C(=NH)—NR$^5$R$^6$, —CN, —SH, —OR$^{11}$, —CONR$^5$R$^6$, —(C$_1$-C$_6$alkyl)-C(=O)—NR$^5$R$^6$, —COOR$^7$, —(C$_1$-C$_6$)alkyl-CO—OR$^7$, —(C$_1$-C$_6$)alkoxy-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—C(=O)—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^7$, —NH—C(=O)—(C$_1$-C$_6$)alkyl-COOR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, —(C$_1$-C$_6$)alkoxy-C(=O)NR$^5$R$^6$, —NH—(C$_1$-C$_6$)alkyl-C(=O)—NR$^5$R$^6$, —C(=O)NH—(C$_1$-C$_6$)alkyl-COOR$^7$, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

each R$^{30}$ is independently selected from —COOR$^7$, —CONR$^{5a}$R$^{6a}$, —(C$_1$-C$_6$)alkyl, CN, -(3- to 12-membered)heteroaryl, ((3- to 12-membered)heteroaryl)-(C$_1$-C$_6$)alkyl-, NH$_2$, halo, and ((6- to 14-membered)aryl)-(C$_1$-C$_6$)alkoxy-;

m is an integer 0, 1, 2, 3, 4, 5, or 6;
n is an integer 0, 1, 2, 3, 4, 5, or 6;
p is an integer 0, 1, 2, 3, 4, 5, or 6:
s is an integer 1, 2, 3, 4, 5, or 6;
w is an integer 0, 1, or 2;
and the pharmaceutically acceptable salts and solvates thereof.

It is to be understood that both the foregoing summary and the following detailed description are exemplary and explanatory only, and are not restrictive of the invention as claimed.

DETAILED DESCRIPTION OF THE INVENTION

Certain Compounds of the Invention are useful for modulating a pharmacodynamic response from one or more opioid receptors (μ, δ, κ, ORL-1) either centrally or peripherally, or both. The pharmacodynamic response may be attributed to the compound either stimulating (agonizing) or inhibiting (antagonizing) the one or more receptors. Certain Compounds of the Invention may antagonize one opioid receptor, while also agonizing one or more other receptors. Compounds of the Invention having agonist activity may be either full or partial agonists.

Another aspect of the invention is based on the use of certain Compounds of the Invention as synthesis intermediates.

In one embodiment, Compounds of the Invention are compounds represented by Formula I:

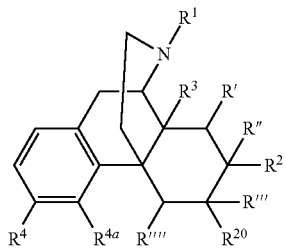

wherein:
R', R'', R''', and R'''' are each hydrogen, or
$R^3$ and R' taken together form a double bond; or
R' and R'' taken together form a double bond; or
R'' and R''' taken together form a double bond; or
R''' and R'''' taken together form a double bond; or
$R^3$ and R' taken together form a double bond and R'' and R''' taken together form a double bond; or
$R^3$ and R' taken together form a double bond and R''' and R'''' taken together form a double bond; or
R' and R'' taken together form a double bond and R''' and R'''' taken together form a double bond;
with the proviso that when R'' and R''' taken together form a double bond or R''' and R'''' taken together form a double bond, then $R^{20}$ is not —OH;
$R^1$ is selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, ($C_3$-$C_{12}$)cycloalkyl-($C_1$-$C_6$)alkyl-, —($C_3$-$C_{12}$)cycloalkenyl, ($C_3$-$C_{12}$)cycloalkenyl-($C_1$-$C_6$)alkyl-, -(6- to 14-membered)aryl, ((6- to 14-membered)aryl)-($C_1$-$C_6$)alkyl-, diphenyl($C_1$-$C_6$)alkyl-, -(3- to 12-membered)heterocycle, ((3- to 12 membered)heterocycle)-($C_1$-$C_6$)alkyl-, —(OCH$_2$CH$_2$)$_s$—O—($C_1$-$C_6$)alkyl, —(CH$_2$CH$_2$O)$_s$—($C_1$-$C_6$)alkyl, ($C_1$-$C_{10}$)alkoxy, C(halo)$_3$, CH(halo)$_2$, CH$_2$(halo), C(O)$R^5$, —C(O)O—($C_1$-$C_{10}$)alkyl, and —(CH$_2$)$_n$—NR$^5$R$^6$; each of which is optionally substituted by 1, 2 or 3 independently selected $R^9$ groups;
$R^3$ is selected from the group consisting of hydrogen, OH, halo, —($C_1$-$C_{10}$)alkoxy, and NR$^{17}$R$^{18}$; any of which is optionally substituted with 1, 2, or 3 substituents, each independently selected from OH, halo, —C(halo)$_3$, —CH(halo)$_2$, CH$_2$(halo), —($C_1$-$C_{10}$)alkyl-(halo)$_w$, —NR$^{17}$R$^{18}$, —COOH, —($C_1$-$C_{10}$)alkoxy, —C(=O)—($C_1$-$C_{10}$)alkoxy, -(5- to 12-membered)aryl, -(5- to 12-membered)heteroaryl, -(3- to 12-membered)heterocycle, —($C_3$-$C_{12}$)cycloalkyl, and —($C_4$-$C_{12}$)cycloalkenyl; wherein the -(5- to 12-membered)aryl, -(5- to 12-membered)heteroaryl, -(3- to 12-membered)heterocycle, —($C_3$-$C_{12}$)cycloalkyl, and —($C_4$-$C_{12}$)cycloalkenyl are optionally substituted with 1, 2, or 3 independently selected $R^{40}$ groups.

$R^4$ and $R^{4a}$ are each independently selected from:
a) hydrogen, OH, halo, —C(halo)$_3$, —CH(halo)$_2$, —CH$_2$(halo), —CN, —COOH, —C(=O)NH$_2$;
b) —($C_1$-$C_{10}$)alkyl, —($C_2$-$C_{10}$)alkenyl, —($C_2$-$C_{10}$)alkynyl, —($C_1$-$C_{10}$)alkoxy, —($C_2$-$C_{10}$)alkenyloxy, —($C_2$-$C_{10}$)alkynyloxy, any of which is optionally substituted with 1, 2, or 3 $R^{32}$ groups; or
c) —O-PG, wherein PG is a hydroxyl protecting group;
each $R^{32}$ is selected from:
a) OH, halo, haloalkyl, NR$^{17}$R$^{18}$, COOH, —($C_1$-$C_{10}$)alkoxy, alkoxycarbonyl; or
b) -(6- to 14-membered)aryl, -(5- to 12-membered)heteroaryl, -(3- to 12-membered)heterocycle, —($C_3$-$C_{12}$)cycloalkyl, and —($C_3$-$C_{12}$)cycloalkenyl, any of which is optionally substituted with 1, 2, or 3 $R^{40}$ groups;
each $R^{40}$ is independently selected from the group consisting of —OH, halo, —($C_1$-$C_{10}$)alkyl, haloalkyl, —NO$_2$, NR$^{17}$R$^{18}$, —COOH, —($C_1$-$C_{10}$)alkoxy, and alkoxycarbonyl;
$R^5$ and $R^6$ are each independently selected from the group consisting of:
a) hydrogen, —OH, halo, —C(halo)$_3$, —CH(halo)$_2$, and —CH$_2$(halo);
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_{39}$ and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_{29}$ and ($C_1$-$C_6$)alkyl-CONH—; and
d) -(6- to 14-membered)aryl optionally substituted with 1, 2, or 3 independently selected $R^{30}$ groups;
or $R^5$ and $R^6$ together with the nitrogen atom to which they are attached form a (3- to 12-membered)heterocycle optionally substituted with 1, 2, or 3 independently selected $R^{30}$ groups;
$R^{5a}$ and $R^{6a}$ are each independently selected from the group consisting of:
a) hydrogen, —OH, halo, —C(halo)$_3$, —CH(halo)$_2$, and —CH$_2$(halo);
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, CH$_2$(halo), —(CH$_2$)$_n$—O(—CH$_2$)$_n$—CH$_3$, and phenyl;
c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—; and
d) -(6- to 14-membered)aryl optionally substituted with 1, 2, or 3 independently selected $R^{30}$ groups;
or $R^{5a}$ and $R^{6a}$ together with the nitrogen atom to which they are attached form a (3- to 12-membered)heterocycle optionally substituted with 1, 2, or 3 independently selected $R^{30}$ groups;
each $R^7$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each $R^8$ is independently selected from the group consisting of hydrogen, —($C_1$-$C_6$)alkyl, —($C_2$-$C_6$)alkenyl, —($C_2$-$C_6$) alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)($C_1$-$C_6$)alkyl, —($C_1$-$C_6$)alkyl-$SO_2$—($C_1$-$C_6$)alkyl, —$SO_2$($C_1$-$C_6$)alkyl, —$SO_2$-(6- to 14-membered)aryl, —$NH_2$, and —($C_1$-$C_6$)alkyl-$NH_2$;

each $R^9$ is independently selected from the group consisting of —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, $CH_2$(halo), —($CH_2$)$_n$—O—($CH_2$)$_n$—$CH_3$, phenyl, and $CONR^{5a}R^{6a}$;

each $R^7$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each $R^{11}$ is independently selected from the group consisting of —C(halo)$_3$, —CH(halo)$_2$, —$CH_2$(halo), —($C_2$-$C_5$)alkenyl, —($C_2$-$C_5$)alkynyl, —($CH_2$)$_n$—O—($CH_2$)$_n$—$CH_3$, (6- to 14-membered)aryl, ((6- to 14-membered)aryl)-($C_1$-$C_6$)alkyl-, and (5- to 12-membered)heteroaryl, and ((5- to 12-membered)heteroaryl)-($C_1$-$C_6$)alkyl-; each of which is optionally substituted with 1, 2, or 3 independently selected $R^9$ groups;

each $R^{14}$ is independently selected from —$COOR^7$, —($C_1$-$C_6$)alkyl-$COOR^7$, —C(=O)—($C_1$-$C_6$)alkyl-$COOR^7$, —($C_1$-$C_6$)alkyl-C(=O)—($C_1$-$C_6$)alkyl-$COOR^7$, $CONH_2$, or —($C_1$-$C_6$)alkyl-$CONH_2$;

each $R^{17}$ and $R^{18}$ are independently selected from the group consisting of hydrogen and —($C_1$-$C_{10}$)alkyl;

$R^2$ is hydrogen, OH, or $Z^1$-$G^1$-$R^{10a}$;

or $R^2$ and R'' taken together with the carbon atom to which they are attached form:

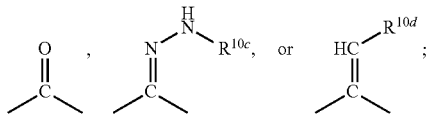

$Z^1$ is ($CH_2$)$_m$, which is optionally substituted with 1 or 2 —($C_1$-$C_6$)alkyl;

$G^1$ is selected from:
 a) a bond, —($C_1$-$C_6$)alkylene, —($C_2$-$C_6$)alkenylene;
 b) —O—, —O—C(=O), —C(=O), =CH; or
 c) $NR^8$, —NH—C(=O), —NH—C(=NH), or =N—NH;

$R^{10a}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —($OCH_2CH_2$)$_s$—O($C_1$-$C_6$)alkyl, —($CH_2CH_2$O)$_s$—($C_1$-$C_6$)alkyl, —NH($C_1$-$C_6$)alkyl, CN, $NR^5R^6$, —($C_1$-$C_6$)alkyl-$NR^5R^6$, —$CONR^5R^6$, —($C_1$-$C_6$)alkyl-CO—$NR^5R^6$, —NH—C(=NH), —($C_1$-$C_6$)alkyl-NH—C(=NH), —($C_1$-$C_6$)alkyl-NH—C(=NH)—$NR^5R^6$, —$COOR^7$, —($C_1$-$C_6$)alkyl-$COOR^7$, —($C_1$-$C_6$)alkoxy-$COOR^7$, —CO—($CH_2$)$_n$—$COOR^7$, —CO—($CH_2$)$_n$—CO—$NR^5R^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricyclo alkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)hetero aryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; each of which is optionally substituted with one, two, or three substituents independently selected from the group consisting of —OH, (=O), halo, —C(halo)$_3$, —CH(halo)$_2$, —$CH_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —$NH_2$, —NH($C_1$-$C_6$)alkyl, —($C_1$-$C_6$)alkyl-NH($C_1$-$C_6$)alkyl-$R^{14}$, —NH—C(=NH)—$NR^5R^6$, —($C_1$-$C_6$)alkyl-NH—C(=NH)—$NR^5R^6$, —CN, —SH, —$OR^{11}$, —$CONR^5R^6$, —($C_1$-$C_6$alkyl)-C(=O)—$NR^5R^6$, —$COOR^7$, —($C_1$-$C_6$)alkyl-CO—$OR^7$, —($C_1$-$C_6$)alkoxy-CO—$OR^7$, —($OCH_2CH_2$)$_s$—O($C_1$-$C_6$)alkyl, —($CH_2CH_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —NH—$SO_2$($C_1$-$C_6$)alkyl, $NH_2$—$SO_2$($C_1$-$C_6$)alkyl-, —N($SO_2$($C_1$-$C_6$)alkyl)$_2$, —C(=NH)$NH_2$, —NH—C(=O)—($C_1$-$C_6$)alkyl, —NH—CO—$NH_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—$OR^7$, —NH—C(=O)—($C_1$-$C_6$)alkyl-$COOR^7$, —NH—C(=O)—CH($NH_2$)—($C_1$-$C_6$)alkyl-CO—$OR^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(=O)$NR^5R^6$, —NH—($C_1$-$C_6$)alkyl-C(=O)—$NR^5R^6$, —C(=O)NH—($C_1$-$C_6$)alkyl-$COOR^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

$R^{20}$ is hydrogen, OH, or $Z^2$-$G^2$-$R^{10b}$;

or $R^{20}$ and R''' taken together with the carbon atom to which they are attached form:

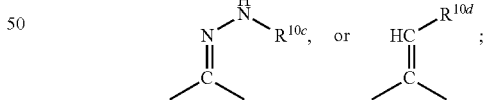

provided that:
$R^2$ and $R^{20}$ are not both H;

$Z^2$ is ($CH_2$)$_m$, which is optionally substituted with 1 or 2 —($C_1$-$C_6$)alkyl;

$G^2$ is selected from:
 a) a bond, —($C_1$-$C_6$)alkylene, —($C_2$-$C_6$)alkenylene;
 b) —O—, —O—C(=O), —C(=O), =CH; or
 c) $NR^8$, —NH—C(=O), —NH—C(=NH), or =N—NH;

$R^{10b}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)

alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —NH—C(=NH), —($C_1$-$C_6$)alkyl-NH—C(=NH), —($C_1$-$C_6$)alkyl-NH—C(=NH)—NR$^5$R$^6$, —COOR$^7$, —($C_1$-$C_6$)alkyl-COOR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —NH—C(=NH)—NR$^5$R$^6$, —($C_1$-$C_6$)alkyl-NH—C(=NH)—NR$^5$R$^6$, —CN, —SH, —OR$^{11}$, —CONR$^5$R$^6$, —($C_1$-$C_6$alkyl)-C(=O)—NR$^5$R$^6$, —COOR$^7$, —($C_1$-$C_6$)alkyl-CO—OR$^7$, —($C_1$-$C_6$)alkoxy-CO—OR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$alkyl)sulfonyl, (($C_1$-$C_6$alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—C(=O)—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-COOR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(=O)NR$^5$R$^6$, —NH—($C_1$-$C_6$)alkyl-C(=O)—NR$^5$R$^6$, —C(=O)NH—($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;
or R$^3$ and R$^{20}$ can be taken together to form a —($C_1$-$C_6$)alkylene bridge or —(CH$_2$)$_w$—O—(CH$_2$)$_w$;
R$^{10c}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —NH—C(=NH), —($C_1$-$C_6$)alkyl-NH—C(=NH), —($C_1$-$C_6$)alkyl-NH—C(=NH)—NR$^5$R$^6$, —COOR$^7$, —($C_1$-$C_6$)alkyl-COOR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —NH—C(=NH)—NR$^5$R$^6$, —($C_1$-$C_6$)alkyl-NH—C(=NH)—NR$^5$R$^6$, —CN, —SH, —OR$^{11}$, —CONR$^5$R$^6$, —($C_1$-$C_6$alkyl)-C(=O)—NR$^5$R$^6$, —COOR$^7$, —($C_1$-$C_6$)alkyl-CO—OR$^7$, —($C_1$-$C_6$)alkoxy-CO—OR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$alkyl)sulfonyl, (($C_1$-$C_6$alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—C(=O)—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-COOR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(=O)NR$^5$R$^6$, —NH—($C_1$-$C_6$)alkyl-C(=O)—NR$^5$R$^6$, —C(=O)NH—($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;
R$^{10d}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$) alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —NH—C(=NH), —($C_1$-$C_6$)alkyl-NH—C(=NH), —($C_1$-$C_6$)alkyl-NH—C(=NH)—NR$^5$R$^6$, —COOR$^7$, —($C_1$-$C_6$)alkyl-COOR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —NH—C(=NH)—NR$^5$R$^6$, —($C_1$-$C_6$)alkyl-NH—C(=NH)—NR$^5$R$^6$, —CN, —SH, —OR$^{11}$, —CONR$^5$R$^6$, —($C_1$-$C_6$alkyl)-C(=O)—NR$^5$R$^6$, —COOR$^7$, —($C_1$-$C_6$)alkyl-CO—OR$^7$, —($C_1$-$C_6$)alkoxy-CO—OR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—C(=O)—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-COOR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(=O)NR$^5$R$^6$, —NH—($C_1$-$C_6$)alkyl-C(=O)—NR$^5$R$^6$, —C(=O)NH—($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

each R$^{30}$ is independently selected from —COOR$^7$, —CONR$^{5a}$R$^{6a}$, —($C_1$-$C_6$)alkyl, CN, -(3- to 12-membered)heteroaryl, ((3- to 12-membered)heteroaryl)-($C_1$-$C_6$)alkyl-, NH$_2$, halo, and ((6- to 14-membered)aryl)-($C_1$-$C_6$)alkoxy-;

m is an integer 0, 1, 2, 3, 4, 5, or 6;
n is an integer 0, 1, 2, 3, 4, 5, or 6;
p is an integer 0, 1, 2, 3, 4, 5, or 6:
s is an integer 1, 2, 3, 4, 5, or 6;
w is an integer 0, 1, or 2;

and the pharmaceutically acceptable salts and solvates thereof.

In another embodiment, the invention provides compounds of Formula II, or pharmaceutically acceptable salts or solvates thereof:

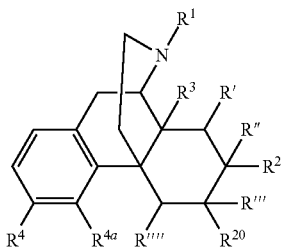

II wherein:
R' is hydrogen, —OH, or —($C_1$-$C_{10}$)alkoxy;
R'', R''', and R'''' are each hydrogen; or
R$^3$ and R' taken together form a double bond; or
R' and R'' taken together form a double bond; or
R'' and R''' taken together form a double bond; or
R''' and R'''' taken together form a double bond; or
R$^3$ and R' taken together form a double bond and R'' and R'''' taken together form a double bond; or
R$^3$ and R' taken together form a double bond and R''' and R'''' taken together form a double bond; or
R' and R'' taken together form a double bond and R''' and R'''' taken together form a double bond;
with the proviso that when R'' and R''' taken together form a double bond or R''' and R'''' taken together form a double bond, then R$^{20}$ is not —OH;

R$^1$ is selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, ($C_3$-$C_{12}$)cycloalkyl-($C_1$-$C_6$)alkyl-, —($C_3$-$C_{12}$)cycloalkenyl, ($C_3$-$C_{12}$)cycloalkenyl-($C_1$-$C_6$)alkyl-, -(6- to 14-membered)aryl, ((6- to 14-membered)aryl)-($C_1$-$C_6$)alkyl-, diphenyl($C_1$-$C_6$)alkyl-, -(3- to 12-membered)heterocycle, ((3- to 12 membered)heterocycle)-($C_1$-$C_6$)alkyl-, —(OCH$_2$CH$_2$)$_s$—O—($C_1$-$C_6$)alkyl, —(CH$_2$CH$_2$O)$_s$—($C_1$-$C_6$)alkyl, ($C_1$-$C_{10}$)alkoxy, C(halo)$_3$, CH(halo)$_2$, CH$_2$(halo), C(O)R$^5$, —C(O)O—($C_1$-$C_{10}$)alkyl, and —(CH$_2$)$_n$—NR$^5$R$^6$; each of which is optionally substituted by 1, 2 or 3 independently selected R$^9$ groups;

R$^3$ is selected from the group consisting of hydrogen, OH, halo, —($C_1$-$C_{10}$)alkoxy, and NR$^{17}$R$^{18}$; any of which is optionally substituted with 1, 2, or 3 substituents, each independently selected from OH, halo, —C(halo)$_3$, —CH(halo)$_2$, CH$_2$(halo), —($C_1$-$C_{10}$)alkyl-(halo), —NR$^{17}$R$^{18}$, —COOH, —($C_1$-$C_{10}$)alkoxy, —C(=O)—($C_1$-$C_{10}$)alkoxy, -(5- to 12-membered)aryl, -(5- to 12-membered)heteroaryl, -(3- to 12-membered)heterocycle, —($C_3$-$C_{12}$)cycloalkyl, and —($C_4$-$C_{12}$)cycloalkenyl; wherein the -(5- to 12-membered)aryl, -(5- to 12-membered)heteroaryl, -(3- to 12-membered)heterocycle, —($C_3$-$C_{12}$)cycloalkyl, and —($C_4$-$C_{12}$)cycloalkenyl are optionally substituted with 1, 2, or 3 independently selected R$^{40}$ groups.

R$^4$ and R$^{4a}$ are each independently selected from:
a) hydrogen, OH, halo, —C(halo)$_3$, —CH(halo)$_2$, —CH$_2$(halo), —CN, —COOH, —C(=O)NH$_2$;
b) —($C_1$-$C_{10}$)alkyl, —($C_2$-$C_{10}$)alkenyl, —($C_2$-$C_{10}$)alkynyl, —($C_1$-$C_{10}$)alkoxy, —($C_2$-$C_{10}$)alkenyloxy, —($C_2$-$C_{10}$)alkynyloxy, any of which is optionally substituted with 1, 2, or 3 R$^{32}$ groups; or c) —O-PG, wherein PG is a hydroxyl protecting group;
each $R^{32}$ is selected from:
a) OH, halo, haloalkyl, $NR^{17}R^{18}$, COOH, —($C_1$-$C_{10}$)alkoxy, alkoxycarbonyl; or
b) -(6- to 14-membered)aryl, -(5- to 12-membered)heteroaryl, -(3- to 12-membered)heterocycle, —($C_3$-$C_{12}$)cycloalkyl, and —($C_3$-$C_{12}$)cycloalkenyl, any of which is optionally substituted with 1, 2, or 3 $R^{40}$ groups;

each $R^{40}$ is independently selected from the group consisting of —OH, halo, —($C_1$-$C_{10}$)alkyl, haloalkyl, —$NO_2$, $NR^{17}R^{18}$, —COOH, —($C_1$-$C_{10}$)alkoxy, and alkoxycarbonyl;

$R^5$ and $R^6$ are each independently selected from the group consisting of:
a) hydrogen, —OH, halo, —C(halo)$_3$, —CH(halo)$_2$, and —CH$_2$(halo);
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, —CH$_2$(halo), —(CH$_2$)$_n$—O—(CH$_2$)$_n$—CH$_3$, phenyl, and —CONR$^{5a}$R$^{6a}$;
c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—; and
d) -(6- to 14-membered)aryl optionally substituted with 1, 2, or 3 independently selected $R^{30}$ groups;

or $R^5$ and $R^6$ together with the nitrogen atom to which they are attached form a (3- to 12-membered)heterocycle optionally substituted with 1, 2, or 3 independently selected $R^{30}$ groups;

$R^{5a}$ and $R^{6a}$ are each independently selected from the group consisting of:
a) hydrogen, —OH, halo, —C(halo)$_3$, —CH(halo)$_2$, and —CH$_2$(halo);
b) —($C_1$-$C_6$)alkyl, —($C_2$-$C_6$)alkenyl, —($C_2$-$C_6$)alkynyl, —(CH$_2$)$_n$—O—(CH$_2$)$_n$—CH$_3$, and —($C_1$-$C_6$)alkoxy, each of which is optionally substituted with 1, 2, or 3 substituents independently selected from —OH, halo, —($C_1$-$C_{10}$)alkyl, —($C_2$-$C_{12}$)alkenyl, —($C_2$-$C_{12}$)alkynyl, —($C_1$-$C_{10}$)alkoxy, —($C_3$-$C_{12}$)cycloalkyl, —CHO, —COOH, —C(halo)$_3$, —CH(halo)$_2$, CH$_2$(halo), —(CH$_2$)$_n$—O—(CH$_2$)$_n$—CH$_3$, and phenyl;
c) —($C_3$-$C_8$)cycloalkyl, (($C_3$-$C_8$)cycloalkyl)-($C_1$-$C_6$)alkyl-, —COOR$^7$, —($C_1$-$C_6$)alkyl-COOR$^7$, —CONH$_2$, and ($C_1$-$C_6$)alkyl-CONH—; and
d) -(6- to 14-membered)aryl optionally substituted with 1, 2, or 3 independently selected $R^{30}$ groups;

or $R^{5a}$ and $R^{6a}$ together with the nitrogen atom to which they are attached form a (3- to 12-membered)heterocycle optionally substituted with 1, 2, or 3 independently selected $R^{30}$ groups;

each $R^7$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each $R^8$ is independently selected from the group consisting of hydrogen, —($C_1$-$C_6$)alkyl, —($C_2$-$C_6$)alkenyl, —($C_2$-$C_6$)alkynyl, —($C_1$-$C_{10}$)alkoxy, —($C_3$-$C_{12}$)cycloalkyl, —($C_3$-$C_{12}$)cycloalkenyl, (($C_3$-$C_{12}$)cycloalkyl)-($C_1$-$C_6$)alkyl-, (($C_3$-$C_{12}$)cycloalkenyl)-($C_1$-$C_6$)alkyl-, —C(=O)($C_1$-$C_6$)alkyl, —($C_1$-$C_6$)alkyl-SO$_2$—($C_1$-$C_6$)alkyl, —SO$_2$($C_1$-$C_6$)alkyl, —SO$_2$-(6- to 14-membered)aryl, —NH$_2$, and —($C_1$-$C_6$)alkyl-NH$_2$;

each $R^9$ is independently selected from the group consisting of —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, CH$_2$(halo), —(CH$_2$)$_n$—O—(CH$_2$)$_n$—CH$_3$, phenyl, and CONR$^{5a}$R$^{6a}$;

each $R^7$ is independently selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$)alkyl-, and (($C_4$-$C_{12}$)cycloalkenyl)-($C_1$-$C_6$)alkyl-;

each $R^{11}$ is independently selected from the group consisting of —C(halo)$_3$, —CH(halo)$_2$, —CH$_2$(halo), —($C_2$-$C_5$)alkenyl, —($C_2$-$C_5$)alkynyl, —(CH$_2$)$_n$—O—(CH$_2$)$_n$—CH$_3$, (6- to 14-membered)aryl, ((6- to 14-membered)aryl)-($C_1$-$C_6$)alkyl-, and (5- to 12-membered)heteroaryl, and ((5- to 12-membered)heteroaryl)-($C_1$-$C_6$)alkyl-; each of which is optionally substituted with 1, 2, or 3 independently selected $R^9$ groups;

each $R^{14}$ is independently selected from COOR$^7$, —($C_1$-$C_6$)alkyl-COOR$^7$, —C(=O)—($C_1$-$C_6$)alkyl-COOR$^7$, —($C_1$-$C_6$)alkyl-C(=O)—($C_1$-$C_6$)alkyl-COOR$^7$, CONH$_2$, or —($C_1$-$C_6$)alkyl-CONH$_2$;

each $R^{17}$ and $R^{18}$ are independently selected from the group consisting of hydrogen and —($C_1$-$C_{10}$)alkyl;

$R^2$ is hydrogen, OH, or $Z^1$-$G^1$-$R^{10a}$;

or $R^2$ and R" taken together with the carbon atom to which they are attached form:

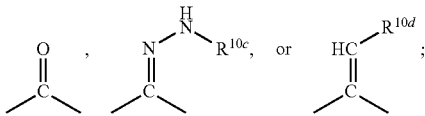

$Z^1$ is —(CH$_2$)$_m$—, which is optionally substituted with 1 or 2 —($C_1$-$C_6$)alkyl;

$G^1$ is selected from:
a) a bond, —($C_1$-$C_6$)alkylene, —($C_2$-$C_6$)alkenylene;
b) —O—, —O—C(=O), —C(=O), =CH; or
c) N(R$^8$)—, —NH—C(=O), —NH—C(=NH), or =N—NH;

$R^{10a}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH($C_1$-$C_6$)alkyl, —CN, —NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —NH—C(=NH), —($C_1$-$C_6$)alkyl-NH—C(=NH), —($C_1$-$C_6$)alkyl-NH—C(=NH)—NR$^5$R$^6$, —COOR$^7$, —($C_1$-$C_6$)alkyl-COOR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, —($C_8$-$C_{20}$)tricycloalkenyl, (($C_8$-$C_{20}$)tricycloalkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)

alkyl-, -(7- to 12-membered)bicyclic aryl, ((7- to 12-membered)bicyclic aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —NR$^5$R$^6$, —($C_1$-$C_6$)alkyl-NH($C_1$-$C_6$)alkyl-R$^{14}$, —NH—C(=NH)—NR$^5$R$^6$, —($C_1$-$C_6$)alkyl-NH—C(=NH)—NR$^5$R$^6$, —CN, —SH, —OR$^{11}$, —CONR$^5$R$^6$, —($C_1$-$C_6$alkyl)-C(=O)—NR$^5$R$^6$, —COOR$^7$, —($C_1$-$C_6$)alkyl-CO—OR$^7$, —($C_1$-$C_6$)alkoxy-CO—OR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—C(=O)—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-COOR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(=O)NR$^5$R$^6$, —NH—($C_1$-$C_6$)alkyl-C(=O)—NR$^5$R$^6$, —C(=O)NH—($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

or R$^{10a}$ and R$^8$, together with the N atom to which they are both attached, form -(3- to 12-membered)heterocycle optionally substituted with one or two substituents independently selected from the group consisting of —OH, (=O), halo, —($C_1$-$C_6$)alkyl, halo($C_1$-$C_6$)alkyl-, hydroxy($C_1$-$C_6$)alkyl-, dihydroxy($C_1$-$C_6$)alkyl-, —($C_1$-$C_6$)alkoxy, (($C_1$-$C_6$)alkoxy)-CO—($C_1$-$C_6$)alkoxy-, phenyl, benzyl, —NH$_2$, and —NH($C_1$-$C_6$)alkyl;

R$^{20}$ is hydrogen, OH, or Z$^2$-G$^2$-R$^{10b}$;

or R$^{20}$ and R''' taken together with the carbon atom to which they are attached form:

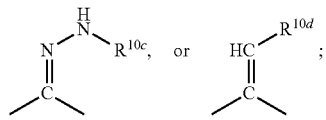

provided that:
R$^2$ and R$^{20}$ are not both H;
Z$^2$ is (CH$_2$)$_m$, which is optionally substituted with 1 or 2 —($C_1$-$C_6$)alkyl;
G$^2$ is selected from:
a) a bond, —($C_1$-$C_6$)alkylene, —($C_2$-$C_6$)alkenylene;
b) —O—, —O—C(=O)—, —C(=O)—, =CH—; or
c) —N(R$^8$)—, —NH—C(=O)—, —NH—C(=NH), or =N—NH—;

R$^{10b}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-$C_{10}$)alkoxy, —(OCH$_2$CH$_2$)$_s$—O($C_1$-$C_6$)alkyl, —(CH$_2$CH$_2$O)$_s$—($C_1$-$C_6$)alkyl, —NH($C_1$-$C_6$)alkyl, CN, NR$^5$R$^6$, —($C_1$-$C_6$)alkyl-NR$^5$R$^6$, —CONR$^5$R$^6$, —($C_1$-$C_6$)alkyl-CO—NR$^5$R$^6$, —NH—C(=NH), —($C_1$-$C_6$)alkyl-NH—C(=NH), —($C_1$-$C_6$)alkyl-NH—C(=NH)—NR$^5$R$^6$, —COOR$^7$, —($C_1$-$C_6$)alkyl-COOR$^7$, —($C_1$-$C_6$)alkoxy-COOR$^7$, —CO—(CH$_2$)$_n$—COOR$^7$, —CO—(CH$_2$)$_n$—CO—NR$^5$R$^6$, —($C_3$-$C_{12}$)cycloalkyl, (($C_3$-$C_{12}$)cycloalkyl)-($C_1$-$C_6$)alkyl-, —($C_4$-$C_{12}$)cycloalkenyl, (($C_4$-$C_{12}$)cycloalkenyl)-($C_1$-$C_6$)alkyl-, —($C_6$-$C_{14}$)bicycloalkyl, (($C_6$-$C_{14}$)bicycloalkyl)-($C_1$-$C_6$)alkyl-, —($C_8$-$C_{20}$)tricycloalkyl, (($C_8$-$C_{20}$)tricycloalkyl)-($C_1$-$C_6$)alkyl-, —($C_7$-$C_{14}$)bicycloalkenyl, (($C_7$-$C_{14}$)bicycloalkenyl)-($C_1$-$C_6$)alkyl-, ($C_8$-$C_{20}$)tricycloalkenyl, (($C_8$-$C_{20}$)tricyclo alkenyl)-($C_1$-$C_6$)alkyl-, -(6- to 14-membered)aryl, ((6- to 14-membered)aryl)-($C_1$-$C_6$)alkyl-, -(7- to 12-membered)bicyclic ring system, ((7- to 12-membered)bicyclic ring system)-($C_1$-$C_6$)alkyl-, -(7- to 12-membered)bicyclic aryl, ((7- to 12-membered)bicyclic aryl)-($C_1$-$C_6$)alkyl-, -(5- to 12-membered)hetero aryl, ((5- to 12-membered)heteroaryl)-($C_1$-$C_6$)alkyl-, -(3- to 12-membered)heterocycle, ((3- to 12 membered)heterocycle)-($C_1$-$C_6$)alkyl-, -(7- to 12-membered)bicycloheterocycle, and ((7- to 12-membered)bicycloheterocycle)-($C_1$-$C_6$)alkyl-; each of which is optionally substituted with one, two, or three substituents independently selected from the group consisting of —OH, (=O), halo, —C(halo)$_3$, —CH(halo)$_2$, —CH$_2$(halo), —($C_1$-$C_6$)alkyl, halo($C_1$-$C_6$)alkyl-, —($C_2$-$C_6$)alkenyl, —($C_2$-$C_6$)alkynyl, hydroxy($C_1$-$C_6$)alkyl-, dihydroxy($C_1$-$C_6$)alkyl-, —($C_1$-$C_6$)alkoxy, (($C_1$-$C_6$)alkoxy)-CO($C_1$-$C_6$)alkoxy-, phenyl, benzyl, —NH$_2$, —NH($C_1$-$C_6$)alkyl, —($C_1$-$C_6$)alkyl-NH($C_1$-$C_6$)alkyl-R$^{14}$, —NH—C(=NH)—NR$^5$R$^6$, —($C_1$-$C_6$)alkyl-NH—C(=NH)—NR$^5$R$^6$, —CN, —SH, —OR$^{11}$, —CONR$^5$R$^6$, —($C_1$-$C_6$alkyl)-C(=O)—NR$^5$R$^6$, —COOR$^7$, —($C_1$-$C_6$)alkyl-CO—OR$^7$, —($C_1$-$C_6$)alkoxy-CO—OR$^7$, —(OCH$_2$CH$_2$)$_s$—O($C_1$-$C_6$)alkyl, —(CH$_2$CH$_2$O)$_s$—($C_1$-$C_6$)alkyl, ($C_1$-$C_6$)alkyl)sulfonyl, (($C_1$-$C_6$)alkyl)sulfonyl($C_1$-$C_6$)alkyl-, —NH—SO$_2$($C_1$-$C_6$)alkyl, NH$_2$—SO$_2$($C_1$-$C_6$)alkyl-, —N(SO$_2$($C_1$-$C_6$)alkyl)$_2$, —C(=NH)NH$_2$, —NH—C(=O)—($C_1$-$C_6$)alkyl, —NH—CO—NH$_2$, —NH—C(=O)—NH—($C_1$-$C_6$)alkyl, —NH—C(=O)-(6- to 14-membered)aryl, —NH—C(=O)—($C_1$-$C_6$)alkyl-(6- to 14-membered)aryl, —NH—($C_1$-$C_6$)alkyl-CO—OR$^7$, —NH—C(=O)—($C_1$-$C_6$)alkyl-COOR$^7$, —NH—C(=O)—CH(NH$_2$)—($C_1$-$C_6$)alkyl-CO—OR$^7$, —($C_3$-$C_{12}$)cycloalkyl, (($C_3$-$C_{12}$)cycloalkyl)-($C_1$-$C_6$)alkyl-, -(6- to 14-membered)aryl, -(6- to 14-membered)aryloxy, —($C_1$-$C_6$)alkoxy-C(=O)NR$^5$R$^6$, —NH—($C_1$-$C_6$)alkyl-C(=O)—NR$^5$R$^6$, —C(=O)NH($C_1$-$C_6$)alkyl-COOR$^7$, ((6- to 14-membered)aryl)-($C_1$-$C_6$)alkyl-, -(5- to 12-membered)heteroaryl, ((5- to 12-membered)heteroaryl)-($C_1$-$C_6$)alkyl-, -(3- to 12-membered)heterocycle, ((3- to 12-membered)heterocycle)-($C_1$-$C_6$)alkyl-, -(7- to 12-membered)bicycloheterocycle, and ((7- to 12-membered)bicycloheterocycle)-($C_1$-$C_6$)alkyl-;

or R$^3$ and R$^{20}$ can be taken together to form a —($C_1$-$C_6$)alkylene bridge or —(CH$_2$)$_w$—O—(CH$_2$)$_w$;

R$^{10c}$ is selected from the group consisting of hydrogen, —($C_1$-$C_{10}$)alkyl, —($C_2$-$C_{12}$)alkenyl, —CH(=O), —C(=O)—($C_1$-$C_6$)alkyl, —C(=O)—($C_2$-$C_6$)alkenyl, —C(=O)-(6- to 14-membered)aryl, —C(=O)—($C_1$-$C_6$)alkyl-(6- to 14-membered)aryl, —($C_2$-$C_{12}$)alkynyl, —($C_1$-

$C_{10}$)alkoxy, —(OCH$_2$CH$_2$)$_s$—O(C$_1$-C$_6$)alkyl, —(CH$_2$CH$_2$O)$_s$(C$_1$-C$_6$)alkyl, —NH(C$_1$-C$_6$)alkyl, CN, NR$^5$R$^6$, —(C$_1$-C$_6$)alkyl-NR$^5$R$^6$, —CONR$^5$R$^6$, —(C$_1$-C$_6$)alkyl-CO—NR$^5$R$^6$, —NH—C(=NH), —(C$_1$-C$_6$)alkyl-NH—C(=NH), —(C$_1$-C$_6$)alkyl-NH—C(=NH)—NR$^5$R$^6$, —COOR$^7$, —(C$_1$-C$_6$)alkyl-COOR$^7$, —(C$_1$-C$_6$)alkoxy-COOR$^7$, —CO—(CH$_2$)$_n$—COOR$^7$, —CO—(CH$_2$)$_n$—CO—NR$^5$R$^6$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(6- to 14-membered)aryl, ((6- to 14-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; each of which is optionally substituted with one, two, or three substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)-CO—(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —NH—C(=NH)—NR$^5$R$^6$, —(C$_1$-C$_6$)alkyl-NH—C(=NH)—NR$^5$R$^6$, —CN, —SH, —OR$^{11}$, —CONR$^5$R$^6$, —(C$_1$-C$_6$alkyl)-C(=O)—NR$^5$R$^6$, —COOR$^7$, —(C$_1$-C$_6$)alkyl-CO—OR$^7$, —(C$_1$-C$_6$)alkoxy-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—C(=O)—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^7$, —NH—C(=O)—(C$_1$-C$_6$)alkyl-COOR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, —(C$_1$-C$_6$)alkoxy-C(=O)NR$^5$R$^6$, —NH—(C$_1$-C$_6$)alkyl-C(=O)—NR$^5$R$^6$, —C(=O)NH—(C$_1$-C$_6$)alkyl-COOR$^7$, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

$R^{10d}$ is selected from the group consisting of hydrogen, —(C$_1$-C$_{10}$)alkyl, —(C$_2$-C$_{12}$)alkenyl, —CH(=O), —C(=O)—(C$_1$-C$_6$)alkyl, —C(=O)—(C$_2$-C$_6$)alkenyl, —C(=O)-(6- to 14-membered)aryl, —C(=O)—(C$_1$-C$_6$)alkyl-(6- to 14-membered)aryl, —(C$_2$-C$_{12}$)alkynyl, —(C$_1$-C$_{10}$)alkoxy, —(OCH$_2$CH$_2$)$_s$—O(C$_1$-C$_6$)alkyl, —(CH$_2$CH$_2$O)$_s$—(C$_1$-C$_6$)alkyl, —NH(C$_1$-C$_6$)alkyl, CN, NR$^5$R$^6$, —(C$_1$-C$_6$)alkyl-NR$^5$R$^6$, —CONR$^5$R$^6$, —(C$_1$-C$_6$)alkyl-CO—NR$^5$R$^6$, —NH—C(=NH), —(C$_1$-C$_6$)alkyl-NH—C(=NH), —(C$_1$-C$_6$)alkyl-NH—C(=NH)—NR$^5$R$^6$, —COOR$^7$, —(C$_1$-C$_6$)alkyl-COOR$^7$, —(C$_1$-C$_6$)alkoxy-COOR$^7$, —CO—(CH$_2$)$_n$—COOR$^7$, —CO—(CH$_2$)$_n$—CO—NR$^5$R$^6$, —(C$_3$-C$_{12}$)cycloalkyl, ((C$_3$-C$_{12}$)cycloalkyl)-(C$_1$-C$_6$)alkyl-, —(C$_4$-C$_{12}$)cycloalkenyl, ((C$_4$-C$_{12}$)cycloalkenyl)-(C$_1$-C$_6$)alkyl-, —(C$_6$-C$_{14}$)bicycloalkyl, ((C$_6$-C$_{14}$)bicycloalkyl)-(C$_1$-C$_6$)alkyl-, —(C$_8$-C$_{20}$)tricycloalkyl, ((C$_8$-C$_{20}$)tricycloalkyl)-(C$_1$-C$_6$)alkyl-, —(C$_7$-C$_{14}$)bicycloalkenyl, ((C$_7$-C$_{14}$)bicycloalkenyl)-(C$_1$-C$_6$)alkyl-, —(C$_8$-C$_{20}$)tricycloalkenyl, ((C$_8$-C$_{20}$)tricycloalkenyl)-(C$_1$-C$_6$)alkyl-, -(6- to 14-membered)aryl, ((6- to 14-membered)aryl)-(C$_1$-C$_6$)alkyl-, -(7- to 12-membered)bicyclic ring system, ((7- to 12-membered)bicyclic ring system)-(C$_1$-C$_6$)alkyl-, -(7- to 12-membered)bicyclic aryl, ((7- to 12-membered)bicyclic aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12 membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-; each of which is optionally substituted with one, two, or three substituents independently selected from the group consisting of —OH, (=O), halo, —C(halo)$_3$, —CH(halo)$_2$, —CH$_2$(halo), —(C$_1$-C$_6$)alkyl, halo(C$_1$-C$_6$)alkyl-, —(C$_2$-C$_6$)alkenyl, —(C$_2$-C$_6$)alkynyl, hydroxy(C$_1$-C$_6$)alkyl-, dihydroxy(C$_1$-C$_6$)alkyl-, —(C$_1$-C$_6$)alkoxy, ((C$_1$-C$_6$)alkoxy)-CO—(C$_1$-C$_6$)alkoxy-, phenyl, benzyl, —NH$_2$, —NH(C$_1$-C$_6$)alkyl, —(C$_1$-C$_6$)alkyl-NH(C$_1$-C$_6$)alkyl-R$^{14}$, —NH—C(=NH)—NR$^5$R$^6$, —(C$_1$-C$_6$)alkyl-NH—C(=NH)—NR$^5$R$^6$, —CN, —SH, —OR$^{11}$, —CONR$^5$R$^6$, —(C$_1$-C$_6$ alkyl)-C(=O)—NR$^5$R$^6$, —COOR$^7$, —(C$_1$-C$_6$)alkyl-CO—OR$^7$, —(C$_1$-C$_6$)alkoxy-CO—OR$^7$, —(OCH$_2$CH$_2$)$_s$—O(C$_1$-C$_6$)alkyl, —(CH$_2$CH$_2$O)$_s$—(C$_1$-C$_6$)alkyl, (C$_1$-C$_6$)alkyl)sulfonyl, ((C$_1$-C$_6$)alkyl)sulfonyl(C$_1$-C$_6$)alkyl-, —NH—SO$_2$(C$_1$-C$_6$)alkyl, NH$_2$—SO$_2$(C$_1$-C$_6$)alkyl-, —N(SO$_2$(C$_1$-C$_6$)alkyl)$_2$, —C(=NH)NH$_2$, —NH—C(=O)—(C$_1$-C$_6$)alkyl, —NH—CO—NH$_2$, —NH—C(=O)—NH—(C$_1$-C$_6$)alkyl, —NH—C(=O)-(6- to 14-membered)aryl, —NH—C(=O)—(C$_1$-C$_6$)alkyl-(6- to 14-membered)aryl, —NH—(C$_1$-C$_6$)alkyl-CO—OR$^7$, —NH—C(=O)—(C$_1$-C$_6$)alkyl-COOR$^7$, —NH—C(=O)—CH(NH$_2$)—(C$_1$-C$_6$)alkyl-CO—OR$^7$, —(C$_3$-C$_{12}$)cycloalkyl, ((C$_3$-C$_{12}$)cycloalkyl)-(C$_1$-C$_6$)alkyl-, -(6- to 14-membered)aryl, -(6- to 14-membered)aryloxy, —(C$_1$-C$_6$)alkoxy-C(=O)NR$^5$R$^6$, —NH—(C$_1$-C$_6$)alkyl-C(=O)—NR$^5$R$^6$, —C(=O)NH—(C$_1$-C$_6$)alkyl-COOR$^7$, ((6- to 14-membered)aryl)-(C$_1$-C$_6$)alkyl-, -(5- to 12-membered)heteroaryl, ((5- to 12-membered)heteroaryl)-(C$_1$-C$_6$)alkyl-, -(3- to 12-membered)heterocycle, ((3- to 12-membered)heterocycle)-(C$_1$-C$_6$)alkyl-, -(7- to 12-membered)bicycloheterocycle, and ((7- to 12-membered)bicycloheterocycle)-(C$_1$-C$_6$)alkyl-;

each $R^{30}$ is independently selected from —COOR$^7$, —CONR$^{5a}$R$^{6a}$, —(C$_1$-C$_6$)alkyl, CN, -(3- to 12-membered)heteroaryl, ((3- to 12-membered)heteroaryl)-(C$_1$-C$_6$)alkyl-, NH$_2$, halo, and ((6- to 14-membered)aryl)-(C$_1$-C$_6$)alkoxy-;

m is an integer 0, 1, 2, 3, 4, 5, or 6;

n is an integer 0, 1, 2, 3, 4, 5, or 6;

p is an integer 0, 1, 2, 3, 4, 5, or 6:

s is an integer 1, 2, 3, 4, 5, or 6; and w is an integer 0, 1, or 2.

In another embodiment, Compounds of the Invention are compounds represented by Formula I-A:

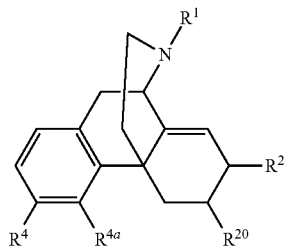

I-A and the pharmaceutically acceptable salts and solvates thereof, wherein $R^1$, $R^2$, $R^4$, $R^{4a}$, and $R^{20}$ are as defined above for Formula I or II.

In another embodiment, Compounds of the Invention are compounds represented by Formula I-B:

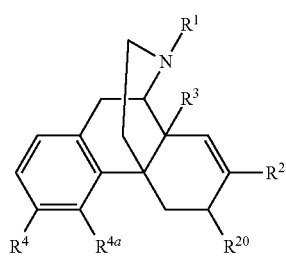

I-B and the pharmaceutically acceptable salts and solvates thereof, wherein $R^1$, $R^2$, $R^3$, $R^4$, $R^{4a}$, and $R^{20}$ are as defined above for Formula I or II.

In another embodiment, Compounds of the Invention are compounds represented by Formula I-C:

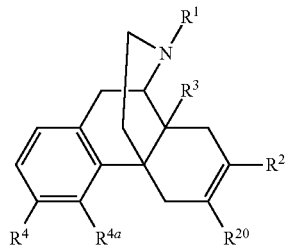

I-C and the pharmaceutically acceptable salts and solvates thereof, wherein $R^1$, $R^2$, $R^3$, $R^4$, $R^{4a}$, and $R^{20}$ are as defined above for Formula I or II.

In another embodiment, Compounds of the Invention are compounds represented by the Formula I-D:

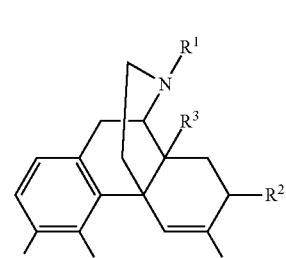

I-D and the pharmaceutically acceptable salts and solvates thereof, wherein $R^1$, $R^2$, $R^3$, $R^4$, $R^{4a}$, and $R^{20}$ are as defined above for Formula I or II.

In another embodiment, Compounds of the Invention are compounds represented by Formula I-E:

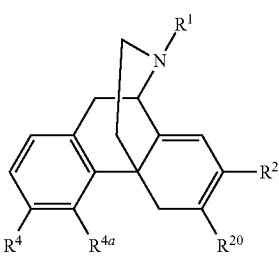

I-E and the pharmaceutically acceptable salts and solvates thereof, wherein $R^1$, $R^2$, $R^4$, $R^{4a}$, and $R^{20}$ are as defined above for Formula I or II.

In another embodiment, Compounds of the Invention are compounds represented by Formula I-F:

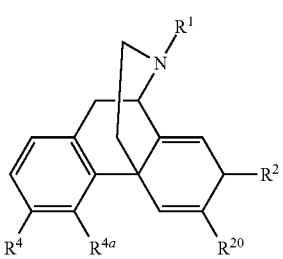

I-F and the pharmaceutically acceptable salts and solvates thereof, wherein $R^1$, $R^2$, $R^4$, $R^{4a}$, and $R^{20}$ are as defined above for Formula I or II.

In another embodiment, Compounds of the Invention are compounds represented by Formula I-G:

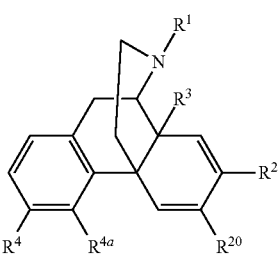

I-G and the pharmaceutically acceptable salts and solvates thereof, wherein $R^1$, $R^2$, $R^3$, $R^4$, $R^{4a}$, and $R^{20}$ are as defined above for Formula I or II.

In one embodiment, Compounds of the Invention are compounds represented by Formula I-H:

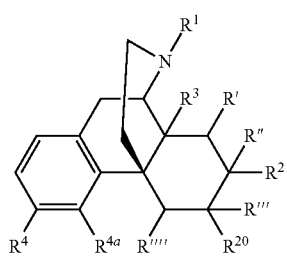

I-H and the pharmaceutically acceptable salts and solvates thereof, wherein R', R'', R''', R'''', R$^1$, R$^2$, R$^3$, R$^4$, R$^{4a}$, and R$^{20}$ are as defined above for Formula I or H.

In another embodiment, Compounds of the Invention are compounds represented by Formula I-I:

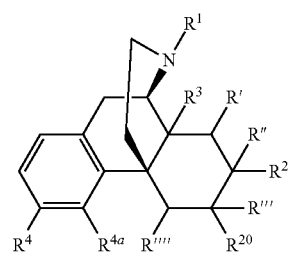

I-I and the pharmaceutically acceptable salts and solvates thereof, wherein R', R'', R''', R'''', R$^1$, R$^2$, R$^3$, R$^4$, R$^{4a}$, and R$^{20}$ are as defined above for Formula I or H.

In another embodiment, Compounds of the Invention are compounds represented by Formula I-J:

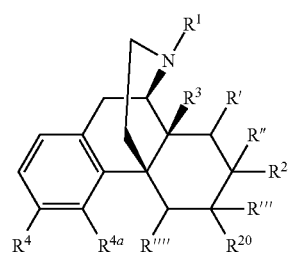

I-J and the pharmaceutically acceptable salts and solvates thereof, wherein R', R'', R''', R'''', R$^1$, R$^2$, R$^3$, R$^4$, R$^{4a}$, and R$^{20}$ are as defined above for Formula I or II.

In another embodiment, Compounds of the Invention are compounds represented by Formula I-K:

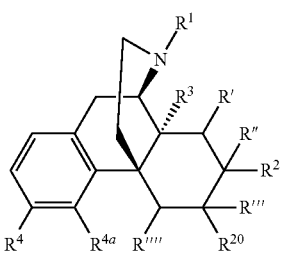

I-K and the pharmaceutically acceptable salts and solvates thereof, wherein R', R'', R''', R'''', R$^1$, R$^2$, R$^3$, R$^4$, R$^{4a}$, and R$^{20}$ are as defined above for Formula I or II.

In another embodiment, Compounds of the Invention are compounds represented by Formula I-L:

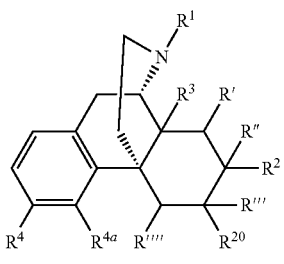

I-L and the pharmaceutically acceptable salts and solvates thereof, wherein R', R'', R''', R'''', R$^1$, R$^2$, R$^3$, R$^4$, R$^{4a}$, and R$^{20}$ are as defined above for Formula I or II.

In another embodiment, Compounds of the Invention are compounds are compounds represented by Formula I-M:

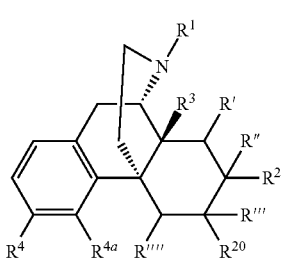

I-M and the pharmaceutically acceptable salts and solvates thereof, wherein R', R'', R''', R'''', R$^1$, R$^2$, R$^3$, R$^4$, R$^{4a}$, and R$^{20}$ are as defined above for Formula I or II.

In another embodiment, Compounds of the Invention are compounds represented by Formula I-N:

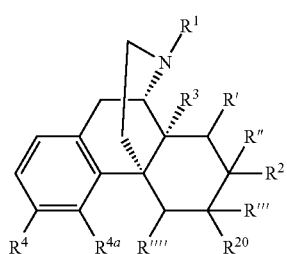

I-N and the pharmaceutically acceptable salts and solvates thereof, wherein R', R", R'", R"", $R^1$, $R^2$, $R^3$, $R^4$, $R^{4a}$, and $R^{20}$ are as defined above for Formula I or II.

In another embodiment, Compounds of the Invention are compounds represented by Formula I-O:

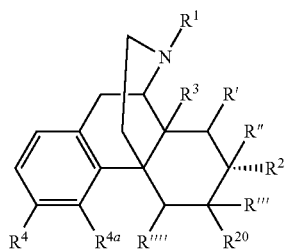

I-O and the pharmaceutically acceptable salts and solvates thereof, wherein R', R", R'", R"", $R^1$, $R^2$, $R^3$, $R^4$, $R^{4a}$, and $R^{20}$ are as defined above for Formula I or II.

In another embodiment, Compounds of the Invention are compounds represented by Formula I-P:

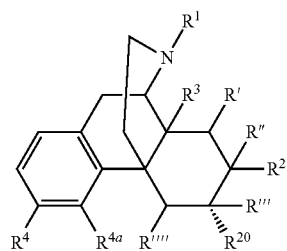

I-P and the pharmaceutically acceptable salts and solvates thereof, wherein R', R", R'", R"", $R^1$, $R^2$, $R^3$, $R^4$, $R^{4a}$, and $R^{20}$ are as defined above for Formula I or II.

In another embodiment, Compounds of the Invention are compounds represented by Formula I-Q:

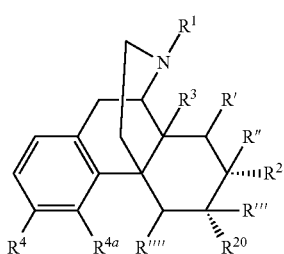

I-Q and the pharmaceutically acceptable salts and solvates thereof, wherein R', R", R'", R"", $R^1$, $R^2$, $R^3$, $R^4$, $R^{4a}$, and $R^{20}$ are as defined above for Formula I or II.

In another embodiment, Compounds of the Invention are compounds represented by Formula I-R:

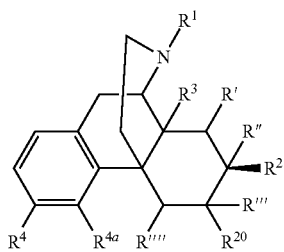

I-R and the pharmaceutically acceptable salts and solvates thereof, wherein R', R", R'", R"", $R^1$, $R^2$, $R^3$, $R^4$, $R^{4a}$, and $R^{20}$ are as defined above for Formula I or II.

In another embodiment, Compounds of the Invention are compounds represented by Formula I-S:

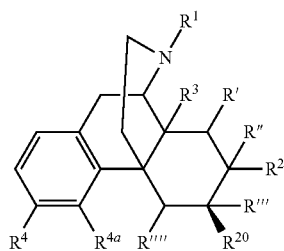

I-S and the pharmaceutically acceptable salts and solvates thereof, wherein R', R", R'", R"", $R^1$, $R^2$, $R^3$, $R^4$, $R^{4a}$, and $R^{20}$ are as defined above for Formula I or II.

In another embodiment, Compounds of the Invention are compounds represented by Formula I-T:

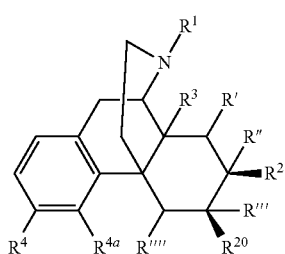

I-T and the pharmaceutically acceptable salts and solvates thereof, wherein R', R'', R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-U:

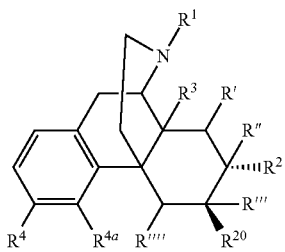

I-U and the pharmaceutically acceptable salts and solvates thereof, wherein R', R'', R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-V:

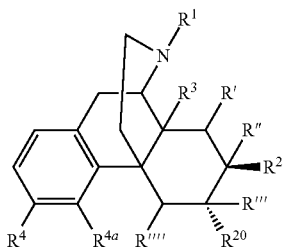

I-V and the pharmaceutically acceptable salts and solvates thereof, wherein R', R'', R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-W:

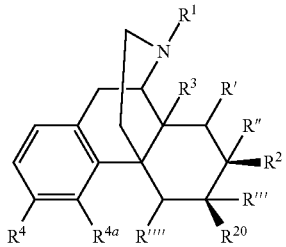

I-W and the pharmaceutically acceptable salts and solvates thereof, wherein R', R'', R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-X:

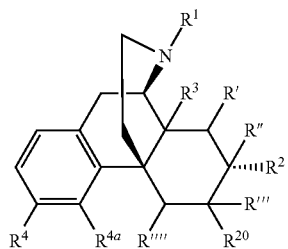

I-X and the pharmaceutically acceptable salts and solvates thereof, wherein R', R'', R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-Y:

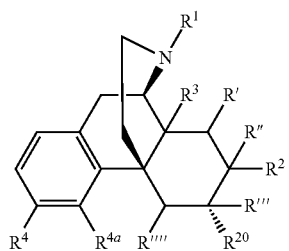

I-Y and the pharmaceutically acceptable salts and solvates thereof, wherein R', R'', R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-Z:

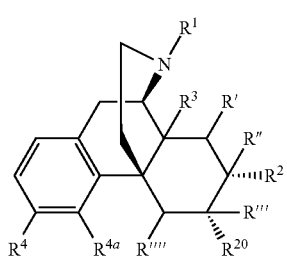

I-Z and the pharmaceutically acceptable salts and solvates thereof, wherein R', R", R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-AA:

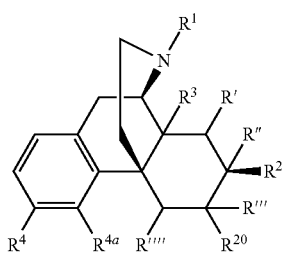

I-AA and the pharmaceutically acceptable salts and solvates thereof, wherein R', R", R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-AB:

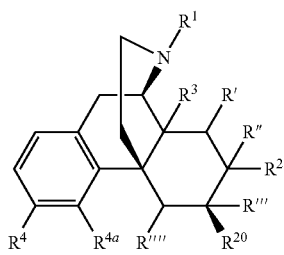

I-AB and the pharmaceutically acceptable salts and solvates thereof, wherein R', R", R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-AC:

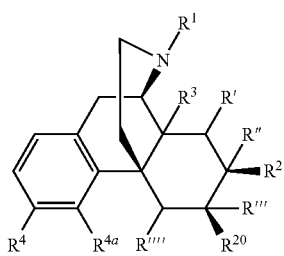

I-AC and the pharmaceutically acceptable salts and solvates thereof, wherein R', R", R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-AD:

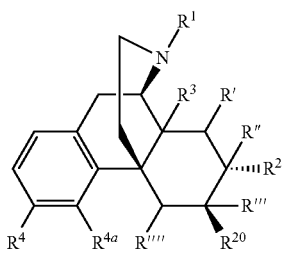

I-AD and the pharmaceutically acceptable salts and solvates thereof, wherein R', R", R''', R'''', $R^1$, $R^2$, $R^3$, $R^4$, $R^{4a}$, and $R^{20}$ are as defined above for Formula I or II.

In another embodiment, Compounds of the Invention are compounds represented by Formula I-AE:

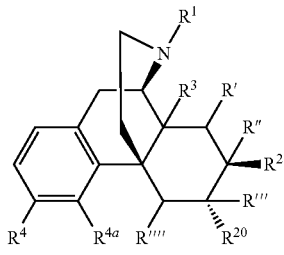

I-AE and the pharmaceutically acceptable salts and solvates thereof, wherein R', R", R''', R'''', $R^1$, $R^2$, $R^3$, $R^4$, $R^{4a}$, and $R^{20}$ are as defined above for Formula I or II.

In certain embodiments in accordance with any one of Formulae I, II, and I-A to I-AE, $R^2$ is hydrogen.

In other embodiments of any one of Formulae I, II, and I-A to I-AE, $R^2$ is OH.

In certain embodiments in accordance with any one of Formulae I, II, and I-A to I-AE, R² and R″ taken together form:

In certain embodiments in accordance with any one of Formulae I, II, and I-A to I-AE, R² is —Z¹-G¹-R¹⁰ᵃ. In certain embodiments of any one of Formulae I, II, and I-A to I-AE, R¹⁰ᵃ is —(C₁-C₁₀)alkyl. In one embodiment, R¹⁰ᵃ is methyl or ethyl.

In other embodiments in accordance with any one of Formulae I, II, and I-A to I-AE, R² is —Z¹-G¹-R¹⁰ᵃ and R¹⁰ᵃ is —(C₁-C₁₀)alkyl substituted with OH. For example, R¹⁰ᵃ is hydroxymethyl. In another example, R¹⁰ᵃ is hydroxyethyl.

In other embodiments in accordance with any one of Formulae I, II, and I-A to I-AE, R² is —Z¹-G¹-R¹⁰ᵃ, and R¹⁰ᵃ is -(6- to 14-membered)aryl. In certain embodiments, R¹⁰ᵃ is selected from the group consisting of phenyl, indenyl, naphthyl, and anthracenyl. In one embodiment, R¹⁰ᵃ is phenyl.

In certain embodiments in accordance with any one of Formulae I, II, and I-A to I-AE, R² is —Z¹-G¹-R¹⁰ᵃ, and R¹⁰ᵃ is -((6- to 14-membered)aryl)-(C₁-C₆)alkyl. In certain embodiments of any one of Formulae I, II, and I-A to I-AE, R² is —Z¹-G¹-R¹⁰ᵃ, and R¹⁰ᵃ is -(3- to 12-membered)cycloalkyl. In certain embodiments, R¹⁰ᵃ is hexyl or propyl.

In other embodiments of any one of Formulae I, II, and I-A to I-AE, R² is —Z¹-G¹-R¹⁰ᵃ, and R¹⁰ᵃ is ((3- to 12-membered)cycloalkyl)-(C₁-C₆)alkyl. As one example, R¹⁰ᵃ is cyclopropylmethyl. Another example provides that R¹⁰ᵃ is cyclopropylethyl.

In certain embodiments of any one of Formulae I, II, and I-A to I-AE, R² is —Z¹-G¹-R¹⁰ᵃ, and R¹⁰ᵃ is —(C₂-C₁₀)alkenyl, such as, ethenyl.

In certain embodiments of any one of Formulae I, II, and I-A to I-AE, R² is —Z¹-G¹-R¹⁰ᵃ, and R¹⁰ᵃ is —(C₁-C₁₀)alkoxy. In one embodiment, R¹⁰ᵃ is methoxy. In another embodiment, R¹⁰ᵃ is ethoxy.

In certain embodiments of any one of Formulae I, II, and I-A to I-AE, R¹⁰ᵃ is -(3- to 12-membered)heterocycle. In certain embodiments, R¹⁰ᵃ is selected from the group consisting of thiazolidinyl, morpholinyl, pyrrolidinyl, piperidinyl, and piperazinyl.

In other embodiments of any one of Formulae I, II, and I-A to I-AE, R² is —Z¹-G¹-R¹⁰ᵃ, and R¹⁰ᵃ is ((3- to 12-membered)heterocycle)-(C₁-C₆)alkyl.

In other embodiments in accordance with any one of Formulae I, II, and I-A to I-AE, R² is —Z¹-G¹-R¹⁰ᵃ, and R¹⁰ᵃ is -(5- to 12-membered)heteroaryl. In certain embodiments, R¹⁰ᵃ is selected from the group consisting of pyridyl, furyl, benzofuranyl, thiophenyl, pyrrolyl, indolyl, oxazolyl, benzoxazolyl, imidazolyl, benzimidazilyl, isoxazolyl, pyrazolyl, pyridazinyl, pyrimidyl, and pyrimidinyl.

In certain embodiments of any one of Formulae I, II, and I-A to I-AE, R² is —Z¹-G¹-R¹⁰ᵃ, and R¹⁰ᵃ is ((5- to 12-membered)heteroaryl)-(C₁-C₆)alkyl.

In certain embodiments of any one of Formulae I, II, and I-A to I-AE, R² is —Z¹-G¹-R¹⁰ᵃ, and R¹⁰ᵃ is —COOR⁷. In other embodiments, R² is —Z¹-G¹-R¹⁰ᵃ, and R¹⁰ᵃ is —(C₁-C₆)alkyl-COOR⁷. One embodiment provides that R⁷ is hydrogen.

In certain embodiments of any one of Formulae I, II, and I-A to I-AE, R² is —Z¹-G¹-R¹⁰ᵃ, and R¹⁰ᵃ is -(6- to 14-membered)aryl substituted with NH—C(=NH)—NR⁵R⁶.

In certain embodiments of any one of Formulae I, II, and I-A to I-AE, R² is —Z¹-G¹-R¹⁰ᵃ, and R¹⁰ᵃ is ((6- to 14-membered)aryl)-(C₁-C₆)alkyl-substituted with —NH—C(=NH)—NR⁵R⁶.

In separate embodiments of any one of Formulae I, II, and I-A to I-AE, R² is —Z¹-G¹-R¹⁰ᵃ, and R¹⁰ᵃ is —NR⁵R⁶. In other embodiments, R² is —Z¹-G¹-R¹⁰ᵃ, and R¹⁰ᵃ is —(C₁-C₆)alkyl-NR⁵R⁶. In yet other embodiments, R² is —Z¹-G¹-R¹⁰ᵃ, and R¹⁰ᵃ is —(C₁-C₆)alkyl-NH—C(=NH)—NR⁵R⁶.

In the above embodiments, one example provides that at least one of R⁵ and R⁶ is hydrogen. In another instance, both R⁵ and R⁶ are hydrogen. In other instances, at least one of R⁵ and R⁶ is —(C₁-C₆)alkyl. In one example, both R⁵ and R⁶ are —(C₁-C₆)alkyl.

In certain embodiments of any one of Formulae I, II, and I-A to I-AE, R² is —Z¹-G¹-R¹⁰ᵃ, and G¹ is a bond.

In other embodiments of any one of Formulae I, II, and I-A to I-AE, R² is —Z¹-G¹-R¹⁰ᵃ, and G¹ is —C(=O).

In other embodiments of any one of Formulae I, II, and I-A to I-AE, R² is —Z¹-G¹-R¹⁰ᵃ, and G¹ is —O—.

In yet other embodiments of any one of Formulae I, II, and I-A to I-AE, R² is —Z¹-G¹-R¹⁰ᵃ, and G¹ is —O—C(=O)—.

In certain embodiments of any one of Formulae I, II, and I-A to I-AE, R² is —Z¹-G¹-R¹⁰ᵃ, and G¹ is selected from the group consisting of —NR⁸, —NH—C(=O)—, and NH—C(=NH)—. In one embodiment, R⁸ is hydrogen.

In certain embodiments of any one of Formulae I, II, and I-A to I-AE, R² is —Z¹-G¹-R¹⁰ᵃ, and Z¹ is (CH₂)ₘ, wherein m is 0 or 1. In certain embodiments, Z¹ is further substituted with one —(C₁-C₆)alkyl. In other embodiments, Z¹ is further substituted with two —(C₁-C₆)alkyl groups, which can be the same or different.

In certain embodiments of any one of Formulae I, II, and I-A to I-AE, R²⁰ is hydrogen or OH.

In other embodiments of any one of Formulae I, II, and I-A to I-AE, R²⁰ and R‴ are taken together to form:

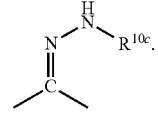

In separate embodiments of any one of Formulae I, II, and I-A to I-AE, R²⁰ is —Z²-G²-R¹⁰ᵇ. In certain embodiments, R²⁰ is —Z²-G²-R¹⁰ᵇ, and R¹⁰ᵇ is —(C₁-C₁₀)alkyl.

In other embodiments of any one of Formulae I, II, and I-A to I-AE, R²⁰ is —Z²-G²-R¹⁰ᵇ, and R¹⁰ᵇ is methyl or ethyl.

In certain embodiments of any one of Formulae I, II, and I-A to I-AE, R²⁰ is —Z²-G²-R¹⁰ᵇ and R¹⁰ᵇ is —(C₁-C₁₀)alkyl substituted with OH. One embodiment provides that R¹⁰ᵇ is hydroxymethyl. Another embodiment provides that R¹⁰ᵇ is hydroxyethyl.

In other embodiments of any one of Formulae I, II, and I-A to I-AE, R²⁰ is —Z²-G²-R¹⁰ᵇ, and R¹⁰ᵇ is -(6- to 14-membered)aryl. In certain embodiments, R¹⁰ᵇ is selected from the group consisting of phenyl, indenyl, naphthyl, and anthracenyl. One example provides that R¹⁰ᵇ is phenyl.

In other embodiments of any one of Formulae I, II, and I-A to I-AE, R²⁰ is —Z²-G²-R¹⁰ᵇ, and R¹⁰ᵇ is ((6- to 14-membered)aryl)-(C₁-C₆)alkyl.

In further separate embodiments of any one of Formulae I, II, and I-A to I-AE, $R^{20}$ is $—Z^2\text{-}G^2\text{-}R^{10b}$, and $R^{10b}$ is -(3- to 12-membered)cycloalkyl. In certain embodiments, $R^{10b}$ is hexyl or propyl.

In other embodiments of any one of Formulae I, II, and I-A to I-AE, $R^{20}$ is $—Z^2\text{-}G^2\text{-}R^{10b}$, and $R^{10b}$ is ((3- to 12-membered)cycloalkyl)-($C_1$-$C_6$)alkyl. As one example, $R^{10b}$ is cyclopropylmethyl. Another example provides that $R^{10b}$ is cyclopropylethyl.

In still other embodiments of any one of Formulae I, II, and I-A to I-AE, $R^{20}$ is $—Z^2\text{-}G^2\text{-}R^{10b}$, and $R^{10b}$ is —($C_2$-$C_{10}$)alkenyl. In one embodiment, $R^{10b}$ is ethenyl.

In certain embodiments of any one of Formulae I, II, and I-A to I-AE, $R^{20}$ is $—Z^2\text{-}G^2\text{-}R^{10b}$, and $R^{10b}$ is —($C_1$-$C_{10}$)alkoxy. In one embodiment, $R^{10b}$ is methoxy. In another embodiment, $R^{10b}$ is ethoxy.

In certain embodiments of any one of Formulae I, II, and I-A to I-AE, $R^{20}$ is $—Z^2\text{-}G^2\text{-}R^{10b}$, and $R^{10b}$ is -(3- to 12-membered)heterocycle. In certain embodiments, $R^{10b}$ is selected from the group consisting of thiazolidinyl, morpholinyl, pyrrolidinyl, piperidinyl, and piperazinyl.

In other embodiments of any one of Formulae I, II, and I-A to I-AE, $R^{20}$ is $—Z^2\text{-}G^2\text{-}R^{10b}$, and $R^{10b}$ is ((3- to 12-membered)heterocycle)-($C_1$-$C_6$)alkyl.

In separate embodiments of any one of Formulae I, II, and I-A to I-AE, $R^{20}$ is $—Z^2\text{-}G^2\text{-}R^{10b}$, and $R^{10b}$ is -(5- to 12-membered)heteroaryl. For example, $R^{10b}$ is selected from the group consisting of pyridyl, furyl, benzofuranyl, thiophenyl, pyrrolyl, indolyl, oxazolyl, benzoxazolyl, imidazolyl, benzimidazilyl, isoxazolyl, pyrazolyl, pyridazinyl, pyrimidyl, and pyrimidinyl.

In certain embodiments of any one of Formulae I, II, and I-A to I-AE, $R^{20}$ is $—Z^2\text{-}G^2\text{-}R^{10b}$, and $R^{10b}$ is ((5- to 12-membered)heteroaryl)-($C_1$-$C_6$)alkyl.

In other embodiments of any one of Formulae I, II, and I-A to I-AE, $R^{20}$ is $—Z^2\text{-}G^2\text{-}R^{10b}$, and $R^{10b}$ is —COOR$^7$. In other embodiments of any one of Formulae I, II, and I-A to I-AE, $R^{20}$ is $—Z^2\text{-}G^2\text{-}R^{10b}$, and $R^{10b}$ is —($C_1$-$C_6$)alkyl-COOR$^7$. In one embodiment, $R^7$ is hydrogen.

In certain embodiments of any one of Formulae I, II, and I-A to I-AE, $R^{20}$ is $—Z^2\text{-}G^2\text{-}R^{10b}$, and $R^{10b}$ is -(6- to 14-membered)aryl substituted with NH—C(=NH)—NR$^5$R$^6$. In other embodiments of any one of Formulae I, II, and I-A to I-AE, $R^{20}$ is $—Z^2\text{-}G^2\text{-}R^{10b}$, and $R^{10b}$ is ((6- to 14-membered)aryl)-($C_1$-$C_6$)alkyl-substituted with NH—C(=NH)—NR$^5$R$^6$. In still other embodiments of any one of Formulae I, II, and I-A to I-AE, $R^{20}$ is $—Z^2\text{-}G^2\text{-}R^{10b}$, and $R^{10b}$ is NR$^5$R$^6$. In separate embodiments, $R^{10b}$ is —($C_1$-$C_6$)alkyl-NR$^5$R$^6$. In other embodiments, $R^{10b}$ is —($C_1$-$C_6$)alkyl-NH—C(=NH)—NR$^5$R$^6$. One embodiment provides that at least one of R$^5$ and R$^6$ is hydrogen. In another embodiment, both R$^5$ and R$^6$ are hydrogen. In yet another embodiment, at least one of R$^5$ and R$^6$ is —($C_1$-$C_6$)alkyl. Another embodiment provides that both R$^5$ and R$^6$ are —($C_1$-$C_6$)alkyl.

In certain embodiments of any one of Formulae I, II, and I-A to I-AE, $R^{20}$ is $—Z^2\text{-}G^2\text{-}R^{10b}$, and $G^2$ is a bond.

In certain embodiments of any one of Formulae I, II, and I-A to I-AE, $R^{20}$ is $—Z^2\text{-}G^2\text{-}R^{10b}$, and $G^2$ is —C(=O)—.

In other embodiments of any one of Formulae I, II, and I-A to I-AE, $R^{20}$ is $—Z^2\text{-}G^2\text{-}R^{10b}$, and $G^2$ is —O—.

In still other embodiments of any one of Formulae I, II, and I-A to I-AE, $R^{20}$ is $—Z^2\text{-}G^2\text{-}R^{10b}$, and $G^2$ is —O—C(=O).

In separate embodiments of any one of Formulae I, II, and I-A to I-AE, $R^{20}$ is $—Z^2\text{-}G^2\text{-}R^{10b}$, and $G^2$ is selected from the group consisting of —NR$^8$—, —NH—C(=O)—, and NH—C(=NH)—. In one embodiment, R$^8$ is hydrogen.

In certain embodiments of any one of Formulae I, II, and I-A to I-AE, $R^{20}$ is $—Z^2\text{-}G^2\text{-}R^{10b}$, and $Z^2$ is (CH$_2$)$_m$, wherein m is 0 or 1. In one embodiment, $Z^2$ is further substituted with one —($C_1$-$C_6$)alkyl. In another embodiment, $Z^2$ is further substituted with two —($C_1$-$C_6$)alkyl groups, which can be the same or different.

In certain embodiments of any one of Formulae I, II, and I-A to I-AE, $R^1$ is —($C_1$-$C_{10}$)alkyl. In certain embodiments, $R^1$ is methyl or ethyl.

In other embodiments of any one of Formulae I, II, and I-A to I-AE, $R^1$ is —($C_2$-$C_{10}$)alkenyl. In certain embodiments, $R^1$ is ethenyl.

In certain embodiments of any one of Formulae I, II, and I-A to I-AE, $R^1$ is —($C_3$-$C_{12}$)cycloalkyl. In certain embodiments, $R^1$ is hexyl or propyl.

In other embodiments of any one of Formulae I, II, and I-A to I-AE, $R^1$ is ((C$_3$-C$_{12}$)cycloalkyl-($C_1$-$C_6$)alkyl-. In one embodiment, $R^1$ is cyclopropylmethyl.

In still other embodiments of any one of Formulae I, II, and I-A to I-AE, $R^1$ is -(6- to 14-membered)aryl. For example, $R^1$ is selected from the group consisting of phenyl, indenyl, naphthyl, and anthracenyl.

In other embodiments of any one of Formulae I, II, and I-A to I-AE, $R^1$ is ((6- to 14-membered)aryl)-($C_1$-$C_6$)alkyl-.

In certain embodiments of any one of Formulae I, II, and I-A to I-AE, $R^1$ is -(3- to 12 membered)heterocycle.

In other embodiments of any one of Formulae I, II, and I-A to I-AE, $R^1$ is ((3- to 12-membered)heterocycle)-($C_1$-$C_6$)alkyl-.

In separate embodiments of any one of Formulae I, II, and I-A to I-AE, $R^1$ is -(5- to 12-membered)heteroaryl.

Certain embodiments of any one of Formulae I, II, and I-A to I-AE provide that R$^4$ is OH. Other embodiments of any one of Formulae I, II, and I-A to I-AE provide that R$^4$ is —($C_1$-$C_{10}$)alkoxy. In certain embodiments, R$^4$ is methoxy or ethoxy.

In certain embodiments of any one of Formulae I, II, and I-A to I-AE, R$^3$ is hydrogen. In other embodiments of any one of Formulae I, II, and I-A to I-AE, R$^3$ is OH.

One embodiment of any one of Formulae I, II, and I-A to I-AE provides that R$^{4a}$ is hydrogen. In other embodiments of any one of Formulae I, II, and I-A to I-AE, R$^{4a}$ is OH.

Further, one embodiment of any one of Formulae I, II, and I-A to I-AE provides that R' is hydrogen.

Another embodiment of any one of Formulae II, and I-A to I-AE provides that R' is —OH. A separate embodiment of any one of Formulae II, and I-A to I-AE provides that R' is —($C_1$-$C_3$)alkoxy.

In one embodiment in accordance with any one of Formulae II, and I-A to I-AE, R' is OH, R" is hydrogen, and R$^2$ is hydrogen. In certain embodiments, $R^{20}$ is $—Z^2\text{-}G^2\text{-}R^{10b}$, and $Z^2$ is (CH$_2$)$_m$ wherein m is 0. One embodiment provides that $G^2$ is —O—, and $R^{10b}$ is —($C_1$-$C_6$)alkyl that is optionally substituted by —OH or —($C_1$-$C_3$)alkoxy.

In a certain embodiment, the invention provides the compounds of Formula I-J:

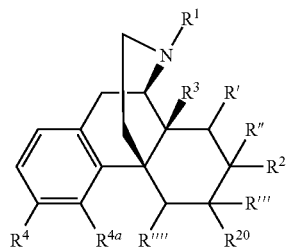

I-J and the pharmaceutically acceptable salts and solvates thereof, wherein

R', R", R''', and R'''' are all H;

$R^1$ is —$(C_1-C_3)$alkyl or $(C_3-C_6)$cycloalkyl-$(C_1-C_3)$alkyl-;

$R^{4a}$ is H;

$R^3$ is —OH;

$R^4$ is —OH or —$(C_1-C_3)$alkoxy; and $R^2$ and $R^{20}$ are as defined above for Formula I or II, including, such as any one of the embodiments above-defined.

In certain embodiments of the afore-defined Formula I-J, $R^{20}$ is —OH, and $R^2$ is H.

In another embodiment of the afore-defined Formula I-J, $R^{20}$ is —OH, and $R^2$ is —$Z^1$-$G^1$-$R^{10a}$, $Z^1$ is $(CH_2)_m$ optionally substituted with —$(C_1-C_6)$alkyl, and m is 0 or 1. In one embodiment, m is 1; $G^1$ is a bond, —O—, or —NH—; and $R^{10a}$ is selected from the group consisting of H, phenyl, phenyl-$(C_1-C_3)$alkyl-, —$(C_3-C_8)$cycloalkyl, and —$(C_1-C_6)$alkyl optionally substituted by —$(C_1-C_3)$alkyl or —COOH. In another embodiment, m is 1; $G^1$ is —N($R^8$)—; and $R^{10a}$ and $R^8$, together with the N atom to which they are both attached, form -(3- to 8-membered)heterocycle.

In another embodiment of the afore-defined Formula I-J, $R^{20}$ is —OH, and $R^2$ is —$Z^1$-$G^1$-$R^{10a}$, $Z^1$ is $(CH_2)_m$, and m is 0, $G^1$ is —NH—C(=O)—, and $R^{10a}$ is —$(C_3-C_8)$cycloalkyl, phenyl, or —$(C_1-C_6)$alkyl optionally substituted by —$(C_1-C_3)$alkyl or —$NR^5R^6$.

In separate embodiments of the afore-defined Formula I-J, $R^{20}$ is —H, and $R^2$ is —$Z^1$-$G^1$-$R^{10a}$, $Z^1$ is $(CH_2)_m$, and m is 0. In one embodiment, $G^1$ is —O— or —NH—; and $R^{10a}$ is H or —$(C_1-C_6)$alkyl optionally substituted by —$(C_1-C_3)$alkyl or —NHC(=NH)$NH_2$. In another embodiment, $G^1$ is —NH—C(=O)—; and $R^{10a}$ is —$(C_1-C_6)$alkyl optionally substituted by —$(C_1-C_3)$alkyl or —NHC(=NH)$NH_2$.

In yet another embodiment of the afore-defined Formula I-J, $R^2$ is —H, and $R^{20}$ is —$Z^2$-$G^2$-$R^{10b}$, $Z^1$ is $(CH_2)_m$, and m is 0. In one embodiment, $G^2$ is —$NR^8$— or —NH—C(=O)—. One embodiment provides that $R^8$ is H. Another embodiment provides that $R^8$ is —$(C_1-C_3)$alkyl. In a separate embodiment, $R^{10b}$ is —$(C_1-C_6)$alkyl or phenyl, each of which is optionally substituted by $NH_2$, —$(C_1-C_3)$alkyl, or —NHC(=NH)$NH_2$.

In a separate embodiment, the invention provides the compounds of Formula I-K, and the pharmaceutically acceptable salts and solvates thereof:

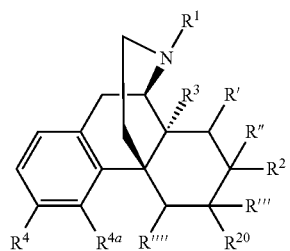

I-K wherein

R' is —OH;

R", R''', and R'''' are all H;

$R^1$ is —$(C_1-C_3)$alkyl or $(C_3-C_6)$cycloalkyl-$(C_1-C_3)$alkyl-;

$R^{4a}$ is H;

$R^3$ is H or OH;

$R^4$ is —OH or —$(C_1-C_3)$alkoxy; and $R^2$ and $R^{20}$ are as defined above for Formula I or II, including, such as any one of the embodiments above-defined.

In certain embodiments of the afore-defined Formula I-K, $R^2$ is hydrogen, and $R^{20}$ is $Z^2$-$G^2$-$R^{10b}$, $Z^2$ is $(CH_2)_m$, and m is 0 or 1. In one embodiment, m is 0. In another embodiment, $G^2$ is —O—, and $R^{10b}$ is —$(C_1-C_6)$alkyl optionally substituted by —OH or —$(C_1-C_3)$alkoxy.

In another embodiment, the compounds of Formula I-J are those presented as follows:

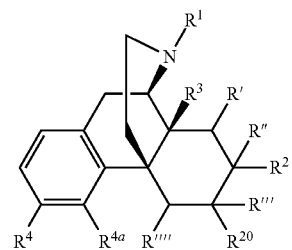

I-J and the pharmaceutically acceptable salts and solvates thereof, wherein

R', R''', and R'''' are all H;

or $R^3$ and R' taken together form a double bond;

$R^3$ is —OH;

$R^1$ is —$(C_1-C_3)$alkyl or $(C_3-C_6)$cycloalkyl-$(C_1-C_3)$alkyl-;

$R^{4a}$ is H;

$R^4$ is —OH or —$(C_1-C_3)$alkoxy; and $R^2$ and R", taken together with the carbon atom to which they are attached, form

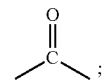

;

$R^{20}$ is as defined above for Formula I or II, including, such as the embodiments as above-defined.

In certain embodiments, representative Compounds of the Invention include:

(4bR,6R,7S,8aS,9R)-11-(cyclopropylmethyl)-3-methoxy-7-methyl-5,6,7,8,9,10-hexahydro-8aH-9,4b-(epiminoethano)phenanthrene-6,8a-diol (Compound 3);

(4bR,6S,8aS,9R)-11-(cyclopropylmethyl)-3-methoxy-5,6,7,8,9,10-hexahydro-8aH-9,4b-(epiminoethano)phenanthrene-6,8a-diol (Compound 4);

(4bR,6R,7R,8aS,9R)-11-(cyclopropylmethyl)-7-(hydroxymethyl)-3-methoxy-5,6,7,8,9,10-hexahydro-8aH-9,4b-(epiminoethano)phenanthrene-6,8a-diol (Compound 7);

2-((4bS,6R,8aS,9R)-11-(cyclopropylmethyl)-8a-hydroxy-3-methoxy-6,7,8,8a,9,10-hexahydro-5H-9,4b-(epiminoethano)phenanthren-6-yl)acetic acid (Compound 9);

(4bR,6S,8aS,9R)-11-(cyclopropylmethyl)-6-(dimethylamino)-5,6,7,8,9,10-hexahydro-8aH-9,4b-(epiminoethano)phenanthrene-3,8a-diol (Compound 10);

(4bR,6R,8aS,9R)-6-((2-aminoethyl)amino)-11-(cyclopropylmethyl)-5,6,7,8,9,10-hexahydro-8aH-9,4b-(epiminoethano)phenanthrene-3,8a-diol (Compound 11);

1-(2-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)ethyl)guanidine (Compound 12);

(4bR,6R,8aS,9R)-6-((3-aminopropyl)amino)-11-(cyclopropylmethyl)-5,6,7,8,9,10-hexahydro-8aH-9,4b-(epiminoethano)phenanthrene-3,8a-diol (Compound 13);

(4bR,6R,8aS,9R)-6-((4-aminobutyl)amino)-11-(cyclopropylmethyl)-5,6,7,8,9,10-hexahydro-8aH-9,4b-(epiminoethano)phenanthrene-3,8a-diol (Compound 14);

1-(3-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)propyl)guanidine (Compound 15);

1-(4-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)butyl)guanidine (Compound 16);

N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-2-guanidinoacetamide (Compound 20);

N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-3-guanidinopropanamide (Compound 21);

N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-4-guanidinobutanamide (Compound 22);

1-(4-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)phenyl)guanidine (Compound 24);

(4bS,8aS,9R)-11-(cyclopropylmethyl)-8a-hydroxy-3-methoxy-5,6,8a,9,10-hexahydro-7H-9,4b-(epiminoethano)phenanthren-7-one (Compound 31);

1-(2-(((4bS,7S,8aS,9R)-11-(cyclopropylmethyl)-3,8a-dihydroxy-6,7,8,8a,9,10-hexahydro-5H-9,4b-(epiminoethano)phenanthren-7-yl)amino)ethyl)guanidine (Compound 32);

(4bR,6S,7R,8aS,9R)-11-(cyclopropylmethyl)-7-(isobutylamino)-3-methoxy-5,6,7,8,9,10-hexahydro-8aH-9,4b-(epiminoethano)phenanthrene-6,8a-diol (Compound 33);

(4bR,6S,7R,8aS,9R)-11-(cyclopropylmethyl)-7-(isobutylamino)-5,6,7,8,9,10-hexahydro-8aH-9,4b-(epiminoethano)phenanthrene-3,6,8a-triol (Compound 34);

(4bR,6S,7R,8aS,9R)-11-(cyclopropylmethyl)-7-(methylamino)-5,6,7,8,9,10-hexahydro-8aH-9,4b-(epiminoethano)phenanthrene-3,6,8a-triol (Compound 35);

(4bR,6S,7R,8aS,9R)-7-(benzylamino)-11-(cyclopropylmethyl)-5,6,7,8,9,10-hexahydro-8aH-9,4b-(epiminoethano)phenanthrene-3,6,8a-triol (Compound 36);

(4bR,6R,7R,8aS,9R)-7-(benzylamino)-11-(cyclopropylmethyl)-5,6,7,8,9,10-hexahydro-8aH-9,4b-(epiminoethano)phenanthrene-3,6,8a-triol (Compound 37);

(4bR,6S,7R,8aS,9R)-11-(cyclopropylmethyl)-7-(pyrrolidin-1-yl)-5,6,7,8,9,10-hexahydro-8aH-9,4b-(epiminoethano)phenanthrene-3,6,8a-triol (Compound 38);

(4bR,6S,7R,8aS,9R)-11-(cyclopropylmethyl)-7-morpholino-5,6,7,8,9,10-hexahydro-8aH-9,4b-(epiminoethano)phenanthrene-3,6,8a-triol (Compound 39);

((4bR,6S,7R,8aS,9R)-11-(cyclopropylmethyl)-3,6,8a-trihydroxy-6,7,8,8a,9,10-hexahydro-5H-9,4b-(epiminoethano)phenanthren-7-yl)glycine (Compound 40);

(4bS,7S,8aS,9R)-11-(cyclopropylmethyl)-7-(isobutylamino)-3-methoxy-5,6,7,8,9,10-hexahydro-8aH-9,4b-(epiminoethano)phenanthren-8a-ol (Compound 41);

(4bS,7S,8aS,9R)-11-(cyclopropylmethyl)-7-(isobutylamino)-5,6,7,8,9,10-hexahydro-8aH-9,4b-(epiminoethano)phenanthrene-3,8a-diol (Compound 42);

N-((4bS,7S,8aS,9R)-11-(cyclopropylmethyl)-8a-hydroxy-3-methoxy-6,7,8,8a,9,10-hexahydro-5H-9,4b-(epiminoethano)phenanthren-7-yl)isobutyramide (Compound 45);

N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)isobutyramide (Compound 46);

N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)acetamide (Compound 47);

N-((4bR,7S,8aS,9R)-11-(cyclopropylmethyl)-6,8a-dihydroxy-3-methoxy-6,7,8,8a,9,10-hexahydro-5H-9,4b-(epiminoethano)phenanthren-7-yl)isobutyramide (Compound 49);

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide (Compound 50);

(4bR,6R,7S,8aS,9R)-11-(cyclopropylmethyl)-7-isobutoxy-3-methoxy-5,6,7,8,9,10-hexahydro-8aH-9,4b-(epiminoethano)phenanthrene-6,8a-diol (Compound 51);

(4bS,7R,8aS,9R)-11-(cyclopropylmethyl)-3-methoxy-5,6,7,8,9,10-hexahydro-8aH-9,4b-(epiminoethano)phenanthrene-7,8a-diol (Compound 52);

(4bR,6R,7S,8aS,9R)-11-(cyclopropylmethyl)-7-(2-methylbutyl)-5,6,7,8,9,10-hexahydro-8aH-9,4b-(epiminoethano)phenanthrene-3,6,8a-triol (Compound 53);

(4bR,6R,7S,8aS,9R)-7-(cyclopentylmethyl)-11-(cyclopropylmethyl)-5,6,7,8,9,10-hexahydro-8aH-9,4b-(epiminoethano)phenanthrene-3,6,8a-triol (Compound 54);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)acetamide (Compound 55);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)propionamide (Compound 56);

N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)propionamide (Compound 57);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide (Compound 58);

(S)—N-((46R,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-2-methylbutanamide (Compound 59);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-3-methylbutanamide (Compound 60);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-4-methylpentanamide (Compound 61);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide (Compound 62);

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide (Compound 63);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclopropanecarboxamide (Compound 64);

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclohexanecarboxamide (Compound 65);

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)benzamide (Compound 66);

(4bR,6R,7S,8aS,9R)-11-(cyclopropylmethyl)-7-isobutyl-5,6,7,8,9,10-hexahydro-8aH-9,4b-(epiminoethano)phenanthrene-3,6,8a-triol (Compound 67);

(4bS,9R)-11-(cyclopropylmethyl)-3-hydroxy-5,6,9,10-tetrahydro-7H-9,4b-(epiminoethano)phenanthren-7-one (Compound 68);

(4bS)-4-hydroxy-3,6-dimethoxy-11-methyl-9,10-dihydro-7H-9,4b-(epiminoethano)phenanthren-7-one (Compound 101);

(4bR,6S,7S,8aS,9R)-7-(benzyloxy)-11-(cyclopropylmethyl)-3-methoxy-5,6,7,8,9,10-hexahydro-9,4b-(epiminoethano)-6,8a-epoxyphenanthrene (Compound 102);

and the pharmaceutically acceptable salts and solvates thereof.

In another embodiment, the Invention also includes representative compounds as follows:

(4bR,6R,7S,8aS,9R)-7-benzyl-11-(cyclopropylmethyl)-5,6,7,8,9,10-hexahydro-8aH-9,4b-(epiminoethano)phenanthrene-3,6,8a-triol (Compound 103);

N-((4bR,6R,7S,8aS,9R)-3,6,8a-trihydroxy-11-methyl-6,7,8,8a,9,10-hexahydro-5H-9,4b-(epiminoethano)phenanthren-7-yl)isobutyramide (Compound 104);

4-methyl-N-((4bR,7S,8aS,9R)-3,6,8a-trihydroxy-11-methyl-6,7,8,8a,9,10-hexahydro-5H-9,4b-(epiminoethano)phenanthren-7-yl)pentanamide (Compound 105);

5-methyl-N-((4bR,7S,8aS,9R)-3,6,8a-trihydroxy-11-methyl-6,7,8,8a,9,10-hexahydro-5H-9,4b-(epiminoethano)phenanthren-7-yl)hexanamide (Compound 106);

(4bR,6R,8aS,9R)-6-(dimethylamino)-11-methyl-5,6,7,8,9,10-hexahydro-8aH-9,4b-(epiminoethano)phenanthrene-3,8a-diol (Compound 107);

N-((4bR,6R,7S,8aS,9R)-3,6,8a-trihydroxy-11-methyl-6,7,8,8a,9,10-hexahydro-5H-9,4b-(epiminoethano)phenanthren-7-yl)benzamide (Compound 108);

(4bR,6R,7S,8aS,9R)-7-isopentyl-11-methyl-5,6,7,8,9,10-hexahydro-8aH-9,4b-(epiminoethano)phenanthrene-3,6,8a-triol (Compound 109);

(4bR,7S,8aS,9R)-7-(cyclopentylmethyl)-11-methyl-5,6,7,8,9,10-hexahydro-8aH-9,4b-(epiminoethano)phenanthrene-3,6,8a-triol (Compound 110);

N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)-2-(dimethylamino)acetamide (Compound 111);

N-((4bS,6R,7S,8aR,9R)-11-(cyclopropylmethyl)-3,6-dihydroxy-6,7,8,8a,9,10-hexahydro-5H-9,4b-(epiminoethano)phenanthren-7-yl)isobutyramide (Compound 112);

(4bR,6R,7S,8aS,9R)-7-(ethylamino)-11-methyl-5,6,7,8,9,10-hexahydro-8aH-9,4b-(epiminoethano)phenanthrene-3,6,8a-triol (Compound 113);

(4bR,6S,7S,8aS,9R)-7-(ethylamino)-11-methyl-5,6,7,8,9,10-hexahydro-8aH-9,4b-(epiminoethano)phenanthrene-3,6,8a-triol (Compound 114);

N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide (Compound 115);

(4bR,6R,7S,8aS,9R)-11-methyl-7-(methylamino)-5,6,7,8,9,10-hexahydro-8aH-9,4b-(epiminoethano)phenanthrene-3,6,8a-triol (Compound 116);

(4bR,6R,7S,8aS,9R)-7-amino-11-(cyclopropylmethyl)-3,8a-dihydroxy-6,7,8,8a,9,10-hexahydro-5H-9,4b-(epiminoethano)phenanthren-6-yl 5-methylhexanoate (Compound 117);

(4bS,6R,8R,8aS,9R)-6-(2-hydroxyethoxy)-3-methoxy-11-methyl-6,7,8,8a,9,10-hexahydro-5H-9,4b-(epiminoethano)phenanthren-8-ol (Compound 118);

(4bS,6S,8R,8aS,9R)-6-(2-hydroxyethoxy)-3-methoxy-11-methyl-6,7,8,8a,9,10-hexahydro-5H-9,4b-(epiminoethano)phenanthren-8-ol (Compound 119);

(4bS,6R,8R,8aS,9R)-6-(2-hydroxyethoxy)-11-methyl-6,7,8,8a,9,10-hexahydro-5H-9,4b-(epiminoethano)phenanthrene-3,8-diol (Compound 120); and (4bS,6S,8R,8aS,9R)-6-(2-hydroxyethoxy)-11-methyl-6,7,8,8a,9,10-hexahydro-5H-9,4b-(epiminoethano)phenanthrene-3,8-diol (Compound 121);

and the pharmaceutically acceptable salts and solvates thereof.

As used herein, the term "alkyl" as used by itself or as part of another group refers to a straight- or branched-chain aliphatic hydrocarbon containing one or more carbon atoms or the number of carbon atoms designated (i.e., a $C_1$ alkyl such as methyl, a $C_2$ alkyl such as ethyl, a $C_3$ alkyl such as propyl or isopropyl, etc.). For example, "—($C_1$-$C_{10}$)alkyl" refers to straight-chain and branched non-cyclic saturated hydrocarbons having from 1 to 10 carbon atoms. Representative straight chain —($C_1$-$C_{10}$) alkyl groups include methyl, -ethyl, -n-propyl, -n-butyl, -n-pentyl, -n-hexyl, n-heptyl, n-octyl, n-nonyl and n-decyl. Representative branched —($C_1$-$C_{10}$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, and the like.

As used herein, the term "—($C_1$-$C_6$)alkyl" refers to straight-chain and branched non-cyclic saturated hydrocarbons having from 1 to 6 carbon atoms. Representative straight chain —($C_1$-$C_6$)alkyl groups include methyl, -ethyl, -n-propyl, -n-butyl, -n-pentyl, and -n-hexyl. Representative branched-chain —($C_1$-$C_6$)alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl, methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, and the like.

As used herein, the term "alkenyl" as used by itself or as part of another group refers to an alkyl group as defined above containing one or more carbon-to-carbon double bonds. As one example, "—($C_2$-$C_{12}$)alkenyl" refers to straight chain and branched non-cyclic hydrocarbons having from 2 to 12 carbon atoms and including at least one carbon-carbon double bond. Representative straight chain and branched —($C_2$-$C_{12}$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, 3-hexenyl, and the like.

As used herein, the term "—($C_2$-$C_6$)alkenyl" refers to straight chain and branched non-cyclic hydrocarbons having from 2 to 6 carbon atoms and including at least one carbon-carbon double bond. Representative straight chain and branched —($C_2$-$C_6$)alkenyl groups include -vinyl, allyl, -1-butenyl, -2-butenyl, -isobutylenyl, -1-pentenyl, -2-pentenyl, -3-methyl-1-butenyl, -2-methyl-2-butenyl, 1-hexenyl, 2-hexenyl, 3-hexenyl and the like.

As used herein, the term "alkynyl" as used by itself or as part of another group refers to an alkyl group as defined above containing one to three carbon-to-carbon triple bonds. For example, "—($C_2$-$C_{12}$)alkynyl" refers to straight chain and branched non-cyclic hydrocarbons having from 2 to 12 carbon atoms and including at least one carbon-carbon triple bond. Representative straight chain and branched —($C_2$-$C_{12}$)alkynyl groups include -ethynyl, -propynyl, -1 butynyl, -2-butynyl, -1-pentynyl, -2-pentynyl, -3-methyl-1-butynyl, -4-pentynyl, -1-hexynyl, -2-hexynyl, -5-hexynyl, and the like.

As used herein, the term "—($C_2$-$C_6$)alkynyl" refers to straight chain and branched non-cyclic hydrocarbons having from 2 to 6 carbon atoms and including at least one carbon-carbon triple bond. Representative straight chain and branched —($C_2$-$C_6$)alkynyl groups include -ethynyl, -propynyl, -1 butynyl, -2-butynyl, -1-pentynyl, -2-pentynyl, -3-methyl-1-butynyl, -4-pentynyl, and the like.

As used herein, the term "alkoxy" as used by itself or as part of another group refers to an optionally substituted alkyl, optionally substituted cycloalkyl, optionally substituted alkenyl or optionally substituted alkynyl attached to a terminal oxygen atom. For example, "—($C_1$-$C_{10}$)alkoxy" means a straight chain or branched non-cyclic hydrocarbon having one or more ether groups and from 1 to 10 carbon atoms. Representative straight chain and branched ($C_1$-$C_{10}$) alkoxys include -methoxy, -ethoxy, -propoxy, -butyloxy, -pentyloxy, -hexyloxy, -heptyloxy, -methoxymethyl, -2-methoxyethyl, -5-methoxypentyl, -3-ethoxybutyl and the like.

As another example, "—($C_1$-$C_6$)alkoxy" means a straight chain or branched non-cyclic hydrocarbon having one or more ether groups and from 1 to 6 carbon atoms. Representative straight chain and branched ($C_1$-$C_5$)alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

Further, "—($C_1$-$C_5$)alkoxy" means a straight chain or branched non-cyclic hydrocarbon having one or more ether groups and from 1 to 5 carbon atoms. Representative straight chain and branched ($C_1$-$C_5$)alkoxys include -methoxy, -ethoxy, -propoxy, -butyloxy, -pentyloxy, -methoxymethyl, -2-methoxyethyl, -5-methoxypentyl, -3-ethoxybutyl and the like.

As used herein, "carbonyl" means —C(=O)—.

As used herein, "alkoxycarbonyl" means a carbonyl group substituted by any one of the above-mentioned ($C_1$-$C_{10}$)alkoxy groups.

As used herein, the term "cycloalkyl" as used by itself or as part of another group refers to saturated cyclic aliphatic hydrocarbons containing one to more rings having three or more carbon atoms or the number of carbons designated. As used herein, "—($C_3$-$C_{12}$)cycloalkyl" refers to cyclic saturated hydrocarbon having from 3 to 12 carbon atoms. Representative ($C_3$-$C_{12}$)cycloalkyls include cyclopropyl, cyclobutyl, cyclopentyl, cyclohexyl, cycloheptyl, cyclooctyl, and cyclononyl, cyclodecyl, cycloundecyl, cyclododecyl, and the like.

As another example, "—($C_6$-$C_{14}$)bicycloalkyl" means a bicyclic hydrocarbon ring system having from 6 to 14 carbon atoms and at least one saturated cyclic alkyl ring. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, and the like.

As used herein, "—($C_8$-$C_{20}$) tricycloalkyl" means a tri-cyclic hydrocarbon ring system having from 8 to 20 carbon atoms and at least one saturated cyclic alkyl ring. Representative —($C_8$-$C_{20}$)tricycloalkyls include -pyrenyl, -adamantyl, -1,2,3,4-tetrahydroanthracenyl, -perhydroanthracenyl, -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e]azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

As used herein, the term "—($C_4$-$C_{12}$)cycloalkenyl" refers to a cyclic, preferably mono- or bicyclic, hydrocarbon having from 4 to 12 carbon atoms, and including at least one carbon-carbon double bond. Representative —($C_3$-$C_{12}$)cycloalkenyls include cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -norbornenyl, and the like.

As used herein, "—($C_7$-$C_{14}$)bicycloalkenyl" means a bi-cyclic hydrocarbon ring system having at least one carbon-carbon double bond in at least one of the rings and from 7 to 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, and the like.

As used herein, "—($C_8$-$C_{20}$)tricycloalkenyl" means a tri-cyclic hydrocarbon ring system having at least one carbon-carbon double bond in one of the rings and from 8 to 20 carbon atoms. Representative —($C_8$-$C_{20}$)tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta[e]indenyl, 2,3,4,7,8,9,10,11-octahydro-1H-cyclohepta[a]naphthalenyl, 8,9,10,11-tetrahydro-7H-cyclohepta[a]naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8,9,10,11,12,13-dodecahydro-1H-dibenzo[a,d]cyclononenyl, and the like.

As used herein, the term "heterocycle" or "heterocyclo" as used by itself or as part of another group refers to saturated or partially unsaturated (e.g., containing one or two double bonds) cyclic groups containing one or more rings having at least one carbon atom of one of the rings is replaced with a heteroatom. In one embodiment, "-(3- to 12-membered)heterocycle" or "-(3- to 12-membered)heterocyclo" means a 3- to 12-membered monocyclic heterocyclic ring which is either saturated, partially unsaturated, or non-aromatic. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(3- to 12-membered)heterocycle can be attached via a nitrogen or carbon atom. Representative -(3- to 12-membered)heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(4- to 8-membered)heterocycle" or "-(4- to 8-membered)heterocyclo" means a 4- to 8-membered monocyclic heterocyclic ring which is either saturated, partially unsaturated, or non-aromatic. A 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(4- to 8-membered)heterocycle can be attached via a nitrogen or carbon atom. Representative -(4- to 8-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(5- to 12-membered)heterocycle" or "-(5- to 12-membered)heterocyclo" means a 5- to 12-membered monocyclic or bicyclic heterocyclic ring which is either saturated, partially unsaturated, or non-aromatic. A 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The -(5- to 12-membered)heterocycle can be attached via a nitrogen or carbon atom. Representative -(5- to 12-membered)heterocycles include morpholinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

As used herein, "-(7- to 12-membered)bicycloheterocycle" or "-(7- to 12-membered)bicycloheterocyclo" means a 7- to 12-membered bicyclic, heterocyclic ring which is either saturated, partially unsaturated, or non-aromatic. At least one ring of the bicycloheterocycle contains at least one heteroatom. A -(7- to 12-membered)bicycloheterocycle contains from 1 to 4 heteroatoms independently selected from nitrogen (which can be quaternized), oxygen, and sulfur (including sulfoxide and sulfone). The -(7- to 12-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, isoindolinyl, -1,2,3,4-tetrahydroquinolinyl, -1,2,3,4-tetrahydroisoquinolinyl, pyrrolopyrrolyl and the like.

As used herein, the term "heteroaryl" or "heteroaromatic" refers to monocyclic and bicyclic aromatic ring systems having 5 or more ring atoms wherein at least one carbon atom of one of the rings is replaced with a heteroatom independently selected from the group consisting of oxygen, nitrogen and sulfur. For example, a "-(6- to 14-membered)aryl" means an aromatic carbocyclic ring containing 6 to 14 carbon atoms, including both mono-, bi-, and tricyclic ring systems. Representative -(6- to 14-membered)aryl groups include indenyl, -phenyl, -naphthyl, anthracenyl and the like.

As used herein a "-(7- to 12-membered)bicyclic aryl" means a bicyclic aromatic carbocyclic ring containing 7 to 12 carbon atoms. Representative -(7- to 12-membered) bicyclic aryl groups include indenyl, -naphthyl, and the like.

As used herein a "-(6- to 14-membered)aryloxy" means an oxygen substituted by an aromatic carbocyclic ring containing 6 to 14 carbon atoms, including both mono-, bi- and tricyclic ring systems. Representative -(6- to 14-membered)aryloxy groups include phenoxy and 4-fluorophenoxy, and the like.

As used herein a "hydroxy($C_1$-$C_6$)alkyl" means any of the above-mentioned $C_{1-6}$ alkyl groups substituted by one or more hydroxy groups. Representative hydroxy($C_1$-$C_6$)alkyl groups include hydroxymethyl, hydroxyethyl, hydroxypropyl and hydroxybutyl groups, and especially hydroxymethyl, 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein a "dihydroxy($C_1$-$C_6$)alkyl" means any of the above-mentioned $C_{1-6}$ alkyl groups substituted by two hydroxy groups. Representative dihydroxy($C_1$-$C_6$)alkyl groups include dihydroxyethyl, dihydroxypropyl and dihydroxybutyl groups, and especially 1,2-dihydroxyethyl, 1,3-dihydroxypropyl, 2,3-dihydroxypropyl, 1,3-dihydroxybutyl, 1,4-dihydroxybutyl, and 1,3-dihydroxyprop-2-yl.

As used herein a "-(5- to 12-membered)carbocyclic ring" means a mono- or bicyclic hydrocarbon ring system having from 5 to 12 carbon atoms, which is either saturated, unsaturated, or non-aromatic.

As used herein a "-(7- to 12-membered)bicyclic ring system" means a 7- to 12-membered a carbocyclic or heterocyclic ring, which may be either unsaturated, saturated, non-aromatic or aromatic.

As used herein, "-(5- to 12-membered)heteroaryl" means an aromatic heterocycle ring of 5 to 12 members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the bicyclic -(5- to 12-membered)heteroaryl rings contains at least one carbon atom. In another embodiment, both of the bicyclic -(5- to 12-membered)heteroaryl rings contain at least one carbon atom. Representative -(5- to 12-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the terms "halo" and "halogen" refer to fluoro, chloro, bromo or iodo.

As used herein, "—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

As used herein, "—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

As used herein, "C(halo)$_3$" means a methyl group where each of the hydrogens of the methyl group has been replaced with a halogen. Representative —C(halo)$_3$ groups include —$CF_3$, —$CCl_3$, —$CBr_3$, and —$CI_3$.

As used herein, the term "optionally substituted" refers to a group that is either unsubstituted or substituted.

Optional substituents on optionally substituted groups, when not otherwise indicated, include 1, 2, or 3 groups each independently selected from the group consisting of —($C_1$-$C_6$)alkyl, OH, halo, —C(halo)$_3$, —CH(halo)$_2$, —$CH_2$(halo), $NH_2$, —NH($C_1$-$C_6$)alkyl, CN, SH, -(5- to 12-membered) carbocyclic ring, -(5- to 12-membered)heterocycle, phenyl, benzyl, (=O), halo($C_1$-$C_6$)alkyl-, —($C_2$-$C_6$)alkenyl-, —($C_2$-$C_6$)alkynyl, hydroxy($C_1$-$C_6$)alkyl-, $OR^4$ (such as —OC(halo)$_3$ and —O($C_1$-$C_6$)alkyl), —$CONR^5R^6$, and —$COOR^7$, where $R^4$ is selected from the group consisting of —($C_1$-$C_6$)alkyl, —($C_2$-$C_6$)alkenyl, —($C_2$-$C_6$)alkynyl, —C(halo)$_3$, hydroxy($C_1$-$C_6$)alkyl-, ($C_3$-$C_{12}$)cycloalkyl, —($C_6$-$C_{14}$)bicycloalkyl, —($C_8$-$C_{20}$)tricycloalkyl, —($C_4$-$C_{12}$)cycloalkenyl, —($C_7$-$C_{14}$)bicycloalkenyl, —($C_8$-$C_{20}$)tricycloalkenyl, -(6- to 14-membered)aryl, -(5- to 12-membered)heteroaryl, -(3- to 12-membered)heterocycle, and -(7- to 12-membered) bicycloheterocycle; $R^5$ and $R^6$ are each independently selected from the group consisting of —($C_1$-$C_6$)alkyl, —($C_3$-$C_8$)cycloalkyl, (($C_3$-$C_8$)cycloalkyl)-($C_1$-$C_6$)alkyl-, or together with the nitrogen atom to which they are attached form a (4- to 8-membered)heterocycle; and $R^7$ is selected from the group consisting of hydrogen, —($C_1$-$C_6$)alkyl, —($C_2$-$C_6$)alkenyl, —($C_2$-$C_6$)alkynyl, —($C_3$-$C_{12}$)cycloalkyl, —($C_4$-$C_{12}$)cycloalkenyl, (($C_3$-$C_{12}$)cycloalkyl)-($C_1$-$C_6$) alkyl-, (($C_4$-$C_{12}$)cycloalkenyl)-($C_1$-$C_6$)alkyl-, —($C_1$-$C_6$) alkoxy-$COOR^7$, —NH—C(=O)—NH—($C_1$-$C_6$)alkyl, —NH—C(=O)-(6- to 14-membered)aryl, —NH—C (=O)—($C_1$-$C_6$)alkyl-(6- to 14-membered)aryl, —NH—($C_1$-$C_6$)alkyl-CO—$OR^7$, —NH—C(=O)—($C_1$-$C_6$)alkyl-CO—$OR^7$, —NH—C(=O)—CH($NH_2$)—($C_1$-$C_6$)alkyl-CO—$OR^7$, —($C_3$-$C_{12}$)cycloalkyl, -(6- to 14-membered) aryl, -(6- to 14-membered)aryloxy, —($C_1$-$C_6$)alkoxy-C(O)—$NR^5R^6$, —NH—($C_1$-$C_6$)alkyl-C(O)—$NR^5R^6$, —C(O)NH—($C_1$-$C_6$)alkyl-$COOR^7$, —($C_1$-$C_6$)alkyl-C(=O)—($C_1$-$C_6$)alkoxy, —($C_1$-$C_6$)alkoxy-C(=O)—($C_1$-$C_6$)alkyl, —($C_1$-$C_6$)alkyl-CN, —($C_1$-$C_6$)alkyl-$COOR^7$, —($C_1$-$C_6$)alkoxy-$COOR^7$, —($C_3$-$C_{12}$)cycloalkyl, (($C_3$-$C_{12}$)cycloalkyl)-($C_1$-$C_6$)alkyl-, (($C_3$-$C_{12}$)cycloalkyl)-($C_1$-$C_6$)alkoxy-, (($C_3$-$C_{12}$) cycloalkyl)-($C_1$-$C_6$)alkoxy-($C_1$-$C_6$)alkyl-, —($C_4$-$C_{12}$) cycloalkenyl, (($C_4$-$C_{12}$)cyclo alkenyl)-($C_1$-$C_6$)alkyl-, (($C_4$-$C_{12}$)cyclo alkenyl)-($C_1$-$C_6$)alkoxy-, (($C_4$-$C_{12}$)cycloalkenyl)-($C_1$-$C_6$)alkoxy-($C_1$-$C_6$)alkyl-, -(6- to 14-membered)aryl, ((6- to 14-membered)aryl)-($C_1$-$C_6$)alkyl-, ((6- to 14-membered)aryl)-($C_1$-$C_6$)alkoxy-, ((6- to 14-membered)aryl)-($C_1$-$C_6$)alkoxy-($C_1$-$C_6$)alkyl-, -(5- to 12-membered)heteroaryl, ((5- to 12-membered)heteroaryl)-($C_1$-$C_6$)alkyl-, ((5- to 12-membered)heteroaryl)-($C_1$-$C_6$)alkoxy-, ((5- to 12-membered)heteroaryl)-($C_1$-$C_6$)alkoxy-($C_1$-$C_6$)alkyl-, -(3- to 12-membered)heterocycle, ((3- to 12 membered)heterocycle)-($C_1$-$C_6$)alkyl-, ((3- to 12 membered)heterocycle)-($C_1$-$C_6$)alkoxy-, and ((3- to 12 membered)heterocycle)-($C_1$-$C_6$)alkoxy-($C_1$-$C_6$)alkyl-.

As used herein, compounds that bind to receptors and mimic the regulatory effects of endogenous ligands are defined as "agonists". Compounds that bind to receptors and are only partly effective as agonists are defined as "partial agonists". Compounds that bind to a receptor without producing any regulatory effect, but rather block the binding of ligands to the receptor are defined as "antagonists". (Ross and Kenakin, "Ch. 2: Pharmacodynamics: Mechanisms of Drug Action and the Relationship Between Drug Concentration and Effect", pp. 31-32, in *Goodman & Gilman's the Pharmacological Basis of Therapeutics*, 10$^{th}$ Ed. (J. G. Hardman, L. E. Limbird and A. Goodman-Gilman eds., 2001).

Compounds of the Invention can be isotopically-labeled (i.e., radio-labeled). Examples of isotopes that can be incorporated into the disclosed compounds include isotopes of hydrogen, carbon, nitrogen, oxygen, phosphorous, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F and $^{36}$Cl, respectively, and preferably $^3$H, $^{11}$C, and $^{14}$C. Isotopically-labeled Compounds of the Invention can be prepared by methods known in the art in view of this disclosure. For example, tritiated Compounds of the Invention can be prepared by introducing tritium into the particular compound by catalytic dehalogenation with tritium. This method may include reacting a suitable halogen-substituted precursor of a Compound of the Invention with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}$C-labeled compounds can be prepared by employing starting materials having a $^{14}$C carbon.

Isotopically labeled Compounds of the Invention, as well as the pharmaceutically acceptable salts, and solvates thereof, can be used as radioligands to test for the binding of compounds to an opioid or ORL-1 receptor. For example, a radio-labeled Compound of the Invention can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid or ORL-1 receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Compounds of the Invention encompass all salts of the disclosed compounds of Formulae I, II, and I-A to I-AE. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of Formulae I, II, and I-A to I-AE.

The term "solvate" as used herein is a combination, physical association and/or solvation of a compound of any one of Formulae I, II, and I-A to I-AE with a solvent molecule such as, e.g. a disolvate, monosolvate or hemisolvate, where the ratio of solvent molecule to a compound of any one of Formulae I, II, and I-A to I-AE is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of any one of Formulae I, II, and I-A to I-AE may be present as a solvated form with a pharmaceutically acceptable solvent, such as water, methanol, ethanol, and the like, and it is intended that the invention include both solvated and unsolvated forms of a compound of any one of Formulae I, II, and I-A to I-AE.

One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.*, 603-604 (2001). A typical, non-limiting, process of preparing a solvate would involve dissolving a compound of any one of Formulae I, II, and I-A to I-AE in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing a Condition. In one embodiment, the Condition is pain, such as acute or chronic pain. In one embodiment, a Compound of the Invention has agonist activity at the μ, δ and/or κ receptors. In another embodiment a Compound of the Invention has agonist activity at the μ receptor. In another embodiment, a Compound of the Invention has agonist activity at the κ receptor. In another embodiment, a Compound of the Invention has antagonist activity at the ORL-1 receptor. In another embodiment, certain Compounds of the invention can stimulate one receptor (e.g., a μ, δ and/or κ agonist) and inhibit a different receptor (e.g., an ORL-1 antagonist).

LIST OF ABBREVIATIONS

ACN acetonitrile
AcCl acetyl chloride
AcOH acetic acid
Ac$_2$O acetic anhydride
aq. aqueous
atm atmosphere(s)
Bn benzyl
Boc tert-butoxycarbonyl
Boc$_2$O di-tert-butyl dicarbonate
° C. degrees Celcius
conc. concentrated
DBU 1,8-diazabicyclo[5.4.0]undec-7-ene DCE 1,2-dichloroethane
DCM dichloromethane
DIPEA diisopropylethylamine
DMAP 4-dimethylaminopyridine
DME 1,2-dimethoxyethane
DMF dimethylformamide
DMSO dimethylsulfoxide
$Et_2O$ diethyl ether
EtOAc ethyl acetate
EtOH ethanol
h hour(s)
HPLC high pressure liquid chromatography
i-PrOH iso-propanol
MeOH methanol
min minute(s)
MPLC medium pressure liquid chromatography
Ms methanesulfonyl
MsCl methanesulfonyl chloride
NaHMDS sodium hexamethyldisilazide
Pd/C palladium on carbon
$PPh_3$ triphenylphosphine
psi pounds per square inch
PyBOP benzotriazol-1-yl-oxytripyrrolidinophosphonium hexafluorophosphate
RT room temperature
satd. saturated
TEA triethylamine
TFA trifluoroacetic acid
THF tetrahydrofuran Synthesis of Compounds Compounds of Formula I or II can be made using conventional organic synthesis in view of this disclosure, or by the illustrative methods shown in the schemes below.

Compound A (as described, for example, in Hupp C. D., et al., *Tetrahedron Lett.* 2010, 51, 2359) is converted to Compound B by reaction with a suitable alkyl halide, triflate, tosylate, mesylate, etc. in the presence of a suitable base such as NaHMDS in a suitable solvent such as THF. Compound A is converted to Compound D by reaction with a suitable base such as NaH in a dialkyl carbonate that functions as both the solvent and electrophile. Compounds B and D can be converted to Compounds C and E, respectively, by treatment with a suitable reducing agent such as $NaBH_4$ in a suitable solvent such as MeOH or EtOH.

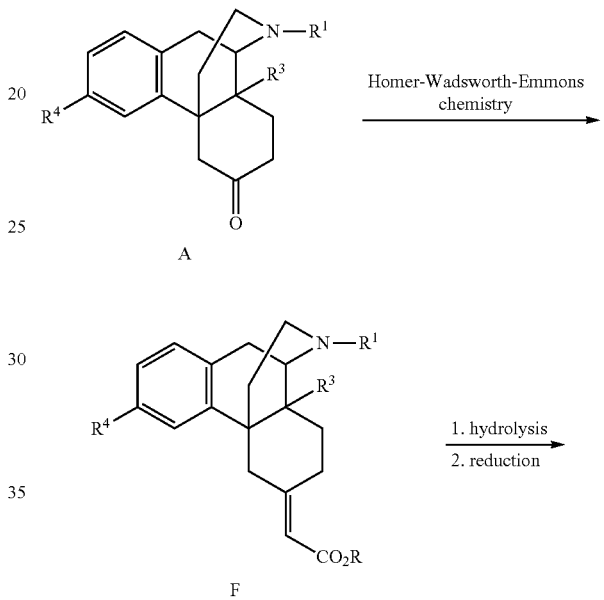

Scheme B

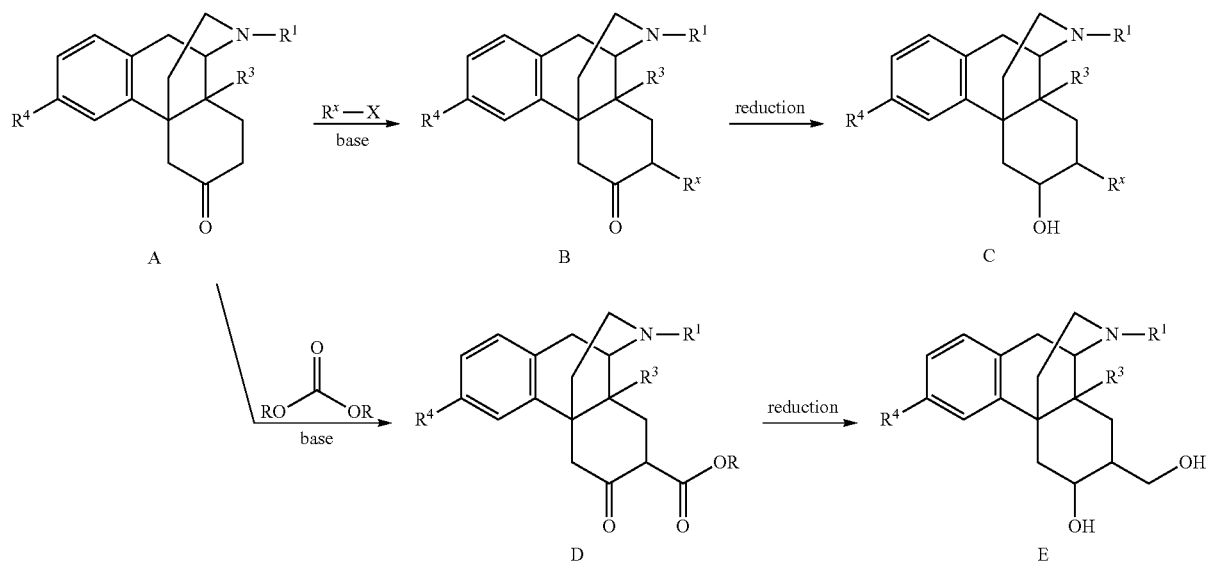

Scheme A

-continued

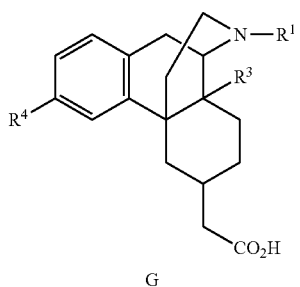

G

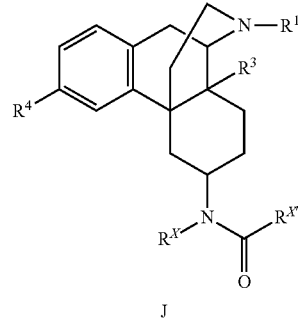

J

Compound A is converted to Compound F by Homer-Wadsworth-Emmons chemistry (e.g. Maryanoff, B. E.; Reitz, A. B. *Chem. Rev.* 1989, 89, 863). Compound F is converted to Compound G by hydrolysis of the ester by treatment with a suitable base such as $NH_3$ in MeOH followed by reduction of the carbon-carbon double bond by hydrogenation in the presence of a suitable catalyst such as Pd/C in a suitable solvent such as MeOH.

Compound I is converted to Compound J by coupling with the appropriate carboxylic acid in the presence of a suitable coupling reagent such as PyBOP in a suitable solvent such as DCM, with or without a base such as DIPEA.

Scheme C

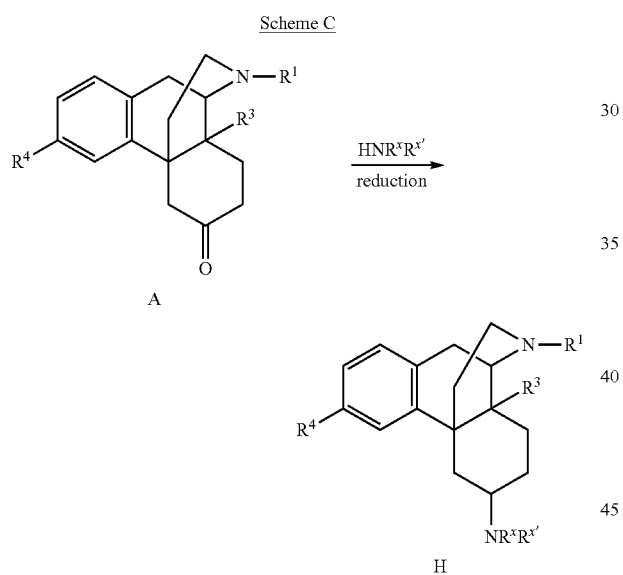

Scheme E

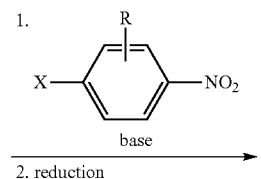

I

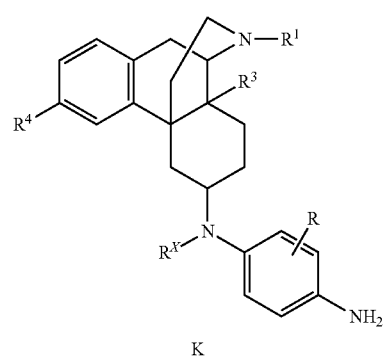

K

Compound A is converted to Compound H by reductive amination using a suitable reducing agent (such as NaBH(OAc)$_3$) in a suitable solvent (such as DCM).

Compound I is converted to Compound K by reaction with a nitroaromatic halide in the presence of a suitable base such as $K_2CO_3$ in a suitable solvent such as ACN followed by reduction of the nitro group by, for example, hydrogenation in the presence of a suitable catalyst such as Pd/C in a suitable solvent such as MeOH.

Scheme D

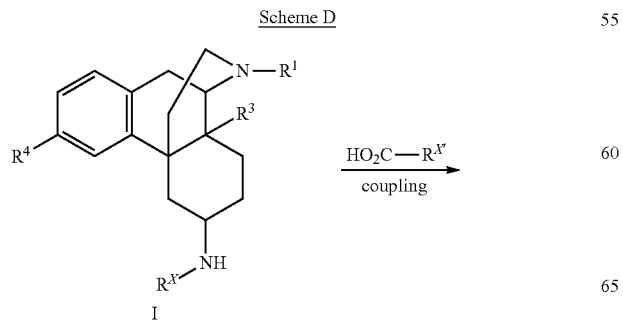

Scheme F

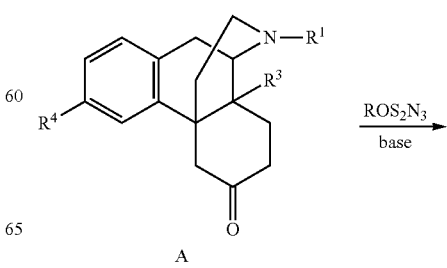

-continued

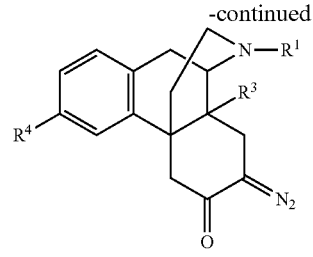

L

1. BnOH, catalyst
2. reduction

Scheme G

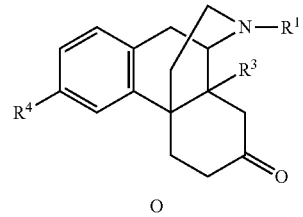

$HNR^XR^{X'}$
reduction

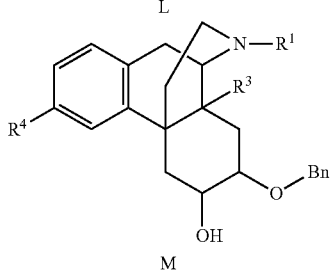

M 1. acylation
2. hydrogenolysis

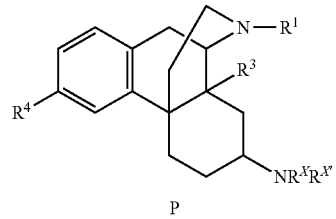

P

Compound O is converted to Compound P by reductive amination using a suitable reducing agent (such as NaBH(OAc)$_3$) in a suitable solvent (such as DCM).

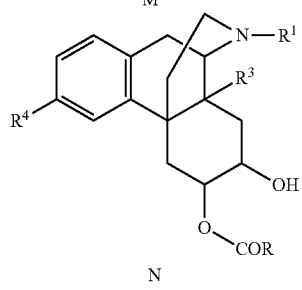

N 1. oxidation
2. reduction

Scheme H

O

Compound A is converted to Compound L by reaction with a suitable sulfonyl azide such as 4-acetamidobenzenesulfonyl azide in the presence of a suitable base such as DBU in a suitable solvent such as ACN. Compound L is converted to Compound M by reaction with benzyl alcohol in the presence of a suitable catalyst such as rhodium acetate dimer in a suitable solvent such as DCE followed by reduction of the ketone by treatment with a suitable reducing agent such as NaBH$_4$ in a suitable solvent such as MeOH or EtOH. Compound M is converted to Compound N by reaction with a suitable acylating agent such as Ac$_2$O in the presence of a suitable base such as pyridine followed by hydrogenolysis of the benzyl ether in the presence of a suitable catalyst such as Pd(OH)$_2$ in a suitable solvent such as AcOH. Compound N is converted to Compound O by oxidation of the alcohol with a suitable oxidizing agent such as Dess-Martin periodane (e.g. Dess, D. B.; Martin, J. C. *J. Org. Chem.* 1983, 48, 4155) in a suitable solvent such as DCM followed by reduction with a suitable reagent such as samarium (II) iodide in a suitable solvent such as THF/MeOH.

Compound L is converted to Compound Q by reaction with the appropriate amide in the presence of a suitable catalyst (such as rhodium acetate dimer) in a suitable solvent (such as DCE). Compound Q is converted to Compound R by reaction with a suitable reducing agent (such as NaBH$_4$) in a suitable solvent (such as MeOH or EtOH).

Scheme I

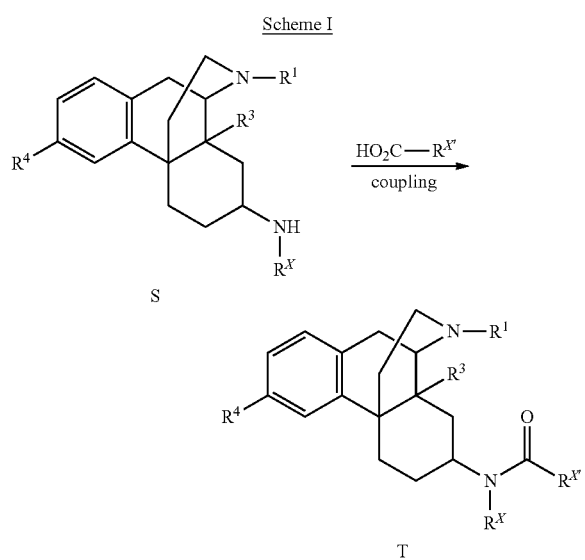

Compound S is converted to Compound T by coupling with the appropriate carboxylic acid in the presence of a suitable coupling reagent (such as PyBOP) in a suitable solvent (such as DCM) with or without a base (such as DIPEA).

Subsequent side chain modifications can be accomplished via appropriate functional group manipulations known to one skilled in the art.

In light of the present disclosure, one of skill in the art would know how to synthesize different stereoisomeric forms (including enantiomers, diastereomers, and other stereoisomeric forms) by using the appropriate reagents and starting materials.

Testing of Compounds

μ-Opioid Receptor Binding Assay Procedures:

Radioligand dose-displacement binding assays for μ-opioid receptors used 0.3 nM [$^3$H]-diprenorphine (Perkin Elmer, Shelton, Conn.), with 5 mg membrane protein/well in a final volume of 500 μl binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 2 hr at room temperature. Binding reactions were terminated by rapid filtration onto 96-well Unifilter GF/C filter plates (Perkin Elmer, Shelton, Conn.), presoaked in 0.5% polyethylenimine using a 96-well tissue harvester (Perkin Elmer, Shelton, Conn.) followed by performing three filtration washes with 500 μl of ice-cold binding buffer. Filter plates were subsequently dried at 50° C. for 2-3 hours. BetaScint scintillation cocktail (Perkin Elmer, Shelton, Conn.) was added (50 μl/well), and plates were counted using a Packard Top-Count for 1 min/well. The data were analyzed using the one-site competition curve fitting functions in GraphPad PRISM™ v. 3.0 or higher (San Diego, Calif.), or an in-house function for one-site competition curve-fitting.

μ-Opioid Receptor Binding Data:

Generally, the lower the Ki value, the more effective the Compounds of the Invention will be at treating or preventing pain or another Condition. Typically, the Compounds of the Invention will have a Ki (nM) of about 1000 or less for binding to μ-opioid receptors. In one embodiment the Compounds of the Invention will have a Ki (nM) of about 300 or less for binding to μ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures:

[$^{35}$S]GTPγS functional assays were conducted using freshly thawed μ-receptor membranes prepared in-house from a cell line expressing recombinant p. opioid receptor in a HEK-293, CHO or U-2 OS cell background, or purchased from a commercial source (Perkin Elmer, Shelton, Conn.; or DiscovRx, Fremont, Calif.). Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; Perkin Elmer, Shelton, Conn.). The prepared membrane solution (190 μl/well) was transferred to 96-shallow well polypropylene plates containing 10 μl of 20× concentrated stock solutions of the agonist [D-Ala$^2$, N-methyl-Phe$^4$ Gly-ol$^5$]-enkephalin (DAMGO) prepared in dimethyl sulfoxide (DMSO). Plates were incubated for 30 min at about 25° C. with shaking. Reactions were terminated by rapid filtration onto 96-well Unifilter GF/B filter plates (Perkin Elmer, Shelton, Conn.) using a 96-well tissue harvester (Perkin Elmer, Shelton, Conn.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Perkin Elmer, Shelton, Conn.) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data:

μ GTP $EC_{50}$ is the concentration of a compound providing 50% of the maximal response for the compound at a μ-opioid receptor. Compounds of the Invention will typically have a μ GTP $EC_{50}$ (nM) of about 5000 or less. In certain embodiments, Compounds of the Invention will have a μ GTP $EC_{50}$ (nM) of about 2000 or less; or about 1000 or less; or about 100 or less; or about 10 or less; or about 1 or less; or about 0.1 or less.

μ GTP $E_{max}$ (%) is the maximal effect elicited by a compound relative to the effect elicited by DAMGO, a standard μ agonist. Generally, the μ GTP $E_{max}$ (%) value measures the efficacy of a compound to treat or prevent pain or other Conditions. Typically, Compounds of the Invention will have a μ GTP $E_{max}$ (%) of greater than about 10%; or greater than about 20%. In certain embodiments, Compounds of the Invention will have a μ GTP $E_{max}$ (%) of greater than about 50%; or greater than about 65%; or greater than about 75%; or greater than about 85%; or greater than about 100%.

κ-Opioid Receptor Binding Assay Procedures:

Membranes from recombinant HEK-293 cells expressing the human κ opioid receptor (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of κ receptor membranes were stored at −80° C.

Radioligand dose displacement assays used 0.4 nM [$^3$H]-U69,593 (GE Healthcare, Piscataway, N.J.; 40 Ci/mmole) with 15 μg membrane protein (recombinant κ opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were terminated by rapid filtration onto 96-well Unifilter GF/C filter plates (Perkin Elmer, Shelton, Conn.) presoaked in 0.5% polyethylenimine (Sigma). Harvesting was performed using a 96-well tissue harvester (Perkin Elmer, Shelton, Conn.) followed by five filtration washes with 200 μl ice-cold binding buffer. Filter plates were subsequently dried at 50° C. for 1-2 hours. Fifty μl/well scintillation cocktail (Perkin Elmer, Shelton, Conn.) was added and plates were counted in a Packard Top-Count for 1 min/well.

κ-Opioid Receptor Binding Data:

In certain embodiments, the Compounds of the Invention will have a Ki (nM) for κ receptors of about 10,000 or more (which, for purposes of this invention, is interpreted as having no binding to the κ receptors). Certain Compounds of the Invention will have a Ki (nM) of about 20,000 or less for κ receptors. In certain embodiments, Compounds of the Invention will have a Ki (nM) of about 10,000 or less; or about 5000 or less; or about 1000 or less; or about 500 or less; or about 450 or less; or about 350 or less; or about 200 or less; or about 100 or less; or about 50 or less; or about 10 or less; or about 1 or less; or about 0.1 or less.

κ-Opioid Receptor Functional Assay Procedures:

Membranes from recombinant HEK-293 cells, CHO or U-2 OS cells expressing the recombinant human κ opioid receptor (κ) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Functional [$^{35}$S]GTPγS binding assays were conducted as follows. κ opioid receptor membrane solution was prepared by sequentially adding final concentrations of 0.026 μg/μl κ membrane protein (in-house), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 mM at a temperature of about 25° C. with shaking. Reactions were terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2-3 hours. Fifty μl/well scintillation cocktail (Perkin Elmer, Shelton, Conn.) was added and plates were counted in a Packard Top-Count for 1 min/well.

κ-Opioid Receptor Functional Data:

κ GTP EC$_{50}$ is the concentration of a compound providing 50% of the maximal response for the compound at a κ receptor. Certain Compounds of the Invention will have a κ GTP EC$_{50}$ (nM) of about 20,000 or less to stimulate κ opioid receptor function. In certain embodiments, Compounds of the Invention will have a κ GTP EC$_{50}$ (nM) of about 10,000 or less; or about 5000 or less; or about 2000 or less; or about 1500 or less; or about 1000 or less; or about 600 or less; or about 100 or less; or about 50 or less; or about 25 or less; or about 10 or less; or about 1 or less; or about 0.1 or less.

κ GTP E$_{max}$ (%) is the maximal effect elicited by a compound relative to the effect elicited by U69,593. Certain Compounds of the Invention will have a κ GTP E$_{max}$ (%) of greater than about 1%; or greater than about 5%; or greater than about 10%; or greater than about 20%. In certain embodiments, Compounds of the Invention will have a κ GTP E$_{max}$ (%) of greater than about 50%; or greater than about 75%; or greater than about 90%; or greater than about 100%.

δ-Opioid Receptor Binding Assay Procedures:

δ-opioid Receptor Binding Assay Procedures can be conducted as follows. Radioligand dose-displacement assays use 0.3 nM [$^3$H]-Naltrindole (Perkin Elmer, Shelton, Conn.; 33.0 Ci/mmole) with 5 μg membrane protein (Perkin Elmer, Shelton, Conn.) in a final volume of 500 μl binding buffer (5 mM MgCl$_2$, 5% DMSO, 50 mM Trizma base, pH 7.4). Non-specific binding is determined in the presence of 25 μM unlabeled naloxone. All reactions are performed in 96-deep well polypropylene plates for 1 hr at a temperature of about 25° C. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by five filtration washes with 500 μl ice-cold binding buffer. Filter plates are subsequently dried at 50° C. for 1-2 hours. Fifty μl/well scintillation cocktail (Perkin Elmer, Shelton, Conn.) is added and plates are counted in a Packard Top-Count for 1 min/well.

δ-Opioid Receptor Binding Data:

In certain embodiments, the Compounds of the Invention will have a Ki (nM) for δ receptors of about 10,000 or more (which, for the purposes of this invention, is interpreted as having no binding to the δ receptors). Certain Compounds of the Invention will have a Ki (nM) of about 20,000 or less for δ receptors. In one embodiment, the Compounds of the Invention will have a Ki (nM) of about 10,000 or less; or of about 9000 or less. In another embodiment, the Compounds of the Invention will have a Ki (nM) of about 7500 or less; or of about 6500 or less; or of about 5000 or less; or of about 3000 or less; or of about 2500 or less. In another embodiment, the Compounds of the Invention will have a Ki (nM) of about 1000 or less; or of about 500 or less; or of about 350 or less; or of about 250 or less; or of about 100 or less; or of about 10 or less.

δ-Opioid Receptor Functional Assay Procedures:

Functional [$^{35}$S]GTPγS binding assays are conducted as follows. δ opioid receptor membrane solution is prepared by sequentially adding final concentrations of 0.026 μg/μl δ membrane protein (Perkin Elmer, Shelton, Conn.), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) is transferred to 96-shallow well polypropylene plates containing 10 μl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates are subsequently dried at 50° C. for 1-2 hours. Fifty μl/well scintillation cocktail (Perkin Elmer, Shelton, Conn.) is added and plates are counted in a Packard Top-count for 1 min/well.

δ-Opioid Receptor Functional Data:

δ GTP $EC_{50}$ is the concentration of a compound providing 50% of the maximal response for the compound at a δ receptor. Certain Compounds of the Invention will have a δ GTP $EC_{50}$ (nM) of about 20,000 or less; or about 10,000 or less. In certain embodiments, the Compounds of the Invention will have a δ GTP $EC_{50}$ (nM) of about 3500 or less; or of about 1000 or less; or of about 500 or less; or of about 100 or less; or of about 90 or less; or of about 50 or less; or of about 25 or less; or of about 10 or less.

δGTP $E_{max}$ (%) is the maximal effect elicited by a compound relative to the effect elicited by met-enkephalin. Certain Compounds of the Invention of the invention will have a δ GTP $E_{max}$ (%) of greater than about 1%; or of greater than about 5%; or of greater than about 10%. In one embodiment, the Compounds of the Invention will have a δ GTP $E_{max}$ (%) of greater than about 30%. In other embodiments, the Compounds of the Invention will have a δ GTP $E_{max}$ (%) of greater than about 50%; or of greater than about 75%; or of greater than about 90%. In another embodiment, the Compounds of the Invention will have a δ GTP $E_{max}$ (%) of about 100% or greater.

ORL-1 Receptor Binding Assay Procedure:

Membranes from recombinant HEK-293 cells expressing the human opioid receptor-like receptor (ORL-1) (Perkin Elmer, Shelton, Conn.) are prepared by lysing cells in ice-cold hypotonic buffer (2.5 mM $MgCl_2$, 50 mM HEPES, pH 7.4) (10 ml/10 cm dish) followed by homogenization with a tissue grinder/Teflon pestle. Membranes are collected by centrifugation at 30,000×g for 15 mM at 4° C. and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Radioligand binding assays (screening and dose-displacement) use 0.1 nM [$^3$H]-nociceptin (Perkin Elmer, Shelton, Conn.; 87.7 Ci/mmole) with 12 μg membrane protein in a final volume of 500 μl binding buffer (10 mM $MgCl_2$, 1 mM EDTA, 5% DMSO, 50 mM HEPES, pH 7.4). Non-specific binding is determined in the presence of 10 nM unlabeled nociceptin (American Peptide Company). All reactions are performed in 96-deep well polypropylene plates for 1 h at room temperature. Binding reactions are terminated by rapid filtration onto 96-well Unifilter GF/C filter plates (Perkin Elmer, Shelton, Conn.) presoaked in 0.5% polyethylenimine (Sigma). Harvesting is performed using a 96-well tissue harvester (Perkin Elmer, Shelton, Conn.) followed by three filtration washes with 500 μl ice-cold binding buffer. Filter plates are subsequently dried at 50° C. for 2-3 hours. Fifty μl/well scintillation cocktail (Perkin Elmer, Shelton, Conn.) is added and plates are counted in a Packard Top-Count for 1 min/well. The data from screening and dose-displacement experiments are analyzed using Microsoft Excel and the curve fitting functions in GraphPad PRISM™, v. 3.0 or higher, respectively, or an in-house function for one-site competition curve-fitting.

ORL-1 Receptor Binding Data:

Certain Compounds of the Invention will have a Ki (nM) of about 1000 or less. In one embodiment, the Compounds of the Invention will have a Ki (nM) of about 500 or less. In other embodiments, the Compounds of the Invention will have a Ki (nM) of about 300 or less; or of about 100 or less; or of about 50 or less; or of about 20 or less. In yet other embodiments, the Compounds of the Invention will have a Ki (nM) of about 10 or less; or of about 1 or less; or of about 0.1 or less.

ORL-1 Receptor Functional Assay Procedure:

Membranes from recombinant HEK-293 cells expressing the human opioid receptor-like (ORL-1) (Perkin Elmer, Shelton, Conn.) are prepared by lysing cells in ice-cold hypotonic buffer (2.5 mM Mg $Cl_2$, 50 mM HEPES, pH 7.4) (10 ml/10 cm dish) followed by homogenization with a tissue grinder/Teflon pestle. Membranes are collected by centrifugation at 30,000×g for 15 min at 4° C., and pellets resuspended in hypotonic buffer to a final concentration of 1-3 mg/ml. Protein concentrations are determined using the BioRad protein assay reagent with bovine serum albumen as standard. Aliquots of the ORL-1 receptor membranes are stored at −80° C.

Functional [$^{35}$S]GTPγS binding assays are conducted as follows. ORL-1 membrane solution is prepared by sequentially adding final concentrations of 0.026 μg/μl ORL-1 membrane protein, 10 μg/ml saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μl/well) is transferred to 96-shallow well polypropylene plates containing 10 μl of 20× concentrated stock solutions of agonist/nociceptin prepared in DMSO. Plates are incubated for 30 min at room temperature with shaking. Reactions are terminated by rapid filtration onto 96-well Unifilter GF/B filter plates (Perkin Elmer, Shelton, Conn.) using a 96-well tissue harvester (Packard) and followed by three filtration washes with 200 μl ice-cold binding buffer (10 mM $NaH_2PO_4$, 10 mM $Na_2HPO_4$, pH 7.4). Filter plates are subsequently dried at 50° C. for 2-3 hours. Fifty μl/well scintillation cocktail (Perkin Elmer, Shelton, Conn.) is added and plates are counted in a Packard Top-Count for 1 min/well. Data are analyzed using the sigmoidal dose-response curve fitting functions in GraphPad PRISM v. 3.0 or higher, or an in-house function for non-linear, sigmoidal dose-response curve-fitting.

ORL-1 Receptor Functional Data:

ORL-1 GTP $EC_{50}$ is the concentration of a compound providing 50% of the maximal response for the compound at an ORL-1 receptor. In certain embodiments, the Compounds of the Invention that have a high binding affinity (i.e. low $K_i$ value) will have an ORL-1 GTP $EC_{50}$ (nM) of greater than about 10,000 (i.e. will not stimulate at therapeutic concentrations) In certain embodiments Compounds of the Invention will have an ORL-1 GTP $EC_{50}$ (nM) of about 20,000 or less. In one embodiment, the Compounds of the Invention will have an ORL-1 GTP $EC_{50}$ (nM) of about 10,000 or less; or of about 5000 or less; or of about 1000 or less. In still other embodiments, the Compounds of the Invention will have an ORL-1 GTP $EC_{50}$ (nM) of about 100 or less; or of about 10 or less; or of about 1 or less; or of about 0.1 or less.

ORL-1 GTP $E_{max}$ % is the maximal effect elicited by a compound relative to the effect elicited by nociceptin, a standard ORL-1 agonist. In certain embodiments, Compounds of the Invention will have an ORL-1 GTP $E_{max}$ of less than 10% (which, for the purposes of this invention, is interpreted as having antagonist activity at ORL-1 receptors). Certain Compounds of the Invention will have an ORL-1 GTP $E_{max}$ (%) of greater than 1%; or of greater than 5%; or of greater than 10%. In other embodiments the Compounds of the Invention will have an ORL-1 GTP $E_{max}$ of greater than 20%; or of greater than 50%; or of greater than 75%; or of greater than 88%; or of greater than 100%.

In Vivo Assays for Prevention or Treatment of Pain

Test Animals:

Each experiment uses rats weighing between 200-260 g at the start of the experiment. The rats are group-housed and have free access to food and water at all times, except prior to oral administration of a Compound of the Invention when food is removed for about 16 hours before dosing. A control group acts as a comparison to rats treated with a Compound of the Invention. The control group is administered the carrier for the Compound of the Invention. The volume of carrier administered to the control group is the same as the volume of carrier and Compound of the Invention administered to the test group.

Acute Pain:

To assess the actions of a Compound of the Invention for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Compound of the Invention. Data are expressed as tail flick latency(s) and the percentage of the maximal possible effect (% MPE), i.e., 20 seconds, is calculated as follows:

$$\% MPE = \frac{[(\text{post administration latency}) - (\text{pre-administration latency})]}{(20\,\text{s} - \text{pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

To assess the actions of a Compound of the Invention for the treatment or prevention of acute pain, the rat hot plate test can also be used. Rats are tested using a hot plate apparatus consisting of a clear plexiglass cylinder with a heated metal floor maintained at a temperature of 48-52° C. (Model 7280, commercially available from Ugo Basile of Italy). A rat is placed into the cylinder on the hot plate apparatus for a maximum duration of 30 s, or until it exhibits a nocifensive behavior (behavioral endpoint), at which time it is removed from the hot plate, and response latency recorded. Hot plate latencies are measured immediately before (pre-treatment) and 1, 3, and 5 hours following administration of a Compound of the Invention. The nocifensive behavioral endpoint is defined as any of the following: 1) paw withdrawal, either as a sustained lift or with shaking or licking; 2) alternating foot lifting; 3) escape or attempted escape from the testing device; or 4) vocalization. Data are expressed as response latency(s) and the percentage of the maximal possible effect is calculated as described above for the tail flick test. The hot plate test is described in G. Woolfe and A. D. Macdonald, *J. Pharmacol. Exp. Ther.* 80:300-307 (1944).

Inflammatory Pain:

To assess the actions of a Compound of the Invention for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of Capsaicin-sensitive Neurones in Hyperalgesia and Enhanced Opioid Antinociception in Inflammation," *Naunyn-Schmiedeberg's Archives of Pharmacol.* 342:666-670 (1990)). The left hind paw of each animal is administered a 50 µL intraplantar injection of 50% FCA. Prior to injection of FCA (baseline) and 24 hours post injection, the animal is assessed for response to noxious mechanical stimuli by determining the PWT, as described below. Rats are then administered a single injection of 1, 3, or 10 mg/kg of either a Compound of the Invention; 30 mg/kg of a control drug selected from Celebrex, indomethacin or naproxen; or carrier. Responses to noxious mechanical stimuli are determined 1, 3, 5 and 24 hours post administration. Percentage reversal of hyperalgesia for each animal is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain:

To assess the actions of a Compound of the Invention for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration. Percentage reversal of neuropathic hyperalgesia is defined as:

$$\% \text{Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia:

The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that is applied to the hind paw is set at 250 g and the end point is taken as complete withdrawal of the paw. PWT is determined once for each rat at each time point and either only the affected (ipsilateral; same side as the injury) rear paw is tested, or both the ipsilateral and contralateral (non-injured; opposite to the injury) rear paw are tested.

Response to Thermal Stimuli as an Assessment of Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia:

To assess tactile allodynia, rats are placed in clear, plexiglass compartments with a wire mesh floor and allowed to habituate for a period of at least 15 minutes. After habituation, a series of von Frey monofilaments are presented to the plantar surface of the affected (ipsilateral) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

Assessment of Respiratory Depression:

To assess respiratory depression, rats can be prepared by implanting a femoral artery cannula via which blood samples are taken. Blood samples are taken prior to drug administration, then 1, 3, 5 and 24 hours post-treatment. Blood samples are processed using an arterial blood gas analyzer (e.g., IDEXX VetStat with Respiratory/Blood Gas test cartridges). Comparable devices are a standard tool for blood gas analysis (e.g., D. Torbati et al., 2000 *Intensive Care Med.* (26) 585-591).

Assessment of Gastric Motility:

Animals are treated with vehicle, reference compound or test article by oral gavage at a volume of 10 mL/kg. At one hour post-dose, all animals are treated with charcoal meal solution (5% non-activated charcoal powder in a solution of 1% carboxymethylcellulose in water) at a volume of 10 mL/kg. At two hours post-dose (one hour post-charcoal), animals are sacrificed by carbon dioxide inhalation or isoflurane overdose and the transit of charcoal meal identified. The stomach and small intestine are removed carefully and each placed on a saline-soaked absorbent surface. The distance between the pylorus and the furthest progression of charcoal meal is measured and compared to the distance between the pylorus and the ileocecal junction. The charcoal meal transit is expressed as a percentage of small intestinal length traveled.

Pharmaceutical Compositions

Due to their activity, the Compounds of the Invention are advantageously useful in human and veterinary medicine. As described above, the Compounds of the Invention are useful for treating or preventing a Condition in an animal (a human patient or non-human subject) in need thereof. The Compounds of the Invention can be administered to any animal requiring modulation of the opioid and/or ORL-1 receptors.

When administered to an animal, a Compound of the Invention can be administered as a component of a pharmaceutical composition that comprises a pharmaceutically acceptable carrier or excipient. A Compound of the Invention can be administered by any appropriate route, as determined by the medical practitioner. Methods of administration may include intradermal, intramuscular, intraperitoneal, parenteral, intravenous, subcutaneous, intranasal, epidural, oral, sublingual, intracerebral, intravaginal, transdermal, transmucosal, rectal, by inhalation, or topical (particularly to the ears, nose, eyes, or skin). Delivery can be either local or systemic. In certain embodiments, administration will result in the release of a Compound of the Invention into the bloodstream.

Pharmaceutical compositions of the invention can take the form of solutions, suspensions, emulsions, tablets, pills, pellets, multi-particulates, capsules, capsules containing liquids, capsules containing powders, capsules containing multi-particulates, lozenges, sustained-release formulations, controlled-release formulations, suppositories, aerosols, sprays, or any other form suitable for use. In one embodiment, the composition is in the form of a capsule (see, e.g., U.S. Pat. No. 5,698,155).

Pharmaceutical compositions of the invention preferably comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Compound of the Invention is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients,* American Pharmaceutical Association (1986). Other examples of suitable pharmaceutical excipients are described in *Remington's Pharmaceutical Sciences* 1447-1676 (Alfonso R. Gennaro ed., 19th ed. 1995), incorporated herein by reference.

In certain embodiments, the Compounds of the Invention are formulated for oral administration. A Compound of the Invention to be orally delivered can be in the form of tablets, capsules, gelcaps, caplets, lozenges, aqueous or oily solutions, suspensions, granules, powders, emulsions, syrups, or elixirs, for example. When a Compound of the Invention is incorporated into oral tablets, such tablets can be compressed, tablet triturates, enteric-coated, sugar-coated, film-coated, multiply compressed or multiply layered.

An orally administered Compound of the Invention can contain one or more additional agents such as, for example, sweetening agents such as fructose, aspartame or saccharin; flavoring agents such as peppermint, oil of wintergreen, or cherry; coloring agents; and preserving agents, and stabilizers, to provide stable, pharmaceutically palatable dosage forms. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16th ed., Mack Publishing, Easton, Pa. 1980). Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and compositions for making liquid oral dosage forms are described in *Pharmaceutical Dosage Forms: Disperse Systems,* (Lieberman, Rieger and Banker, eds.) published by Marcel Dekker, Inc.

When a Compound of the Invention is formulated for parenteral administration by injection (e.g., continuous infusion or bolus injection), the formulation can be in the form of a suspension, solution, or emulsion in an oily or aqueous vehicle, and such formulations can further comprise pharmaceutically necessary additives such as one or more stabilizing agents, suspending agents, dispersing agents, and the like. When a Compound of the Invention is to be injected parenterally, it can be, e.g., in the form of an isotonic sterile solution. A Compound of the Invention can also be in the form of a powder for reconstitution as an injectable formulation.

In certain embodiments, a Compound of the Invention is formulated into a pharmaceutical composition for intravenous administration. Typically, such compositions comprise sterile isotonic aqueous buffer. Where necessary, the compositions can also include a solubilizing agent. A Compound of the Invention for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Compound of the Invention is to be administered by infusion, it can be dispensed, for example, with an infusion bottle containing sterile pharmaceutical grade water or saline. Where a Compound of the Invention is administered by injection, an ampule of sterile water for injection or saline can be provided so that the ingredients can be mixed prior to administration.

When a Compound of the Invention is to be administered by inhalation, it can be formulated into a dry aerosol, or an aqueous or partially aqueous solution.

In another embodiment, a Compound of the Invention can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In certain embodiments, a Compound of the Invention is administered locally. This can be achieved, for example, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, a Compound of the Invention can be delivered in an immediate release form. In other embodiments, a Compound of the Invention can be delivered in a controlled-release system or sustained-release system. Controlled- or sustained-release pharmaceutical compositions can have a common goal of improving drug therapy over the results achieved by their non-controlled or non-sustained-release counterparts. In one embodiment, a controlled- or sustained-release composition comprises a minimal amount of a Compound of the Invention to treat or prevent the Condition (or a symptom thereof) in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Compound of the Invention, and can thus reduce the occurrence of adverse side effects.

Controlled- or sustained-release compositions can initially release an amount of a Compound of the Invention that promptly produces the desired therapeutic or prophylactic effect, and gradually and continually release other amounts of the Compound of the Invention to maintain a level of therapeutic or prophylactic effect over an extended period of time. To maintain a constant level of the Compound of the Invention in the body, the Compound of the Invention can be released from the dosage form at a rate that will replace the amount of Compound of the Invention being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release means for use according to the present invention may be selected from those known in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in *Medical Applications of Controlled Release, Vol. 2, Applications and Evaluation,* R. S. Langer and D. L. Wise eds., CRC Press (1984). Other controlled- or sustained-release systems that are discussed in the review by Langer, *Science* 249:1527-1533 (1990) can be selected for use according to the present invention. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Compound of the Invention, e.g., the spinal column, brain, or gastrointestinal tract, thus requiring only a fraction of the systemic dose.

When in tablet or pill form, a pharmaceutical composition of the invention can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

Pharmaceutical compositions of the invention include single unit dosage forms suitable for oral administration such as, but not limited to, tablets, capsules, gelcaps, and caplets that are adapted for controlled- or sustained-release.

The amount of the Compound of the Invention that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the extent of the Condition to be treated, and can be decided according to the judgment of a practitioner and/or each animal's circumstances. Variations in dosing may occur depending upon typical factors such as the weight, age, gender and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts can range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Compound of the Invention, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the Condition is abated. In another embodiment, an effective dosage amount is administered about every 12 h until the Condition is abated. In another embodiment, an effective dosage amount is administered about every 8 h until the Condition is abated. In another embodiment, an effective dosage amount is administered about every 6 h until the Condition is abated. In another embodiment, an effective dosage amount is administered about every 4 h until the Condition is abated. The effective dosage amounts described herein refer to total amounts administered; that is, if more than one Compound of the Invention is administered, the effective dosage amounts correspond to the total amount administered.

Where a cell capable of expressing the ORL-1 receptor is contacted with a Compound of the Invention in vitro, the amount effective for inhibiting or activating the ORL-1 receptor function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the compound in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the n-opioid receptors is contacted with a Compound of the Invention in vitro, the amount effective for inhibiting or activating the µ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the δ-opioid receptors is contacted with a Compound of the Invention in vitro, the amount effective for inhibiting or activating the δ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

Where a cell capable of expressing the κ-opioid receptors is contacted with a Compound of the Invention in vitro, the amount effective for inhibiting or activating the κ-opioid receptors function in a cell will typically range from about $10^{-12}$ mol/L to about $10^{-4}$ mol/L, or from about $10^{-12}$ mol/L to about $10^{-5}$ mol/L, or from about $10^{-12}$ mol/L to about $10^{-6}$ mol/L, or from about $10^{-12}$ mol/L to about $10^{-9}$ mol/L of a solution or suspension of the Compound of the Invention in a pharmaceutically acceptable carrier or excipient. In one embodiment, the volume of solution or suspension comprising the Compound of the Invention will be from about 0.01 µL to about 1 mL. In another embodiment, the volume of solution or suspension will be about 200 µL.

The Compounds of the Invention can be assayed in vitro or in vivo for the desired therapeutic or prophylactic activity prior to use in humans. Animal model systems can be used to demonstrate safety and efficacy. Certain Compounds of the Invention will have an $ED_{50}$ for treating inflammatory pain ranging from about 0.5 mg/kg to about 20 mg/kg. Certain Compounds of the Invention will produce significant analgesia and/or anti-hyperalgesia at doses that do not induce respiratory depression. In contrast, oxygen tension, oxygen saturation and pH are significantly decreased, while carbon dioxide is significantly increased, in blood samples from rats given effective doses of conventional opioids, such as morphine.

According to the invention, methods for treating or preventing a Condition in an animal in need thereof can further comprise co-administering to the animal an effective amount of a second therapeutic agent in addition to a Compound of the Invention (i.e., a first therapeutic agent). An effective amount of the second therapeutic agent will be known or determinable by a medical practitioner in view of this disclosure and published clinical studies. In one embodiment of the invention, where a second therapeutic agent is administered to an animal for treatment of a Condition (e.g., pain), the minimal effective amount of the Compound of the Invention (i.e., the first therapeutic agent) will be less than its minimal effective amount would be in circumstances where the second therapeutic agent is not administered. In this embodiment, the Compound of the Invention and the second therapeutic agent can act either additively or synergistically to treat or prevent a Condition. Alternatively, the second therapeutic agent may be used to treat or prevent a disorder that is different from the Condition for which the first therapeutic agent is being administered, and which disorder may or may not be a Condition as defined hereinabove. In one embodiment, a Compound of the Invention is administered concurrently with a second therapeutic agent as a single composition comprising an effective amount of a Compound of the Invention and an effective amount of the second therapeutic agent. Alternatively, a composition comprising an effective amount of a Compound of the Invention and a second composition comprising an effective amount of the second therapeutic agent are concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for treating, preventing or inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Inset, *Analgesic-Antipyretic and Anti-inflammatory Agents and Drugs Employed in the Treatment of Gout*, in *Goodman & Gilman's The Pharmacological Basis of Therapeutics* 617-57 (Perry B. Molinhoff and Raymond W. Ruddon eds., 9$^{th}$ ed 1996); and Glen R. Hanson, *Analgesic, Antipyretic and Anti-Inflammatory Drugs in Remington: The Science and Practice of Pharmacy* Vol IA 1196-1221 (A. R. Gennaro ed. 19$^{th}$ ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethyl-barbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Compound of the Invention (or a pharmaceutically acceptable salt, prodrug or solvate thereof) with a pharmaceutically acceptable carrier or excipient. Admixing can be accomplished using methods known for admixing a compound (or derivative) and a pharmaceutically acceptable carrier or excipient. In one embodiment, the Compound of the Invention (or pharmaceutically acceptable salt, prodrug or solvate thereof) is present in the composition in an effective amount.

EXAMPLES

Example 1

(4bR,6R,7S,8aS,9R)-11-(cyclopropylmethyl)-3-methoxy-7-methyl-5,6,7,8,9,10-hexahydro-8aH-9,4b-(epiminoethano)phenanthrene-6,8a-diol (Compound 3)

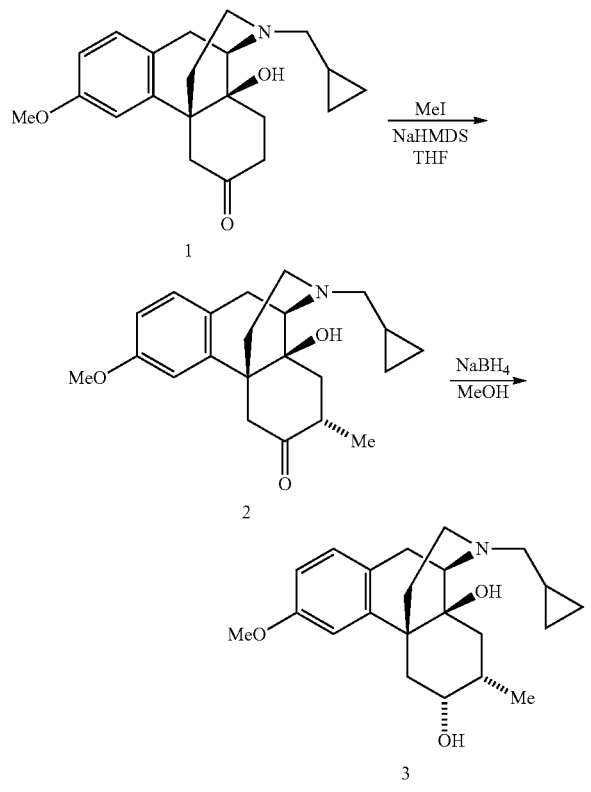

To a −78° C. solution of 1.0M NaHMDS in THF (1.2 mL, 1.21 mmol) in anhydrous THF (4.3 mL) was added a solution of Compound 1 (0.180 g, 0.527 mmol) in THF (1 mL) dropwise via syringe. The light yellow solution was maintained at −78° C. for 1 h whereupon methyl iodide (0.050 mL, 0.791 mmol) was added dropwise. The reaction mixture was allowed to warm to RT overnight. The reaction was quenched with satd. aq. NaHCO$_3$ and diluted with DCM. The layers were separated and the aqueous layer extracted with DCM. The combined organic extracts were washed with brine, dried over Na$_2$SO$_4$, filtered, and concentrated. Purification of the residue by flash chromatography (SiO$_2$, 0-15% acetone/hexanes) gave 40 mg (21%) of Compound 2 as a clear oil: LC/MS, m/z=356.4 [M+H]$^+$ (Calc: 355.5).

To a 0° C. solution of Compound 2 (0.040 g, 0.113 mmol) in MeOH (1.5 mL) was added NaBH$_4$ (10 mg, 0.270 mmol) in one portion. The reaction mixture was allowed to warm to RT and stirred for 1 h. The reaction was quenched with H$_2$O and diluted with DCM. The layers were separated and the aqueous layer extracted with DCM. The combined organic extracts were washed with brine, dried over Na$_2$SO$_4$, filtered, and concentrated. Purification of the residue by prep HPLC (C18, 0-60% 0.1% TFA in ACN/0.1% TFA in water) gave 25 mg (62%) of Compound 3 as a white solid (after neutralization with ammonium carbonate resin and lyophilization): $^1$H NMR (400 MHz, CD$_3$OD): δ 7.05-6.95 (m, 2H), 6.70 (dd, 1H), 3.85 (d, 1H), 3.75 (s, 3H), 3.07 (m, 2H), 3.00-2.80 (brm, 1H), 2.70-2.58 (brm, 2H), 2.53 (dd, 1H), 2.49-2.35 (brm, 1H), 2.30-2.15 (m, 1H), 2.10-1.95 (m, 3H), 1.67 (app t, 1H), 1.21 (dd, 1H), 1.11 (d, 1H), 1.00-0.87 (m, 1H), 0.86 (d, 3H), 0.65-0.45 (m, 2H), 0.27-0.10 (m, 2H). LC/MS, m/z=358.2 [M+H]$^+$ (Calc: 357.5).

In a similar manner the following compounds were prepared:

(4bR,6S,8aS,9R)-11-(cyclopropylmethyl)-3-methoxy-5,6,7,8,9,10-hexahydro-8aH-9,4b-(epiminoethano)phenanthrene-6,8a-diol (Compound 4): $^1$H NMR (400 MHz, CD$_3$OD): δ 7.00 (d, J=8.3 Hz, 1H), 6.96 (d, J=2.6 Hz, 1H), 6.69 (dd, J=8.6, 2.6 Hz, 1H), 4.01 (t, J=2.6 Hz, 1H), 3.68 (s, 3H), 3.65-3.68 (m, 1H), 3.16-3.19 (m, 3H), 2.87 (dd, J=12.5, 4.2 Hz, 1H), 2.73 (dd, J=13.6, 7.7 Hz, 1H), 2.39-2.50 (m, 2H), 2.30 (td, J=13.4, 4.5 Hz, 1H), 2.00-2.10 (m, 1H), 1.91-2.00 (m, 2H), 1.45-1.52 (m, 1H), 1.30-1.38 (m, 1H), 1.13-1.20 (m, 1H), 0.94-1.06 (m, 1H), 0.67-0.76 (m, 1H), 0.59-0.67 (m, 1H), 0.34-0.46 (m, 2H). LC/MS, m/z=344.4 [M+H]$^+$ (Calc: 343.5).

Example 2

(4bR,6R,7R,8aS,9R)-11-(cyclopropylmethyl)-7-(hydroxymethyl)-3-methoxy-5,6,7,8,9,10-hexahydro-8aH-9,4b-(epiminoethano)phenanthrene-6,8a-diol (Compound 7)

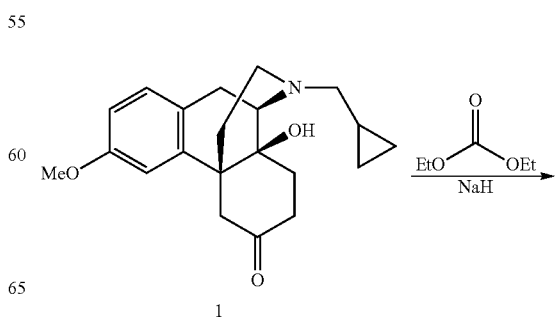

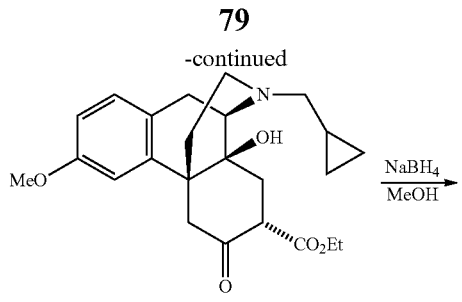

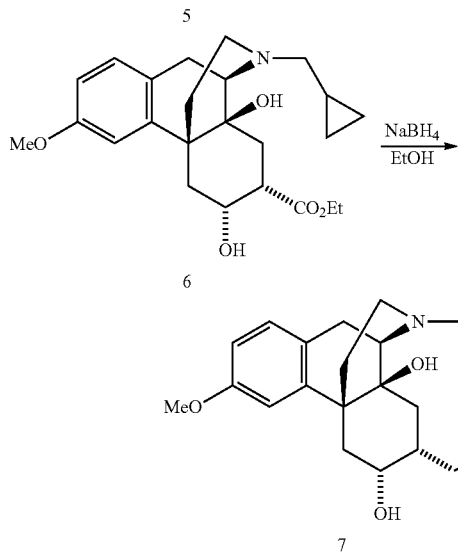

To a suspension of 60% NaH in mineral oil (0.246 g, 10.3 mmol) in diethyl carbonate (7 mL) was added a solution of Compound 1 (1.4 g, 4.10 mmol) in diethyl carbonate (7 mL) dropwise via syringe. The resulting mixture was heated to 90° C. for 0.5 h. The reaction mixture was cooled to 0° C. and treated with H₂O dropwise. The mixture was basified with conc. NH₄OH and extracted (3×) with DCM. The combined organic extracts were washed with brine, dried over Na₂SO₄, filtered, and concentrated. Purification of the residue by flash chromatography (SiO₂, 0-15% acetone/hexanes) gave 625 mg (37%) of Compound 5 as a white foam: LC/MS, m/z=414.3 [M+H]$^+$ (Calc: 413.5).

To a 0° C. solution of Compound 5 (0.190 g, 0.459 mmol) in MeOH (6 mL) was added NaBH₄ (37 mg, 0.965 mmol). The reaction mixture was warmed to RT and stirred for 1 h. The reaction was quenched with satd. aq. NaHCO₃ and extracted with DCM (3×). The combined organic extracts were washed with brine, dried over Na₂SO₄, filtered, and concentrated. Purification of the residue by flash chromatography (SiO₂, 0-1% MeOH/DCM) gave 81 mg (42%) of Compound 6 as white foam: LC/MS, m/z=416.2 [M+H]$^+$ (Calc: 415.5).

To a 0° C. solution of Compound 6 (0.064 g, 0.154 mmol) in EtOH (1.5 mL) was added NaBH₄ (0.035 g, 0.924 mmol) in one portion. The reaction mixture was warmed to RT, stirred for 18 h and heated to 50° C. for 24 h. The reaction was quenched with H₂O at 0° C. and diluted with DCM. The layers were separated and aqueous extracted with DCM (2×). The combined organic extracts were washed with brine, dried over Na₂SO₄, filtered, and concentrated. Purification of the residue by prep HPLC (C18, 0-40% 0.1% TFA in ACN/0.1% TFA in water) gave 26 mg (45%) of Compound 7 as a fluffy, white solid (after neutralization with ammonium carbonate resin and lyophilization): $^1$H NMR (400 MHz, CD₃OD): δ 7.05-6.90 (m, 2H), 6.69 (dd, 1H), 4.15-4.10 (m, 1H), 3.75 (s, 3H), 3.51 (dd, 1H), 3.39 (dd, 1H), 3.08 (m, 2H), 3.00-2.85 (brm, 1H), 2.70-2.55 (brm, 2H), 2.53 (dd, 1H), 2.49-2.35 (brm, 1H), 2.30-2.15 (m, 1H), 2.10-1.95 (m, 3H), 1.71 (app t, 1H), 1.31 (dd, 1H), 1.11 (d, 1H), 0.95-0.80 (m, 1H), 0.60-0.49 (m, 2H), 0.25-0.10 (m, 2H). LC/MS, m/z=374.1 [M+H]$^+$ (Calc: 373.5).

Example 3

2-((4bS,6R,8aS,9R)-11-(cyclopropylmethyl)-8a-hydroxy-3-methoxy-6,7,8,8a,9,10-hexahydro-5H-9,4b-(epiminoethano)phenanthren-6-yl)acetic Acid (Compound 9)

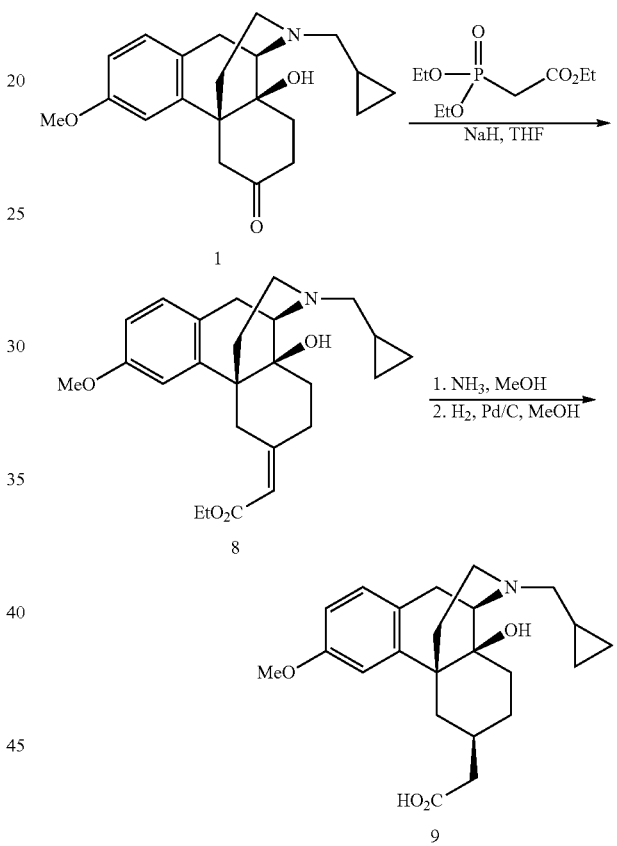

To a 0° C. suspension of 60% NaH in mineral oil (0.181 g, 4.53 mmol) in THF (10 mL) was added triethyl phosphonoacetate (0.88 mL, 4.44 mol). The mixture was stirred at 0° C. for 10 min and for 25 min at RT. A mixture of Compound 1 (0.503 g, 1.47 mmol) in THF (5 mL) was added and the mixture was heated at reflux overnight. After cooling, the reaction mixture was quenched with satd. aq. NH₄Cl solution (2 mL) then diluted with 25 mL water and 2 mL conc. NH₄OH and extracted with DCM. The organic extracts were washed with brine, dried over MgSO₄, filtered and concentrated. Purification of the residue by flash chromatography (SiO₂, 0-50% acetone/hexanes) gave 0.375 g (62%) of Compound 8 as a pale yellow oil: LC/MS, m/z=412.4 [M+H]$^+$ (Calc: 411.5).

A mixture of Compound 8 (0.371 g, 0.902 mmol) in 7M NH₃ in MeOH (10 mL) was sealed in a pressure reaction tube and stirred at RT overnight then at 50° C. for 12 days.

5N aq. NaOH (2 mL) was added and the mixture heated again at 50° C. overnight. After cooling the mixture was concentrated, dissolved in MeOH (50 mL). 10% Pd/C (0.265 g) was added and the mixture hydrogenated at 50 psi for 3 days. 1N aq. HCl (25 mL), conc. HCl (3 mL) and fresh 10% Pd/C (0.508 g) were added and the hydrogenation was continued for 7 more days. The reaction mixture was filtered through Celite and the filtrate concentrated. The residue was taken up in MeOH, filtered and concentrated. The residue was taken up in ACN, filtered and concentrated. Purification of the residue by prep HPLC (C18, 0-40% 0.1% TFA in ACN/0.1% TFA in water) gave 0.044 g (98%) of Compound 9 TFA salt as a white powder.

Compound 9 TFA salt: $^1$H NMR (400 MHz, CD$_3$OD): δ 7.14 (d, J=8.5 Hz, 1H), 7.00 (d, J=2.2 Hz, 1H), 6.82 (dd, J=8.6, 2.4 Hz, 1H), 3.83-3.76 (m, 4H), 3.36-3.18 (m, 3H, overlap with MeOH), 3.00 (dd, J=12.5, 4.4 Hz, 1H), 2.87 (dd, J=13.5, 7.3 Hz, 1H), 2.66 (td, J=13.1, 3.4 Hz, 1H), 2.40 (td, J=13.5, 4.9 Hz, 1H), 2.33-2.14 (m, 3H), 1.99-1.84 (m, 1H), 1.78-1.47 (m, 5H), 1.31-1.22 (m, 1H), 1.15-1.04 (m, 1H), 0.86-0.78 (m, 1H), 0.77-0.67 (m, 1H), 0.55-0.42 (m, 2H). LC/MS, m/z=386.2 [M+H]$^+$ (Calc: 385.5).

Example 4

(4bR,6S,8aS,9R)-11-(cyclopropylmethyl)-6-(dimethylamino)-5,6,7,8,9,10-hexahydro-8aH-9,4b-(epiminoethano)phenanthrene-3,8a-diol (Compound 10)

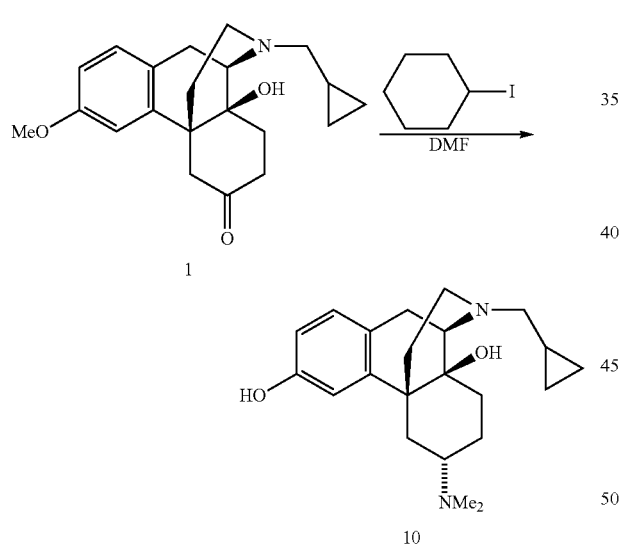

A mixture of Compound 1 (as the HCl salt) (0.501 g, 1.33 mmol) in DMF (3 mL) and iodocyclohexane (0.90 mL, 6.96 mmol, 5 eq) was heated at reflux for 3.5 h. Additional iodocyclohexane (0.45 mL, 3.48 mmol, 2.5 eq) was added and refluxing continued overnight. After cooling, the reaction mixture was concentrated and the residue diluted with 25 mL 2N aq. HCl and washed twice with DCM. The aqueous layer was basified with 5 mL conc. NH$_4$OH and extracted twice with DCM. The organic extracts were concentrated and the residue purified by flash chromatography (SiO$_2$, 0-50% (10% NH$_4$OH in MeOH) in DCM) followed by trituration with 2 mL of MeOH to give 0.104 g (22%) of Compound 10 as a tan powder: $^1$H NMR (400 MHz, DMSO-d$_6$): δ 9.05 (s, 1H), 6.88 (d, J=8.1 Hz, 1H), 6.65 (d, J=2.4 Hz, 1H), 6.51 (dd, J=8.1, 2.4 Hz, 1H), 4.33 (s, 1H), 2.92 (d, J=18.0 Hz, 1H), 2.84 (d, J=5.7 Hz, 1H), 2.61 (dd, J=18.2, 6.1 Hz, 1H), 2.55-2.43 (m, 1H, overlap with DMSO), 2.38-2.25 (m, 2H), 2.25-2.12 (m, 7H), 2.02-1.86 (m, 3H), 1.78-1.58 (m, 2H), 1.48-1.27 (m, 3H), 0.97-0.87 (m, 1H), 0.87-0.76 (m, 1H), 0.50-0.39 (m, 2H), 0.14-0.03 (m, 2H). LC/MS, m/z=357.3 [M+H]$^+$ (Calc: 356.5).

Example 5

(4bR,6R,8aS,9R)-6-((2-aminoethyl)amino)-11-(cyclopropylmethyl)-5,6,7,8,9,10-hexahydro-8aH-9,4b-(epiminoethano)phenanthrene-3,8a-diol TFA salt (Compound 11) and 1-(2-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)ethyl)guanidine Tris-TFA Salt (Compound 12)

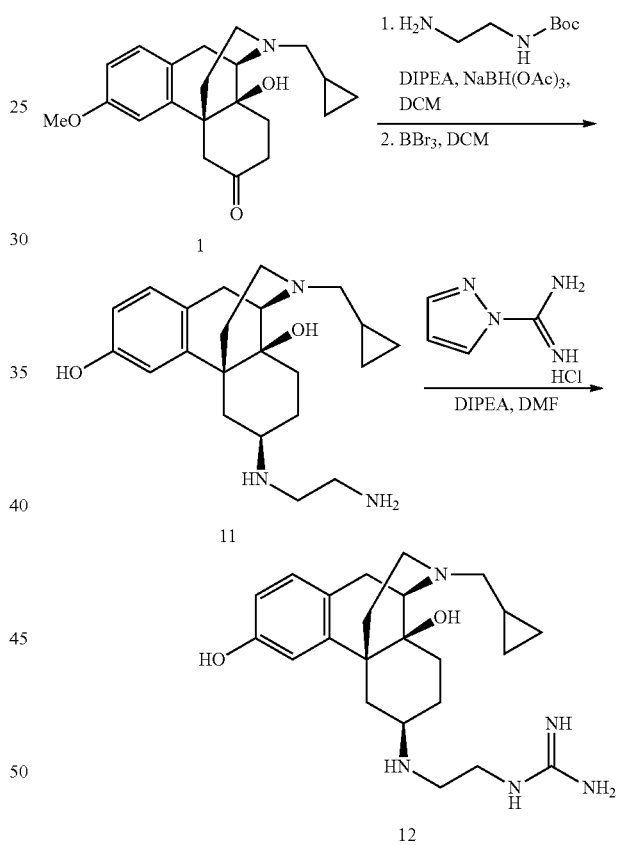

DIPEA (0.52 mL, 3 mmol) was added to a solution of Compound 1 (378 mg, 1 mmol) and tert-butyl N-(2-aminoethyl)carbamate (0.19 mL, 1.2 mmol) in DCE (5 mL) and the solution was stirred at RT for 15 min NaBH(OAc)$_3$ (318 mg, 1.5 mmol) was added and the solution was stirred at RT for 20 h, quenched with MeOH, and concentrated. Purification by MPLC (SiO$_2$, 0-20% MeOH/DCM) gave the desired intermediate. This material was dissolved in DCM (10 mL) followed by BBr$_3$ (1M in DCM, 8 mL, 8 mmol) at 0° C. The reaction mixture was allowed to warm to RT over 4 h, quenched with MeOH, concentrated, and purified by MPLC (SiO$_2$, 0-20% (10% NH$_4$OH in MeOH) in DCM) followed by further purification by preparatory HPLC (C18, 0-40% 0.1% TFA in ACN/0.1% TFA in water) to give Compound 11 as its TFA salt: $^1$H NMR (600 MHz, CD$_3$OD): δ 7.19 (d, J=8.4 Hz, 1H), 7.01 (s, 1H), 6.84 (d, J=8.4 Hz, 1H), 5.52 (s, 1H), 3.87 (br. s., 1H), 3.63 (br. s., 1H), 3.49-3.35 (m, 4H), 3.24-3.14 (m, 2H), 3.06 (dd, J=12.4, 3.2 Hz, 1H), 2.90 (dd, J=13.6, 7.5 Hz, 1H), 2.73 (d, J=15.8 Hz, 1H), 2.65-2.54 (m, 1H), 2.50-2.33 (m, 3H), 2.12-2.02 (m, 1H), 1.89 (d, J=15.6 Hz, 1H), 1.68 (d, J=14.7 Hz, 1H), 1.38 (d, J=12.8 Hz, 1H), 1.17-1.09 (m, 1H), 0.89-0.83 (m, 1H), 0.79-0.74 (m, 1H), 0.58-0.47 (m, 2H). LC/MS, m/z=372 [M+H]$^+$ (Calc: 371).

DIPEA (0.155 mL, 0.89 mmol) was added to a solution of Compound 11 (110 mg, 0.30 mmol) and 1H-pyrazole-1-carboxamidine hydrochloride (52 mg, 0.36 mmol) in DMF (1.5 mL). The reaction mixture was stirred at 80° C. for 65 h, concentrated, and triturated with DCM. The resulting solid was purified by preparatory HPLC (C18, 0-40% 0.1% TFA in ACN/0.1% TFA in water) to give Compound 12 as its tris-TFA salt: $^1$H NMR (400 MHz, CD$_3$OD): δ 7.17 (d, J=8.4 Hz, 1H), 7.01 (d, J=1.8 Hz, 1H), 6.82 (dd, J=8.3, 1.9 Hz, 1H), 3.87 (br. s., 1H), 3.67 (br. s., 1H), 3.46-3.58 (m, 2H), 3.28-3.41 (m, 5H), 3.06 (dd, J=12.6, 3.7 Hz, 1H), 2.89 (dd, J=13.5, 7.6 Hz, 1H), 2.78 (d, J=16.0 Hz, 1H), 2.58 (td, J=13.0, 3.1 Hz, 1H), 2.35-2.50 (m, 3H), 2.15 (td, J=14.1, 4.0 Hz, 1H), 1.94 (d, J=15.2 Hz, 1H), 1.68 (d, J=14.5 Hz, 1H), 1.34-1.42 (m, 1H), 1.09-1.17 (m, 1H), 0.82-0.88 (m, 1H), 0.73-0.80 (m, 1H), 0.48-0.57 (m, 2H). LC/MS, m/z=414 [M+H]$^+$ (Calc: 413).

In a similar manner, the following compounds were prepared:

(4bR,6R,8aS,9R)-6-((3-aminopropyl)amino)-11-(cyclopropylmethyl)-5,6,7,8,9,10-hexahydro-8aH-9,4b-(epiminoethano)phenanthrene-3,8a-diol TFA salt (Compound 13) $^1$H NMR (600 MHz, CD$_3$OD): δ 7.21 (d, J=8.4 Hz, 1H), 7.03 (d, J=1.8 Hz, 1H), 6.86 (dd, J=8.3, 1.7 Hz, 1H), 5.52 (s, 1H), 3.88 (br. s., 1H), 3.63 (br. s., 1H), 3.39-3.35 (m, 3H), 3.31-3.24 (m, 1H), 3.20-3.12 (m, 1H), 3.10-3.01 (m, 3H), 2.90 (dd, J=13.7, 7.6 Hz, 1H), 2.75 (d, J=16.1 Hz, 1H), 2.63-2.55 (m, 1H), 2.50-2.37 (m, 3H), 2.10-1.93 (m, 3H), 1.89 (d, J=15.6 Hz, 1H), 1.69 (d, J=14.7 Hz, 1H), 1.42-1.36 (m, 1H), 1.18-1.08 (m, 1H), 0.89-0.81 (m, 1H), 0.81-0.74 (m, 1H), 0.58-0.48 (m, 2H). LC/MS, m/z=386 [M+H]$^+$ (Calc: 385).

(4bR,6R,8aS,9R)-6-((4-aminobutyl)amino)-11-(cyclopropylmethyl)-5,6,7,8,9,10-hexahydro-8aH-9,4b-(epiminoethano)phenanthrene-3,8a-diol TFA salt (Compound 14): $^1$H NMR (600 MHz, CD$_3$OD): δ 7.21 (d, J=8.4 Hz, 1H), 7.02 (d, J=1.8 Hz, 1H), 6.86 (dd, J=8.4, 1.8 Hz, 1H), 5.52 (s, 1H), 3.88 (br. s., 1H), 3.61 (br. s., 1H), 3.35 (br. s., 3H), 3.26 (td, J=11.6, 5.5 Hz, 1H), 3.10-3.03 (m, 2H), 3.00 (t, J=7.8 Hz, 2H), 2.90 (dd, J=13.6, 7.7 Hz, 1H), 2.78 (d, J=16.0 Hz, 1H), 2.58 (td, J=13.0, 3.3 Hz, 1H), 2.50-2.39 (m, 2H), 2.37 (dd, J=16.2, 5.0 Hz, 1H), 2.03 (td, J=14.1, 3.8 Hz, 1H), 1.88 (d, J=15.2 Hz, 1H), 1.82-1.72 (m, 2H), 1.72-1.59 (m, 3H), 1.39 (d, J=12.1 Hz, 1H), 1.16-1.09 (m, 1H), 0.89-0.82 (m, 1H), 0.81-0.74 (m, 1H), 0.58-0.49 (m, 2H). LC/MS, m/z=400 [M+H]$^+$ (Calc: 399).

1-(3-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)propyl)guanidine tris-TFA salt (Compound 15): $^1$H NMR (400 MHz, CD$_3$OD): δ 7.21 (d, J=8.4 Hz, 1H), 7.03 (s, 1H), 6.85 (dd, J=8.4, 2.3 Hz, 1H), 3.88 (br. s., 1H), 3.62 (br. s., 1H), 3.28-3.40 (m, 4H), 3.20-3.27 (m, 1H), 3.09-3.16 (m, 1H), 3.07 (dd, J=12.6, 3.6 Hz, 1H), 2.90 (dd, J=13.6, 7.5 Hz, 1H), 2.75 (d, J=16.0 Hz, 1H), 2.58 (td, J=13.0, 3.1 Hz, 1H), 2.34-2.50 (m, 3H), 1.99-2.08 (m, 1H), 1.82-1.93 (m, 3H), 1.69 (d, J=14.4 Hz, 1H), 1.38 (d, J=13.4 Hz, 1H), 1.08-1.17 (m, 1H), 0.82-0.89 (m, 1H), 0.74-0.81 (m, 1H), 0.48-0.58 (m, 2H). LC/MS, m/z=428 [M+H]$^+$ (Calc: 427).

1-(4-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)butyl)guanidine tris-TFA salt (Compound 16): $^1$H NMR (400 MHz, CD$_3$OD): δ 7.21 (d, J=8.4 Hz, 1H), 7.02 (s, 1H), 6.85 (dd, J=8.3, 2.2 Hz, 1H), 3.87 (br. s., 1H), 3.61 (br. s., 1H), 3.37 (d, J=7.3 Hz, 1H), 3.18-3.27 (m, 3H), 3.07 (d, J=9.7 Hz, 2H), 2.90 (dd, J=13.7, 7.6 Hz, 1H), 2.76 (d, J=16.0 Hz, 1H), 2.58 (td, J=13.0, 3.1 Hz, 1H), 2.34-2.50 (m, 3H), 2.03 (td, J=14.3, 4.1 Hz, 1H), 1.88 (d, J=15.0 Hz, 1H), 1.57-1.73 (m, 5H), 1.39 (d, J=13.7 Hz, 1H), 1.08-1.16 (m, 1H), 0.82-0.89 (m, 1H), 0.74-0.80 (m, 1H), 0.47-0.57 (m, 2H). LC/MS, m/z=442 [M+H]$^+$ (Calc: 441).

Example 6

N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-2-guanidinoacetamide Tris-TFA Salt (Compound 20)

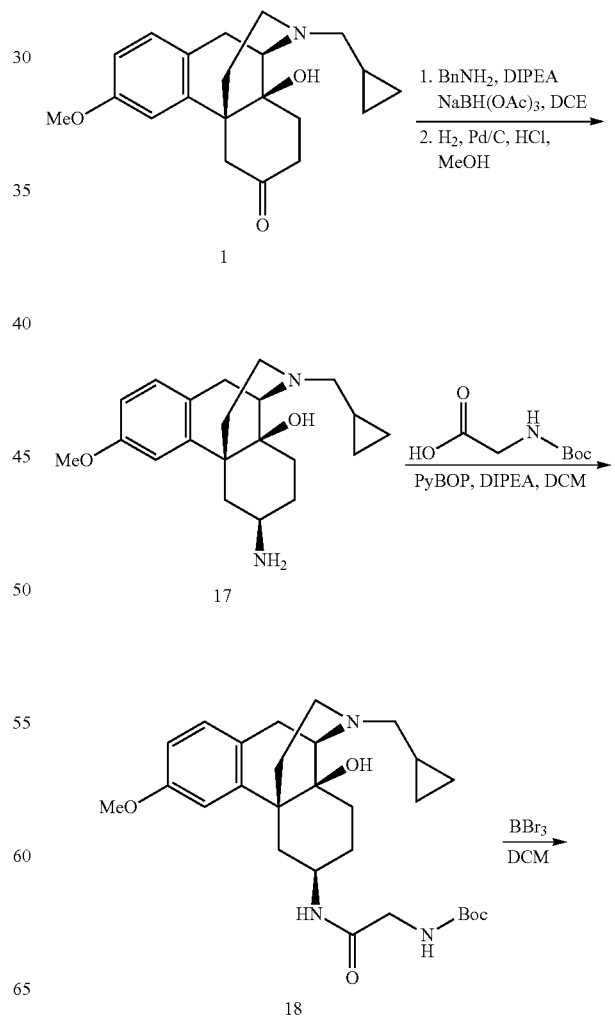

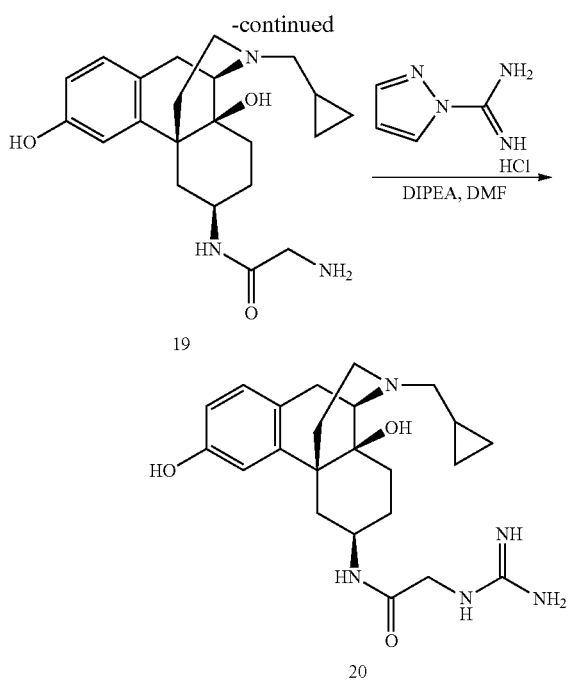

NaBH(OAc)₃ (3.18 g, 15 mmol) was added to a solution of Compound 1 (3.78 g, 10 mmol), benzylamine (1.31 mL, 12 mmol), and DIPEA (5.24 mL, 30 mmol) in DCE (40 mL). The reaction was stirred at RT for 7 h, DCM was added and the layers separated. The organic phase was washed with satd. aq. NaHCO₃, dried over Na₂SO₄, and concentrated. The resulting material was dissolved in 40 mL MeOH and carefully added to 10% Pd/C (400 mg). Conc. HCl was added until the solution was at pH 1-2 and the mixture was hydrogenated at 50 psi for 7 days. Filtration through Celite and concentration of the filtrate yielded a white foam that was purified by MPLC (SiO₂, 0-20% MeOH/DCM) followed by treatment with HCl in Et₂O to give 3.01 g of Compound 17 as its HCl salt: LC/MS, m/z=343 [M+H]⁺ (Calc: 342).

DIPEA (0.52 mL, 3 mmol) was added to Compound 17 HCl salt (379 mg, 1 mmol), Boc-glycine (210 mg, 1.2 mmol), and PyBOP (624 mg, 1.2 mmol) in DCM (5 mL) and the resulting solution was stirred at RT for 18 h. The reaction mixture was concentrated and purified by MPLC (SiO₂, 0-100% EtOAc/hexanes) to give Compound 18. DCM (5 mL) was added to Compound 18 (300 mg, 0.60 mmol) and BBr₃ (1M in DCM, 8 mL, 8 mmol) was added at 0° C. The mixture was stirred at 0° C. for 4 h, quenched with MeOH, concentrated, and purified by MPLC (SiO₂, 0-20% (10% NH₄OH in MeOH) in DCM) to give Compound 19: LC/MS, m/z=386 [M+H]⁺ (Calc: 385).

DIPEA (0.169 mL, 0.97 mmol) was added to a solution of Compound 19 (124 mg, 0.32 mmol) and 1H-pyrazole-1-carboxamidine hydrochloride (57 mg, 0.39 mmol) in DMF (1.5 mL). The reaction mixture was stirred at 80° C. for 65 h, concentrated, and triturated with DCM. The resulting solid was purified by preparatory HPLC (C18, 0-40% 0.1% TFA in ACN/0.1% TFA in water) to give Compound 20 as its tris-TFA salt: ¹H NMR (400 MHz, CD₃OD): δ 7.13 (d, J=8.3 Hz, 1H), 6.75-6.81 (m, 2H), 4.08 (br. s., 1H), 3.82 (br. s., 1H), 3.69 (d, J=16.5 Hz, 1H), 3.45 (d, J=16.7 Hz, 1H), 3.30-3.37 (m, 3H), 3.02 (dd, J=12.6, 3.9 Hz, 1H), 2.88 (dd, J=13.6, 7.5 Hz, 1H), 2.76 (d, J=14.9 Hz, 1H), 2.60 (td, J=13.0, 3.2 Hz, 1H), 2.42 (td, J=13.4, 4.7 Hz, 1H), 2.34 (tt, J=14.1, 4.3 Hz, 1H), 2.04 (d, J=14.7 Hz, 2H), 1.53-1.64 (m, 2H), 1.28 (d, J=13.4 Hz, 1H), 1.08-1.17 (m, 1H), 0.82-0.88 (m, 1H), 0.73-0.80 (m, 1H), 0.47-0.58 (m, 2H). LC/MS, m/z=428 [M+H]⁺ (Calc: 427).

In a similar manner, the following compounds were prepared:

N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-3-guanidinopropanamide tris-TFA salt (Compound 21): ¹H NMR (400 MHz, CD₃OD): δ 7.11 (d, J=8.3 Hz, 1H), 6.71-6.79 (m, 2H), 4.06 (br. s., 1H), 3.81 (br. s., 1H), 3.47-3.54 (m, 1H), 3.29-3.42 (m, 4H), 3.01 (dd, J=12.5, 3.9 Hz, 1H), 2.87 (dd, J=13.6, 7.5 Hz, 1H), 2.74 (d, J=14.7 Hz, 1H), 2.58 (td, J=13.0, 3.2 Hz, 1H), 2.42 (td, J=13.6, 4.6 Hz, 1H), 2.16-2.36 (m, 3H), 2.00-2.12 (m, 2H), 1.58 (d, J=13.9 Hz, 1H), 1.54 (d, J=13.8 Hz, 1H), 1.26 (d, J=12.8 Hz, 1H), 1.09-1.17 (m, 1H), 0.81-0.88 (m, 1H), 0.72-0.79 (m, 1H), 0.47-0.57 (m, 2H). LC/MS, m/z=442 [M+H]⁺ (Calc: 441).

N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-4-guanidinobutanamide tris-TFA salt (Compound 22): ¹H NMR (400 MHz, CD₃OD): δ 7.08-7.14 (m, 1H), 6.76 (s, 1H), 6.74 (d, J=8.4 Hz, 1H), 4.06 (br. s., 1H), 3.81 (d, J=3.9 Hz, 1H), 3.30-3.37 (m, 3H), 3.14-3.24 (m, 2H), 3.01 (dd, J=12.8, 3.9 Hz, 1H), 2.86 (dd, J=13.6, 7.5 Hz, 1H), 2.72 (d, J=15.0 Hz, 1H), 2.57 (td, J=13.0, 3.2 Hz, 1H), 2.42 (td, J=13.4, 4.4 Hz, 1H), 2.31 (tt, J=14.2, 4.3 Hz, 1H), 1.98-2.11 (m, 4H), 1.74-1.88 (m, 2H), 1.58 (d, J=14.1 Hz, 1H), 1.54 (d, J=14.3 Hz, 1H), 1.26 (d, J=13.2 Hz, 1H), 1.08-1.17 (m, 1H), 0.81-0.88 (m, 1H), 0.73-0.80 (m, 1H), 0.47-0.57 (m, 2H). LC/MS, m/z=456 [M+H]⁺ (Calc: 455).

Example 7

1-(4-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)phenyl)guanidine Bis-TFA Salt (Compound 24)

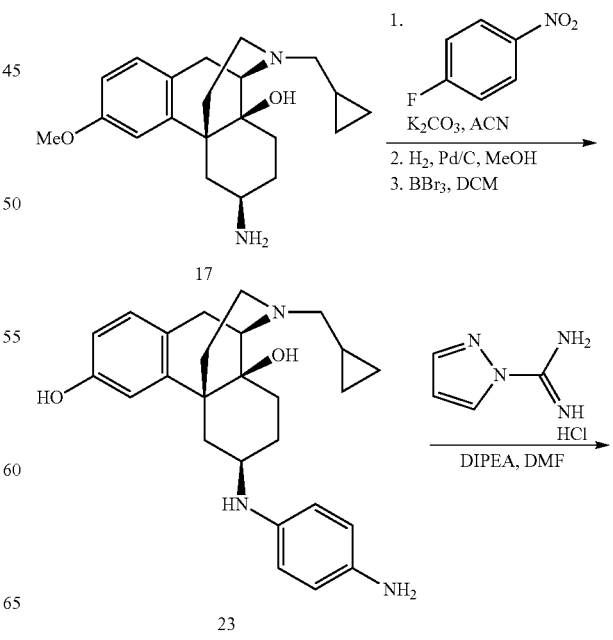

87

-continued

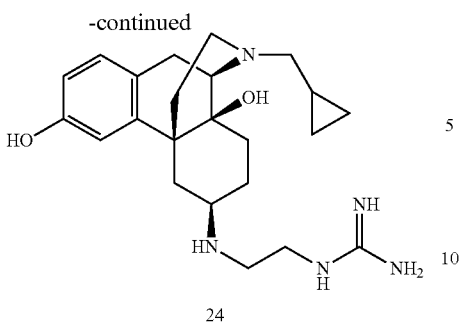

24

A solution of Compound 17 (379 mg, 1 mmol), 1-fluoro-4-nitrobenzene (0.127 mL, 1.2 mmol), and K₂CO₃ (415 mg, 3 mmol) in ACN (5 mL) was heated at 60° C. for 17 h and at reflux for an additional 4 days. The reaction was cooled to RT, filtered and purified by MPLC (SiO₂, 0-100% EtOAc/hexanes). The resulting yellow oil was dissolved in 1:1 MeOH:EtOAc (20 mL) and carefully added to 10% Pd/C (106 mg). Cyclohexene (0.304 mL, 3 mmol) was added and the solution heated at reflux for 15 h. The mixture was filtered through Celite and concentrated to give 320 mg of a white foam that was carried on without further purification. DCM (10 mL) was added followed by BBr₃ (1M in DCM, 3 mL, 4 equiv) at 0° C. The mixture was stirred at 0° C. for 50 min, quenched with MeOH, and concentrated. Purification by MPLC (SiO₂, 0-20% (10% NH₄OH in MeOH) in DCM) gave Compound 23 as a dark purple foam: LC/MS, m/z=420 [M+H]⁺ (Calc: 419).

DIPEA (0.37 mL, 2.1 mmol) was added to a solution of Compound 23 (296 mg, 0.71 mmol) and 1H-pyrazole-1-carboxamidine hydrochloride (124 mg, 0.85 mmol) in DMF (1.5 mL). The reaction mixture was stirred at 80° C. for 65 h, concentrated, and triturated with DCM. The resulting solid was purified by preparatory HPLC (C18, 0-60% 0.1% TFA in ACN/0.1% TFA in water) to give Compound 24 as its bis-TFA salt: $^1$H NMR (400 MHz, CD₃OD): δ 7.11 (d, J=8.4 Hz, 1H), 7.01 (d, J=8.6 Hz, 2H), 6.71 (dd, J=8.3, 2.0 Hz, 1H), 6.51 (d, J=2.0 Hz, 1H), 6.38 (d, J=8.6 Hz, 2H), 3.88 (br. s., 1H), 3.81 (d, J=5.6 Hz, 1H), 3.25-3.41 (m, 3H), 3.00 (dd, J=12.1, 3.2 Hz, 1H), 2.86 (dd, J=13.4, 7.6 Hz, 1H), 2.63-2.69 (m, 1H), 2.55 (td, J=12.8, 3.0 Hz, 1H), 2.46 (dd, J=13.4, 4.3 Hz, 1H), 2.36 (tt, J=14.1, 4.1 Hz, 1H), 2.07-2.18 (m, 2H), 1.73 (d, J=14.9 Hz, 1H), 1.58 (d, J=14.2 Hz, 1H), 1.23 (d, J=11.7 Hz, 1H), 1.08-1.18 (m, 1H), 0.83-0.89 (m, 1H), 0.72-0.81 (m, 1H), 0.47-0.58 (m, 2H). LC/MS, m/z=462 [M+H]⁺ (Calc: 461).

Example 8

(4bS,8aS,9R)-11-(cyclopropylmethyl)-8a-hydroxy-3-methoxy-5,6,8,8a,9,10-hexahydro-7H-9,4b-(epiminoethano)phenanthren-7-one TFA salt (Compound 31)

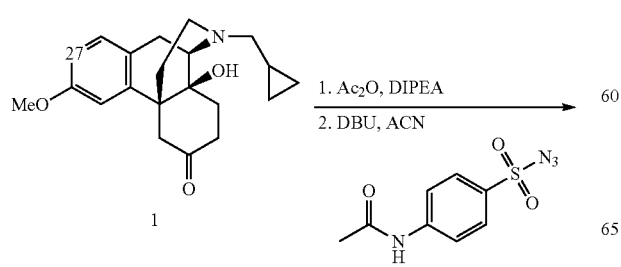

88

-continued

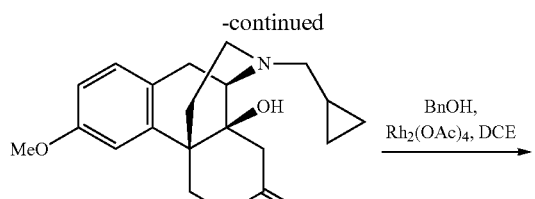

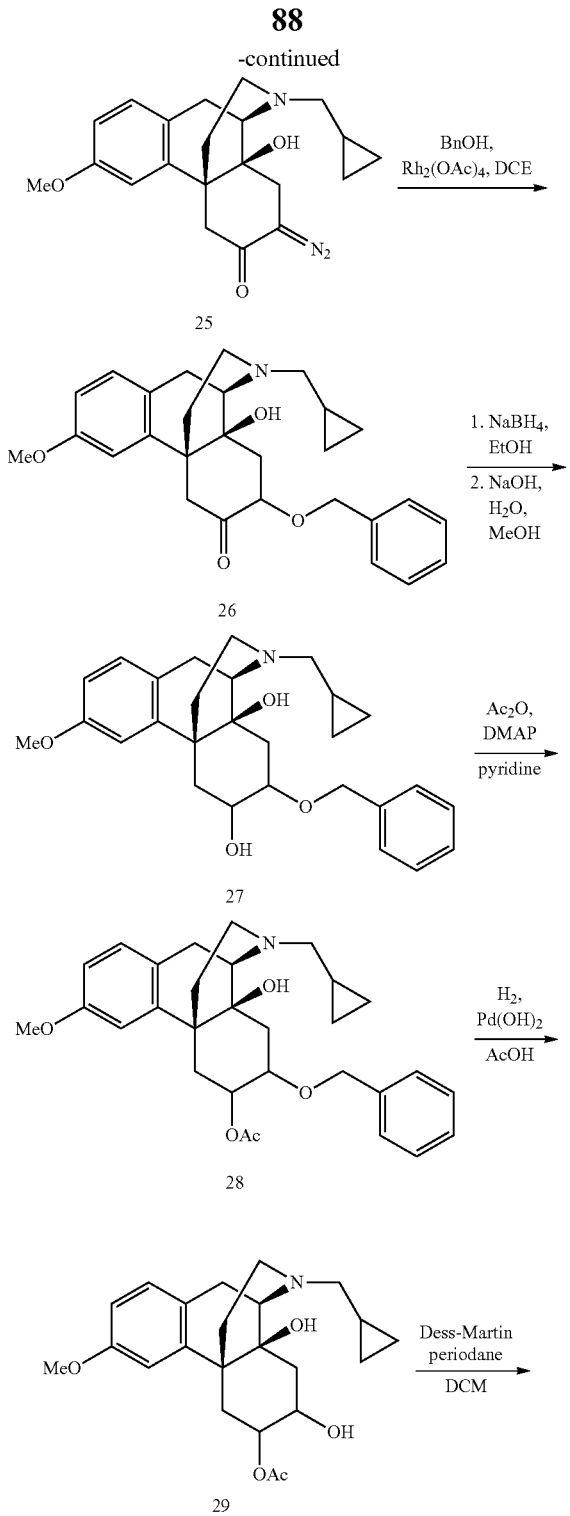

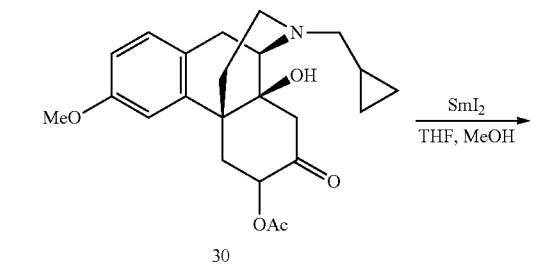

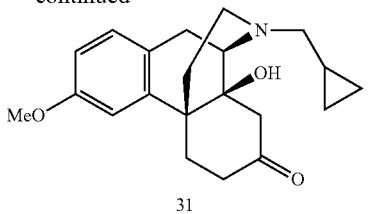

31

DIPEA (13.3 mL, 76 mmol) was added to Compound 1 (27.4 g, 72.5 mmol) in Ac₂O (68.4 mL, 725 mmol). The solution was heated at 120° C. for 2 h. The reaction mixture was diluted with EtOAc, washed with two portions of satd. aq. NaHCO₃, dried over Na₂SO₄ and concentrated. ACN (300 mL) and 4-acetamidobenzenesulfonyl azide (34.8 g, 145 mmol) were added, followed by DBU (32.8 mL, 218 mmol) at 0° C. The reaction was allowed to warm to RT over 18 h and concentrated. EtOAc was added, washed with two portions of 1M aq. NaOH, dried over Na₂SO₄ and concentrated. The resulting brown solid was triturated with acetone and filtered to give 17.28 g of Compound 25 as a yellow solid which was carried on without further purification: LC/MS, m/z=410 [M+H]⁺ (Calc: 409).

Compound 25 (8.19 g, 20 mmol) in DCE (40 mL) was added dropwise at 80° C. to a solution of benzyl alcohol (2.5 mL, 24 mmol) and rhodium acetate dimer (88 mg, 0.2 mmol) in DCE (60 mL). The solution was heated at 80° C. for 30 min and concentrated to give Compound 26, which was used without purification. EtOH (100 mL) was added followed by NaBH₄ (2.27 g, 60 mmol) at 0° C. The solution was stirred at 0° C. for 30 min. A 10% aq. solution of NaOH (20 mL, 50 mmol) was added slowly at 0° C. and the reaction mixture heated at reflux for 90 min EtOH was removed under vacuum and EtOAc was added. The organics were washed with satd. aq. NaHCO₃, dried over Na₂SO₄ and concentrated to give 9.75 g of Compound 27 as a brown oil that was carried on without purification. Compound 27 (9.75 g, 20 mmol) and DMAP (244 mg, 2 mmol) were dissolved in 1:1 DCM:pyridine (100 mL) and Ac₂O (9.44 g, 100 mmol) was added slowly at 0° C. The solution was allowed to warm to RT over 16 h after which additional Ac₂O (6 mL) was added. After 60 h the reaction was diluted with DCM, washed with 10% aq. NH₄OH and 10% aq. CuSO₄. The NH₄OH layer was back extracted with DCM and the combined organic layers were dried over Na₂SO₄, concentrated, and the residue purified by MPLC (SiO₂, 0-40% acetone/hexanes) to give 6.13 g of Compound 28 as a pale yellow foam: LC/MS, m/z=492 [M+H]⁺ (Calc: 491).

20% Pd(OH)₂/C (610 mg) was added to Compound 28 (6.13 g, 12.5 mmol) in AcOH (120 mL) and the reaction mixture was hydrogenated at 50 psi for 16 h. The mixture was filtered through Celite and concentrated. The resulting oil was dissolved in EtOAc, washed with 10% aq. NH₄OH, dried over Na₂SO₄ and concentrated to give 5.36 g of Compound 29 as a white foam that was carried on without purification. DCM (60 mL) was added followed by Dess-Martin periodane (6.35 g, 15 mmol). The reaction was stirred at RT for 24 h, after which an additional aliquot of Dess-Martin periodane (6.35 g, 15 mmol) was added. The reaction was stirred for an additional 24 h and concentrated. EtOAc was added, washed with 1M aq. NaOH (2×). The aqueous layer was back extracted with EtOAc, and the combined organic extracts were dried over Na₂SO₄, concentrated, and the residue purified by MPLC (SiO₂, 0-100% acetone/hexanes) to give 2.81 g of Compound 30 as a yellow foam: LC/MS, m/z=400 [M+H]⁺ (Calc: 399).

Compound 30 (2.41 g, 6.0 mmol) was added to THF (12 mL) and MeOH (3 mL) and the mixture purged with argon for 10 min. Samarium(II) iodide (0.1M in THF, 200 mL, 20 mmol) was added dropwise over 1 h. at 0° C. The resulting blue solution was allowed to warm to RT over 19 h and concentrated. EtOAc was added to the residue and washed with satd. aq. NaHCO₃. The aqueous layer was back extracted with DCM. The combined organic extracts were dried over Na₂SO₄, and concentrated to give 2.15 g of a dark orange oil. Purification by preparatory HPLC (C18, 0-60% 0.1% TFA in ACN/0.1% TFA in water) gave Compound 31 as its TFA salt: ¹H NMR (400 MHz, DMSO-d₆): δ 7.00 (d, J=8.4 Hz, 1H), 6.82 (d, J=2.4 Hz, 1H), 6.69 (dd, J=8.5, 2.5 Hz, 1H), 4.43 (d, J=1.8 Hz, 1H), 3.64 (s, 3H), 2.95 (d, J=18.5 Hz, 1H), 2.81 (d, J=5.9 Hz, 1H), 2.62 (dd, J=18.5, 6.2 Hz, 1H), 2.52-2.44 (m, 1H), 2.32-2.15 (m, 4H), 2.12-1.97 (m, 3H), 1.92 (d, J=15.0 Hz, 1H), 1.88-1.78 (m, 2H), 1.08-0.99 (m, 1H), 0.80-0.68 (m, 1H), 0.42-0.31 (m, 2H), 0.05-0.05 (m, 2H). LC/MS, m/z=398 [M+H]⁺ (Calc: 397).

Example 9

1-(2-(((4bS,7S,8aS,9R)-11-(cyclopropylmethyl)-3, 8a-dihydroxy-6,7,8,8a,9,10-hexahydro-5H-9,4b-(epiminoethano)phenanthren-7-yl)amino)ethyl) guanidine Tris-TFA Salt (Compound 32)

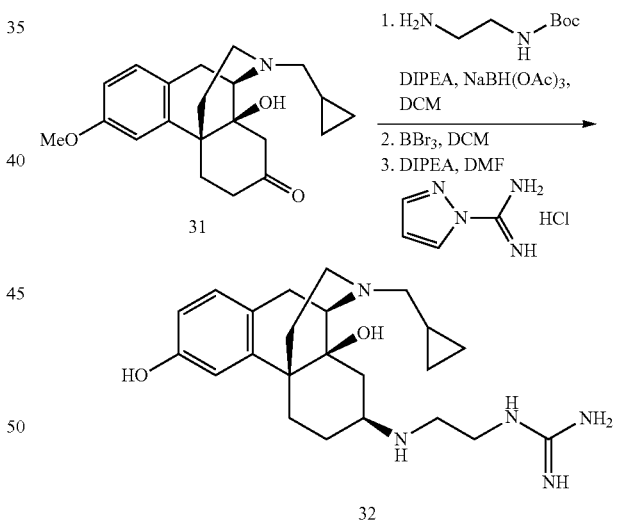

Compound 32 tris-TFA salt was prepared in a similar manner to the preparation of Compound 12 in Example 5.

Compound 32 tris-TFA salt: ¹H NMR (400 MHz, DMSO-d₆): δ 9.42 (br. s., 1H), 9.00 (br. s., 1H), 8.41 (br. s., 1H), 8.16 (br. s., 1H), 7.87 (br. s., 1H), 7.42 (br. s., 4H), 7.02 (d, J=8.4 Hz, 1H), 6.76 (d, J=2.0 Hz, 1H), 6.61-6.73 (m, 2H), 3.87 (br. s., 1H), 2.93-3.66 (m, 9H), 2.35-2.47 (m, 1H), 2.19-2.32 (m, 1H), 2.07-2.19 (m, 1H), 2.01 (d, J=16.3 Hz, 2H), 1.82-1.94 (m, 1H), 1.49-1.70 (m, 2H), 1.24 (d, J=12.8 Hz, 1H), 1.05 (br. s., 1H), 0.56-0.70 (m, 2H), 0.34-0.50 (m, 2H). LC/MS, m/z=414 [M+H]⁺ (Calc: 413).

Example 10

(4bR,6S,7R,8aS,9R)-11-(cyclopropylmethyl)-7-(isobutylamino)-3-methoxy-5,6,7,8,9,10-hexahydro-8aH-9,4b-(epiminoethano)phenanthrene-6,8a-diol Bis-TFA Salt (Compound 33) and (4bR,6S,7R,8aS,9R)-11-(cyclopropylmethyl)-7-(isobutylamino)-5,6,7,8,9,10-hexahydro-8aH-9,4b-(epiminoethano)phenanthrene-3,6,8a-triol Bis-TFA Salt (Compound 34)

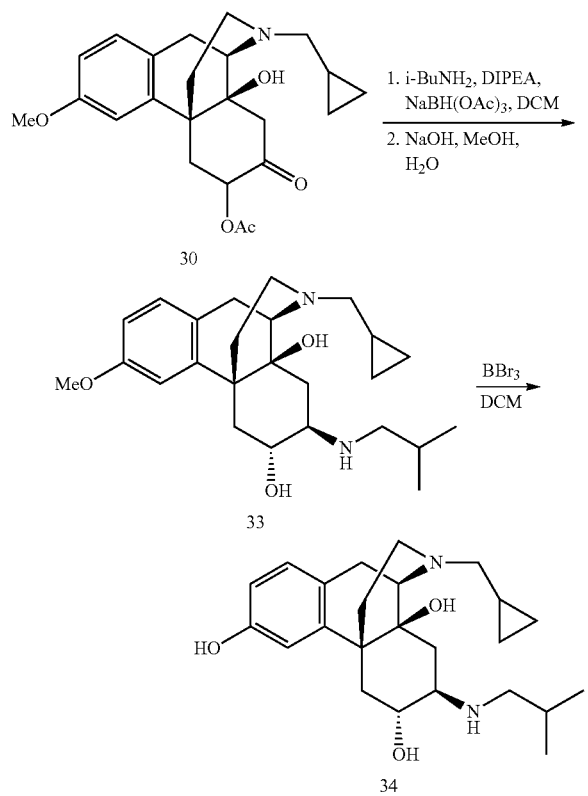

DIPEA (0.35 mL, 2.0 mmol) was added to Compound 30 (400 mg, 1.0 mmol) and isobutylamine (0.12 mL, 1.2 mmol) in DCM (5 mL) and the resulting solution was stirred at RT for 5 min. NaBH(OAc)$_3$ (318 mg, 1.5 mmol) was added and the reaction mixture was stirred at RT for 21 h. The mixture was diluted with DCM, washed with satd. aq. NaHCO$_3$, dried over Na$_2$SO$_4$, and concentrated. MeOH (3 mL) was added followed by 2.5M aq. NaOH (1.2 mL, 3.0 mmol) and the mixture was heated at 60° C. for 90 min EtOAc was added, washed with satd. aq. NaHCO$_3$, dried over Na$_2$SO$_4$, and concentrated. The residue was purified by MPLC (SiO$_2$, 0-60% acetone/hexanes followed by 0-20% MeOH/DCM) followed by preparatory HPLC (C18, 0-40% 0.1% TFA in ACN/0.1% TFA in water) to give Compound 33 as its bis-TFA salt: $^1$H NMR (400 MHz, DMSO-d$_6$): δ 9.03 (br. s., 1H), 7.75 (br. s., 1H), 7.37 (br. s., 1H), 7.15 (d, J=8.6 Hz, 1H), 6.97 (d, J=2.2 Hz, 1H), 6.90 (dd, J=8.4, 2.2 Hz, 1H), 6.69 (br. s., 1H), 5.92 (br. s., 1H), 4.00 (br. s., 1H), 3.77 (s, 3H), 3.74-3.67 (m, 2H), 3.44-3.26 (m, 3H), 3.26-3.09 (m, 2H), 3.09-2.90 (m, 5H), 2.42-2.13 (m, 5H), 2.13-1.99 (m, 1H), 1.64 (d, J=14.1 Hz, 1H), 1.34 (d, J=11.7 Hz, 1H), 1.11-1.02 (m, 1H), 0.98 (d, J=6.6 Hz, 3H), 0.94 (d, J=6.6 Hz, 3H), 0.73-0.57 (m, 2H), 0.48-0.36 (m, 2H). LC/MS, m/z=415 [M+H]$^+$ (Calc: 414).

A 1M solution of BBr$_3$ in DCM (0.36 mL, 0.36 mmol) was added slowly to Compound 33 (40 mg, 0.096 mmol) in DCM (0.5 mL). The solution was stirred at RT for 45 min. then slowly quenched with MeOH. The resulting salts were filtered off, the filtrate concentrated and the resulting residue purified by preparatory HPLC (C18, 0-40% 0.1% TFA in ACN/0.1% TFA in water) to give Compound 34 as its bis-TFA salt: $^1$H NMR (400 MHz, DMSO-d$_6$): δ 9.39 (br. s., 1H), 8.96 (br. s., 1H), 7.66 (br. s., 1H), 7.38 (br. s., 1H), 6.95 (d, J=8.4 Hz, 1H), 6.80 (br. s., 1H), 6.75 (d, J=2.0 Hz, 1H), 6.68-6.60 (m, 1H), 6.64 (dd, J=8.3, 2.1 Hz, 1H), 5.84 (br. s., 1H), 3.94 (d, J=4.4 Hz, 1H), 3.71-3.60 (m, 1H), 3.37-3.28 (m, 1H), 3.27-3.08 (m, 2H), 2.96 (d, J=6.6 Hz, 5H), 2.37-1.94 (m, 6H), 1.59 (d, J=12.5 Hz, 1H), 1.21 (d, J=12.1 Hz, 1H), 1.04-0.95 (m, 1H), 0.91 (d, J=6.6 Hz, 3H), 0.87 (d, J=6.6 Hz, 3H), 0.63-0.47 (m, 2H), 0.39-0.24 (m, 2H). LC/MS, m/z=401 [M+H]$^+$ (Calc: 400).

In a similar manner, the following compounds were prepared:

(4bR,6S,7R,8aS,9R)-11-(cyclopropylmethyl)-7-(methylamino)-5,6,7,8,9,10-hexahydro-8aH-9,4b-(epiminoethano)phenanthrene-3,6,8a-triol bis-TFA salt (Compound 35): $^1$H NMR (400 MHz, DMSO-d$_6$): δ 9.46 (s, 1H), 8.90 (br. s., 1H), 8.19 (br. s., 1H), 7.63 (br. s., 1H), 7.01 (d, J=8.4 Hz, 1H), 6.80 (d, J=2.0 Hz, 1H), 6.71 (dd, J=8.4, 2.2 Hz, 1H), 6.34 (s, 1H), 5.85 (br. s., 1H), 3.96 (d, J=5.5 Hz, 1H), 3.71 (d, J=10.3 Hz, 1H), 3.33-3.13 (m, 3H), 3.13-2.93 (m, 3H), 2.69 (t, J=5.2 Hz, 3H), 2.43-2.15 (m, 3H), 2.15-1.98 (m, 2H), 1.62 (dd, J=15.7, 4.1 Hz, 1H), 1.27 (d, J=12.3 Hz, 1H), 1.09-0.97 (m, 1H), 0.71-0.57 (m, 2H), 0.48-0.35 (m, 2H). LC/MS, m/z=359 [M+H]$^+$ (Calc: 358).

(4bR,6S,7R,8aS,9R)-7-(benzylamino)-11-(cyclopropylmethyl)-5,6,7,8,9,10-hexahydro-8aH-9,4b-(epiminoethano)phenanthrene-3,6,8a-triol bis-TFA salt (Compound 36): $^1$H NMR (400 MHz, DMSO-d$_6$): δ 9.43 (br. s., 1H), 9.01 (br. s., 1H), 8.58 (br. s., 1H), 8.04 (br. s., 1H), 7.61-7.50 (m, 2H), 7.49-7.36 (m, 3H), 6.99 (d, J=8.4 Hz, 1H), 6.79 (d, J=2.2 Hz, 1H), 6.69 (dd, J=8.3, 2.3 Hz, 1H), 6.50 (br. s., 1H), 5.81 (br. s., 1H), 4.46-4.28 (m, 2H), 3.98 (br. s., 1H), 3.85-3.59 (m, 1H), 3.31-3.13 (m, 3H), 3.13-2.94 (m, 3H), 2.46-2.12 (m, 5H), 1.63 (d, J=13.4 Hz, 1H), 1.28 (d, J=12.3 Hz, 1H), 1.13-1.01 (m, 1H), 0.73-0.57 (m, 2H), 0.49-0.36 (m, 2H). LC/MS, m/z=435 [M+H]$^+$ (Calc: 434).

(4bR,6R,7R,8aS,9R)-7-(benzylamino)-11-(cyclopropylmethyl)-5,6,7,8,9,10-hexahydro-8aH-9,4b-(epiminoethano)phenanthrene-3,6,8a-triol bis-TFA salt (Compound 37): $^1$H NMR (400 MHz, DMSO-d$_6$): δ 9.12 (br. s., 1H), 8.88 (br. s., 1H), 8.68 (br. s., 1H), 8.38 (br. s., 1H), 7.40-7.26 (m, 5H), 6.87 (d, J=8.4 Hz, 1H), 6.72 (d, J=1.5 Hz, 1H), 6.55 (dd, J=8.4, 2.0 Hz, 1H), 6.27 (br. s., 1H), 5.08 (br. s., 1H), 4.29-4.19 (m, 1H), 4.12-4.00 (m, 2H), 3.92-3.84 (m, 1H), 3.24-3.06 (m, 3H), 2.98-2.84 (m, 2H), 2.84-2.71 (m, 1H), 2.31-2.01 (m, 5H), 1.90 (d, J=12.1 Hz, 1H), 1.19 (d, J=12.8 Hz, 1H), 1.05-0.93 (m, 1H), 0.66-0.50 (m, 2H), 0.45-0.29 (m, 2H). LC/MS, m/z=435 [M+H]$^+$ (Calc: 434).

(4bR,6S,7R,8aS,9R)-11-(cyclopropylmethyl)-7-(pyrrolidin-1-yl)-5,6,7,8,9,10-hexahydro-8aH-9,4b-(epiminoethano)phenanthrene-3,6,8a-triol bis-TFA salt (Compound 38): $^1$H NMR (400 MHz, DMSO-d$_6$): δ 9.45 (br. s., 1H), 8.88 (br. s., 1H), 8.67 (br. s., 1H), 7.01 (d, J=8.4 Hz, 1H), 6.82 (d, J=2.2 Hz, 1H), 6.71 (dd, J=8.4, 2.0 Hz, 1H), 6.28 (br. s., 1H), 5.69 (br. s., 1H), 4.16-3.97 (m, 3H), 3.73 (d, J=12.1 Hz, 1H), 3.61-3.33 (m, 3H), 3.26 (d, J=19.8 Hz, 1H), 3.19-2.95 (m, 6H), 2.40-2.24 (m, 3H), 2.22-2.09 (m, 2H), 2.01-1.88 (m, 3H), 1.88-1.66 (m, 2H), 1.27 (d, J=9.5

Hz, 1H), 1.12-0.98 (m, 1H), 0.71-0.59 (m, 2H), 0.49-0.33 (m, 2H). LC/MS, m/z=399 [M+H]+ (Calc: 398).

(4bR,6S,7R,8aS,9R)-11-(cyclopropylmethyl)-7-morpholino-5,6,7,8,9,10-hexahydro-8aH-9,4b-(epiminoethano)phenanthrene-3,6,8a-triol bis-TFA salt (Compound 39): $^1$H NMR (400 MHz, CD$_3$OD): δ 7.08 (d, J=8.4 Hz, 1H), 6.98 (d, J=2.4 Hz, 1H), 6.73 (dd, J=8.4, 2.4 Hz, 1H), 4.60-4.50 (m, 1H), 3.99 (d, J=4.0 Hz, 1H), 3.93-3.75 (m, 4H), 3.42-3.34 (m, 1H), 3.30-3.24 (m, 1H), 3.19-2.87 (m, 6H), 2.87-2.75 (m, 1H), 2.68-2.42 (m, 3H), 2.36-2.18 (m, 2H), 1.99 (dd, J=14.7, 6.4 Hz, 1H), 1.44 (d, J=12.8 Hz, 1H), 1.18-1.05 (m, 1H), 0.90-0.71 (m, 2H), 0.57-0.44 (m, 2H). LC/MS, m/z=415 [M+H]+ (Calc: 414).

((4bR,6S,7R,8aS,9R)-11-(cyclopropylmethyl)-3,6,8a-trihydroxy-6,7,8,9,8a,9,10-hexahydro-5H-9,4b-(epiminoethano)phenanthren-7-yl)glycine bis-TFA salt (Compound 40): $^1$H NMR (400 MHz, CD$_3$OD): δ 7.11 (d, J=8.4 Hz, 1H), 6.94 (d, J=2.2 Hz, 1H), 6.77 (dd, J=8.4, 2.4 Hz, 1H), 4.03 (d, J=5.9 Hz, 1H), 4.00-3.91 (m, 1H), 3.87 (d, J=9.5 Hz, 2H), 3.52-3.46 (m, 1H), 3.39-3.18 (m, 3H), 3.10 (dd, J=12.5, 3.7 Hz, 1H), 3.01 (dd, J=13.6, 7.0 Hz, 1H), 2.67 (td, J=13.0, 3.4 Hz, 1H), 2.52 (td, J=13.6, 4.5 Hz, 1H), 2.45 (dd, J=14.3, 4.2 Hz, 1H), 2.24-2.14 (m, 2H), 2.24-2.14 (m, 2H), 1.92 (dd, J=15.7, 4.1 Hz, 1H), 1.43 (d, J=11.9 Hz, 1H), 1.16-1.04 (m, 1H), 0.88-0.73 (m, 2H), 0.56-0.46 (m, 2H). LC/MS, m/z=403 [M+H]+ (Calc: 402).

Example 11

(4bS,7S,8aS,9R)-11-(cyclopropylmethyl)-7-(isobutylamino)-3-methoxy-5,6,7,8,9,10-hexahydro-8aH-9,4b-(epiminoethano)phenanthren-8a-ol Bis-TFA Salt (Compound 41) and (4bS,7S,8aS,9R)-11-(cyclopropylmethyl)-7-(isobutylamino)-5,6,7,8,9,10-hexahydro-8aH-9,4b-(epiminoethano)phenanthrene-3,8a-diol Bis-TFA Salt (Compound 42)

DIPEA (0.21 mL, 1.2 mmol) was added to Compound 31 (200 mg, 0.59 mmol) and isobutylamine (0.07 mL, 0.7 mmol) in DCM (3 mL). NaBH(OAc)$_3$ (318 mg, 1.5 mmol) was added and the mixture stirred at RT for 16 h. The reaction was quenched with MeOH, concentrated, and purified by MPLC (SiO$_2$, 0-20% MeOH/DCM) followed by preparatory HPLC (C18, 0-60% 0.1% TFA in ACN/0.1% TFA in water) to give Compound 41 as its bis-TFA salt: $^1$H NMR (400 MHz, DMSO-d$_6$): δ 9.05 (br. s., 1H), 8.19 (br. s., 1H), 7.66-7.54 (m, 1H), 7.15 (d, J=8.4 Hz, 1H), 6.92 (d, J=2.2 Hz, 1H), 6.88 (dd, J=8.5, 2.3 Hz, 1H), 6.83 (s, 1H), 3.98 (d, J=5.3 Hz, 1H), 3.75 (s, 3H), 3.40-3.28 (m, 2H), 3.23-3.13 (m, 2H), 3.13-2.96 (m, 4H), 2.86-2.74 (m, 1H), 2.45-2.05 (m, 5H), 2.05-1.84 (m, 2H), 1.65-1.52 (m, 2H), 1.27 (d, J=12.5 Hz, 1H), 1.12-1.03 (m, 1H), 1.00 (d, J=6.6 Hz, 3H), 0.96 (d, J=6.8 Hz, 3H), 0.93-0.85 (m, 1H), 0.70-0.58 (m, 2H), 0.47-0.36 (m, 2H). LC/MS, m/z=399 [M+H]+ (Calc: 398).

A 1M solution of BBr$_3$ in DCM (0.44 mL, 0.44 mmol) was added slowly to Compound 41 (43 mg, 0.11 mmol) in DCM (0.5 mL). The solution was stirred at RT for 45 min then slowly quenched with MeOH. The resulting salts were filtered off and the filtrate purified by preparatory HPLC (C18, 0-40% 0.1% TFA in ACN/0.1% TFA in water) to give Compound 42 as its bis-TFA salt: $^1$H NMR (400 MHz, DMSO-d$_6$): δ 9.40 (br. s., 1H), 9.00 (br. s., 1H), 8.16 (br. s., 1H), 7.61 (s, 1H), 7.02 (d, J=8.4 Hz, 1H), 6.76 (d, J=2.0 Hz, 1H), 6.72 (s, 1H), 6.70 (dd, J=8.3, 2.1 Hz, 1H), 3.94 (d, J=5.1 Hz, 1H), 3.35 (br. s., 1H), 3.29 (d, J=19.8 Hz, 1H), 3.24-3.13 (m, 1H), 3.12-2.96 (m, 4H), 2.90-2.76 (m, 1H), 2.47-2.36 (m, 1H), 2.34-2.17 (m, 2H), 2.08 (d, J=15.4 Hz, 1H), 2.04-1.88 (m, 3H), 1.67-1.53 (m, 2H)), 1.24 (d, J=12.5 Hz, 1H), 1.11-1.03 (m, 1H), 1.00 (d, J=6.6 Hz, 3H), 0.97 (d, J=6.8 Hz, 3H), 0.71-0.57 (m, 2H), 0.47-0.36 (m, 2H). LC/MS, m/z=385 [M+H]+ (Calc: 384).

Example 12

N-((4bS,7S,8aS,9R)-11-(cyclopropylmethyl)-8a-hydroxy-3-methoxy-6,7,8,8a,9,10-hexahydro-5H-9,4b-(epiminoethano)phenanthren-7-yl)isobutyramide TFA Salt (Compound 45) and N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)isobutyramide TFA Salt (Compound 46)

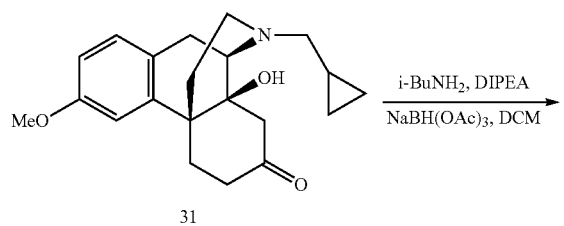

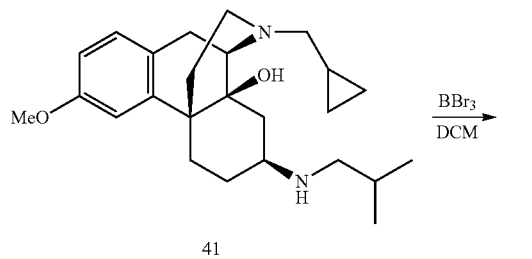

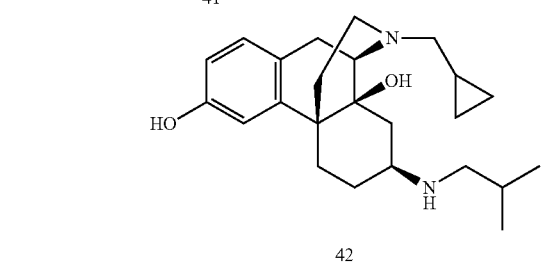

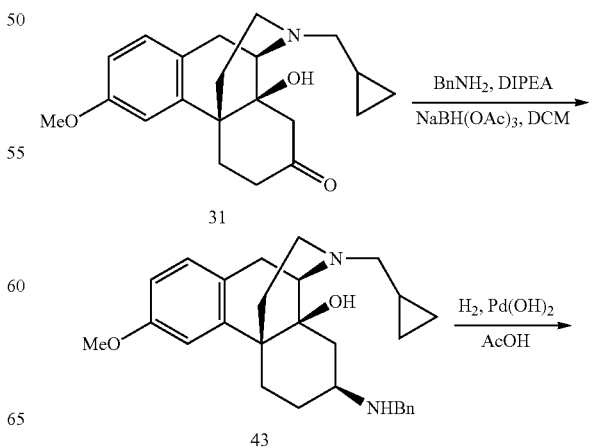

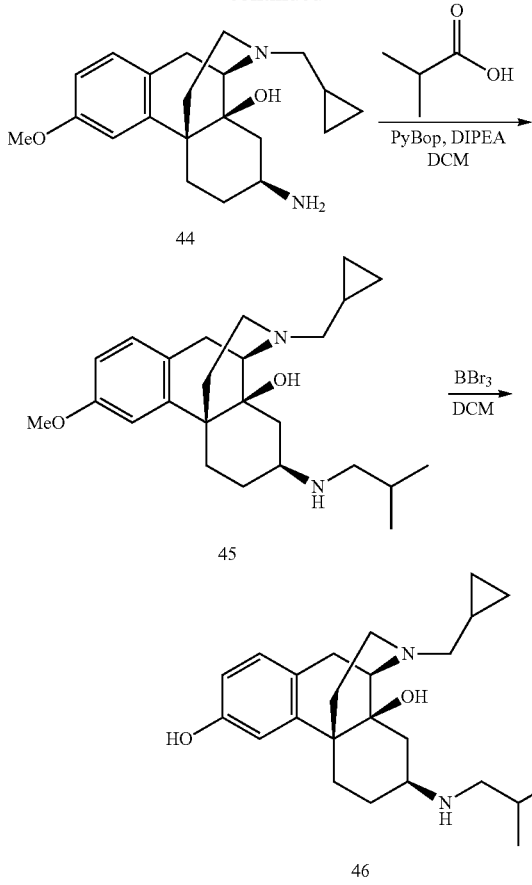

DIPEA (1.6 mL, 9.1 mmol) was added to Compound 31 (1.55 g, 4.5 mmol) and benzylamine (0.60 mL, 5.5 mmol) in DCM (25 mL). NaBH(OAc)₃ (1.44 g, 6.8 mmol) was added and the reaction mixture was stirred at RT for 2 h. Satd. aq. NaHCO₃ was added followed by additional DCM. The aqueous layer was washed with DCM and the combined organic layers dried over Na₂SO₄ and concentrated. Purification of the residue by MPLC (SiO₂, 0-20% MeOH/DCM) gave 920 mg of Compound 43 as a yellow oil. AcOH (25 mL) and 20% Pd(OH)₂/C (200 mg) were added and the suspension hydrogenated at 50 psi for 46 h. The mixture was filtered through Celite and concentrated. EtOAc was added to the residue and the solution washed with 10% aq. NH₄OH (3×), dried over Na₂SO₄, and concentrated to give Compound 44. DIPEA (0.23 mL, 1.3 mmol) was added to Compound 44 (150 mg, 0.44 mmol), isobutyric acid (0.05 mL, 0.53 mmol), and PyBop (274 mg, 0.53 mmol) in DCM (2 mL). The solution was stirred at RT for 16 h and concentrated. Purification of the residue by MPLC (SiO₂, 0-20% (10% NH₄OH in MeOH) followed by preparatory HPLC (C18, 0-40% 0.1% TFA in ACN/0.1% TFA in water) gave Compound 45 as its TFA salt.

Compound 45 TFA salt: $^1$H NMR (400 MHz, DMSO-d₆): δ 8.84 (br. s., 1H), 7.43 (d, J=7.9 Hz, 1H), 7.13 (d, J=8.1 Hz, 1H), 6.92-6.83 (m, 2H), 5.94 (br. s., 1H), 3.92 (br. s., 1H), 3.78 (d, J=5.9 Hz, 1H), 3.74 (s, 3H), 3.34-3.18 (m, 2H), 3.17-3.08 (m, 1H), 2.98 (d, J=11.7 Hz, 1H), 2.93-2.84 (m, 1H), 2.45-2.32 (m, 2H), 2.32-2.21 (m, 1H), 2.14-1.98 (m, 2H), 1.70-1.64 (m, 1H), 1.62-1.53 (m, 1H), 1.53-1.37 (m, 2H), 1.22 (d, J=12.8 Hz, 1H), 1.07 (d, J=5.5 Hz, 3H), 1.05 (d, J=5.5 Hz, 3H), 1.04-1.01 (m, 1H), 0.72-0.56 (m, 2H), 0.49-0.36 (m, 2H). LC/MS, m/z=413 [M+H]⁺ (Calc: 412).

A 1M solution of BBr₃ in DCM (0.9 mL, 0.9 mmol) was added slowly to Compound 45 (90 mg, 0.22 mmol) in DCM (1 mL). The solution was stirred at RT for 2.5 h, then slowly quenched with MeOH. The resulting salts were filtered off and the filtrate purified by preparatory HPLC (C18, 0-40% 0.1% TFA in ACN/0.1% TFA in water) to give Compound 46 as its TFA salt: $^1$H NMR (400 MHz, DMSO-d₆): δ 9.33 (br. s., 1H), 8.80 (br. s., 1H), 7.42 (d, J=7.9 Hz, 1H), 7.00 (d, J=8.4 Hz, 1H), 6.73 (d, J=2.2 Hz, 1H), 6.67 (dd, J=8.4, 2.2 Hz, 1H), 5.92 (s, 1H), 3.93 (br. s., 1H), 3.75 (d, J=5.7 Hz, 1H), 3.34-3.14 (m, 2H), 3.14-3.03 (m, 1H), 2.97 (d, J=11.4 Hz, 1H), 2.91-2.84 (m, 1H), 2.46-2.31 (m, 2H), 2.30-2.20 (m, 1H), 2.13-2.02 (m, 1H), 1.87 (d, J=14.1 Hz, 1H), 1.69-1.52 (m, 2H), 1.52-1.38 (m, 2H), 1.17 (d, J=12.1 Hz, 1H), 1.07 (d, J=4.6 Hz, 3H), 1.05 (d, J=4.4 Hz, 3H), 1.04-0.99 (m, 1H), 0.73-0.56 (m, 2H), 0.51-0.33 (m, 2H).

LC/MS, m/z=399 [M+H]⁺ (Calc: 398).

In a similar manner, the following compound was prepared.

N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)acetamide TFA salt (Compound 47) $^1$H NMR (400 MHz, DMSO-d₆): δ 9.25 (br. s., 1H), 8.62 (br. s., 1H), 7.51 (d, J=8.1 Hz, 1H), 6.93 (d, J=8.4 Hz, 1H), 6.65 (d, J=2.2 Hz, 1H), 6.60 (dd, J=8.3, 2.3 Hz, 1H), 5.69 (s, 1H), 3.84 (br. s., 1H), 3.63 (d, J=5.5 Hz, 1H), 3.25-3.11 (m, 2H), 3.05-2.97 (m, 1H), 2.88 (d, J=12.3 Hz, 1H), 2.82-2.71 (m, 1H), 2.41-2.24 (m, 1H), 2.24-2.04 (m, 2H), 1.83-1.80 (m, 1H), 1.79 (s, 3H), 1.62 (d, J=14.3 Hz, 1H), 1.50-1.36 (m, 3H), 1.09 (d, J=12.1 Hz, 1H), 1.01-0.90 (m, 1H), 0.64-0.49 (m, 2H), 0.43-0.28 (m, 2H). LC/MS, m/z=371 [M+H]⁺ (Calc: 370).

Example 13

N-((4bR,7S,8aS,9R)-11-(cyclopropylmethyl)-6,8a-dihydroxy-3-methoxy-6,7,8,8a,9,10-hexahydro-5H-9,4b-(epiminoethano)phenanthren-7-yl)isobutyramide TFA Salt (Compound 49) and N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide TFA Salt (Compound 50)

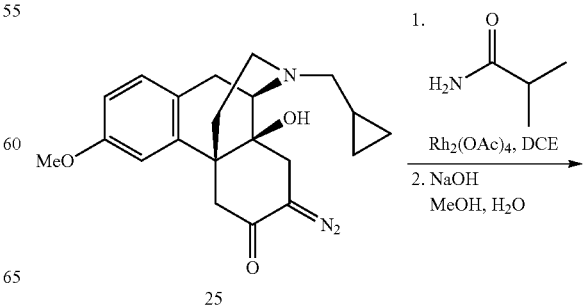

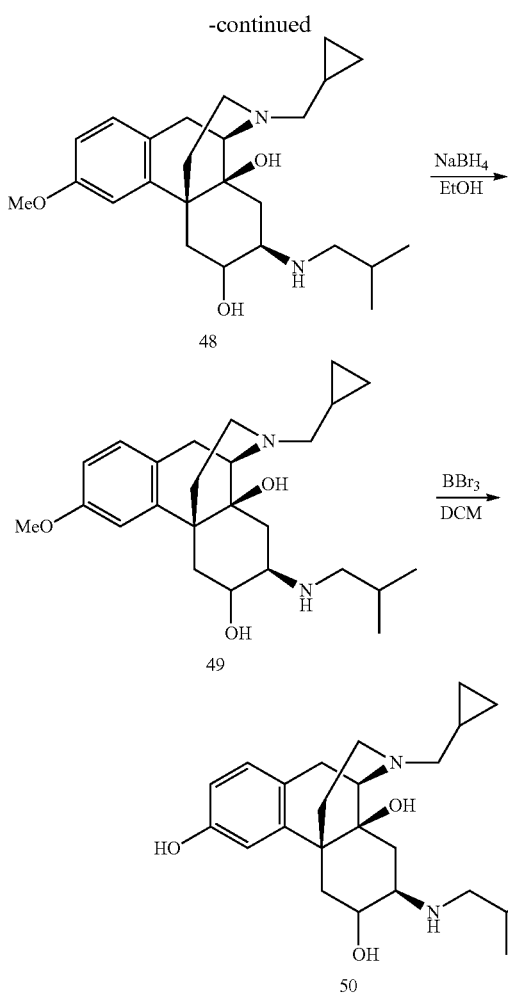

1H), 1.72 (dd, J=13.3, 4.7 Hz, 1H), 1.43-1.36 (m, 0.2H), 1.24 (t, J=12.5 Hz, 0.8H), 1.17 (d, J=12.3 Hz, 1H), 0.98-0.90 (m, 1H), 0.88 (s, 3H), 0.84 (d, J=6.6 Hz, 3H), 0.63-0.55 (m, 1H), 0.55-0.47 (m, 1H), 0.42-0.34 (m, 1H), 0.34-0.27 (m, 1H). LC/MS, m/z=429 [M+H]$^+$ (Calc: 428).

A 1M solution of BBr$_3$ in DCM (1.3 mL, 1.3 mmol) was added slowly to Compound 49 (140 mg, 0.32 mmol) in DCM (1 mL). The solution was stirred at RT for 2 h then slowly quenched with MeOH. The resulting salts were filtered off and the filtrate purified by preparatory HPLC (C18, 0-40% 0.1% TFA in ACN/0.1% TFA in water) to give Compound 50 as its TFA salt: $^1$H NMR (400 MHz, DMSO-d$_6$): δ 9.34 (s, 1H), 8.76 (br. s., 1H), 7.41 (d, J=8.6 Hz, 1H), 6.98 (d, J=8.4 Hz, 1H), 6.81 (d, J=2.2 Hz, 1H), 6.65 (dd, J=8.4, 2.4 Hz, 1H), 5.95 (s, 1H), 4.59 (br. s., 1H), 4.11-4.01 (m, 1H), 3.75 (d, J=6.2 Hz, 1H), 3.34-3.16 (m, 4H), 3.03 (dd, J=19.4, 6.4 Hz, 1H), 2.89 (d, J=12.3 Hz, 1H), 2.82-2.73 (m, 1H), 2.44-2.30 (m, 1H), 2.29-2.15 (m, 3H), 1.98-1.90 (m, 1H), 1.78 (dd, J=13.1, 4.3 Hz, 1H), 1.33 (t, J=12.7 Hz, 1H), 1.19 (d, J=12.1 Hz, 1H), 1.05-0.98 (m, 1H), 0.95 (d, J=6.8 Hz, 3H), 0.92 (d, J=7.0 Hz, 3H), 0.69-0.61 (m, 1H), 0.61-0.51 (m, 1H), 0.49-0.41 (m, 1H), 0.41-0.32 (m, 1H). LC/MS, m/z=415 [M+H]$^+$ (Calc: 414).

In a similar manner the following compounds were prepared.

(4bR,6R,7S,8aS,9R)-11-(cyclopropylmethyl)-7-isobutoxy-3-methoxy-5,6,7,8,9,10-hexahydro-8aH-9,4b-(epiminoethano)phenanthrene-6,8a-diol TFA salt (Compound 51) $^1$H NMR (400 MHz, DMSO-d$_6$): δ 8.78 (br. s., 1H), 7.05-6.97 (m, 2H), 6.74 (dd, J=8.4, 2.4 Hz, 1H), 5.84 (br. s., 1H), 4.07 (d, J=2.9 Hz, 1H), 3.74-3.68 (m, 5H), 3.35-3.12 (m, 5H), 3.07 (dd, J=9.1, 6.9 Hz, 1H), 2.90 (d, J=11.9 Hz, 1H), 2.81-2.72 (m, 1H), 2.55 (d, J=2.6 Hz, 1H), 2.33-2.20 (m, 1H), 2.18-2.09 (m, 1H), 1.86 (dd, J=14.7, 2.4 Hz, 1H), 1.80-1.64 (m, 3H), 1.20 (d, J=12.8 Hz, 1H), 1.09-0.99 (m, 1H), 0.83 (d, J=2.6 Hz, 3H), 0.81 (d, J=2.6 Hz, 3H), 0.71-0.63 (m, 1H), 0.63-0.54 (m, 1H), 0.52-0.44 (m, 1H), 0.44-0.36 (m, 1H). LC/MS, m/z=416 [M+H]$^+$ (Calc: 415).

(4bS,7R,8aS,9R)-11-(cyclopropylmethyl)-3-methoxy-5,6,7,8,9,10-hexahydro-8aH-9,4b-(epiminoethano)phenanthrene-7,8a-diol TFA salt (Compound 52): $^1$H NMR (400 MHz, DMSO-d$_6$): δ 8.69 (br. s., 1H), 7.06 (d, J=8.1 Hz, 1H), 6.83-6.74 (m, 2H), 5.73 (br. s., 1H), 3.89-3.79 (m, 1H), 3.67 (s, 3H), 3.60 (d, J=5.9 Hz, 1H), 3.29-3.18 (m, 2H), 3.12-3.01 (m, 1H), 2.88 (d, J=12.3 Hz, 1H), 2.78-2.69 (m, 1H), 2.36-2.24 (m, 1H), 2.14-2.03 (m, 2H), 1.86-1.72 (m, 2H), 1.62 (d, J=9.9 Hz, 1H), 1.21-1.11 (m, 2H), 1.11-0.93 (m, 2H), 0.65-0.57 (m, 1H), 0.57-0.48 (m, 1H), 0.44-0.37 (m, 1H), 0.37-0.28 (m, 1H). LC/MS, m/z=344 [M+H]$^+$ (Calc: 343).

(4bR,6R,7S,8aS,9R)-11-(cyclopropylmethyl)-7-(2-methylbutyl)-5,6,7,8,9,10-hexahydro-8aH-9,4b-(epiminoethano)phenanthrene-3,6,8a-triol TFA salt (Compound 53): $^1$H NMR (400 MHz, DMSO-d$_6$): δ 9.04 (s, 1H), 8.70 (br. s., 1H), 6.90 (d, J=8.4 Hz, 1H), 6.86 (d, J=2.0 Hz, 1H), 6.57 (dd, J=8.1, 2.0 Hz, 1H), 5.55 (d, J=12.8 Hz, 1H), 3.79-3.51 (m, 3H), 3.30-3.05 (m, 3H), 2.88 (d, J=11.2 Hz, 1H), 2.80-2.71 (m, 1H), 2.42-2.12 (m, 3H), 2.12-1.99 (m, 1H), 1.94-1.82 (m, 1H), 1.62-1.44 (m, 1H), 1.42-1.22 (m, 3H), 1.13-0.93 (m, 4H), 0.85-0.78 (m, 6H), 0.78-0.62 (m, 1H), 0.62-0.54 (m, 1H), 0.52-0.43 (m, 1H), 0.43-0.35 (m, 1H). LC/MS, m/z=400 [M+H]$^+$ (Calc: 399).

(4bR,6R,7S,8aS,9R)-7-(cyclopentylmethyl)-11-(cyclopropylmethyl)-5,6,7,8,9,10-hexahydro-8aH-9,4b-(epiminoethano)phenanthrene-3,6,8a-triol TFA salt (Compound 54): $^1$H NMR (400 MHz, DMSO-d$_6$): δ 9.04 (s, 1H), 8.71 (br. s., 1H), 6.90 (d, J=8.4 Hz, 1H), 6.86 (d, J=2.2 Hz, 1H), A solution of Compound 25 (500 mg, 1.2 mmol) in DCE (2 mL) was added dropwise to isobutyramide (177 mg, 1.34 mmol) and rhodium (II) acetate dimer (11 mg, 0.02 mmol) in DCE (2 mL) at 80° C. The solution was stirred at 80° C. for 90 min then concentrated. MeOH (2 mL) was added followed by 2.5M aq. NaOH (1.5 mL, 3.7 mmol) and the resulting solution stirred at RT for 72 h. DCM was added followed by satd. aq. NaHCO$_3$ and the mixture was passed through a phase separation column (Biotage Isolute 120-1906-D). Concentration followed by purification by MPLC (SiO$_2$, 0-60% acetone/hexanes) and preparatory HPLC (C18, 0-60% 0.1% TFA in ACN/0.1% TFA in water) gave Compound 48: LC/MS, m/z=427 [M+H]$^+$ (Calc: 426).

NaBH$_4$ (56 mg, 1.5 mmol) was added to Compound 48 (210 mg, 0.5 mmol) in 2 mL EtOH (2 mL) and the solution was stirred at RT for 45 min EtOAc was added, washed with satd. aq. NaHCO$_3$, dried over Na$_2$SO$_4$ and concentrated. Purification of the residue by preparatory HPLC (C18, 0-40% 0.1% TFA in ACN/0.1% TFA in water) gave Compound 49 as its TFA salt: $^1$H NMR (400 MHz, DMSO-d$_6$): δ 8.74 (br. s., 1H), 7.32 (d, J=8.6 Hz, 0.8H), 7.30 (d, J=10.1 Hz, 0.8H), 7.05 (d, J=8.4 Hz, 0.8H), 6.97-6.92 (m, 0.4H), 6.87 (d, J=2.4 Hz, 0.8H), 6.78 (dd, J=8.4, 2.4 Hz, 0.8H), 6.66 (dd, J=8.5, 2.5 Hz, 0.2H), 5.92 (s, 0.8H), 5.80 (s, 0.8), 4.29-4.21 (m, 0.2H), 4.05-3.94 (m, 0.8H), 3.78-3.69 (m, 1H), 3.68 (s, 0.2H), 3.66 (s, 0.6H), 3.28-3.16 (m, 3H), 3.10-2.97 (m, 1H), 2.83 (d, J=11.4 Hz, 1H), 2.77-2.67 (m, 1H), 2.34-2.21 (m, 2H), 2.21-2.08 (m, 2H), 1.92-1.84 (m, 6.57 (dd, J=8.1, 2.2 Hz, 1H), 5.52 (s, 1H), 3.78 (br. s., 1H), 3.63 (br. s., 1H), 3.54 (br. s., 1H), 3.30-3.04 (m, 3H), 2.88 (d, J=11.9 Hz, 1H), 2.80-2.70 (m, 1H), 2.44-2.12 (m, 4H), 2.05-1.95 (m, 1H), 1.87 (d, J=11.9 Hz, 1H), 1.83-1.64 (m, 3H), 1.61-1.40 (m, 5H), 1.35 (d, J=10.1 Hz, 1H), 1.31-1.20 (m, 1H), 1.17-0.92 (m, 5H), 0.72-0.63 (m, 1H), 0.63-0.53 (m, 1H), 0.53-0.43 (m, 1H), 0.43-0.35 (m, 1H). LC/MS, m/z=412 [M+H]$^+$ (Calc: 411).

N-((4bR,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)acetamide TFA salt (Compound 55): $^1$H NMR (400 MHz, DMSO-d$_6$): δ 9.07 (s, 1H), 8.77 (br. s., 1H), 7.52 (d, J=8.8 Hz, 1H), 6.92-6.84 (m, 2H), 6.56 (dd, J=8.1, 2.2 Hz, 1H), 5.83 (s, 1H), 4.33-4.25 (m, 1H), 4.23 (d, J=4.2 Hz, 1H), 3.82 (br. s., 1H), 3.69 (d, J=5.3 Hz, 1H), 3.28-3.17 (m, 2H), 3.13-3.03 (m, 1H), 2.90 (d, J=11.7 Hz, 1H), 2.81-2.70 (m, 1H), 2.40 (d, J=12.8 Hz, 1H), 2.34-2.22 (m, 1H), 2.21-2.10 (m, 1H), 1.94 (d, J=11.9 Hz, 1H), 1.82 (t, J=12.5 Hz, 1H), 1.75 (s, 3H), 1.45 (dd, J=12.4, 3.9 Hz, 1H), 1.15 (d, J=11.9 Hz, 1H), 1.08-0.98 (m, 1H), 0.70-0.61 (m, 1H), 0.61-0.53 (m, 1H), 0.50-0.42 (m, 1H), 0.42-0.33 (m, 1H). LC/MS, m/z=387 [M+H]$^+$ (Calc: 386).

N-((4bR,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)propionamide TFA salt (Compound 56): $^1$H NMR (400 MHz, DMSO-d$_6$): δ 9.07 (br. s., 1H), 8.78 (br. s., 1H), 7.42 (d, J=8.6 Hz, 1H), 6.96-6.83 (m, 2H), 6.56 (dd, J=8.4, 2.2 Hz, 1H), 5.83 (s, 1H), 4.35-4.25 (m, 1H), 4.21 (br. s., 1H), 3.82 (br. s., 1H), 3.69 (d, J=4.4 Hz, 1H), 3.31-3.16 (m, 2H), 3.14-3.03 (m, 1H), 2.90 (d, J=11.2 Hz, 1H), 2.80-2.71 (m, 1H), 2.40 (d, J=12.3 Hz, 1H), 2.36-2.22 (m, 1H), 2.16 (td, J=13.1, 3.9 Hz, 1H), 2.06-1.90 (m, 3H), 1.83 (t, J=12.5 Hz, 1H), 1.45 (dd, J=12.5, 3.7 Hz, 1H), 1.15 (d, J=12.5 Hz, 1H), 1.08-0.98 (m, 1H), 0.94 (t, J=7.6 Hz, 3H), 0.70-0.61 (m, 1H), 0.61-0.53 (m, 1H), 0.49-0.42 (m, 1H), 0.42-0.34 (m, 1H). LC/MS, m/z=401 [M+H]$^+$ (Calc: 400).

N-((4bR,6S,7S,8aS,9R)-11-(cyclopropylmethyl)-3,6,8a-trihydroxy-6,7,8,8a,9,10-hexahydro-5H-9,4b-(epimi-noethano)phenanthren-7-yl)propionamide TFA salt (Compound 57): $^1$H NMR (400 MHz, DMSO-d$_6$): δ 9.34 (s, 1H), 8.76 (br. s., 1H), 7.45 (d, J=8.4 Hz, 1H), 6.98 (d, J=8.4 Hz, 1H), 6.81 (d, J=2.0 Hz, 1H), 6.65 (dd, J=8.4, 2.2 Hz, 1H), 5.96 (s, 1H), 4.59 (br. s, 1H), 4.12-3.98 (m, 1H), 3.75 (d, J=5.7 Hz, 1H), 3.35-3.18 (m, 3H), 3.08-3.00 (m, 1H), 2.90 (d, J=11.9 Hz, 1H), 2.84-2.73 (m, 1H), 2.45-2.32 (m, 1H), 2.28-2.15 (m, 2H), 2.04-1.88 (m, 3H), 1.80 (dd, J=13.2, 4.4 Hz, 1H), 1.32 (t, J=12.5 Hz, 1H), 1.20 (d, J=12.8 Hz, 1H), 1.06-0.97 (m, 1H), 0.94 (t, J=7.6 Hz, 3H), 0.71-0.62 (m, 1H), 0.62-0.54 (m, 1H), 0.50-0.41 (m, 1H), 0.40-0.33 (m, 1H). LC/MS, m/z=401 [M+H]$^+$ (Calc: 400).

N-((4bR,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)isobutyramide TFA salt (Compound 58): $^1$H NMR (400 MHz, DMSO-d$_6$): δ 9.07 (br. s., 1H), 8.78 (br. s., 1H), 7.35 (d, J=8.8 Hz, 1H), 6.94-6.85 (m, 2H), 6.57 (dd, J=8.4, 2.2 Hz, 1H), 5.83 (s, 1H), 4.36-4.26 (m, 1H), 4.18 (br. s., 1H), 3.82 (br. s., 1H), 3.70 (d, J=4.6 Hz, 1H), 3.33-3.03 (m, 3H), 2.89 (d, J=11.0 Hz, 1H), 2.81-2.69 (m, 1H), 2.40 (d, J=12.5 Hz, 1H), 2.36-2.24 (m, 2H), 2.22-2.11 (m, 1H), 1.99-1.90 (m, 1H), 1.85 (t, J=12.7 Hz, 1H), 1.45 (dd, J=12.5, 3.7 Hz, 1H), 1.15 (d, J=12.1 Hz, 1H), 1.08-0.98 (m, 1H), 0.95 (d, J=4.8 Hz, 2H), 0.93 (d, J=5.1 Hz, 2H), 0.71-0.61 (m, 1H), 0.62-0.53 (m, 1H), 0.50-0.43 (m, 1H), 0.43-0.33 (m, 1H). LC/MS, m/z=415 [M+H]$^+$ (Calc: 414).

(S)—N-((46R,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)-2-methylbutanamide TFA salt (Compound 59): $^1$H NMR (400 MHz, DMSO-d$_6$): δ 9.06 (s, 1H), 8.77 (br. s., 1H), 7.37 (d, J=9.0 Hz, 1H), 6.92-6.84 (m, 2H), 6.57 (dd, J=8.4, 2.2 Hz, 1H), 5.83 (s, 1H), 4.41-4.29 (m, 1H), 4.10 (br. s., 1H), 3.82 (br. s., 1H), 3.70 (d, J=3.7 Hz, 1H), 3.31-3.03 (m, 3H), 2.89 (d, J=11.2 Hz, 1H), 2.81-2.69 (m, 1H), 2.41 (d, J=12.3 Hz, 1H), 2.35-2.23 (m, 1H), 2.22-2.05 (m, 2H), 1.95 (d, J=12.1 Hz, 1H), 1.85 (t, J=12.5 Hz, 1H), 1.55-1.38 (m, 2H), 1.30-1.18 (m, 1H), 1.15 (d, J=12.3 Hz, 1H), 1.08-0.96 (m, 1H), 0.92 (d, J=6.8 Hz, 3H), 0.77 (t, J=7.4 Hz, 3H), 0.71-0.62 (m, 1H), 0.61-0.52 (m, 1H), 0.50-0.42 (m, 1H), 0.42-0.32 (m, 1H). LC/MS, m/z=429 [M+H]$^+$ (Calc: 428).

N-((4bR,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)-3-methylbutanamide TFA salt (Compound 60): $^1$H NMR (400 MHz, DMSO-d$_6$): δ 9.07 (br. s., 1H), 8.77 (br. s., 1H), 7.41 (d, J=8.8 Hz, 1H), 6.93-6.84 (m, 2H), 6.57 (dd, J=8.1, 2.2 Hz, 1H), 5.83 (s, 1H), 4.41-4.28 (m, 1H), 4.15 (br. s., 1H), 3.82 (br. s., 1H), 3.70 (d, J=4.6 Hz, 1H), 3.31-3.03 (m, 3H), 2.89 (d, J=11.2 Hz, 1H), 2.81-2.68 (m, 1H), 2.40 (d, J=12.5 Hz, 1H), 2.34-2.23 (m, 1H), 2.22-2.10 (m, 1H), 2.00-1.78 (m, 6H), 1.46 (dd, J=12.5, 3.7 Hz, 1H), 1.15 (d, J=12.3 Hz, 1H), 1.07-0.99 (m, 1H), 0.83 (t, J=6.9 Hz, 6H), 0.70-0.62 (m, 1H), 0.62-0.53 (m, 1H), 0.49-0.42 (m, 1H), 0.42-0.34 (m, 1H). LC/MS, m/z=429 [M+H]$^+$ (Calc: 428).

N-((4bR,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)-4-methylpentanamide TFA salt (Compound 61): $^1$H NMR (400 MHz, DMSO-d$_6$): δ 9.00 (s, 1H), 8.70 (br. s., 1H), 7.38 (d, J=8.6 Hz, 1H), 6.87-6.77 (m, 2H), 6.49 (dd, J=8.3, 2.3 Hz, 1H), 5.76 (s, 1H), 4.29-4.19 (m, 1H), 4.10 (d, J=4.0 Hz, 1H), 3.74 (br. s., 1H), 3.63 (d, J=4.8 Hz, 1H), 3.24-2.96 (m, 4H), 2.82 (d, J=10.8 Hz, 1H), 2.73-2.63 (m, 1H), 2.33 (d, J=12.1 Hz, 1H), 2.29-2.15 (m, 1H), 2.15-2.04 (m, 1H), 2.01-1.82 (m, 3H), 1.76 (t, J=12.5 Hz, 1H), 1.46-1.33 (m, 2H), 1.32-1.21 (m, 2H), 1.08 (d, J=12.8 Hz, 1H), 1.02-0.88 (m, 1H), 0.76 (s, 3H), 0.74 (s, 3H), 0.63-0.55 (m, 1H), 0.54-0.45 (m, 1H), 0.42-0.35 (m, 1H), 0.34-0.28 (m, 1H). LC/MS, m/z=443 [M+H]$^+$ (Calc: 443).

N-((4bR,6R,7S,8aS,9R)-11-(cyclopropylmethyl)-3,6,8a-trihydroxy-6,7,8,8a,9,10-hexahydro-5H-9,4b-(epimi-noethano)phenanthren-7-yl)-5-methylhexanamide TFA salt (Compound 62): $^1$H NMR (400 MHz, DMSO-d$_6$): δ 9.06 (s, 1H), 8.77 (br. s., 1H), 7.42 (d, J=8.8 Hz, 1H), 6.93-6.83 (m, 2H), 6.56 (dd, J=8.3, 2.3 Hz, 1H), 5.82 (s, 1H), 4.36-4.27 (m, 1H), 4.16 (br. s., 1H), 3.82 (br. s., 1H), 3.69 (d, J=4.4 Hz, 1H), 3.31-3.03 (m, 3H), 2.89 (d, J=11.4 Hz, 1H), 2.81-2.70 (m, 1H), 2.40 (d, J=13.0 Hz, 1H), 2.36-2.22 (m, 2H), 2.20-2.10 (m, 1H), 2.03-1.90 (m, 3H), 1.83 (t, J=12.4 Hz, 1H), 1.53-1.37 (m, 4H), 1.19-0.95 (m, 4H), 0.83 (d, J=6.8 Hz, 6H), 0.70-0.61 (m, 1H), 0.61-0.53 (m, 1H), 0.49-0.41 (m, 1H), 0.41-0.34 (m, 1H). LC/MS, m/z=457 [M+H]$^+$ (Calc: 456).

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide TFA salt (Compound 63): $^1$H NMR (400 MHz, DMSO-$d_6$): δ 9.35 (s, 0.4H), 9.07 (s, 0.6H), 8.77 (br. s., 1H), 7.48 (d, J=8.4 Hz, 0.4H), 7.43 (d, J=8.8 Hz, 0.6H), 6.98 (d, J=8.4 Hz, 0.4H), 6.92-6.85 (m, 1.2H), 6.80 (d, J=2.2 Hz, 0.4H), 6.65 (dd, J=8.3, 2.3 Hz, 0.4H), 6.56 (dd, J=8.3, 2.3 Hz, 0.6H), 6.54 (s, 0.6H), 5.96 (s, 0.4H), 5.82 (s, 0.6H), 4.61 (d, J=5.1 Hz, 0.4H), 4.35-4.26 (m, 0.6H), 4.17 (d, J=4.0 Hz, 0.6H), 4.13-4.00 (m, 0.4H), 3.85-3.79 (m, 0.6H), 3.77-3.67 (m, 1H), 3.30-3.17 (m, 3H), 3.13-2.98 (m, 1H), 2.89 (d, J=10.8 Hz, 1H), 2.81-2.70 (m, 1H), 2.44-2.10 (m, 4H), 2.03-1.88 (m, 3H), 1.88-1.75 (m, 1H), 1.53-1.37 (m, 4H), 1.31 (t, J=12.7 Hz, 0.6H), 1.23-0.96 (m, 5H), 0.83 (d, J=1.8 Hz, 3H), 0.81 (d, J=1.8 Hz, 3H), 0.70-0.61 (m, 1H), 0.61-0.53 (m, 1H), 0.49-0.41 (m, 1H), 0.41-0.33 (m, 1H). LC/MS, m/z=457 [M+H]$^+$ (Calc: 456).

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclopropanecarboxamide TFA salt (Compound 64): $^1$H NMR (400 MHz, DMSO-$d_6$): δ 9.08 (s, 1H), 8.78 (br. s., 1H), 7.80 (d, J=9.0 Hz, 1H), 6.94-6.85 (m, 2H), 6.57 (dd, J=8.3, 2.3 Hz, 1H), 5.82 (s, 1H), 4.41-4.31 (m, 1H), 4.29 (d, J=4.2 Hz, 1H), 3.80 (br. s., 1H), 3.68 (d, J=4.2 Hz, 1H), 3.30-3.04 (m, 3H), 2.89 (d, J=11.0 Hz, 1H), 2.79-2.70 (m, 1H), 2.40 (d, J=11.9 Hz, 1H), 2.35-2.23 (m, 1H), 2.21-2.10 (m, 1H), 1.94 (d, J=11.9 Hz, 1H), 1.86 (t, J=12.5 Hz, 1H), 1.59-1.49 (m, 1H), 1.46 (dd, J=12.5, 4.0 Hz, 1H), 1.15 (d, J=12.8 Hz, 1H), 1.09-0.98 (m, 1H), 0.71-0.51 (m, 6H), 0.49-0.42 (m, 1H), 0.41-0.32 (m, 1H). LC/MS, m/z=413 [M+H]$^+$ (Calc: 412).

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclohexanecarboxamide TFA salt (Compound 65): $^1$H NMR (400 MHz, DMSO-$d_6$): δ 9.35 (br. s., 0.3H), 9.07 (br. s., 0.7H), 8.77 (br. s., 1H), 7.36 (d, J=8.4 Hz, 0.3H), 7.26 (d, J=8.6 Hz, 0.7H), 6.98 (d, J=8.6 Hz, 0.3H), 6.94-6.84 (m, 1.4H), 6.80 (d, J=2.0 Hz, 0.3H), 6.66 (dd, J=8.1, 2.2 Hz, 0.3H), 6.57 (dd, J=8.4, 2.2 Hz, 0.7H), 5.94 (s, 0.3H), 5.82 (s, 0.7H), 4.36-4.25 (m, 1H), 4.14 (br. s., 1H), 4.07-4.00 (m, 0.3H), 3.81 (br. s., 0.7H), 3.75 (d, J=6.2 Hz, 0.3H), 3.70 (d, J=4.4 Hz, 0.7H), 3.36-2.97 (m, 3H), 2.89 (d, J=11.4 Hz, 1H), 2.82-2.69 (m, 1H), 2.40 (d, J=12.5 Hz, 1H), 2.36-1.73 (m, 5H), 1.72-1.52 (m, 5H), 1.44 (dd, J=12.4, 3.4 Hz, 1H), 1.36-1.08 (m, 6H), 1.07-0.96 (m, 1H), 0.70-0.62 (m, 1H), 0.62-0.52 (m, 1H), 0.48-0.42 (m, 1H), 0.42-0.33 (m, 1H). LC/MS, in/z=449 [M+H]$^+$ (Calc: 448).

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)benzamide TFA salt (Compound 66): $^1$H NMR (400 MHz, DMSO-$d_6$): δ 9.03 (s, 1H), 8.76 (br. s., 1H), 7.88 (d, J=8.4 Hz, 1H), 7.81-7.75 (m, 2H), 7.44-7.38 (m, 1H), 7.37-7.30 (m, 2H), 6.89-6.81 (m, 2H), 6.54-6.50 (m, 1H), 5.84 (s, 1H), 4.55-4.46 (m, 1H), 4.24 (d, J=4.0 Hz, 1H), 3.90 (br. s., 1H), 3.65 (d, J=4.6 Hz, 1H), 3.27-3.13 (m, 3H), 3.10-2.99 (m, 1H), 2.85 (d, J=11.2 Hz, 1H), 2.75-2.66 (m, 1H), 2.39 (d, J=13.9 Hz, 1H), 2.31-2.08 (m, 2H), 2.04 (t, J=12.7 Hz, 1H), 1.95 (d, J=12.1 Hz, 1H), 1.48 (dd, J=12.5, 3.5 Hz, 1H), 1.10 (d, J=12.3 Hz, 1H), 0.63-0.55 (m, 1H), 0.55-0.47 (m, 1H), 0.44-0.36 (m, 1H), 0.36-0.28 (m, 1H). LC/MS, m/z=449 [M+H]$^+$ (Calc: 448).

(4bR,6R,7S,8aS,9R)-11-(cyclopropylmethyl)-7-isobutyl-5,6,7,8,9,10-hexahydro-8 aH-9,4b-(epiminoethano)phenanthrene-3,6,8a-triol TFA salt (Compound 67): $^1$H NMR (400 MHz, DMSO-$d_6$): δ 8.98 (s, 1H), 8.63 (br. s., 1H), 6.86-6.76 (m, 2H), 6.50 (dd, J=8.3, 2.3 Hz, 1H), 5.49 (s, 1H), 3.68 (br. s., 1H), 3.56 (d, J=4.0 Hz, 1H), 3.48 (br. s., 1H), 3.26-3.00 (m, 3H), 2.81 (d, J=11.7 Hz, 1H), 2.74-2.62 (m, 1H), 2.33-2.27 (m, 1H), 2.27-2.15 (m, 1H), 2.15-2.06 (m, 1H), 2.03-1.91 (m, 1H), 1.81 (dd, J=14.4, 2.8 Hz, 1H), 1.56-1.43 (m, 2H), 1.23 (dd, J=12.8, 2.9 Hz, 1H), 1.10-0.99 (m, 2H), 0.99-0.90 (m, 1H), 0.87-0.80 (m, 1H), 0.78 (d, J=1.5 Hz, 3H), 0.76 (d, J=1.3 Hz, 3H), 0.64-0.55 (m, 1H), 0.55-0.47 (m, 1H), 0.44-0.37 (m, 1H), 0.36-0.28 (m, 1H). LC/MS, m/z=386 [M+H]$^+$ (Calc: 385).

Example 14

(4bS,9R)-11-(cyclopropylmethyl)-3-hydroxy-5,6,9,10-tetrahydro-7H-9,4b-(epiminoethano)phenanthren-7-one (Compound 68)

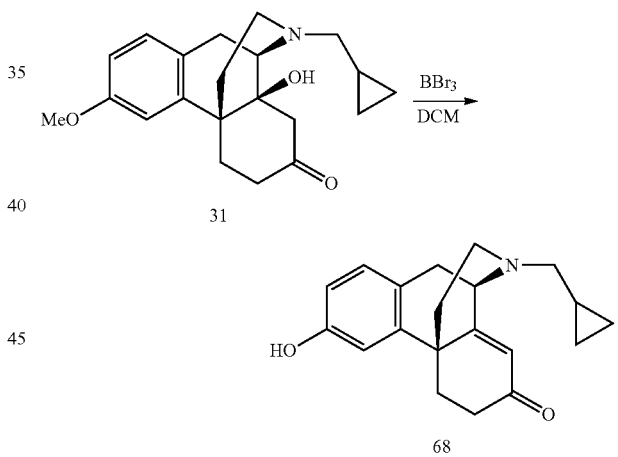

A 1M solution of BBr$_3$ in DCM (2.0 mL, 2.0 mmol) was added slowly to Compound 31 (171 mg, 0.50 mmol) in DCM (2 mL). The solution was stirred at RT for 2.5 h then slowly quenched with MeOH, concentrated, and purified by MPLC (SiO$_2$, 0-20% (10% NH$_4$OH in MeOH) in DCM) to give Compound 68: $^1$H NMR (400 MHz, DMSO-$d_6$): δ 9.12 (s, 1H), 6.83 (d, J=8.4 Hz, 1H), 6.62 (d, J=2.4 Hz, 1H), 6.51 (dd, J=8.3, 2.3 Hz, 1H), 5.76 (s, 1H), 3.66 (d, J=6.2 Hz, 1H), 3.09 (d, J=17.6 Hz, 1H), 2.73 (dd, J=17.6, 6.4 Hz, 1H), 2.64 (dd, J=12.7, 3.2 Hz, 1H), 2.40-2.18 (m, 5H), 2.09-1.88 (m, 3H), 1.33 (d, J=12.3 Hz, 1H), 0.77-0.65 (m, 1H), 0.42-0.29 (m, 2H), 0.08-0.07 (m, 2H). LC/MS, m/z=310 [M+H]$^+$ (Calc: 309).

Example 15

Synthesis of (4bS,6R,8R,8aS,9R)-6-(2-hydroxyethoxy)-3-methoxy-11-methyl-6,7,8,8a,9,10-hexahydro-5H-9,4b-(epiminoethano)phenanthren-8-ol (Compound 118), (4bS,6S,8R,8aS,9R)-6-(2-hydroxyethoxy)-3-methoxy-11-methyl-6,7,8,8a,9,10-hexahydro-5H-9,4b-(epiminoethano)phenanthren-8-ol (Compound 119), (4bS,6R,8R,8aS,9R)-6-(2-hydroxyethoxy)-11-methyl-6,7,8,8a,9,10-hexahydro-5H-9,4b-(epiminoethano)phenanthrene-3,8-diol (Compound 120), and (4bS,6S,8R,8aS,9R)-6-(2-hydroxyethoxy)-11-methyl-6,7,8,8a,9,10-hexahydro-5H-9,4b-(epiminoethano)phenanthrene-3,8-diol (Compound 121)

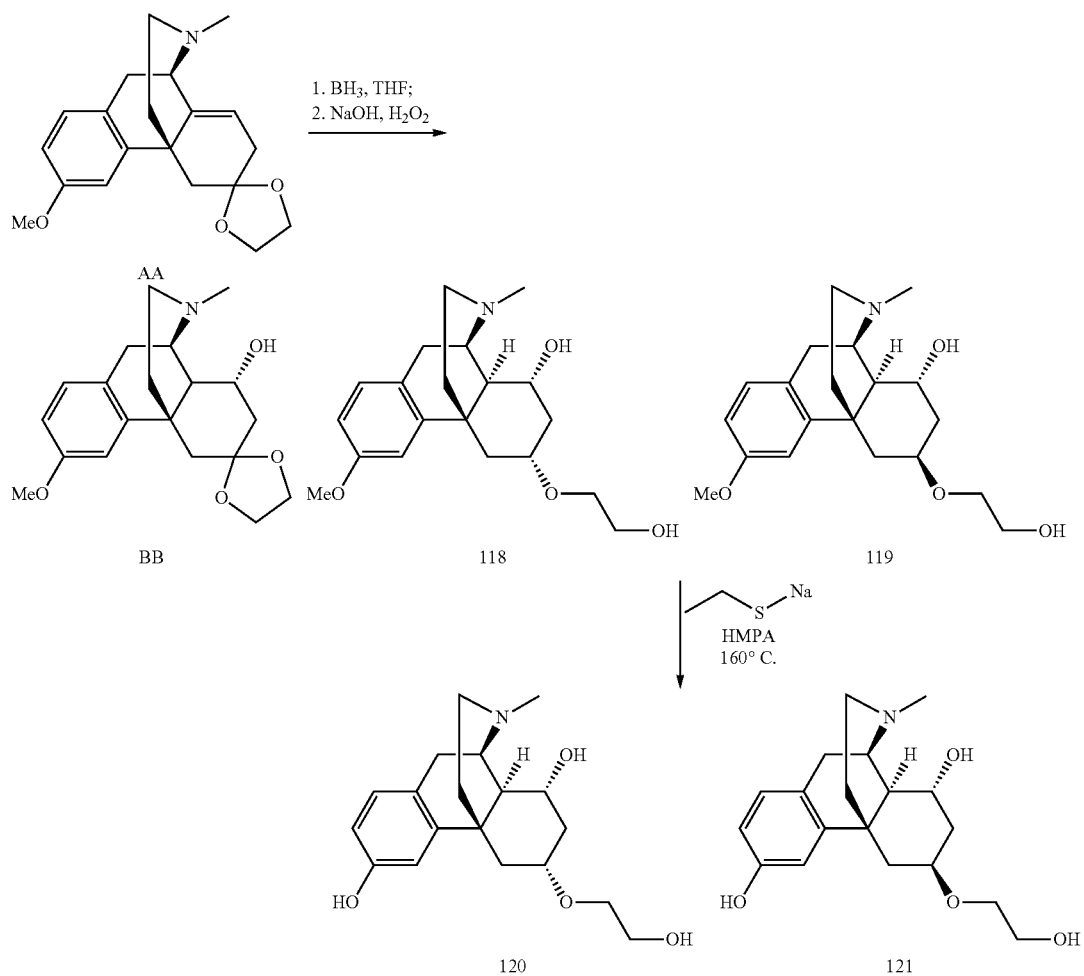

BH$_3$-THF complex (1N in THF, 275 mL, 275 mmol, 10 eq, Sigma-Aldrich) was added to a solution of olefin AA (9 g, 27.5 mmol, 1 eq) in THF (200 mL) at 0° C. The mixture was stirred at room temperature (RT) overnight. The mixture was cooled to 0° C. 10% NaOH (50 mL) then H$_2$O$_2$ (25 mL) were added and stirred for 3 hr at RT. The condenser was placed and the mixture was heated to reflux for 1 hr. THF was removed. DCM and water were added. The layer was separated and the aq. layer was extracted with DCM. The organic layer was dried over MgSO4 and concentrated. The concentrated crude oil was purified by flash chromatography (SiO$_2$, 0-100%, Hexane/Acetone) to obtain white foam. 1.73 g (18% yield) of the mixture of Compound 118 and 119 were obtained. The mixture of diastereoisomers (100 mg) were separated by reverse-phase prep HPLC (C18, 0-100% 0.1% TFA in water/0.1% TFA in ACN).

Compound 118: $^1$H NMR (METHANOL-d$_4$) δ: 7.02 (d, J=8.5 Hz, 1H), 6.77 (d, J=2.5 Hz, 1H), 6.67-6.74 (m, 1H), 3.99 (td, J=11.2, 4.2 Hz, 1H), 3.89 (d, J=5.5 Hz, 1H), 3.67 (s, 3H), 3.53-3.66 (m, 5H), 3.22-3.30 (m, 1H), 2.95 (dd, J=18.8, 5.9 Hz, 1H), 2.79-2.86 (m, 1H), 2.67 (s, 3H), 2.62-2.65 (m, 1H), 2.38-2.50 (m, 2H), 2.06 (td, J=13.6, 4.8 Hz, 1H), 1.63 (d, J=10.9 Hz, 1H), 1.36 (t, J=12.1 Hz, 1H), 1.28 (d, J=14.1 Hz, 1H), 1.19 (q, J=11.5 Hz, 1H). LC/MS, m/z=348.4 [M+H]$^+$ (Calc: 347.45).

Compound 119: $^1$H NMR (METHANOL-d$_4$) δ: 7.02 (d, J=8.5 Hz, 1H), 6.76 (d, J=2.5 Hz, 1H), 6.71 (dd, J=8.4, 2.5 Hz, 1H), 4.25 (td, J=11.2, 4.1 Hz, 1H), 4.03 (d, J=5.7 Hz, 1H), 3.83-3.89 (m, 1H), 3.67 (s, 3H), 3.58-3.64 (m, 2H), 3.47-3.57 (m, 2H), 3.23-3.31 (m, 1H), 3.03 (dd, J=19.0, 6.0 Hz, 1H), 2.83-2.94 (m, 2H), 2.74 (s, 3H), 2.61 (d, J=14.6 Hz, 1H), 2.41-2.53 (m, 1H), 2.30-2.38 (m, 1H), 1.73 (d, J=11.1 Hz, 1H), 1.57 (dd, J=14.5, 3.6 Hz, 1H), 1.34-1.43 (m, 1H), 1.28 (dd, J=14.1, 2.8 Hz, 1H). LC/MS, m/z=348.1 [M+H]$^+$ (Calc: 347.45).

The mixture of Compound 118 and 119 (200 mg, 0.57 mmol, 1 eq) and sodium ethanolate (169 mg, 2.01 mmol, 3.5 eq, Sigma-Aldrich) in HMPA (2 mL) was stirred at 120° C.

for 3 hr. The mixture was quenched with sat. NH$_4$Cl and DCM were added. The aq. layer was extracted with DCM. The organic layer was dried over MgSO4 and purified by flash chromatography (SiO$_2$, 0-40%, DCM/10% NH4OH in MeOH). The mixture of diastereoisomers were separated by reverse-phase prep HPLC (C18, 0-100% 0.1% TFA in water/0.1% TFA in ACN). 20-30 mg (32-41% yield) of the Compound 120 and Compound 121 were obtained.

Compound 120: $^1$H NMR (DMSO-d$_6$) δ: 6.82 (d, J=8.3 Hz, 1H), 6.56 (d, J=2.4 Hz, 1H), 6.46 (dd, J=8.2, 2.4 Hz, 1H), 3.92-4.04 (m, 1H), 3.49-3.62 (m, 1H), 3.44 (s, 4H), 3.31 (d, J=5.0 Hz, 1H), 2.99 (d, J=17.9 Hz, 1H), 2.35-2.42 (m, 2H), 2.26 (t, J=6.1 Hz, 2H), 2.20 (s, 3H), 1.80-1.96 (m, 2H), 1.20 (d, J=10.1 Hz, 1H), 0.94-1.15 (m, 2H), 0.89 (d, J=9.7 Hz, 1H). LC/MS, m/z=334.2 [M+H]$^+$ (Calc: 333.42).

Compound 121: $^1$H NMR (METHANOL-d$_4$) δ: 7.04 (d, J=8.3 Hz, 1H), 6.76 (d, J=2.5 Hz, 1H), 6.68 (dd, J=8.3, 2.4 Hz, 1H), 4.31 (td, J=11.2, 4.1 Hz, 1H), 4.16 (d, J=4.8 Hz, 1H), 3.94-4.03 (m, 1H), 3.70-3.78 (m, 2H), 3.59-3.67 (m, 2H), 3.38 (s, 1H), 3.08-3.19 (m, 1H), 2.93-3.06 (m, 2H), 2.88 (s, 3H), 2.57-2.72 (m, 2H), 2.48 (d, J=13.5 Hz, 1H), 1.86 (d, J=11.0 Hz, 1H), 1.69 (dd, J=14.5, 3.6 Hz, 1H), 1.45-1.58 (m, 1H), 1.39 (d, J=14.4 Hz, 1H). LC/MS, m/z=334.2 [M+H]$^+$ (Calc: 333.42).

Example 16

Synthesis of (4bR,6R,8aS,9R)-6-(dimethylamino)-11-methyl-5,6,7,8,9,10-hexahydro-8aH-9,4b-(epiminoethano)phenanthrene-3,8a-diol (Compound 107)

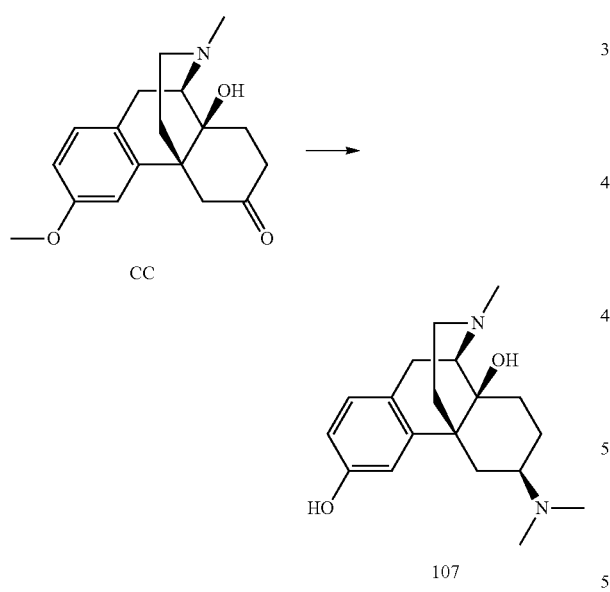

To a suspension of Compound CC (15.04 g, 49.9 mmol, 1 eq) in DMF (100 mL) was added iodocyclohexane (60 mL). A Dean-Starke distillation trap was added and the reaction heated at reflux for 5 hours while periodically draining the distillate from the trap. The reaction mixture was concentrated in vacuo, methanol was added and the mixture concentrated a second time in vacuo. The residue was diluted with 50 mL water and washed twice with 50 mL DCM then the layers were allowed to stand overnight. The aqueous layer was basified with 40 mL concentrated NH$_4$OH and extracted three times with 50 mL 3:1 CHCl$_3$/EtOH. The combined organics were washed once with 25 mL water and 5 mL concentrated NH$_4$OH, then concentrated down to 20-25 mL volume and the solid that formed was filtered off, rinsed once with 10 mL EtOH and purified over silica gel with 0-22% (10% NH$_4$OH in MeOH) in DCM. The product fractions were evaporated in vacuo to a residue.

The residue was triturated with 20 mL EtOH, filtered and washed with an additional 5 mL EtOH then dried under vacuum at 60 C to give Compound 107 as a light tan powder (2.605 g, 8.23 mmol, 16% yield).

Compound 107: $^1$H NMR δ$_H$ (400 MHz, DMSO-d$_6$): 9.06 (s, 1H), 6.90 (d, J=8.3 Hz, 1H), 6.65 (d, J=2.4 Hz, 1H), 6.51 (dd, J=8.2, 2.4 Hz, 1H), 4.25 (s, 1H), 3.04-2.94 (m, 1H), 2.63-2.53 (m, 2H), 2.30-2.18 (m, 5H), 2.16 (s, 6H), 2.01-1.86 (m, 3H), 1.76-1.59 (m, 2H), 1.45-1.27 (m, 3H), 0.95-0.85 (m, 1H). LC/MS, m/z=317.3 [M+H]$^+$ (Calc: 316).

Example 17

Synthesis of (4bR,6R,7S,8aS,9R)-11-methyl-7-(methylamino)-5,6,7,8,9,10-hexahydro-8aH-9,4b-(epiminoethano)phen-anthrene-3,6,8a-triol (Compound 116)

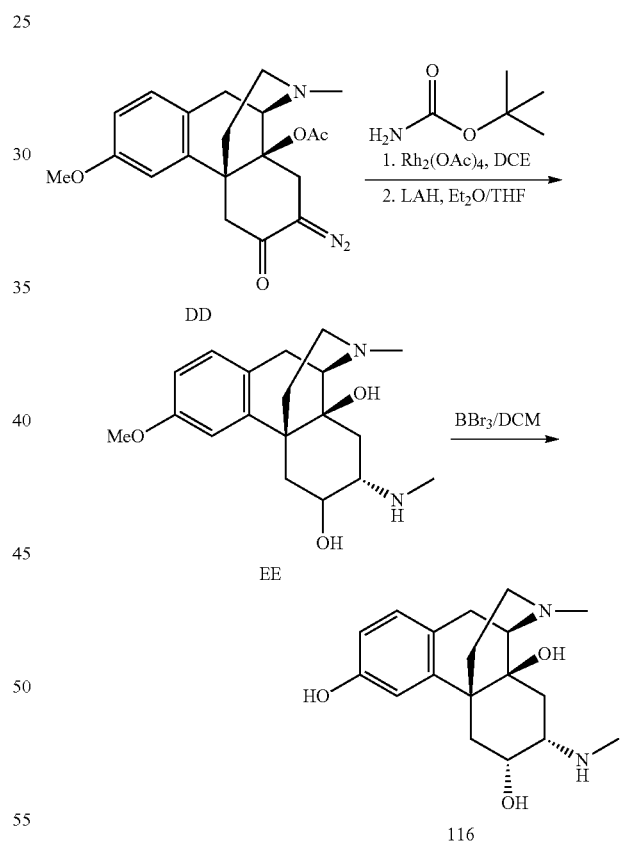

Compound DD (369 mg, 1 mmol) in 3 mL DCE was added dropwise to O-t-butyl carbamate (141 mg, 1.2 mmol) and Rh$_2$(OAc)$_4$ (9 mg, 0.02 mmol) in 2 mL DCE at 80° C. and the solution was heated at 80° C. for 30 min. The reaction mixture was concentrated and 5 mL THF was added. LAH (1M in THF, 2 mL, 2 mmol) was added slowly at 0° C. and the solution was stirred at 0° C. for 90 min. Additional LAH (2 mL, 2 mmol) was added and the solution allowed to warm to RT over 2.5 h. Another aliquot of LAH (2 mL, 2 mmol) was added and the solution heated at 60° C.

Additional LAH (2 mL, 2 mmol) was added after 20 h and 28 h and heating continued for 48 h. The reaction mixture was cooled to room temperature (RT), slowly quenched with MeOH, and concentrated. Purification by MPLC (0-20% (10% NH$_4$OH/MeOH)/DCM) led to the isolation of Compound EE as a yellow foam. (163 mg, 49%).

A 1M solution of BBr$_3$ in DCM (2 mL, 2 mmol) was added to Compound EE (163 mg, 0.5 mmol) in 2 mL DCM. The solution was stirred at RT for 3.75 h and an additional aliquot of BBr$_3$ in DCM (1 mL, 1 mmol) was added. The solution was stirred at RT for an additional 3.25 h, quenched with 7M ammonia in MeOH, filtered over celite, and concentrated. Purification by MPLC (0-20% (10% NH$_4$OH/MeOH)/DCM) followed by preparatory HPLC [0-20% MeCN/H$_2$O (0.01% TFA)] yielded Compound 116 as its bis-TFA salt.

Compound 116—2TFA salt: $^1$H NMR (DMSO-d$_6$) δ: 9.15 (br. s, 2H), 8.44-8.34 (m, 1H), 8.34-8.23 (m, 1H), 6.93 (d, J=8.4 Hz, 1H), 6.87 (d, J=2.3 Hz, 1H), 6.60 (dd, J=8.3, 2.3 Hz, 1H), 5.92 (s, 1H), 5.20 (d, J=3.7 Hz, 1H), 4.12 (br. s., 1H), 3.45-3.40 (m, 3H, overlapped with water), 3.25 (d, J=19.6 Hz, 1H), 3.05 (dd, J=19.4, 5.4 Hz, 1H), 2.97 (d, J=12.0 Hz, 1H), 2.78 (d, J=5.0 Hz, 3H), 2.48-2.43 (m, 3H), 2.38-2.27 (m, 1H), 2.10 (td, J=13.7, 4.5 Hz, 1H), 1.90 (d, J=12.7 Hz, 1H), 1.79 (d, J=8.3 Hz, 2H), 1.21 (d, J=11.8 Hz, 1H). LC/MS, m/z=319 [M+H]$^+$ (Calc: 318).

Likewise, the following compounds were prepared from Compound DD and acetamides:

Compound 113—2TFA Salt: $^1$H NMR (DMSO-d$_6$) δ: 9.18 (br. s., 2H), 8.39-8.17 (m, 2H), 6.93 (d, J=8.4 Hz, 1H), 6.89 (d, J=2.2 Hz, 1H), 6.60 (dd, J=8.3, 2.3 Hz, 1H), 6.02 (s, 1H), 5.22 (d, J=3.6 Hz, 1H), 4.12 (br. s., 1H), 3.54-3.48 (m, 2H), 3.45 (d, J=4.8 Hz, 2H), 3.26 (d, J=19.6 Hz, 1H), 3.06 (d, J=5.7 Hz, 1H), 3.04-2.94 (m, 1H), 2.91-2.82 (m, 2H), 2.78 (d, J=4.8 Hz, 3H), 2.50 (br. s., 3H), 2.39-2.27 (m, 1H), 2.11 (td, J=13.4, 4.4 Hz, 1H), 1.96-1.90 (m, 1H), 1.88-1.75 (m, 2H), 1.20 (d, J=12.0 Hz, 1H), 1.14 (t, J=7.2 Hz, 3H). LC/MS, m/z=333 [M+H]$^+$ (Calc: 332).

Compound 114—2TFA salt: $^1$H NMR (DMSO-d$_6$) δ: 9.46 (br. s., 1H), 9.21 (br. s., 1H), 8.26 (br. s., 2H), 7.04 (d, J=8.4 Hz, 1H), 6.80 (d, J=2.3 Hz, 1H), 6.70 (dd, J=8.3, 2.3 Hz, 1H), 6.20 (s, 1H), 5.61 (br. s., 1H), 3.49-3.43 (m, 1H), 3.31 (d, J=19.7 Hz, 1H), 3.26-3.17 (m, 1H), 3.08-2.84 (m, 4H), 2.81 (d, J=4.8 Hz, 3H), 2.46-2.29 (m, 2H), 2.16 (td, J=13.5, 4.5 Hz, 1H), 2.06 (dd, J=13.1, 4.1 Hz, 1H), 1.93 (t, J=12.5 Hz, 1H), 1.47 (t, J=12.6 Hz, 1H), 1.26 (d, J=12.0 Hz, 1H), 1.15 (t, J=7.2 Hz, 3H). LC/MS, m/z=333 [M+H]$^+$ (Calc: 332).

Example 18

In similar manners as those set forth in the above examples, the following compounds were also made:

(4bS)-4-hydroxy-3,6-dimethoxy-11-methyl-9,10-dihydro-7H-9,4b-(epiminoethano)phenanthren-7-one (Compound 101): LC/MS, m/z=[M+H]$^+$ (Calc: 327.37).

(4bR,6S,7S,8aS,9R)-7-(benzyloxy)-11-(cyclopropylmethyl)-3-methoxy-5,6,7,8,9,10-hexahydro-9,4b-(epiminoethano)-6,8a-epoxyphenanthrene (Compound 102): Elemental Analysis: C$_{19}$H$_{21}$O$_4$N: Calc.: C, 69.71%; H, 6.47%; N, 4.28%. Found: C, 69.64%; H, 6.56%; N, 4.30%.

Compound 103—TFA salt: $^1$H NMR (DMSO-d$_6$) δ: 9.06 (br. s., 1H), 8.68 (br. s., 1H), 7.29-7.23 (m, 2H), 7.21-7.14 (m, 3H), 6.91 (d, J=8.3 Hz, 1H), 6.87 (d, J=2.3 Hz, 1H), 6.59 (dd, J=8.3, 2.3 Hz, 1H), 5.54 (s, 1H), 3.74 (br. s., 1H), 3.70 (br. s., 1H), 3.61 (d, J=3.5 Hz, 1H), 3.30-3.20 (m, 1H), 3.20-3.06 (m, 2H), 2.87 (d, J=12.2 Hz, 1H), 2.78-2.69 (m, 1H), 2.59 (dd, J=12.9, 7.0 Hz, 1H), 2.41-2.22 (m, 4H), 2.16 (dd, J=13.3, 4.1 Hz, 1H), 1.87-1.79 (m, 1H), 1.68 (t, J=12.5 Hz, 1H), 1.37-1.27 (m, 1H), 1.09 (d, J=11.8 Hz, 1H), 1.05-0.96 (m, 1H), 0.68-0.60 (m, 1H), 0.59-0.51 (m, 1H), 0.47-0.41 (m, 1H), 0.40-0.32 (m, 1H). LC/MS, m/z=420 [M+H]$^+$ (Calc: 419).

Compound 104—TFA salt: $^1$H NMR (DMSO-d$_6$) δ: 9.13 (br. s., 1H), 9.07 (s, 1H), 7.38 (d, J=8.7 Hz, 1H), 6.90 (d, J=8.3 Hz, 1H), 6.87 (d, J=2.3 Hz, 1H), 6.56 (dd, J=8.3, 2.3 Hz, 1H), 5.72 (s, 1H), 4.32-4.22 (m, 1H), 4.17 (d, J=3.6 Hz, 1H), 3.81 (br. s., 1H), 3.32 (d, J=4.3 Hz, 1H), 3.24-3.16 (m, 1H), 3.10-2.99 (m, 1H), 2.91 (d, J=12.9 Hz, 1H), 2.74 (d, J=5.0 Hz, 3H), 2.39 (d, J=12.4 Hz, 1H), 2.35-2.24 (m, 2H), 2.12 (td, J=13.2, 4.1 Hz, 1H), 1.96-1.90 (m, 1H), 1.83 (t, J=12.6 Hz, 1H), 1.38 (dd, J=12.6, 3.9 Hz, 1H), 1.13 (d, J=11.6 Hz, 1H), 0.94 (d, J=4.3 Hz, 3H), 0.93 (d, J=4.3 Hz, 3H). LC/MS, m/z=375 [M+H]$^+$ (Calc: 374).

Compound 105—TFA salt (5:1 mixture of 6-α-OH:6-β-OH): $^1$H NMR (DMSO-d$_6$) δ: 9.35 (s, 0.2H), 9.12 (br. s., 1H), 9.07 (s, 1H), 7.46 (d, J=8.9 Hz, 1H), 7.00 (d, J=8.3 Hz, 0.2H), 6.90 (d, J=8.4 Hz, 1H), 6.86 (d, J=2.3 Hz, 1H), 6.80 (d, J=2.5 Hz, 0.2H), 6.66 (dd. J=7.9, 2.1 Hz, 0.2H), 6.56 (dd, J=8.3, 2.3 Hz, 1H), 5.86 (s, 0.2H), 5.72 (s, 1H), 4.32-4.22 (m, 1H), 4.16 (d, J=3.1 Hz, 1H), 4.04 (br. s., 0.2H), 3.81 (br. s., 1H), 3.33 (d, J=4.7 Hz, 1H), 3.20 (d, J=18.9 Hz, 1H), 3.03 (dd, J=19.8, 5.5 Hz, 1H), 2.91 (d, J=12.3 Hz, 1H), 2.73 (d, J=5.0 Hz, 3H), 2.44-2.24 (m, 2H), 2.23-2.06 (m, 2H), 2.00 (dd, J=7.6, 3.9 Hz, 4H), 1.81 (t, J=12.5 Hz, 1H), 1.70 (dd, J=13.6, 4.7 Hz, 0.2H), 1.50-1.28 (m, 5H), 1.29-1.20 (m, 0.2H), 1.18-1.09 (m, 1H), 0.81 (d, J=6.5 Hz, 7H). LC/MS, m/z=403 [M+H]$^+$ (Calc: 402).

Compound 106—TFA salt (9:1 mixture of 6-α-OH:6-β-OH): $^1$H NMR (DMSO-d$_6$, 400 MHz): δ=9.29 (s, 0.1H), 9.05 (br. s., 0.9H), 9.01 (br. s., 0.9H), 7.33-7.45 (m, 1.0H), 6.93 (d, J=8.4 Hz, 0.2H), 6.83 (d, J=8.4 Hz, 1.0H), 6.80 (d, J=2.2 Hz, 1.0H), 6.73 (d, J=2.1 Hz, 0.2H), 6.59 (dd, J=8.3, 2.3 Hz, 0.2H), 6.49 (dd, J=8.3, 2.3 Hz, 1.0H), 5.79 (s, 0.1H), 5.66 (s, 0.9H), 4.15-4.26 (m, 1.0H), 4.09 (br. s., 1.0H), 3.74 (br. s., 1.1H), 3.24-3.31 (m, 1.3H), 3.13 (d, J=19.1 Hz, 1.1H), 2.96 (dd, J=19.5, 5.5 Hz, 1.2H), 2.85 (d, J=12.3 Hz, 1.2H), 2.62-2.71 (m, 3.2H), 2.32 (d, J=12.4 Hz, 1.1H), 2.17-2.28 (m, 1.2H), 2.00-2.16 (m, 1.4H), 1.81-1.94 (m, 3.3H), 1.75 (t, J=12.6 Hz, 1.0H), 1.26-1.46 (m, 4.4H), 0.95-1.12 (m, 3.3H), 0.75 ppm (d, J=6.6 Hz, 6.6H). LC/MS, m/z=417 [M+H]$^+$ (Calc: 416).

Compound 108—TFA salt: $^1$H NMR (DMSO-d$_6$) δ: 9.09 (br. s., 1H), 9.03 (s, 1H), 7.89 (d, J=8.4 Hz, 1H), 7.81-7.76 (m, 2H), 7.44-7.39 (m, 1H), 7.38-7.29 (m, 2H), 6.87 (d, J=8.4 Hz, 1H), 6.82 (d, J=2.3 Hz, 1H), 6.51 (dd, J=8.3, 2.3 Hz, 1H), 5.72 (s, 1H), 4.53-4.41 (m, 1H), 4.23 (d, J=4.2 Hz, 1H), 3.89 (br. s., 1H), 3.16 (d, J=19.1 Hz, 1H), 2.99 (dd, J=19.2, 5.4 Hz, 1H), 2.87 (d, J=11.8 Hz, 1H), 2.69 (d, J=5.0 Hz, 3H), 2.37 (d, J=12.3 Hz, 1H), 2.31-2.18 (m, 1H), 2.16-1.98 (m, 2H), 1.93 (d, J=12.0 Hz, 1H), 1.42 (dd, J=12.7, 3.9 Hz, 1H), 1.14-1.05 (m, 1H). LC/MS, m/z=409 [M+H]$^+$ (Calc: 408).

Compound 109—TFA salt: $^1$H NMR (DMSO-d$_6$) δ: 9.05 (br. s., 2H), 6.90 (d, J=8.3 Hz, 1H), 6.85 (d, J=2.3 Hz, 1H), 6.57 (dd, J=8.3, 2.3 Hz, 1H), 5.44 (s, 1H), 3.78 (br. s., 1H), 3.27 (d, J=4.0 Hz, 1H), 3.21-3.12 (m, 1H), 3.12-3.02 (m, 1H), 2.91 (d, J=12.0 Hz, 1H), 2.74 (d, J=5.0 Hz, 3H), 2.36 (dd, J=14.4, 2.2 Hz, 1H), 2.32-2.23 (m, 1H), 2.12 (td, J=13.3, 4.3 Hz, 1H), 1.92-1.79 (m, 2H), 1.54 (t, J=12.7 Hz, 1H), 1.50-1.38 (m, 1H), 1.33-0.95 (m, 6H), 0.83 (d, J=6.5 Hz, 6H). 2 protons under water peak. LC/MS, m/z=360 [M+H]$^+$ (Calc: 359).

Compound 110—TFA salt (5:1 mixture of 6-α-OH:6-β-OH): $^1$H NMR (DMSO-$d_6$, 400 MHz): δ=9.31 (s, 0.1H), 9.05 (br. s., 1.9H), 6.98 (d, J=8.4 Hz, 0.1H), 6.90 (d, J=8.3 Hz, 0.8H), 6.85 (d, J=2.3 Hz, 0.9H), 6.76 (d, J=2.3 Hz, 0.2H), 6.64 (dd, J=8.3, 2.3 Hz, 0.2H), 6.57 (dd, J=8.3, 2.3 Hz, 1.0H), 5.58 (s, 0.1H), 5.44 (s, 0.8H), 4.17-4.68 (m, 0.3H), 3.78 (br. s., 1.0H), 3.27 (d, J=4.1 Hz, 1.4H), 3.14-3.21 (m, 1.2H), 3.03-3.11 (m, 1.3H), 2.92 (d, J=11.3 Hz, 1.4H), 2.77 (br. s., 0.3H), 2.74 (d, J=5.0 Hz, 2.7H), 2.20-2.44 (m, 2.8H), 2.08-2.20 (m, 1.5H), 1.92-2.03 (m, 1.1H), 1.63-1.90 (m, 5.3H), 1.54 (br. s., 5.9H), 1.20-1.34 (m, 2.1H), 0.89-1.19 ppm (m, 5.0H). LC/MS, m/z=372 [M+H]$^+$ (Calc: 371).

Compound 111—2TFA salt: $^1$H NMR (DMSO-$d_6$) δ: 9.65 (br. s., 1H), 9.12 (br. s., 1H), 8.81 (br. s., 1H), 8.36 (d, J=8.5 Hz, 1H), 6.93-6.86 (m, 2H), 6.58 (dd, J=8.3, 2.2 Hz, 1H), 5.93 (s, 1H), 4.47 (br. s., 1H), 4.38-4.28 (m, 1H), 3.87 (br. s., 1H), 3.77 (br. s., 2H), 3.72 (d, J=4.8 Hz, 1H), 3.32-3.15 (m, 2H), 3.13-3.03 (m, 1H), 2.92 (d, J=11.9 Hz, 1H), 2.83-2.78 (m, 1H), 2.76 (br. s., 6H), 2.43 (d, J=12.5 Hz, 1H), 2.37-2.25 (m, 1H), 2.16 (td, J=13.3, 4.1 Hz, 1H), 1.97 (d, J=12.2 Hz, 1H), 1.85 (t, J=12.5 Hz, 1H), 1.50 (dd, J=12.4, 3.8 Hz, 1H), 1.18 (d, J=12.2 Hz, 1H), 1.08-0.97 (m, 1H), 0.70-0.61 (m, 1H), 0.61-0.52 (m, 1H), 0.50-0.32 (m, 2H). LC/MS, m/z=430 [M+H]$^+$ (Calc: 429).

Compound 112—TFA salt: $^1$H NMR (DMSO-$d_6$) δ: 9.20 (br. s., 1H), 8.99 (s, 1H), 7.22 (d, J=8.3 Hz, 1H), 6.82 (d, J=8.3 Hz, 1H), 6.79 (d, J=2.3 Hz, 1H), 6.49 (dd, J=8.2, 2.4 Hz, 1H), 4.20 (br. s., 1H), 3.83-3.72 (m, 2H), 3.72-3.63 (m, 1H), 3.14 (br. s., 3H), 3.01-2.82 (m, 3H), 2.67-2.50 (m, 1H), 2.26 (d, J=6.7 Hz, 3H), 1.98 (d, J=12.0 Hz, 1H), 1.72-1.62 (m, 1H), 1.50-1.42 (m, 2H), 1.39 (d, J=12.1 Hz, 1H), 1.37-1.28 (m, 1H), 1.05-0.93 (m, 1H), 0.90-0.83 (m, 6H), 0.63-0.50 (m, 2H), 0.37-0.24 (m, 2H). LC/MS, m/z=399 [M+H]$^+$ (Calc: 398).

Compound 117—TFA salt: $^1$H NMR (DMSO-$d_6$) δ: 9.24 (s, 1H), 8.79 (br. s., 1H), 7.84 (d, J=4.4 Hz, 2H), 6.92 (d, J=8.4 Hz, 1H), 6.58 (dd, J=8.3, 2.3 Hz, 1H), 6.45 (d, J=2.2 Hz, 1H), 6.16 (s, 1H), 4.95 (d, J=3.0 Hz, 1H), 3.77 (d, J=4.5 Hz, 1H), 3.74-3.66 (m, 1H), 3.31-3.16 (m, 2H, overlapped with water), 3.11-3.03 (m, 1H), 2.89 (d, J=10.9 Hz, 1H), 2.79-2.70 (m, 1H), 2.55 (d, J=13.0 Hz, 1H), 2.25-2.15 (m, 1H), 2.14-2.05 (m, 1H), 1.97 (d, J=13.0 Hz, 1H), 1.86 (dd, J=9.7, 6.7 Hz, 1H), 1.81-1.68 (m, 3H), 1.46-1.34 (m, 2H), 1.33-1.22 (m, 1H), 1.16 (d, J=12.5 Hz, 1H), 1.06-0.94 (m, 3H), 0.77 (d, J=6.6 Hz, 6H), 0.64-0.57 (m, 1H), 0.57-0.49 (m, 1H), 0.44-0.29 (m, 2H). LC/MS, m/z=457 [M+H]$^+$ (Calc: 456).

Compound 115—TFA salt: $^1$H NMR (DMSO-$d_6$) δ: 9.37 (br. s., 1H), 8.78 (br. s., 1H), 7.49 (d, J=8.4 Hz, 1H), 6.98 (d, J=8.4 Hz, 1H), 6.81 (d, J=2.3 Hz, 1H), 6.66 (dd, J=8.3, 2.3 Hz, 1H), 5.97 (br. s., 1H), 4.11-4.00 (m, 1H), 3.76 (d, J=5.6 Hz, 1H), 3.34-3.16 (m, 3H), 3.06-2.97 (m, 1H), 2.90 (d, J=12.4 Hz, 1H), 2.83-2.73 (m, 1H), 2.44-2.32 (m, 1H), 2.26-2.15 (m, 2H), 1.94 (br. s., 3H), 1.85-1.73 (m, 1H), 1.56-1.37 (m, 4H), 1.31 (t, J=12.6 Hz, 1H), 1.07 (d, J=8.6 Hz, 4H), 0.82 (d, J=6.6 Hz, 6H), 0.70-0.61 (m, 1H), 0.61-0.53 (m, 1H), 0.48-0.41 (m, 1H), 0.40-0.33 (m, 1H). LC/MS, m/z=457 [M+H]$^+$ (Calc: 456).

Example 19

The following Tables provide results on the efficacy of binding and activity response of exemplified Compounds of the Invention at the μ- and κ-opioid receptors.

In TABLE 1, binding affinity of certain Compounds of the Invention to the μ-, and κ-opioid receptors in HEK-293 or CHO cells was determined as described above.

In TABLE 2, activity response of certain Compounds of the Invention at the μ- and κ-opioid receptors using HEK-293 or CHO cells was determined as described above for functional assays.

In TABLE 2A, activity response of certain Compounds of the Invention at the μ- and κ-opioid receptors using U-2 OS cells was determined as described above for functional assays.

In TABLE 3, the structures of certain exemplified compounds are shown.

TABLE 1

Binding Affinity of 7-Substituted Morphinan Compounds in HEK-293 or CHO cells

| | Ki (nM) | |
|---|---|---|
| Cpd. No. | μ | κ |
| 3 | 6137.00 ± 962.70 | 3015.00 ± 339.30 |
| 4 | 4586.00 ± 355.80 | 172.00 ± 12.80 |
| 7 | 10814.00 ± 843.20 | 7304.00 ± 1642.00 |
| 9 | | 597.00 ± 162.70 |
| 10 | 3.84 ± 1.36 | 0.057 ± 0.01 |
| 11 | 71.00 ± 28.10 | 0.29 ± 0.049 |
| 12 | 53.20 ± 8.90 | 0.29 ± 0.13 |
| 13 | 80.00 ± 27.10 | 0.51 ± 0.073 |
| 14 | 124.30 ± 43.50 | 0.56 ± 0.052 |
| 15 | 54.10 ± 10.10 | 0.53 ± 0.13 |
| 16 | 70.50 ± 13.80 | 0.48 ± 0.055 |
| 20 | 448.80 ± 53.50 | 3.23 ± 0.70 |
| 21 | 1012.00 ± 220.50 | 4.61 ± 1.05 |
| 22 | 250.90 ± 29.40 | 1.85 ± 0.22 |
| 24 | 8.42 ± 2.88 | 0.24 ± 0.021 |
| 55 | 200.80 ± 62.10 | 54.80 ± 8.83 |
| 56 | 54.20 ± 12.50 | 7.19 ± 0.87 |
| 57 | 44.90 ± 7.71 | 16.70 ± 2.61 |
| 63 | | 11.5 ± 0.97 |

TABLE 2

Activity Response of 7-Substituted Morphinan Compounds in HEK-293 or CHO cells

| | GTPγS (EC$_{50}$: nM, E$_{max}$: %) | | | |
|---|---|---|---|---|
| | μ | | κ | |
| Cpd. No. | EC$_{50}$ | E$_{max}$ | EC$_{50}$ | E$_{max}$ |
| 3 | 2749.00 ± 705.30 | 58.70 ± 4.18 | | |
| 4 | 6135.00 ± 1040.00 | 33.70 ± 2.96 | 7858.00 ± 435.50 | 55.80 ± 5.88 |
| 7 | 4912.00 ± 944.40 | 53.70 ± 4.37 | | |
| 9 | | | 597.0 ± 162.7 | |
| 10 | >20 μM | 2.50 | | |
| 11 | >20 μM | 6.33 ± 1.67 | | |

TABLE 2-continued

Activity Response of 7-Substituted Morphinan Compounds in HEK-293 or CHO cells

GTPγS (EC$_{50}$: nM, E$_{max}$: %)

| Cpd. No. | μ EC$_{50}$ | μ E$_{max}$ | κ EC$_{50}$ | κ E$_{max}$ |
|---|---|---|---|---|
| 12 | >20 μM | 5.33 ± 0.88 | | |
| 14 | >20 μM | 8.67 ± 2.96 | | |
| 15 | 1112 ± 446.6 | 11.3 ± 0.33 | | |
| 16 | 811.4 ± 441.9 | 9.00 ± 0.58 | | |
| 20 | >20 μM | 7.33 ± 0.88 | | |
| 22 | >20 μM | 5.00 ± 1.53 | | |
| 24 | >20 μM | 4.33 ± 1.45 | | |
| 34 | >20 μM | 1.00 ± 0.00 | 0.55 ± 0.23 | 32.00 ± 1.35 |
| 42 | 20.2 ± 7.83 | 16.6 ± 1.63 | | |
| 45 | 307.6 ± 121.7 | 15.3 ± 1.86 | | |
| 46 | >20 μM | 7.67 ± 3.48 | | |
| 50 | >20 μM | 1.00 ± 0.00 | 29.20 ± 2.21 | 45.70 ± 2.19 |
| 55 | >20 μM | 1.00 ± 0.00 | 203.10 ± 20.20 | 13.30 ± 0.88 |
| 56 | >20 μM | 1.00 ± 0.00 | 71.80 ± 8.76 | 53.00 ± 0.58 |
| 57 | >20 μM | 1.50 ± 0.00 | 26.10 ± 6.87 | 37.20 ± 3.07 |
| 58 | | | | |
| 62 | 54.7 ± 4.52 | 23.3 ± 0.67 | | |
| 63 | 81.2 ± 8.25 | 23.3 ± 1.33 | 23.0 ± 4.32 | 21.2 ± 0.44 |
| 68 | >20 μM | 6.00 ± 3.00 | | |
| 102 | 1519 ± 465.3 | 10.5 ± 1.26 | | |
| 103 | >20 μM | 1.00 ± 0.00 | | |
| 104 | 15454 ± 1323 | 23.0 ± 1.53 | | |
| 105 | 3653 ± 293.6 | 77.0 ± 2.65 | | |
| 106 | 635.5 ± 43.7 | 82.3 ± 1.86 | | |
| 107 | 1294 ± 20.3 | 36.3 ± 1.20 | | |
| 108 | 2188 ± 211.5 | 48.4 ± 0.66 | | |
| 109 | 1875 ± 203.1 | 41.1 ± 3.25 | | |
| 110 | >20 μM | 42.7 ± 32.7 | | |
| 111 | >20 μM | 1.67 ± 0.67 | | |
| 112 | 66.7 ± 27.5 | 8.61 ± 0.31 | | |
| 113 | >20 μM | 3.62 ± 3.99 | | |
| 114 | >20 μM | 9.47 ± 0.74 | | |
| 115 | >20 μM | −1.04 | | |
| 116 | 13757 ± 599.7 | 28.9 ± 1.26 | | |
| 117 | 23.0 ± 3.59 | 14.1 ± 1.20 | | |
| 118 | >20 μM | 31.8 ± 5.76 | | |
| 119 | >20 μM | 24.2 ± 3.04 | | |
| 120 | 436.2 ± 34.7 | 36.3 ± 1.43 | | |
| 121 | 1961 ± 876.4 | 16.6 ± 1.97 | | |

TABLE 2A

Activity Response of 7-Substituted Morphinan Compounds in U2-OS cells

GTPγS (EC$_{50}$: nM, E$_{max}$: %)

| Cpd. No. | μ EC$_{50}$ | μ E$_{max}$ | κ EC$_{50}$ | κ E$_{max}$ |
|---|---|---|---|---|
| 9 | 573.80 ± 87.20 | 36.30 ± 0.88 | | |
| 10 | 4.69 ± 0.74 | 33.00 ± 1.15 | 0.79 ± 0.07 | 100.70 ± 6.23 |
| 11 | 37.90 ± 12.00 | 70.00 ± 8.08 | 2.75 ± 0.48 | 119.00 ± 0.58 |
| 12 | 32.70 ± 2.82 | 64.70 ± 5.17 | 5.06 ± 0.29 | 104.70 ± 1.76 |
| 13 | 38.90 ± 4.90 | 66.30 ± 5.78 | 2.13 ± 0.41 | 117.30 ± 1.86 |
| 14 | 85.60 ± 3.31 | 74.30 ± 2.19 | 5.47 ± 0.30 | 112.00 ± 5.13 |
| 15 | 41.50 ± 8.55 | 76.30 ± 3.38 | 12.80 ± 1.30 | 108.00 ± 2.65 |
| 16 | 53.70 ± 11.50 | 78.00 ± 3.61 | 15.00 ± 1.15 | 105.00 ± 2.89 |
| 20 | 393.50 ± 57.80 | 62.70 ± 4.26 | 62.30 ± 2.37 | 111.30 ± 2.40 |
| 21 | | | 120.20 ± 2.94 | 105.30 ± 0.88 |
| 22 | 246.80 ± 25.50 | 60.00 ± 5.51 | 27.10 ± 4.18 | 107.30 ± 2.33 |
| 24 | 8.14 ± 0.94 | 55.30 ± 2.91 | 2.91 ± 0.18 | 104.00 ± 4.04 |
| 31 | 739.90 ± 49.50 | 57.30 ± 2.73 | 633.00 ± 87.10 | 107.70 ± 3.76 |
| 32 | >20 μM | 5.33 ± 1.45 | >20 μM | −1.00 ± 0.00 |
| 33 | 503.30 ± 43.50 | 43.00 ± 3.79 | 327.60 ± 22.10 | 93.70 ± 1.76 |
| 34 | 3.84 ± 1.53 | 20.30 ± 1.76 | 0.81 ± 0.12 | 71.00 ± 1.53 |
| 35 | 2.55 ± 0.33 | 25.70 ± 0.88 | 0.20 ± 0.042 | 97.30 ± 2.85 |
| 36 | 2.36 ± 0.64 | 24.30 ± 0.88 | 0.34 ± 0.033 | 62.00 ± 3.06 |

TABLE 2A-continued

Activity Response of 7-Substituted Morphinan Compounds in U2-OS cells

| | GTPγS ($EC_{50}$: nM, $E_{max}$: %) | | | |
|---|---|---|---|---|
| | μ | | κ | |
| Cpd. No. | $EC_{50}$ | $E_{max}$ | $EC_{50}$ | $E_{max}$ |
| 37 | 3.35 ± 0.41 | 24.30 ± 0.88 | 0.50 ± 0.039 | 87.70 ± 2.19 |
| 38 | 1.27 ± 0.19 | 23.30 ± 1.86 | 0.33 ± 0.022 | 80.00 ± 3.79 |
| 39 | >20 μM | 2.00 ± 0.00 | >20 μM | 1.00 ± 0.00 |
| 40 | >20 μM | 2.00 ± 0.00 | 7.24 ± 0.65 | 43.00 ± 3.06 |
| 41 | 674.10 ± 63.80 | 74.70 ± 4.67 | 41.60 ± 2.25 | 102.30 ± 2.19 |
| 42 | 2.81 ± 0.16 | 67.30 ± 2.85 | 0.25 ± 0.029 | 110.00 ± 0.00 |
| 45 | 72.00 ± 15.90 | 71.00 ± 5.69 | 10.60 ± 2.10 | 106.00 ± 1.00 |
| 46 | 0.38 ± 0.11 | 54.00 ± 6.03 | 0.10 ± 0.021 | 102.30 ± 5.24 |
| 47 | 0.61 ± 0.17 | 44.00 ± 1.73 | 0.14 ± 0.027 | 105.30 ± 1.76 |
| 49 | 8460.00 ± 627.10 | 27.00 ± 1.53 | 7945.00 ± 222.60 | 90.30 ± 1.67 |
| 50 | 113.00 ± 60.80 | 12.80 ± 0.85 | 47.30 ± 3.70 | 91.70 ± 1.33 |
| 51 | >20 μM | 7.00 ± 0.00 | 14534 ± 1680 | 86.70 ± 3.18 |
| 52 | 1255.00 ± 203.90 | 23.20 ± 4.07 | 1566.00 ± 97.40 | 91.30 ± 0.67 |
| 53 | >20 μM | 3.00 ± 0.00 | 73.80 ± 11.80 | 62.00 ± 1.53 |
| 54 | >20 μM | 3.00 ± 0.00 | 32.10 ± 2.76 | 97.70 ± 3.93 |
| 55 | >20 μM | 4.00 ± 0.00 | 194.30 ± 54.40 | 77.70 ± 5.49 |
| 56 | 95.00 ± 16.40 | 19.30 ± 1.45 | 29.30 ± 4.34 | 104.70 ± 3.38 |
| 57 | 77.70 ± 10.30 | 9.00 ± 0.58 | 33.10 ± 3.53 | 113.00 ± 5.86 |
| 58 | 80.90 ± 15.10 | 19.30 ± 1.45 | 38.10 ± 2.20 | 100.70 ± 1.20 |
| 59 | 45.00 ± 8.96 | 22.30 ± 1.45 | 35.60 ± 4.27 | 98.30 ± 3.18 |
| 60 | 54.70 ± 8.10 | 25.30 ± 0.33 | 31.40 ± 3.70 | 106.30 ± 6.06 |
| 61 | 61.60 ± 5.41 | 26.70 ± 0.88 | 15.40 ± 2.43 | 97.70 ± 2.19 |
| 62 | 43.30 ± 5.60 | 60.30 ± 0.88 | 17.40 ± 1.46 | 90.20 ± 1.65 |
| 63 | 63.20 ± 8.31 | 58.70 ± 1.33 | 38.80 ± 7.82 | 84.30 ± 1.67 |
| 64 | 111.80 ± 19.30 | 7.33 ± 0.33 | 48.30 ± 3.10 | 93.70 ± 2.33 |
| 65 | 68.40 ± 13.00 | 26.70 ± 0.67 | 15.90 ± 2.09 | 106.20 ± 1.89 |
| 66 | 114.10 ± 14.50 | 15.00 ± 0.58 | 39.20 ± 4.27 | 71.70 ± 1.20 |
| 67 | >20 μM | 2.00 ± 0.00 | 55.50 ± 8.50 | 89.30 ± 1.67 |
| 68 | 4.54 ± 1.28 | 31.30 ± 1.33 | 1.67 ± 0.099 | 104.00 ± 2.31 |
| 102 | 470.20 ± 69.90 | 42.00 ± 1.73 | 1917.00 ± 150.90 | 58.30 ± 0.67 |

The in vitro test results of Tables 1, 2 and 2A show that representative Compounds of the Invention generally bind to opioid receptors, and that these compounds activate these receptors as partial to full agonists. Compounds of the Invention are therefore expected to be useful to treat Conditions, particularly pain, that are responsive to activation of one or more opioid receptors.

TABLE 3

Exemplified 7-Substituted Morphinan Compounds

| Cpd. No. | Compound name and structure |
|---|---|
| 3 | 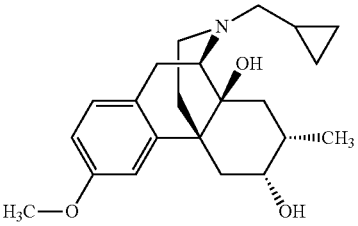 [SMILES: COc1ccc2c(c1)[C@]13CCN(CC4CC4)[C@H](C2)[C@]1(O)C[C@H](C)[C@H](O)C3] (4bR,6R,7S,8aS,9R)-11-(cyclopropylmethyl)-3-methoxy-7-methyl-5,6,7,8,9,10-hexahydro-8aH-9,4b-(epiminoethano)phenanthrene-6,8a-diol |

TABLE 3-continued

Exemplified 7-Substituted Morphinan Compounds

| Cpd. No. | Compound name and structure | |
|---|---|---|
| 4 | 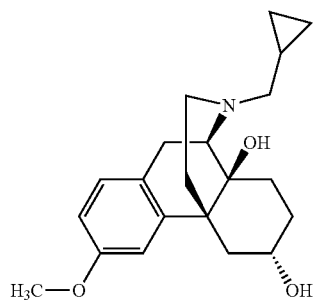 [SMILES: COc1ccc2c(c1)[C@]13CCN(CC4CC4)[C@H](C2)[C@]1(O)CC[C@H](O)C3] | (4bR,6S,8aS,9R)-11-(cyclopropylmethyl)-3-methoxy-5,6,7,8,9,10-hexahydro-8aH-9,4b-(epiminoethano)phenanthrene-6,8a-diol |
| 7 | 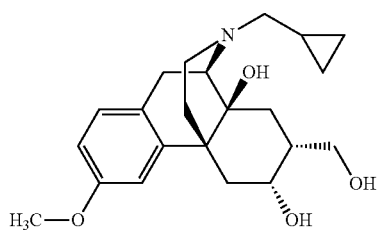 [SMILES: COc1ccc2c(c1)[C@]13CCN(CC4CC4)[C@H](C2)[C@]1(O)C[C@H](CO)[C@H](O)C3] | (4bR,6R,7R,8aS,9R)-11-(cyclopropylmethyl)-7-(hydroxymethyl)-3-methoxy-5,6,7,8,9,10-hexahydro-8aH-9,4b-(epiminoethano)phenanthrene-6,8a-diol |
| 9 | 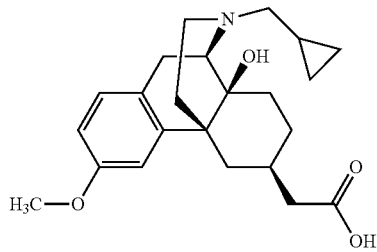 [SMILES: COc1ccc2c(c1)[C@]13CCN(CC4CC4)[C@H](C2)[C@]1(O)CC[C@@H](CC(=O)O)C3] | 2-((4bS,6R,8aS,9R)-11-(cyclopropylmethyl)-8a-hydroxy-3-methoxy-6,7,8,8a,9,10-hexahydro-5H-9,4b-(epiminoethano)phenanthren-6-yl)acetic acid |
| 10 | 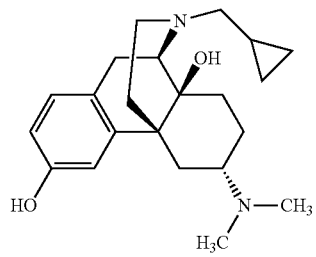 [SMILES: CN(C)[C@H]1CC[C@@]2(O)[C@H]3Cc4ccc(O)cc4[C@@]2(CCN3CC2CC2)C1] | (4bR,6S,8aS,9R)-11-(cyclopropylmethyl)-6-(dimethylamino)-5,6,7,8,9,10-hexahydro-8aH-9,4b-(epiminoethano)phenanthrene-3,8a-diol |
| 11 | 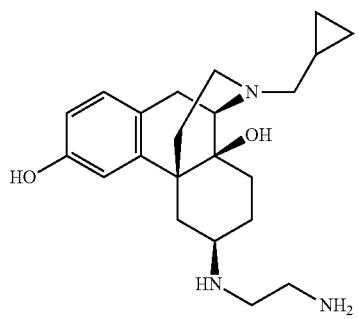 [SMILES: NCCN[C@@H]1CC[C@@]2(O)[C@H]3Cc4ccc(O)cc4[C@@]2(CCN3CC2CC2)C1] | (4bR,6R,8aS,9R)-6-((2-aminoethyl)amino)-11-(cyclopropylmethyl)-5,6,7,8,9,10-hexahydro-8aH-9,4b-(epiminoethano)phenanthrene-3,8a-diol |

TABLE 3-continued

Exemplified 7-Substituted Morphinan Compounds

| Cpd. No. | Compound name and structure | |
|---|---|---|
| 12 | 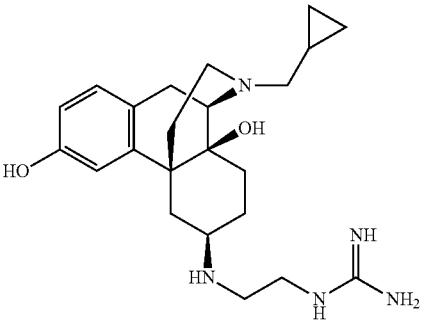 [SMILES: N=C(N)NCCN[C@@H]1CC[C@@]2(O)[C@H]3Cc4ccc(O)cc4[C@@]2(CCN3CC2CC2)C1] | 1-(2-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)ethyl)guanidine |
| 13 | 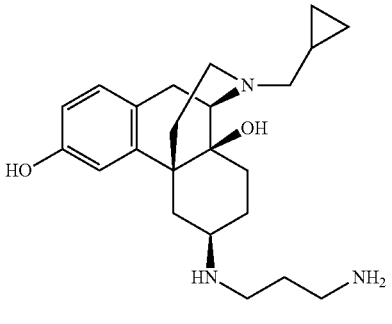 [SMILES: NCCCN[C@@H]1CC[C@@]2(O)[C@H]3Cc4ccc(O)cc4[C@@]2(CCN3CC2CC2)C1] | (4bR,6R,8aS,9R)-6-((3-aminopropyl)amino)-11-(cyclopropylmethyl)-5,6,7,8,9,10-hexahydro-8aH-9,4b-(epiminoethano)phenanthrene-3,8a-diol |
| 14 | 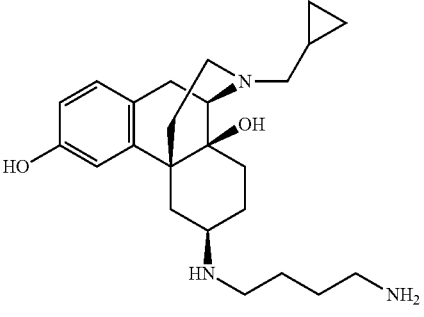 [SMILES: NCCCCN[C@@H]1CC[C@@]2(O)[C@H]3Cc4ccc(O)cc4[C@@]2(CCN3CC2CC2)C1] | (4bR,6R,8aS,9R)-6-((4-aminobutyl)amino)-11-(cyclopropylmethyl)-5,6,7,8,9,10-hexahydro-8aH-9,4b-(epiminoethano)phenanthrene-3,8a-diol |
| 15 | 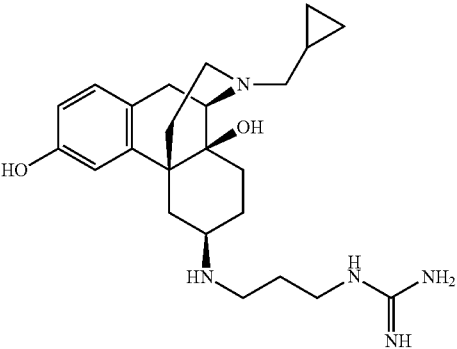 [SMILES: N=C(N)NCCCN[C@@H]1CC[C@@]2(O)[C@H]3Cc4ccc(O)cc4[C@@]2(CCN3CC2CC2)C1] | 1-(3-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)propyl)guanidine |

TABLE 3-continued

Exemplified 7-Substituted Morphinan Compounds

| Cpd. No. | Compound name and structure |
|---|---|
| 16 | 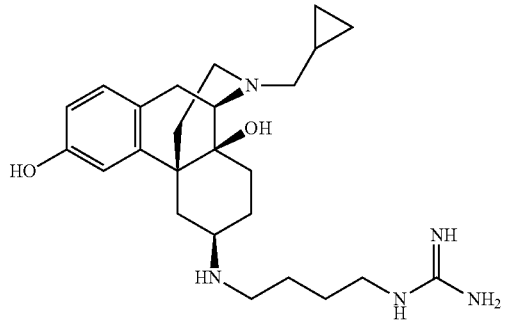 [SMILES: N=C(N)NCCCCN[C@@H]1CC[C@@]2(O)[C@H]3Cc4ccc(O)cc4[C@@]2(CCN3CC2CC2)C1] 1-(4-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)butyl)guanidine |
| 20 | 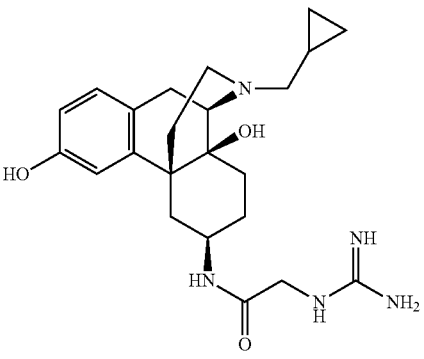 [SMILES: N=C(N)NCC(=O)N[C@@H]1CC[C@@]2(O)[C@H]3Cc4ccc(O)cc4[C@@]2(CCN3CC2CC2)C1] N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-2-guanidinoacetamide |
| 21 | 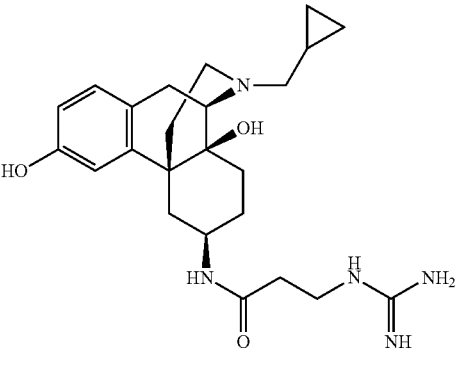 [SMILES: N=C(N)NCCC(=O)N[C@@H]1CC[C@@]2(O)[C@H]3Cc4ccc(O)cc4[C@@]2(CCN3CC2CC2)C1] N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-3-guanidinopropanamide |
| 22 | 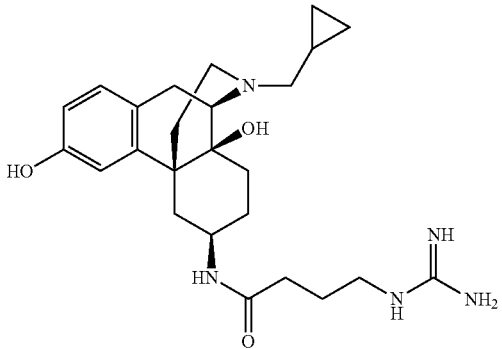 [SMILES: N=C(N)NCCCC(=O)N[C@@H]1CC[C@@]2(O)[C@H]3Cc4ccc(O)cc4[C@@]2(CCN3CC2CC2)C1] N-((4bR,6R,8aS,9R)-11-(cyclopropylmethyl)-3,8a-dihydroxy-6,7,8,8a,9,10-hexahydro-5H-9,4b-(epiminoethano)phenanthren-6-yl)-4-guanidinobutanamide |

TABLE 3-continued

Exemplified 7-Substituted Morphinan Compounds

| Cpd. No. | Compound name and structure |
|---|---|
| 24 | 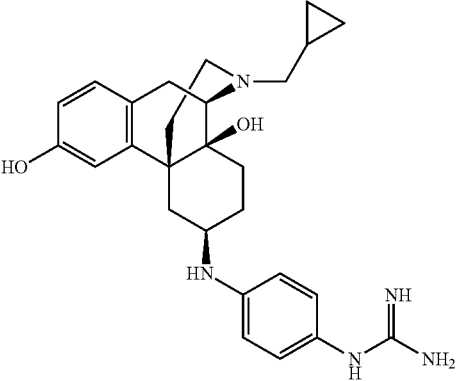 [SMILES: N=C(N)Nc1ccc(N[C@@H]2CC[C@@]3(O)[C@H]4Cc5ccc(O)cc5[C@@]3(CCN4CC3CC3)C2)cc1] 1-(4-(((4bR,6R,8aS,9R)-11-(cyclopropylmethyl)-3,8a-dihydroxy-6,7,8,8a,9,10-hexahydro-5H-9,4b-(epiminoethano)phenanthren-6-yl)amino)phenyl)guanidine |
| 31 | 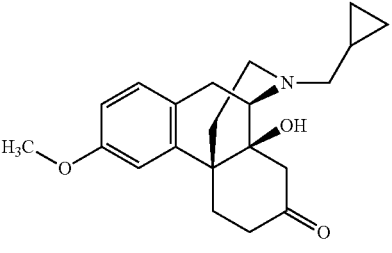 [SMILES: COc1ccc2c(c1)[C@@]13CCC(=O)C[C@@]1(O)[C@@H](C2)N(CC1CC1)CC3] (4bS,8aS,9R)-11-(cyclopropylmethyl)-8a-hydroxy-3-methoxy-5,6,8,8a-9,10-hexahydro-7H-9,4b-(epiminoethano)phenanthren-7-one |
| 32 | 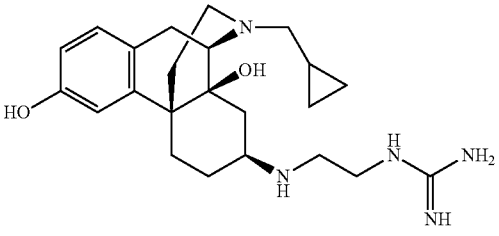 [SMILES: N=C(N)NCCN[C@H]1CC[C@]23CCN(CC4CC4)[C@H](Cc4ccc(O)cc42)[C@]3(O)C1] 1-(2-(((4bS,7S,8aS,9R)-11-(cyclopropylmethyl)-3,8a-dihydroxy-6,7,8,8a,9,10-hexahydro-5H-9,4b-(epiminoethano)phenanthren-7-yl)amino)ethyl)guanidine |
| 33 | 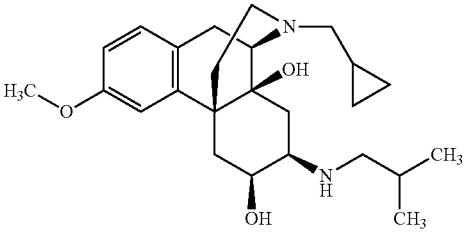 [SMILES: COc1ccc2c(c1)[C@]13CCN(CC4CC4)[C@H](C2)[C@]1(O)C[C@@H](NCC(C)C)[C@@H](O)C3] (4bR,6S,7R,8aS,9R)-11-(cyclopropylmethyl)-7-(isobutylamino)-3-methyl-5,6,7,8,9,10-hexahydro-8aH-9,4b-(epiminoethano)phenanthrene-6,8a-diol |
| 34 | 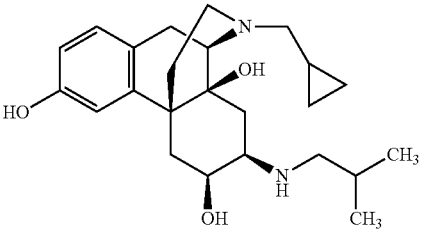 [SMILES: CC(C)CN[C@@H]1C[C@@]2(O)[C@H]3Cc4ccc(O)cc4[C@@]2(CCN3CC2CC2)C[C@@H]1O] (4bR,6S,7R,8aS,9R)-11-(cyclopropylmethyl)-7-(isobutylamino)-5,6,7,8,9,10-hexahydro-8aH-9,4b-(epiminoethano)phenanthrene-3,6,8a-triol |

TABLE 3-continued

Exemplified 7-Substituted Morphinan Compounds

| Cpd. No. | Compound name and structure | |
|---|---|---|
| 35 | 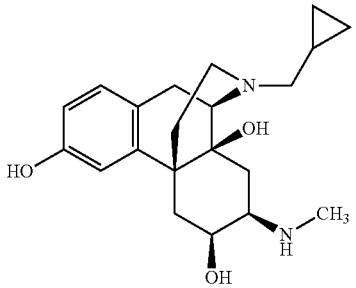 [SMILES: CN[C@@H]1C[C@@]2(O)[C@H]3Cc4ccc(O)cc4[C@@]2(CCN3CC2CC2)C[C@@H]1O] | (4bR,6S,7R,8aS,9R)-11-(cyclopropylmethyl)-7-(methylamino)-5,6,7,8,9,10-hexahydro-8aH-9,4b-(epiminoethano)phenanthrene-3,6,8a-triol |
| 36 | 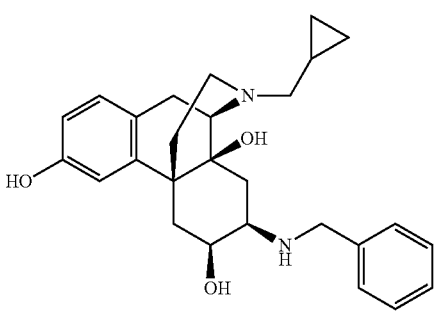 [SMILES: Oc1ccc2c(c1)[C@]13CCN(CC4CC4)[C@H](C2)[C@]1(O)C[C@@H](NCc1ccccc1)[C@@H](O)C3] | (4bR,6S,7R,8aS,9R)-7-(benzylamino)-11-(cyclopropylmethyl)-5,6,7,8,9,10-hexahydro-8aH-9,4b-(epiminoethano)phenanthrene-3,6,8a-triol |
| 37 | 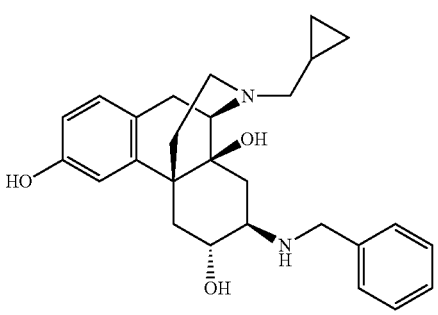 [SMILES: Oc1ccc2c(c1)[C@]13CCN(CC4CC4)[C@H](C2)[C@]1(O)C[C@@H](NCc1ccccc1)[C@H](O)C3] | (4bR,6R,7R,8aS,9R)-7-(benzylamino)-11-(cyclopropylmethyl)-5,6,7,8,9,10-hexahydro-8aH-9,4b-(epiminoethano)phenanthrene-3,6,8a-triol |
| 38 | 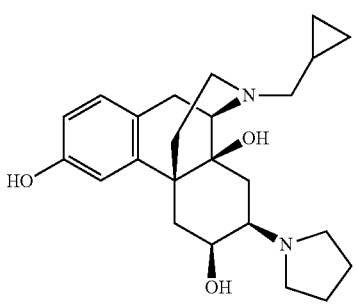 [SMILES: Oc1ccc2c(c1)[C@]13CCN(CC4CC4)[C@H](C2)[C@]1(O)C[C@@H](N1CCCC1)[C@@H](O)C3] | (4bR,6S,7R,8aS,9R)-11-(cyclopropylmethyl)-7-(pyrrolidin-1-yl)-5,6,7,8,9,10-hexahydro-8aH-9,4b-(epiminoethano)phenanthrene-3,6,8a-triol |
| 39 | 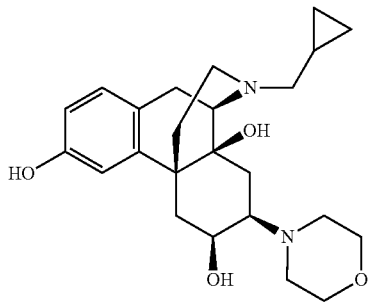 [SMILES: Oc1ccc2c(c1)[C@]13CCN(CC4CC4)[C@H](C2)[C@]1(O)C[C@@H](N1CCOCC1)[C@@H](O)C3] | (4bR,6S,7R,8aS,9R)-11-(cyclopropylmethyl)-7-morpholino-5,6,7,8,9,10-hexahydro-8aH-9,4b-(epiminoethano)phenanthrene-3,6,8a-triol |

TABLE 3-continued

Exemplified 7-Substituted Morphinan Compounds

| Cpd. No. | Compound name and structure |
|---|---|
| 40 | 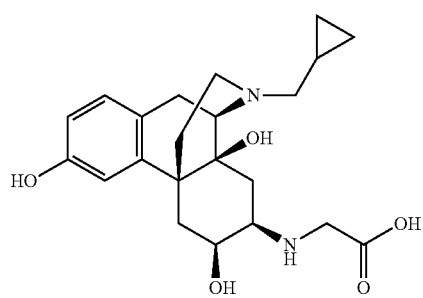 [SMILES: O=C(O)CN[C@@H]1C[C@@]2(O)[C@H]3Cc4ccc(O)cc4[C@@]2(CCN3CC2CC2)C[C@@H]1O] ((4bR,6S,7R,8aS,9R)-11-(cyclopropylmethyl)-3,6,8a-trihydroxy-6,7,8,8a,9,10-hexahydro-5H-9,4b-(epiminoethano)phenanthren-7-yl)glycine |
| 41 | 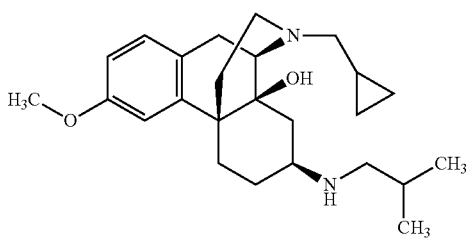 [SMILES: COc1ccc2c(c1)[C@@]13CC[C@H](NCC(C)C)C[C@@]1(O)[C@@H](C2)N(CC1CC1)CC3] (4bS,7S,8aS,9R)-11-(cyclopropylmethyl)-7-(isobutylamino)-3-methoxy-5,6,7,8,9,10-hexahydro-8aH-9,4b-(epiminoethano)phenanthren-8a-ol |
| 42 | 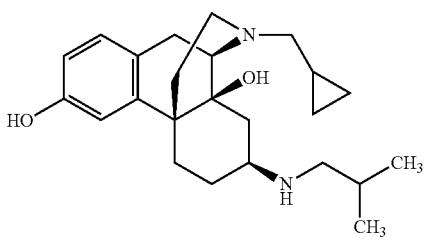 [SMILES: CC(C)CN[C@H]1CC[C@]23CCN(CC4CC4)[C@H](Cc4ccc(O)cc42)[C@]3(O)C1] (4bS,7S,8aS,9R)-11-(cyclopropylmethyl)-7-(isobutylamino)-5,6,7,8,9,10-hexahydro-8aH-9,4b-(epiminoethano)phenanthrene-3,8a-diol |
| 45 | 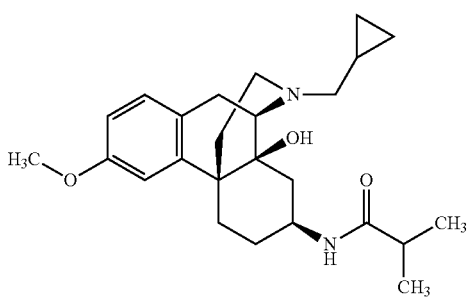 [SMILES: COc1ccc2c(c1)[C@@]13CC[C@H](NC(=O)C(C)C)C[C@@]1(O)[C@@H](C2)N(CC1CC1)CC3] N-((4bS,7S,8aS,9R)-11-(cyclopropylmethyl)-8a-hydroxy-3-methoxy-6,7,8,8a,9,10-hexahydro-5H-9,4b-(epiminoethano)phenanthren-7-yl)isobutyramide |
| 46 | 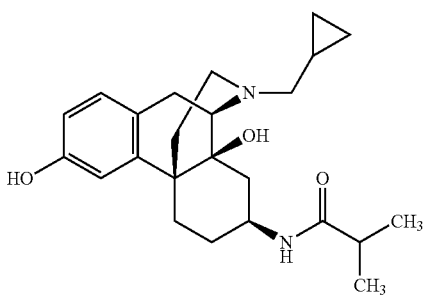 [SMILES: CC(C)C(=O)N[C@H]1CC[C@]23CCN(CC4CC4)[C@H](Cc4ccc(O)cc42)[C@]3(O)C1] N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)isobutyramide |

TABLE 3-continued

Exemplified 7-Substituted Morphinan Compounds

| Cpd. No. | Compound name and structure | |
|---|---|---|
| 47 | 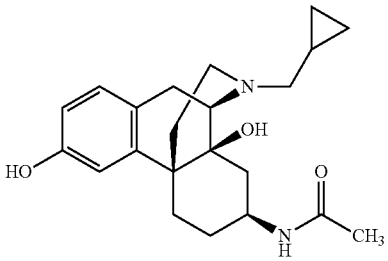 [SMILES: CC(=O)N[C@H]1CC[C@]23CCN(CC4CC4)[C@H](Cc4ccc(O)cc42)[C@]3(O)C1] | N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)acetamide |
| 49 | 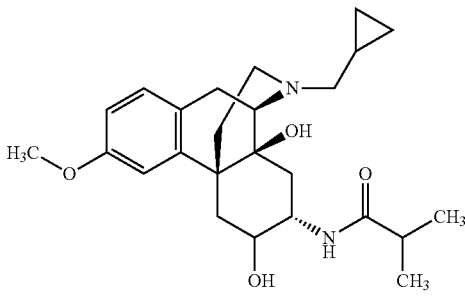 [SMILES: COc1ccc2c(c1)[C@]13CCN(CC4CC4)[C@H](C2)[C@]1(O)C[C@H](NC(=O)C(C)C)C(O)C3] | N-((4bR,7S,8aS,9R)-11-(cyclopropylmethyl)-6,8a-dihydroxy-3-methoxy-6,7,8,8a,9,10-hexahydro-5H-9,4b-(epiminoethano)phenanthren-7-yl)isobutyramide |
| 50 | 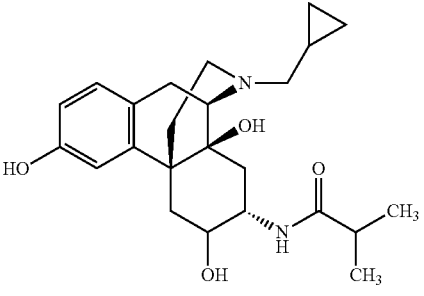 [SMILES: CC(C)C(=O)N[C@H]1C[C@@]2(O)[C@H]3Cc4ccc(O)cc4[C@@]2(CCN3CC2CC2)CC1O] | N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide |
| 51 | 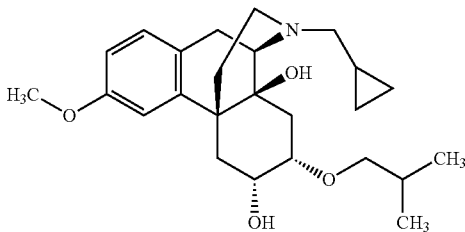 [SMILES: COc1ccc2c(c1)[C@]13CCN(CC4CC4)[C@H](C2)[C@]1(O)C[C@H](OCC(C)C)[C@H](O)C3] | (4bR,6R,7S,8aS,9R)-11-(cyclopropylmethyl)-7-isobutoxy-3-methoxy-5,6,7,8,9,10-hexahydro-8aH-9,4b-(epiminoethano)phenanthrene-6,8a-diol |
| 52 | 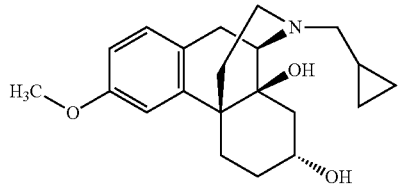 [SMILES: COc1ccc2c(c1)[C@@]13CC[C@@H](O)C[C@@]1(O)[C@@H](C2)N(CC1CC1)CC3] | (4bS,7R,8aS,9R)-11-(cyclopropylmethyl)-3-methoxy-5,6,7,8,9,10-hexahydro-8aH-9,4b-(epiminoethano)phenanthrene-7,8a-diol |

TABLE 3-continued

Exemplified 7-Substituted Morphinan Compounds

| Cpd. No. | Compound name and structure | |
|---|---|---|
| 53 | 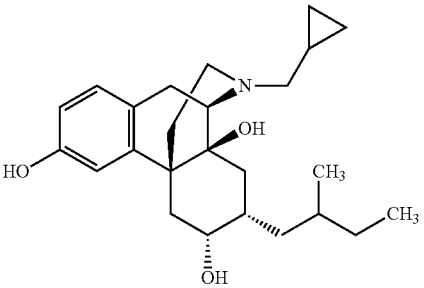 [SMILES: CCC(C)C[C@H]1C[C@@]2(O)[C@H]3Cc4ccc(O)cc4[C@@]2(CCN3CC2CC2)C[C@H]1O] | (4bR,6R,7S,8aS,9R)-11-(cyclopropylmethyl)-7-(2-methylbutyl)-5,6,7,8,9,10-hexahydro-8aH-9,4b-(epiminoethano)phenanthrene-3,6,8a-triol |
| 54 | 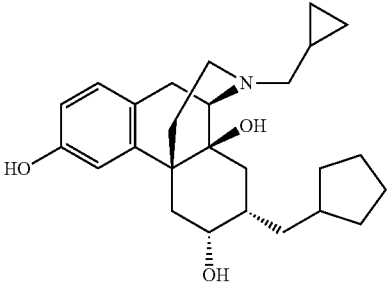 [SMILES: Oc1ccc2c(c1)[C@]13CCN(CC4CC4)[C@H](C2)[C@]1(O)C[C@H](CC1CCCC1)[C@H](O)C3] | (4bR,6R,7S,8aS,9R)-7-(cyclopentylmethyl)-11-(cyclopropylmethyl)-5,6,7,8,9,10-hexahydro-8aH-9,4b-(epiminoethano)phenanthrene-3,6,8a-triol |
| 55 | 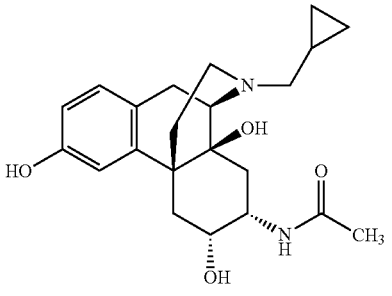 [SMILES: CC(=O)N[C@H]1C[C@@]2(O)[C@H]3Cc4ccc(O)cc4[C@@]2(CCN3CC2CC2)C[C@H]1O] | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)acetamide |
| 56 | 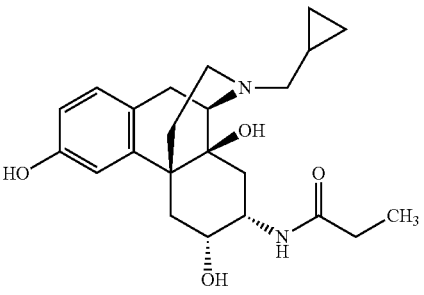 [SMILES: CCC(=O)N[C@H]1C[C@@]2(O)[C@H]3Cc4ccc(O)cc4[C@@]2(CCN3CC2CC2)C[C@H]1O] | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)propionamide |
| 57 | 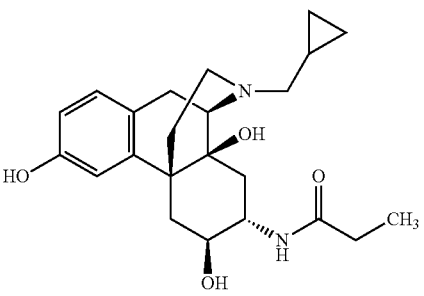 [SMILES: CCC(=O)N[C@H]1C[C@@]2(O)[C@H]3Cc4ccc(O)cc4[C@@]2(CCN3CC2CC2)C[C@@H]1O] | N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)propionamide |

TABLE 3-continued

Exemplified 7-Substituted Morphinan Compounds

| Cpd. No. | Compound name and structure | |
|---|---|---|
| 58 | 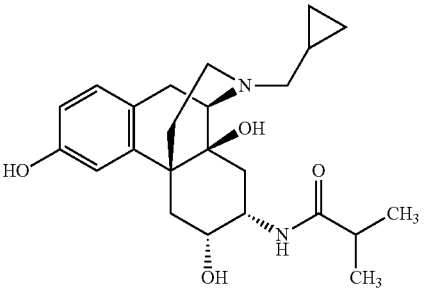 [SMILES: CC(C)C(=O)N[C@H]1C[C@@]2(O)[C@H]3Cc4ccc(O)cc4[C@@]2(CCN3CC2CC2)C[C@H]1O] | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide |
| 59 | 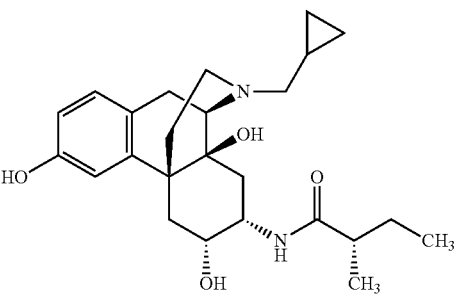 [SMILES: CC[C@H](C)C(=O)N[C@H]1C[C@@]2(O)[C@H]3Cc4ccc(O)cc4[C@@]2(CCN3CC2CC2)C[C@H]1O] | (S)-N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-2-methylbutanamide |
| 60 | 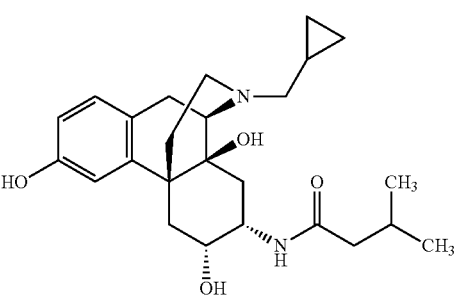 [SMILES: CC(C)CC(=O)N[C@H]1C[C@@]2(O)[C@H]3Cc4ccc(O)cc4[C@@]2(CCN3CC2CC2)C[C@H]1O] | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-3-methylbutanamide |
| 61 | 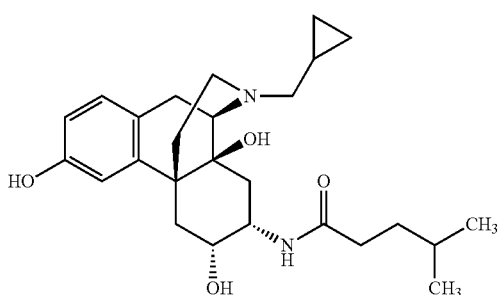 | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-4-methylpentanamide |
| 62 | 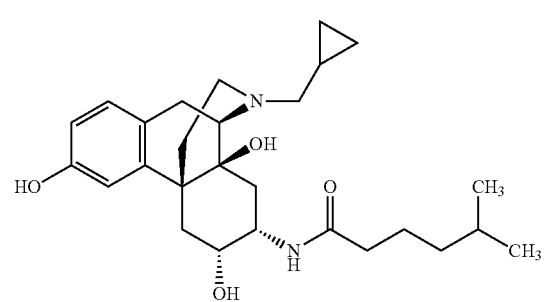 [SMILES: CC(C)CCCC(=O)N[C@H]1C[C@@]2(O)[C@H]3Cc4ccc(O)cc4[C@@]2(CCN3CC2CC2)C[C@H]1O] | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide |

TABLE 3-continued

Exemplified 7-Substituted Morphinan Compounds

| Cpd. No. | Compound name and structure |
|---|---|
| 63 | N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide |
| 64 | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclopropanecarboxamide |
| 65 | N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclohexanecarboxamide |
| 66 | N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)benzamide |
| 67 | (4bR,6R,7S,8aS,9R)-11-(cyclopropylmethyl)-7-isobutyl-5,6,7,8,9,10-hexahydro-8aH-9,4b-(epiminoethano)phenanthrene-3,6,8a-triol |

TABLE 3-continued

Exemplified 7-Substituted Morphinan Compounds

| Cpd. No. | Compound name and structure | |
|---|---|---|
| 68 | 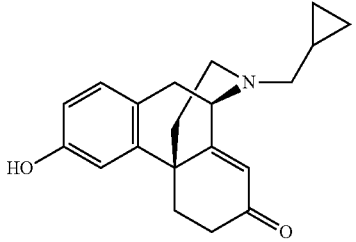 [SMILES: O=C1C=C2[C@H]3Cc4ccc(O)cc4[C@]2(CC1)CCN3CC1CC1] | (4bS,9R)-11-(cyclopropylmethyl)-3-hydroxy-5,6,9,10-tetrahydro-7H-9,4b-(epiminoethano)phenanthren-7-one |
| 101 | 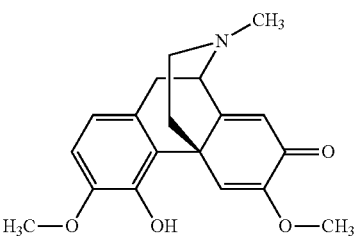 | (4bS)-4-hydroxy-3,6-dimethoxy-11-methyl-9,10-dihydro-7H-9,4b-(epiminoethano)phenanthren-7-one |
| 102 | 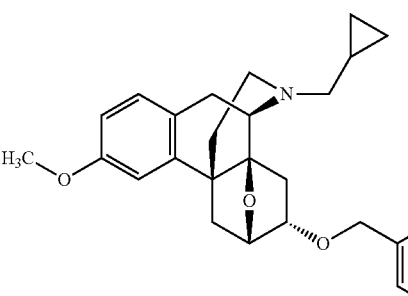 | (4bR,6S,7S,8aS,9R)-7-(benzyloxy)-11-(cyclopropylmethyl)-3-methoxy-5,6,7,8,9,10-hexahydro-9,4b-(epiminoethano)-6,8a-epoxyphenanthrene |

TABLE 3A

Exemplified Compounds Of the Invention

| Cpd. No. | Compound name and structure | |
|---|---|---|
| 103 | 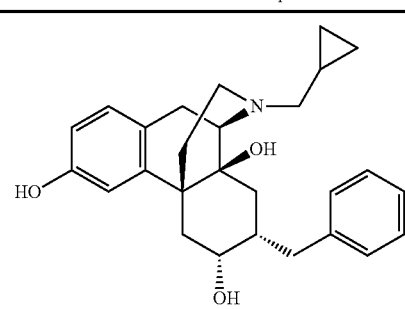 | (4bR,6R,7S,8aS,9R)-7-benzyl-11-(cyclopropylmethyl)-5,6,7,8,9,10-hexahydro-8aH-9,4b-(epimino-ethano)phenanthrene-3,6,8a-triol |
| 104 | 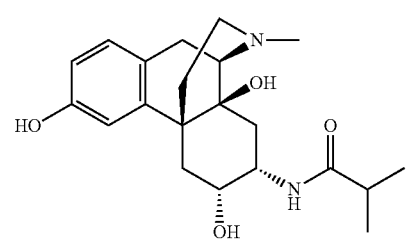 [SMILES: CC(C)C(=O)N[C@H]1C[C@@]2(O)[C@H]3Cc4ccc(O)cc4[C@@]2(CCN3C)C[C@H]1O] | N-((4bR,6R,7S,8aS,9R)-3,6,8a-trihydroxy-11-methyl-6,7,8,8a,9,10-hexahydro-5H-9,4b-(epiminoethano)phenanthren-7-yl)isobutyramide |

TABLE 3A-continued

Exemplified Compounds Of the Invention

| Cpd. No. | Compound name and structure | |
|---|---|---|
| 105 | 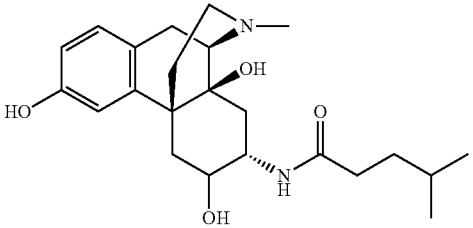 [SMILES: CC(C)CCC(=O)N[C@H]1C[C@@]2(O)[C@H]3Cc4ccc(O)cc4[C@@]2(CCN3C)CC1O] | 4-methyl-N-((4bR,7S,8aS,9R)-3,6,8a-trihydroxy-11-methyl-6,7,8,8a,9,10-hexahydro-5H-9,4b-(epiminoethano)phenanthren-7-yl)pentanamide |
| 106 | 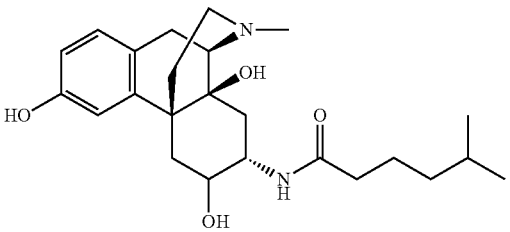 [SMILES: CC(C)CCCC(=O)N[C@H]1C[C@@]2(O)[C@H]3Cc4ccc(O)cc4[C@@]2(CCN3C)CC1O] | 5-methyl-N-((4bR,7S,8aS,9R)-3,6,8a-trihydroxy-11-methyl-6,7,8,8a,9,10-hexahydro-5H-9,4b-(epiminoethano)phenanthren-7-yl)hexanamide |
| 107 | 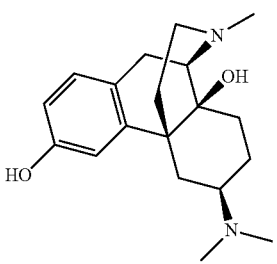 [SMILES: CN(C)[C@@H]1CC[C@@]2(O)[C@H]3Cc4ccc(O)cc4[C@@]2(CCN3C)C1] | (4bR,6R,8aS,9R)-6-(dimethylamino)-11-methyl-5,6,7,8,9,10-hexahydro-8aH-9,4b-(epiminoethano)phenanthrene-3,8a-diol |
| 108 | 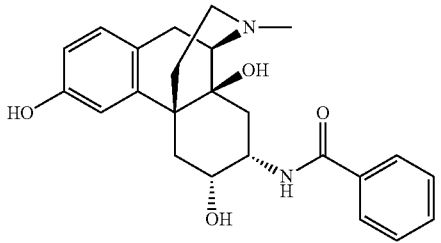 [SMILES: CN1CC[C@]23C[C@@H](O)[C@@H](NC(=O)c4ccccc4)C[C@@]2(O)[C@H]1Cc1ccc(O)cc13] | N-((4bR,6R,7S,8aS,9R)-3,6,8a-trihydroxy-11-methyl-6,7,8,8a,9,10-hexahydro-5H-9,4b-(epiminoethano)phenanthren-7-yl)benzamide |
| 109 | 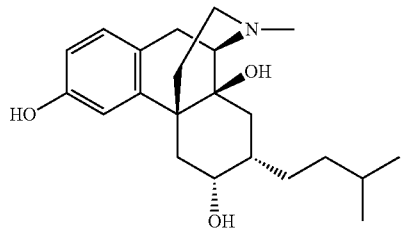 [SMILES: CC(C)CC[C@H]1C[C@@]2(O)[C@H]3Cc4ccc(O)cc4[C@@]2(CCN3C)C[C@H]1O] | (4bR,6R,7S,8aS,9R)-7-isopentyl-11-methyl-5,6,7,8,9,10-hexahydro-8aH-9,4b-(epiminoethano)phenanthrene-3,6,8a-triol |
| 110 | 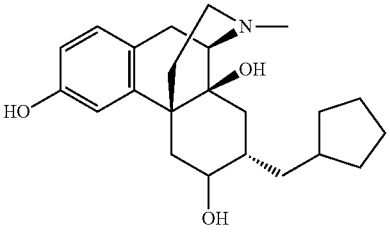 [SMILES: CN1CC[C@]23CC(O)[C@@H](CC4CCCC4)C[C@@]2(O)[C@H]1Cc1ccc(O)cc13] | (4bR,7S,8aS,9R)-7-(cyclopentylmethyl)-11-methyl-5,6,7,8,9,10-hexahydro-8aH-9,4b-(epiminoethano)phenanthrene-3,6,8a-triol |

TABLE 3A-continued

Exemplified Compounds Of the Invention

| Cpd. No. | Compound name and structure | |
|---|---|---|
| 111 | 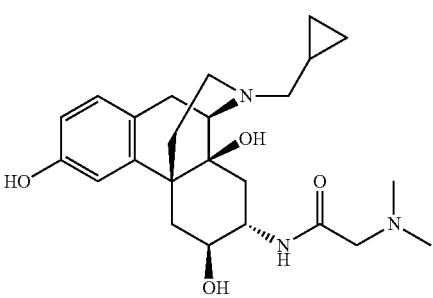 [SMILES: CN(C)CC(=O)N[C@H]1C[C@@]2(O)[C@H]3Cc4ccc(O)cc4[C@@]2(CCN3CC2CC2)C[C@@H]1O] | N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)-2-(dimethylamino)acetamide |
| 112 | 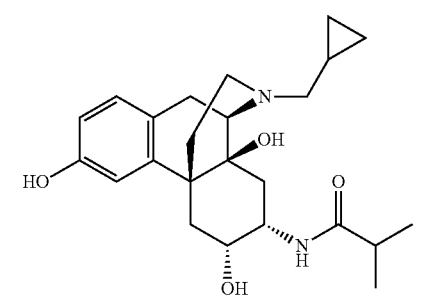 [SMILES: CC(C)C(=O)N[C@H]1C[C@@]2(O)[C@H]3Cc4ccc(O)cc4[C@@]2(CCN3CC2CC2)C[C@H]1O] | N-((4bS,6R,7S,8aR,9R)-11-(cyclopropylmethyl)-3,6-dihydroxy-6,7,8,8a,9,10-hexahydro-5H-9,4b-(epiminoethano)phenanthren-7-yl)isobutyramide |
| 113 | 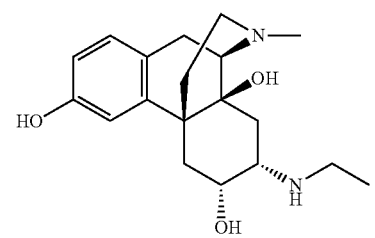 [SMILES: CCN[C@H]1C[C@@]2(O)[C@H]3Cc4ccc(O)cc4[C@@]2(CCN3C)C[C@H]1O] | (4bR,6R,7S,8aS,9R)-7-(ethylamino)-11-methyl-5,6,7,8,9,10-hexahydro-8aH-9,4b-(epiminoethano)phenanthrene-3,6,8a-triol |
| 114 | 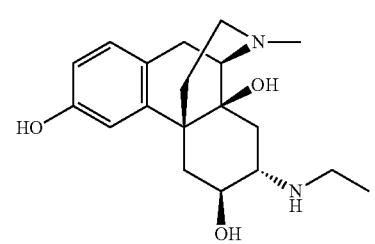 [SMILES: CCN[C@H]1C[C@@]2(O)[C@H]3Cc4ccc(O)cc4[C@@]2(CCN3C)C[C@@H]1O] | (4bR,6S,7S,8aS,9R)-7-(ethylamino)-11-methyl-5,6,7,8,9,10-hexahydro-8aH-9,4b-(epiminoethano)phenanthrene-3,6,8a-triol |
| 115 | 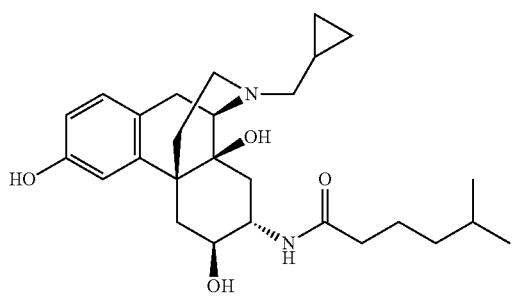 [SMILES: CC(C)CCCC(=O)N[C@H]1C[C@@]2(O)[C@H]3Cc4ccc(O)cc4[C@@]2(CCN3CC2CC2)C[C@@H]1O] | N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide |

TABLE 3A-continued

Exemplified Compounds Of the Invention

| Cpd. No. | Compound name and structure | |
|---|---|---|
| 116 | 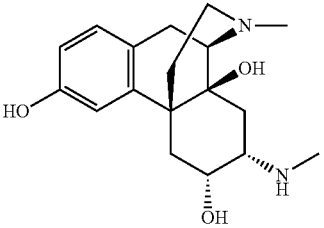 [SMILES: CN[C@H]1C[C@@]2(O)[C@H]3Cc4ccc(O)cc4[C@@]2(CCN3C)C[C@H]1O] | (4bR,6R,7S,8aS,9R)-11-methyl-7-(methylamino)-5,6,7,8,9,10-hexahydro-8aH-9,4b-(epiminoethano)phen-anthrene-3,6,8a-triol |
| 117 | 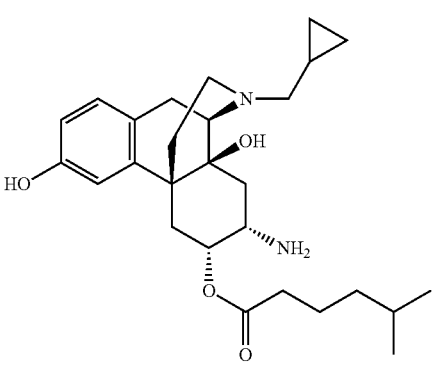 [SMILES: CC(C)CCCC(=O)O[C@@H]1C[C@]23CCN(CC4CC4)[C@H](Cc4ccc(O)cc42)[C@]3(O)C[C@@H]1N] | (4bR,6R,7S,8aS,9R)-7-amino-11-(cyclopropylmethyl)-3,8a-dihydroxy-6,7,8,8a,9,10-hexahydro-5H-9,4b-(epiminoethano)phenanthren-6-yl 5-methylhexanoate |
| 118 | 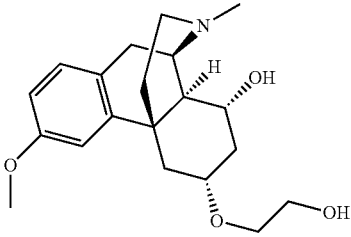 [SMILES: COc1ccc2c(c1)[C@]13CCN(C)[C@H](C2)[C@H]1[C@H](O)C[C@H](OCCO)C3] | (4bS,6R,8R,8aS,9R)-6-(2-hydroxyethoxy)-3-methoxy-11-methyl-6,7,8,8a,9,10-hexahydro-5H-9,4b-(epiminoethano)phenanthren-8-ol |
| 119 | 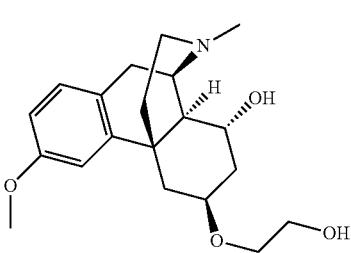 [SMILES: COc1ccc2c(c1)[C@]13CCN(C)[C@H](C2)[C@H]1[C@H](O)C[C@@H](OCCO)C3] | (4bS,6S,8R,8aS,9R)-6-(2-hydroxyethoxy)-3-methoxy-11-methyl-6,7,8,8a,9,10-hexahydro-5H-9,4b-(epiminoethano)phenanthren-8-ol |
| 120 | 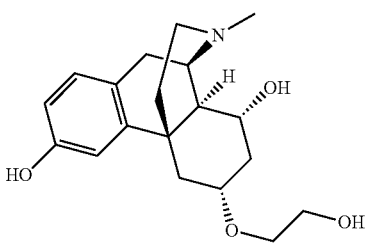 [SMILES: CN1CC[C@]23C[C@@H](OCCO)C[C@@H](O)[C@@H]2[C@H]1Cc1ccc(O)cc13] | (4bS,6R,8R,8aS,9R)-6-(2-hydroxyethoxy)-11-methyl-6,7,8,8a,9,10-hexahydro-5H-9,4b-(epiminoethano)phenanthrene-3,8-diol |

TABLE 3A-continued

Exemplified Compounds Of the Invention

| Cpd. No. | Compound name and structure |
|---|---|
| 121 | 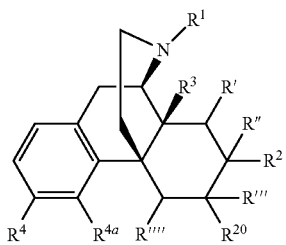 (4bS,6S,8R,8aS,9R)-6-(2-hydroxyethoxy)-11-methyl-6,7,8,8a,9,10-hexahydro-5H-9,4b-(epiminoethano)phenanthrene-3,8-diol |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed:
1. A compound of Formula I-J:

I-J or a pharmaceutically acceptable salt or solvate thereof, wherein
R', R", R''', and R'''' are all H;
$R^1$ is $(C_3-C_6)$cycloalkyl-$(C_1-C_3)$alkyl-;
$R^{4a}$ is H;
$R^3$ is —OH;
$R^4$ is —OH or —$(C_1-C_3)$alkoxy; and
$R^{20}$ is —OH;
$R^2$ is —$Z^1$-$G^1$-$R^{10a}$;
$Z^1$ is $(CH_2)_m$ optionally substituted with —$(C_1-C_6)$alkyl;
m is 0 or 1; and
when a) $R^2$ is —$Z^1$-$G^1$-$R^{10a}$ and m is 1,
then $G^1$ is a bond, —O—, or —NH—, and $R^{10a}$ is selected from the group consisting of H, phenyl, phenyl-$(C_1-C_3)$alkyl-, —$(C_3-C_8)$cycloalkyl, and —$(C_1-C_6)$alkyl optionally substituted by —$(C_1-C_3)$alkyl or —COOH; and
b) $R^2$ is —$Z^1$-$G^1$-$R^{10a}$ and m is 0,
then $G^1$ is —NH—C(═O)—, and $R^{10a}$ is —$(C_3-C_8)$cycloalkyl, phenyl, or —$(C_1-C_6)$alkyl optionally substituted by —$(C_1-C_3)$alkyl or —$NR^5R^6$; wherein $R^5$ and $R^6$, respectively, are H or —$(C_1-C_6)$alkyl.

2. A compound selected from the group consisting of:
(4bR,6R,7S,8aS,9R)-11-(cyclopropylmethyl)-3-methoxy-7-methyl-5,6,7,8,9,10-hexahydro-8aH-9,4b-(epiminoethano)phenanthrene-6,8a-diol;
(4bR,6R,7R,8aS,9R)-11-(cyclopropylmethyl)-7-(hydroxymethyl)-3-methoxy-5,6,7,8,9,10-hexahydro-8aH-9,4b-(epiminoethano)phenanthrene-6,8a-diol;
1-(2-(((4bS,7S,8aS,9R)-11-(cyclopropylmethyl)-3,8a-dihydroxy-6,7,8,8a,9,10-hexahydro-5H-9,4b-(epiminoethano)phenanthren-7-yl)amino)ethyl)guanidine;
(4bR,6S,7R,8aS,9R)-11-(cyclopropylmethyl)-7-(isobutylamino)-3-methoxy-5,6,7,8,9,10-hexahydro-8aH-9,4b-(epiminoethano)phenanthrene-6,8a-diol;
(4bR,6S,7R,8aS,9R)-11-(cyclopropylmethyl)-7-(isobutylamino)-5,6,7,8,9,10-hexahydro-8aH-9,4b-(epiminoethano)phenanthrene-3,6,8a-triol;
(4bR,6S,7R,8aS,9R)-11-(cyclopropylmethyl)-7-(methylamino)-5,6,7,8,9,10-hexahydro-8aH-9,4b-(epiminoethano)phenanthrene-3,6,8a-triol;
(4bR,6S,7R,8aS,9R)-7-(benzylamino)-11-(cyclopropylmethyl)-5,6,7,8,9,10-hexahydro-8aH-9,4b-(epiminoethano)phenanthrene-3,6,8a-triol;
(4bR,6R,7R,8aS,9R)-7-(benzylamino)-11-(cyclopropylmethyl)-5,6,7,8,9,10-hexahydro-8aH-9,4b-(epiminoethano)phenanthrene-3,6,8a-triol;
(4bR,6S,7R,8aS,9R)-11-(cyclopropylmethyl)-7-(pyrrolidin-1-yl)-5,6,7,8,9,10-hexahydro-8aH-9,4b-(epiminoethano)phenanthrene-3,6,8a-triol;
(4bR,6S,7R,8aS,9R)-11-(cyclopropylmethyl)-7-morpholino-5,6,7,8,9,10-hexahydro-8aH-9,4b-(epiminoethano)phenanthrene-3,6,8a-triol;
((4bR,6S,7R,8aS,9R)-11-(cyclopropylmethyl)-3,6,8a-trihydroxy-6,7,8,8a,9,10-hexahydro-5H-9,4b-(epiminoethano)phenanthren-7-yl)glycine;
(4bS,7S,8aS,9R)-11-(cyclopropylmethyl)-7-(isobutylamino)-3-methoxy-5,6,7,8,9,10-hexahydro-8aH-9,4b-(epiminoethano)phenanthren-8a-ol;
(4bS,7S,8aS,9R)-11-(cyclopropylmethyl)-7-(isobutylamino)-5,6,7,8,9,10-hexahydro-8aH-9,4b-(epiminoethano)phenanthrene-3,8a-diol;
N-((4bS,7S,8aS,9R)-11-(cyclopropylmethyl)-8a-hydroxy-3-methoxy-6,7,8,8a,9,10-hexahydro-5H-9,4b-(epiminoethano)phenanthren-7-yl)isobutyramide;
N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)isobutyramide;
N-((4bS,7S,8aS,9R)-11-(cyclopropylmethyl)-3,8a-dihydroxy-6,7,8,8a,9,10-hexahydro-5H-9,4b-(epiminoethano)phenanthren-7-yl)acetamide;
N-((4bR,7S,8aS,9R)-11-(cyclopropylmethyl)-6,8a-dihydroxy-3-methoxy-6,7,8,8a,9,10-hexahydro-5H-9,4b-(epiminoethano)phenanthren-7-yl)isobutyramide;

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide;

(4bR,6R,7S,8aS,9R)-11-(cyclopropylmethyl)-7-isobutoxy-3-methoxy-5,6,7,8,9,10-hexahydro-8aH-9,4b-(epiminoethano)phenanthrene-6,8a-diol;

(4bS,7R,8aS,9R)-11-(cyclopropylmethyl)-3-methoxy-5,6,7,8,9,10-hexahydro-8aH-9,4b-(epiminoethano)phenanthrene-7,8a-diol;

(4bR,6R,7S,8aS,9R)-11-(cyclopropylmethyl)-7-(2-methylbutyl)-5,6,7,8,9,10-hexahydro-8aH-9,4b-(epiminoethano)phenanthrene-3,6,8a-triol;

(4bR,6R,7S,8aS,9R)-7-(cyclopentylmethyl)-11-(cyclopropylmethyl)-5,6,7,8,9,10-hexahydro-8aH-9,4b-(epiminoethano)phenanthrene-3,6,8a-triol;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)acetamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)propionamide;

N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)propionamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)isobutyramide;

(S)—N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-2-methylbutanamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-3-methylbutanamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-4-methylpentanamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide;

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclopropanecarboxamide;

N-((4bR,7S,8aS,9R)-11-(cyclopropylmethyl)-3,6,8a-trihydroxy-6,7,8,8a,9,10-hexahydro-5H-9,4b-(epiminoethano)phenanthren-7-yl)cyclohexanecarboxamide;

N-((4bR,6R,7S,8aS,9R)-11-(cyclopropylmethyl)-3,6,8a-trihydroxy-6,7,8,8a,9,10-hexahydro-5H-9,4b-(epiminoethano)phenanthren-7-yl)benzamide;

(4bR,6R,7S,8aS,9R)-11-(cyclopropylmethyl)-7-isobutyl-5,6,7,8,9,10-hexahydro-8aH-9,4b-(epiminoethano)phenanthrene-3,6,8a-triol;

(4bR,6S,7S,8aS,9R)-7-(benzyloxy)-11-(cyclopropylmethyl)-3-methoxy-5,6,7,8,9,10-hexahydro-9,4b-(epiminoethano)-6,8a-epoxyphenanthrene;

(4bR,6R,7S,8aS,9R)-7-benzyl-11-(cyclopropylmethyl)-5,6,7,8,9,10-hexahydro-8aH-9,4b-(epiminoethano)phenanthrene-3,6,8a-triol (Compound 103);

N-((4bR,6R,7S,8aS,9R)-3,6,8a-trihydroxy-11-methyl-6,7,8,8a,9,10-hexahydro-5H-9,4b-(epiminoethano)phenanthren-7-yl)isobutyramide (Compound 104);

4-methyl-N-((4bR,7S,8aS,9R)-3,6,8a-trihydroxy-11-methyl-6,7,8,8a,9,10-hexahydro-5H-9,4b-(epiminoethano)phenanthren-7-yl)pentanamide (Compound 105);

5-methyl-N-((4bR,7S,8aS,9R)-3,6,8a-trihydroxy-11-methyl-6,7,8,8a,9,10-hexahydro-5H-9,4b-(epiminoethano)phenanthren-7-yl)hexanamide (Compound 106);

N-((4bR,6R,7S,8aS,9R)-3,6,8a-trihydroxy-11-methyl-6,7,8,8a,9,10-hexahydro-5H-9,4b-(epiminoethano)phenanthren-7-yl)benzamide (Compound 108);

(4bR,6R,7S,8aS,9R)-7-isopentyl-11-methyl-5,6,7,8,9,10-hexahydro-8aH-9,4b-(epiminoethano)phenanthrene-3,6,8a-triol (Compound 109);

(4bR,7S,8aS,9R)-7-(cyclopentylmethyl)-11-methyl-5,6,7,8,9,10-hexahydro-8aH-9,4b-(epiminoethano)phenanthrene-3,6,8a-triol (Compound 110);

N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)-2-(dimethylamino)acetamide (Compound 111);

N-((4bS,6R,7S,8aR,9R)-11-(cyclopropylmethyl)-3,6-dihydroxy-6,7,8,8a,9,10-hexahydro-5H-9,4b-(epiminoethano)phenanthren-7-yl)isobutyramide (Compound 112);

(4bR,6R,7S,8aS,9R)-7-(ethylamino)-11-methyl-5,6,7,8,9,10-hexahydro-8aH-9,4b-(epiminoethano)phenanthrene-3,6,8a-triol (Compound 113);

(4bR,6S,7S,8aS,9R)-7-(ethylamino)-11-methyl-5,6,7,8,9,10-hexahydro-8aH-9,4b-(epiminoethano)phenanthrene-3,6,8a-triol (Compound 114);

N-((4bR,6S,7S,8aS,9R)-11-(cyclopropylmethyl)-3,6,8a-trihydroxy-6,7,8,8a,9,10-hexahydro-5H-9,4b-(epiminoethano)phenanthren-7-yl)-5-methylhexanamide (Compound 115);

(4bR,6R,7S,8aS,9R)-11-methyl-7-(methylamino)-5,6,7,8,9,10-hexahydro-8aH-9,4b-(epiminoethano)phenanthrene-3,6,8a-triol (Compound 116); and (4bR,6R,7S,8aS,9R)-7-amino-11-(cyclopropylmethyl)-3,8a-dihydroxy-6,7,8,8a,9,10-hexahydro-5H-9,4b-(epiminoethano)phenanthren-6-yl 5-methylhexanoate (Compound 117);

or a pharmaceutically acceptable salt or solvate thereof.

3. A pharmaceutical composition comprising an effective amount of a compound of claim 1, or a pharmaceutically acceptable salt or solvate thereof, and a pharmaceutically acceptable carrier or excipient.

4. A method of treating a Condition in an animal in need thereof, comprising administering to such animal in need thereof an effective amount of a compound of claim 1, or a pharmaceutically acceptable salt or solvate thereof, wherein the Condition is pain.

5. The compound of claim 1, wherein $R^{10a}$ is phenyl.

6. The compound of claim 1, wherein $R^4$ is —OH.

7. The compound of claim 1, wherein $R^4$ is methoxy.

8. The compound of claim 1, wherein $R^1$ is cyclopropylmethyl.

9. A pharmaceutical composition comprising an effective amount of a compound of claim 2, or a pharmaceutically acceptable salt or solvate thereof, and a pharmaceutically acceptable carrier or excipient.

10. A method of treating a Condition in an animal in need thereof, comprising administering to such animal in need thereof an effective amount of a compound of claim 2, or a pharmaceutically acceptable salt or solvate thereof, wherein the Condition is pain.

* * * * *